US012630522B2

(12) United States Patent
Kim et al.

(10) Patent No.: US 12,630,522 B2
(45) Date of Patent: May 19, 2026

(54) COMPOUND FOR ORGANIC OPTOELECTRONIC DEVICE, COMPOSITION FOR ORGANIC OPTOELECTRONIC DEVICE, AND ORGANIC OPTOELECTRONIC DEVICE AND DISPLAY DEVICE

(71) Applicant: SAMSUNG SDI CO., LTD., Yongin-si (KR)

(72) Inventors: Byungku Kim, Suwon-si (KR); Yunsoo Kim, Suwon-si (KR); Sunwoong Shin, Suwon-si (KR); Namheon Lee, Suwon-si (KR); Byoungkwan Lee, Suwon-si (KR); Kipo Jang, Suwon-si (KR); Hyunjung Kim, Suwon-si (KR); Eunhye An, Suwon-si (KR); Mijin Lee, Suwon-si (KR); Suyong Lim, Suwon-si (KR); Sung-Hyun Jung, Suwon-si (KR); Youngkyoung Jo, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 1044 days.

(21) Appl. No.: 17/741,653

(22) Filed: May 11, 2022

(65) Prior Publication Data

US 2022/0388976 A1 Dec. 8, 2022

(30) Foreign Application Priority Data

May 12, 2021 (KR) ........................ 10-2021-0061606
May 10, 2022 (KR) ........................ 10-2022-0057504

(51) Int. Cl.
*C07D 333/76* (2006.01)
*C07D 251/24* (2006.01)
(Continued)

(52) U.S. Cl.
CPC ......... *C07D 333/76* (2013.01); *C07D 251/24* (2013.01); *C07D 307/91* (2013.01);
(Continued)

(58) Field of Classification Search
CPC ................ C07D 251/24; C07D 333/76; C07D 307/91; H10K 85/6574; H10K 85/6576; H10K 85/636
See application file for complete search history.

(56) References Cited

U.S. PATENT DOCUMENTS 5,061,569 A 10/1991 Vanslyke et al.
2016/0093810 A1* 3/2016 Miyake ............. H10K 85/6574 548/440
(Continued)

FOREIGN PATENT DOCUMENTS

CN 106749198 A 5/2017
CN 107936957 A * 4/2018 ........... C07D 409/12
(Continued)

OTHER PUBLICATIONS

Machine-generated English-language translation of CN-107936957-A.*
(Continued)

*Primary Examiner* — Vu A Nguyen
(74) *Attorney, Agent, or Firm* — Lee IP Law, P.C.

(57) ABSTRACT

A compound, a composition for an organic optoelectronic device, an organic optoelectronic device, and a display device, the compound being represented by Chemical Formula 1:
(Continued)

[Chemical Formula 1]

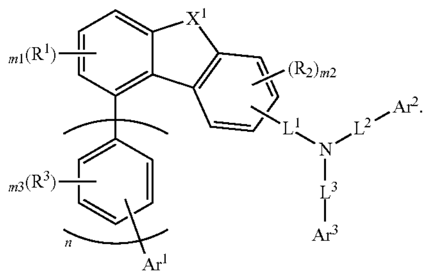

20 Claims, 1 Drawing Sheet

(51) Int. Cl.

| | |
|---|---|
| ***C07D 307/91*** | (2006.01) |
| ***C07D 403/04*** | (2006.01) |
| ***C07D 403/10*** | (2006.01) |
| ***C07D 405/04*** | (2006.01) |
| ***C07D 405/10*** | (2006.01) |
| ***C07D 405/14*** | (2006.01) |
| ***C07D 409/04*** | (2006.01) |
| ***C07D 409/10*** | (2006.01) |
| ***C07D 409/12*** | (2006.01) |
| ***C07D 409/14*** | (2006.01) |
| ***C07D 413/12*** | (2006.01) |
| ***C07F 7/08*** | (2006.01) |
| ***H10K 50/11*** | (2023.01) |
| ***H10K 85/40*** | (2023.01) |
| ***H10K 85/60*** | (2023.01) |

(52) U.S. Cl.

CPC ......... *C07D 403/04* (2013.01); *C07D 403/10* (2013.01); *C07D 405/04* (2013.01); *C07D 405/10* (2013.01); *C07D 405/14* (2013.01); *C07D 409/04* (2013.01); *C07D 409/10* (2013.01); *C07D 409/12* (2013.01); *C07D 409/14* (2013.01); *C07D 413/12* (2013.01); *C07F 7/0812* (2013.01); *H10K 50/11* (2023.02); *H10K 85/40* (2023.02); *H10K 85/657* (2023.02); *H10K 85/6572* (2023.02); *H10K 85/6574* (2023.02); *H10K 85/6576* (2023.02); *C07B 2200/05* (2013.01)

(56) References Cited

U.S. PATENT DOCUMENTS

| | | | | |
|---|---|---|---|---|
| 2017/0012204 | A1 | 1/2017 | Jin et al. | |
| 2019/0288206 | A1 | 9/2019 | Parham et al. | |
| 2021/0359216 | A1 | 11/2021 | Kim et al. | |
| 2022/0199911 | A1 * | 6/2022 | Lee | H10K 85/615 |
| 2022/0278284 | A1 | 9/2022 | So et al. | |

FOREIGN PATENT DOCUMENTS

| | | | | | |
|---|---|---|---|---|---|
| CN | 108101896 | A | | 6/2018 | |
| CN | 108178763 | A | | 6/2018 | |
| CN | 108623545 | A | | 10/2018 | |
| CN | 111354873 | A | | 6/2020 | |
| CN | 111732578 | A | | 10/2020 | |
| CN | 113045434 | A | * | 6/2021 | C07C 211/61 |
| CN | 114907298 | A | | 8/2022 | |
| EP | 3792255 | A1 | * | 3/2021 | H10K 85/6574 |
| JP | 1993-009471 | A | | 1/1993 | |
| JP | 1995-126615 | A | | 5/1995 | |
| JP | 1998-095973 | A | | 4/1998 | |
| KR | 10-2017-0007683 | A | | 1/2017 | |
| KR | 10-2018-0010167 | A | | 1/2018 | |
| KR | 20180010167 | A | * | 1/2018 | C07D 405/04 |
| KR | 10-2019-0060914 | A | | 6/2019 | |
| KR | 10-2019-0079181 | A | | 7/2019 | |
| KR | 10-2019-0079646 | A | | 9/2019 | |
| KR | 10-2078171 | B1 | | 2/2020 | |
| KR | 10-2020-0026079 | A | | 3/2020 | |
| KR | 10-2020-0072211 | A | | 6/2020 | |
| KR | 10-2020-0131646 | A | | 11/2020 | |
| KR | 10-2020-0131681 | A | | 11/2020 | |
| WO | WO 1995/09147 | A1 | | 4/1995 | |
| WO | WO-2020231197 | A1 | * | 11/2020 | C07D 409/12 |

OTHER PUBLICATIONS

Machine-generated English-language translation of KR-20180010167-A.*

Machine-generated English-language translation of CN-113045434-A.*

Korean Office action dated Aug. 29, 2024.

Chinese Office action dated Apr. 29, 2024.

Korean Notice of Allowance dated Apr. 28, 2025.

* cited by examiner

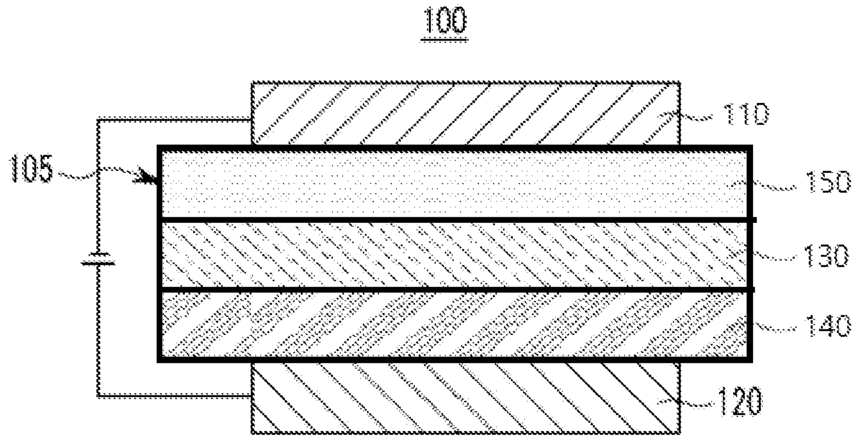
100
110
105
150
130
140
120

COMPOUND FOR ORGANIC OPTOELECTRONIC DEVICE, COMPOSITION FOR ORGANIC OPTOELECTRONIC DEVICE, AND ORGANIC OPTOELECTRONIC DEVICE AND DISPLAY DEVICE

CROSS-REFERENCE TO RELATED APPLICATIONS

This application claims priority to and the benefit of Korean Patent Application No. 10-2021-0061606 filed in the Korean Intellectual Property Office on May 12, 2021, and Korean Patent Application No. 10-2022-0057504 filed in the Korean Intellectual Property Office on May 10, 2022, the entire contents of which are incorporated herein by reference.

BACKGROUND

1. Field

Embodiments relate to a compound for an organic optoelectronic device, a composition for an organic optoelectronic device, an organic optoelectronic device, and a display device.

2. Description of the Related Art

An organic optoelectronic device (e.g., an organic optoelectronic diode) is a device capable of converting electrical energy and optical energy to each other.

An organic optoelectronic device may be classified as follows in accordance with its driving principles. One is a photoelectric device that generates electrical energy by separating excitons formed by light energy into electrons and holes, and transferring the electrons and holes to different electrodes, respectively and the other is light emitting device that generates light energy from electrical energy by supplying voltage or current to the electrodes.

Examples of the organic optoelectronic device may include an organic photoelectric element, an organic light emitting diode, an organic solar cell, and an organic photo conductor drum.

Of these, an organic light emitting diode (OLED) has recently drawn attention due to an increase in demand for flat panel displays. The organic light emitting diode is a device that converts electrical energy into light, and the performance of the organic light emitting diode is greatly influenced by an organic material between electrodes.

SUMMARY

The embodiments may be realized by providing a compound for an organic optoelectronic device represented by Chemical Formula 1:

[Chemical Formula 1]

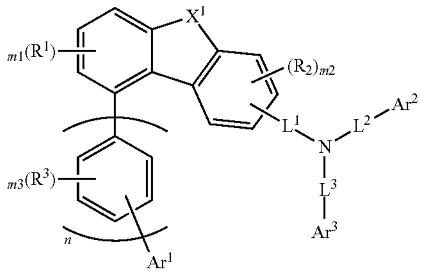

wherein, in Chemical Formula 1, $X^1$ is O or S, $L^1$ to $L^3$ are each independently a single bond, a substituted or unsubstituted C6 to C20 arylene group, or a substituted or unsubstituted C2 to C30 heterocyclic group, $Ar^1$ is a substituted or unsubstituted C7 to C20 aryl group, $Ar^2$ and $Ar^3$ are each independently a substituted or unsubstituted C6 to C20 aryl group or a substituted or unsubstituted C2 to C30 heterocyclic group, $R^1$ to $R^3$ are each independently hydrogen, deuterium, a halogen, a substituted or unsubstituted C1 to C10 alkyl group, or a substituted or unsubstituted C6 to C12 aryl group, m1 and m2 are each independently an integer of 1 to 3, m3 is an integer of 1 to 4, and n is 0 or 1.

The embodiments may be realized by providing a composition for an organic optoelectronic device, the composition including a first compound; and a second compound, wherein the first compound is the compound for an organic optoelectronic device according to an embodiment, the second compound is a compound for an organic optoelectronic device represented by Chemical Formula 2:

[Chemical Formula 2]

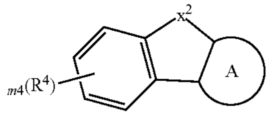

in Chemical Formula 2, $X^2$ is O, S, N-$L^a$-$R^a$, $CR^bR^c$, or $SiR^dR^e$, $L^a$ is a single bond or a substituted or unsubstituted C6 to C12 arylene group, $R^a$, $R^b$, $R^c$, $R^d$, $R^e$ and $R^4$ are each independently hydrogen, deuterium, a substituted or unsubstituted C1 to C30 alkyl group, a substituted or unsubstituted C6 to C30 aryl group, or a substituted or unsubstituted C2 to C30 heterocyclic group, m4 is an integer of 1 to 4, and A is a ring of Group II,

[Group II]

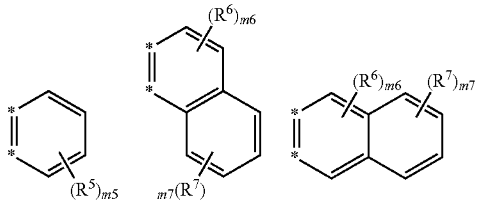

-continued

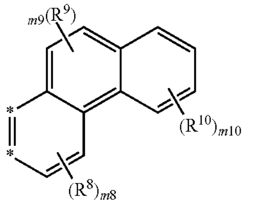

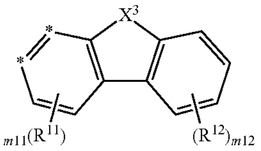

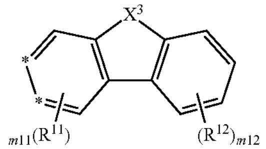

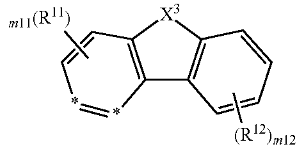

in Group II, * is a linking point, $X^3$ is O or S, $R^5$ to $R^{12}$ are each independently hydrogen, deuterium, a substituted or unsubstituted C1 to C30 alkyl group, a substituted or unsubstituted C6 to C30 aryl group, or a substituted or unsubstituted C2 to C30 heterocyclic group, m5, m7, m10, and m12 are each independently an integer of 1 to 4, m6, m8, m9, and m11 are each independently 1 or 2, and at least one of $R^a$ and $R^4$ to $R'^2$ is a substituted heterocyclic group represented by Chemical Formula a,

[Chemical Formula a]

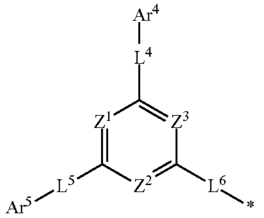

in Chemical Formula a, $Z^1$ to $Z^3$ are each independently N or $CR^f$, provided that at least two of $Z^1$ to $Z^3$ are N, $R^f$ is hydrogen, deuterium, a substituted or unsubstituted C1 to C10 alkyl group, or a substituted or unsubstituted C6 to C20 aryl group, $L^4$ to $L^6$ are each independently a single bond or a substituted or unsubstituted C6 to C30 arylene group, $Ar^4$ and $Ar^5$ are each independently a substituted or unsubstituted C6 to C30 aryl group or a substituted or unsubstituted C2 to C30 heterocyclic group, and * is a linking point.

The embodiments may be realized by providing an organic optoelectronic device including an anode and a cathode facing each other, and at least one organic layer between the anode and the cathode, wherein the at least one organic layer includes the compound for an organic optoelectronic device according to an embodiment.

The embodiments may be realized by providing an organic optoelectronic device including an anode and a cathode facing each other, and at least one organic layer between the anode and the cathode, wherein the at least one organic layer includes the composition for an organic optoelectronic device according to an embodiment.

The embodiments may be realized by providing a display device including the organic optoelectronic device according to an embodiment.

BRIEF DESCRIPTION OF THE DRAWING

Features will become apparent to those of skill in the art by describing in detail exemplary embodiments with reference to the attached drawing in which:

the FIGURE is a cross-sectional view of an organic light emitting diode according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

In one example of the present disclosure, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In specific example of the present disclosure, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In specific example of the present disclosure, the "substituted" refers to replacement of at least one hydrogen of a substituent or a compound by deuterium, a C1 to C20 alkyl group, a C6 to C30 aryl group, or a cyano group. In specific example of the present disclosure, the "substituted" refers to replacement of at least one hydrogen of a substituent or a compound by deuterium, a C1 to C5 alkyl group, a C6 to C18 aryl group, or a cyano group. In specific example of the present disclosure, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, "unsubstituted" refers to non-replacement of a hydrogen atom by another substituent and remaining of the hydrogen atom.

As used herein, "hydrogen substitution (—H)" may include deuterium substitution (-D) or "tritium substitution (-T).

As used herein, when a definition is not otherwise provided, "hetero" refers to one including one to three heteroatoms selected from N, O, S, P, and Si, and remaining carbons in one functional group.

As used herein, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic, or fused ring polycyclic (i.e., rings sharing adjacent pairs of carbon atoms) functional group.

As used herein, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted benzophenanthrenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, a substituted or unsubstituted benzonaphthofuranyl group, a substituted or unsubstituted benzonaphthothiophenyl group, a substituted or unsubstituted benzofuranofluorenyl group, a substituted or unsubstituted benzothiophenefluorenyl group, or a combination thereof, but is not limited thereto.

As used herein, "hydrogen substitution (—H)" may include "deuterium substitution (-D)" or "tritium substitution (-T)".

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment may be represented by, e.g., Chemical Formula 1.

[Chemical Formula 1]

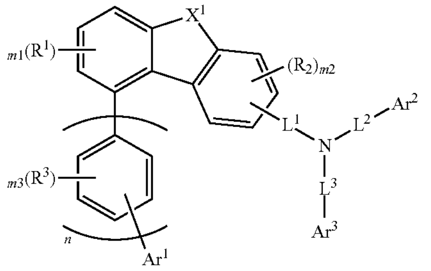

In Chemical Formula 1, $X^1$ may be, e.g., O or S.

$L^1$ to $L^3$ may each independently be or include, e.g., a single bond, a substituted or unsubstituted C6 to C20 arylene group, or a substituted or unsubstituted C2 to C30 heterocyclic group. As used herein, the term "or" is not an exclusive term, e.g., "A or B" would include A, B, or A and B.

$Ar^1$ may be or may include, e.g., a substituted or unsubstituted C7 to C20 aryl group.

$Ar^2$ and $Ar^3$ may each independently be or include, e.g., a substituted or unsubstituted C6 to C20 aryl group or a substituted or unsubstituted C2 to C30 heterocyclic group.

$R^1$ to $R^3$ may each independently be or include, e.g., hydrogen, deuterium, a halogen, a substituted or unsubstituted C1 to C10 alkyl group, or a substituted or unsubstituted C6 to C12 aryl group.

m1 and m2 may each independently be, e.g., an integer of 1 to 3.

m3 may be, e.g., an integer of 1 to 4.

n may be, e.g., 0 or 1.

The compound represented by Chemical Formula 1 may have excellent thermal stability by including a substituted or unsubstituted C7 to C20 aryl group (e.g., not an unsubstituted phenyl group) at a 1$^{st}$ position of dibenzofuran (or dibenzothiophene), and may have a low deposition process temperature compared to molecular weight due to the dibenzofuran (or dibenzothiophene).

Accordingly, stability of the device in the device manufacturing process and a stable film against Joule heat generated during device driving may be maintained, so that an organic light emitting diode including the compound represented by Chemical Formula 1 may secure a stable driving voltage and excellent life-span characteristics.

In Chemical Formula 1, n may be 0 or 1. When n is 0, it means a structure in which a substituted or unsubstituted C7 to C20 aryl group is directly linked at the 1st position of dibenzofuran (or dibenzothiophene).

In an implementation, the compound may be represented by, e.g., Chemical Formula 1A.

[Chemical Formula 1A]

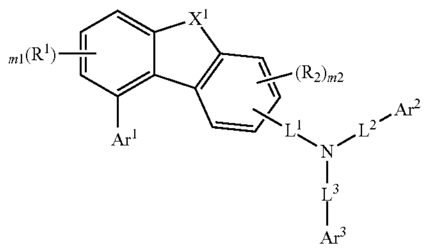

In Chemical Formula 1A, $X^1$, $L^1$ to $L^3$, $Ar^1$ to $Ar^3$, $R^1$, $R^2$, m1, and m2 may be defined the same as those described above.

In an implementation, when n is 1, it means a structure in which a substituted or unsubstituted C7 to C20 aryl group is substituted at the 1$^{st}$ position of dibenzofuran (or dibenzothiophene) via a phenylene linking group.

In an implementation, the compound may be represented by, e.g., Chemical Formula 1B.

[Chemical Formula 1B]

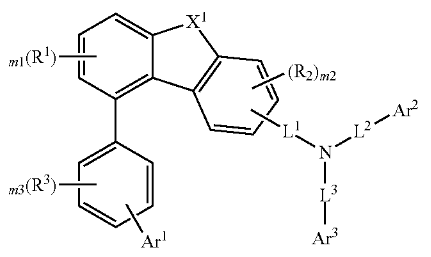

In Chemical Formula 1B, $X^1$, $L^1$ to $L^3$, $Ar^1$ to $Ar^3$, $R^1$ to $R^3$, and m1 to m3 may be defined the same as those described above.

In an implementation, the compound represented by Chemical Formula 1 may be represented by, e.g., one of Chemical Formula 1-I to Chemical Formula 1-IV, depending on the substitution position of the amine group.

[Chemical Formula 1-I]

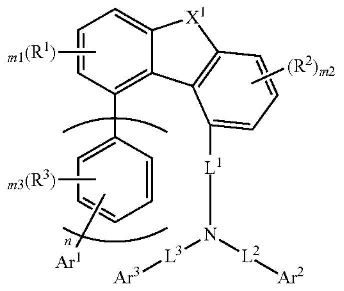

[Chemical Formula 1-II]

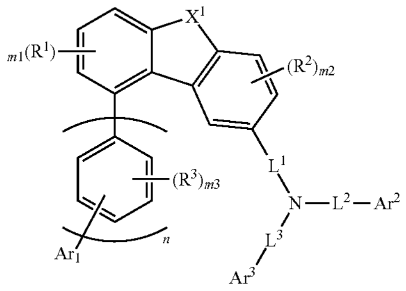

[Chemical Formula 1-III]

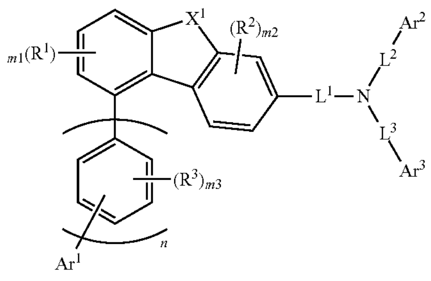

[Chemical Formula 1-IV]

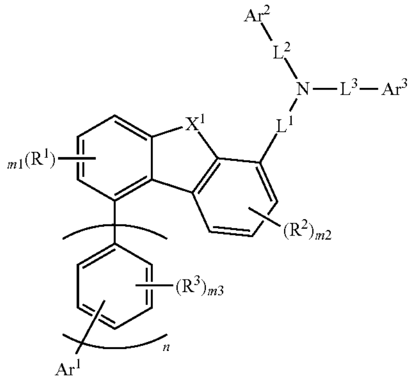

In Chemical Formula 1-I to Chemical Formula 1-IV, $X^1$, $L^1$ to $L^3$, $Ar^1$ to $Ar^3$, $R^1$ to $R^3$, m1 to m3, and n may be defined the same as those described above.

In an implementation, Chemical Formula 1-I may be represented by Chemical Formula 1-IA or Chemical Formula 1-IB.

[Chemical Formula 1-IA]

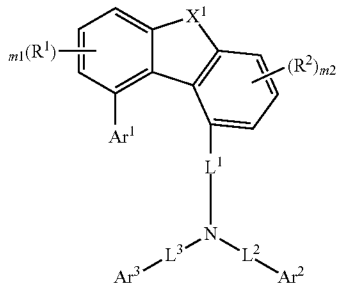

[Chemical Formula 1-IB]

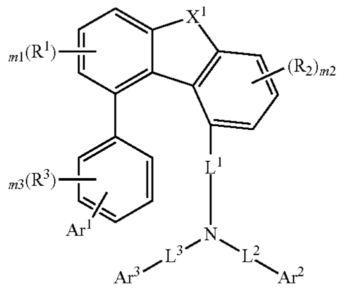

In an implementation, Chemical Formula 1-II may be represented by Chemical Formula 1-IIA or Chemical Formula 1-IIB.

[Chemical Formula 1-IIA]

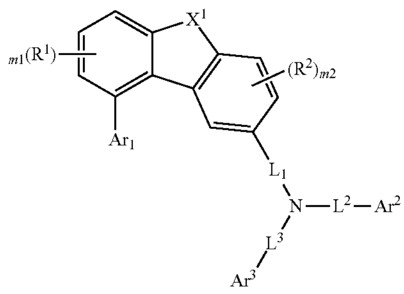

[Chemical Formula 1-IIB]

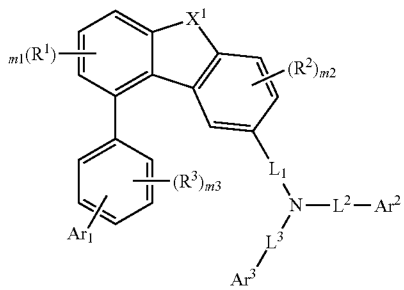

In an implementation, Chemical Formula 1-III may be represented by Chemical Formula 1-IIIA or Chemical Formula 1-IIIB

[Chemical Formula 1-IIIA]

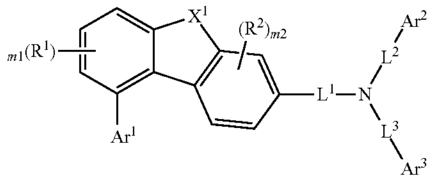

[Chemical Formula 1-IIIB]

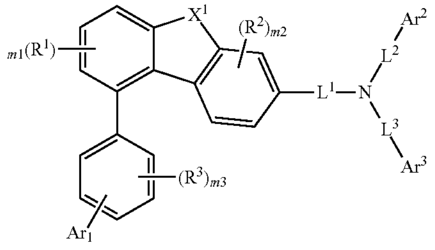

In an implementation, Chemical Formula 1-IV may be represented by Chemical Formula 1-IVA or Chemical Formula 1-IVB.

[Chemical Formula 1-IVA]

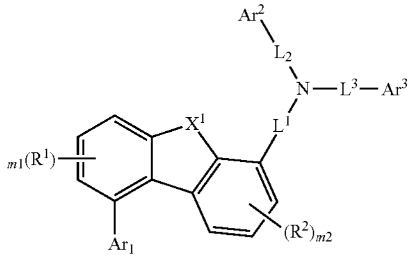

[Chemical Formula 1-IVB]

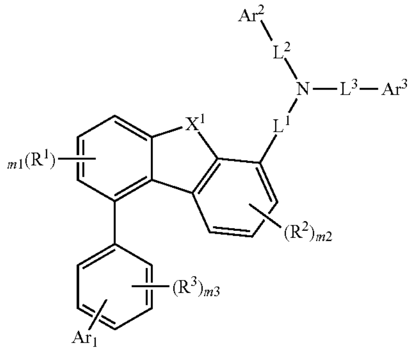

In Chemical Formula 1-IA to Chemical Formula 1-IVA and Chemical Formula 1-IB to Chemical Formula 1-IVB, $X^1$, $L^1$ to $L^3$, $Ar^1$ to $Ar^3$, $R^1$ to $R^3$, and m1 to m3 may be defined the same as those described above.

In an implementation, the compound represented by Chemical Formula 1 may be represented by any one of Chemical Formula 1-II to Chemical Formula 1-IV.

In an implementation, the compound represented by Chemical Formula 1 may be represented by Chemical Formula 1-II or Chemical Formula 1-III.

In an implementation, the compound represented by Chemical Formula 1 may be represented by Chemical Formula 1-II.

In an implementation, $Ar^1$ may be, e.g., a substituted or unsubstituted C10 to C20 aryl group.

In an implementation, $Ar^1$ may be, e.g., a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted chrysenyl group, a substituted or unsubstituted fluorenyl group, or a substituted or unsubstituted triphenylene group.

In an implementation, $Ar^1$ may be, e.g., a substituted or unsubstituted biphenyl group, a substituted or unsubstituted terphenyl group, a substituted or unsubstituted naphthyl group, or a substituted or unsubstituted phenanthrenyl group.

In an implementation, $Ar^1$ may be, e.g., unsubstituted or substituted with deuterium or a C6 to C12 aryl group.

In an implementation, $Ar^1$ may be, e.g., a biphenyl group that is unsubstituted or substituted with deuterium or a C6 to C12 aryl group, a terphenyl group that is unsubstituted or substituted with deuterium or a C6 to C12 aryl group, a naphthyl group that is unsubstituted or substituted with deuterium or a C6 to C12 aryl group, or a phenanthrenyl group that is unsubstituted or substituted with deuterium or a C6 to C12 aryl group.

In an implementation, $Ar^2$ and $Ar^3$ may each independently be, e.g., a substituted or unsubstituted phenyl group, a substituted or unsubstituted biphenyl group, a substituted or unsubstituted naphthyl group, a substituted or unsubstituted phenanthrenyl group, a substituted or unsubstituted chrysenyl group, a substituted or unsubstituted fluorenyl group, a substituted or unsubstituted benzofluorenyl group, a substituted or unsubstituted benzophenanthrenyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuranyl group, a substituted or unsubstituted benzonaphthothiophenyl group, a substituted or unsubstituted benzooxazolyl group, or a substituted or unsubstituted phenanthrooxazolyl group.

In an implementation, $Ar^2$ and $Ar^3$ may each independently be, e.g., a substituted or unsubstituted phenyl group, a substituted or unsubstituted biphenyl group, a substituted or unsubstituted naphthyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuranyl group, or a substituted or unsubstituted benzonaphthothiophenyl group.

In an implementation, $L^1$ to $L^3$ may each independently be, e.g., a single bond or a substituted or unsubstituted C6 to C12 arylene group.

In an implementation, $L^1$ may be, e.g., a single bond, and $L^2$ and $L^3$ may each independently be, e.g., a single bond or a substituted or unsubstituted C6 to C12 arylene group.

In an implementation, moieties $L^2$-$Ar^2$ and $L^3$-$Ar^3$ of Chemical Formula 1 may each independently be, e.g., a moiety of Group I.

[Group I]

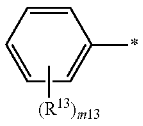

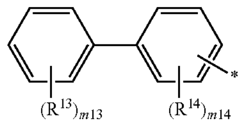

-continued

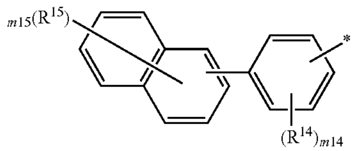

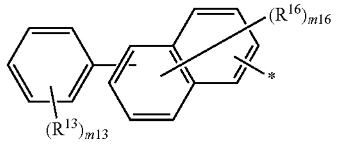

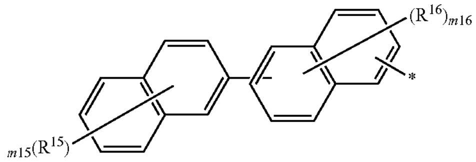

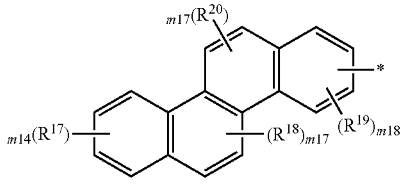

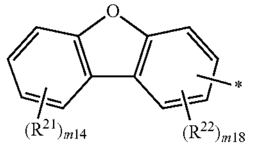

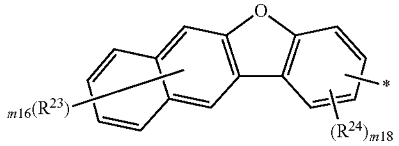

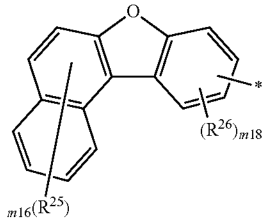

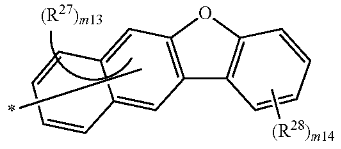

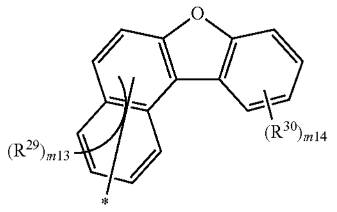

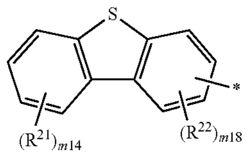

-continued

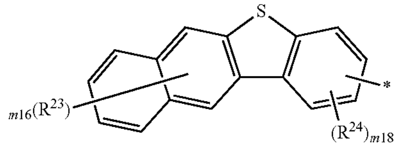

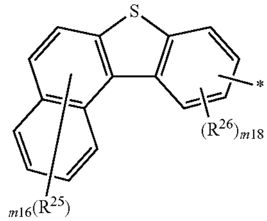

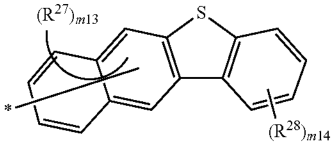

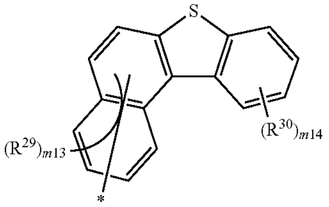

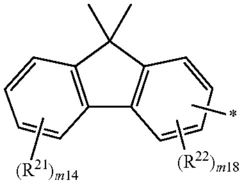

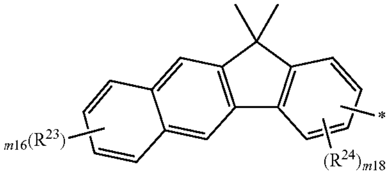

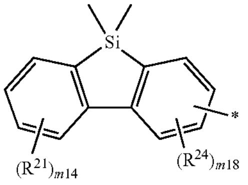

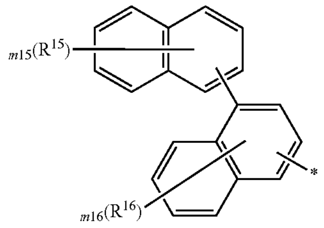

-continued

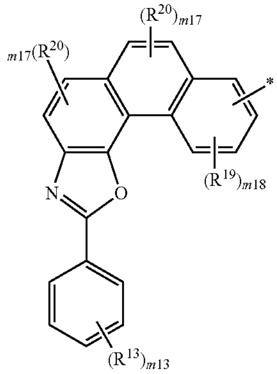

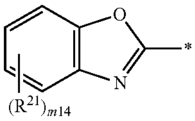

In Group I, $R^{13}$ to $R^{30}$ may each independently be, e.g., hydrogen, deuterium, a C1 to C10 alkyl group or a C6 to C12 aryl group, m13 may be, e.g., an integer of 1 to 5, m14 may be, e.g., an integer of 1 to 4, m15 may be, e.g., an integer of 1 to 7, m16 may be, e.g., an integer of 1 to 6, m17 may be, e.g., an integer of 1 or 2, m18 may be, e.g., an integer of 1 to 3, and * is a connection or linking point.

In an implementation, $R^1$ to $R^3$ may each independently be, e.g., hydrogen, deuterium, or a substituted or unsubstituted C1 to C5 alkyl group.

In an implementation, $R^1$ to $R^3$ may each independently be, e.g., hydrogen or deuterium.

In an implementation, the compound for an organic optoelectronic device represented by Chemical Formula 1 may include, e.g., a compound of Group 1.

[Group 1]

1-1

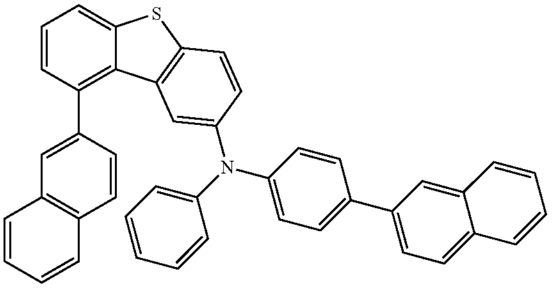

1-2

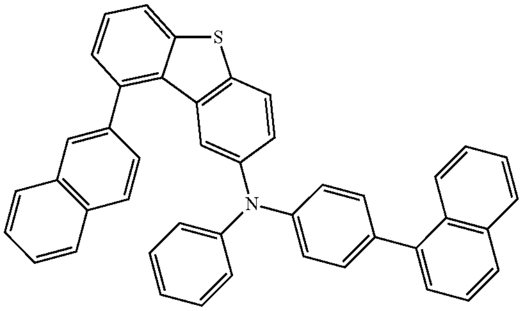

-continued
1-3
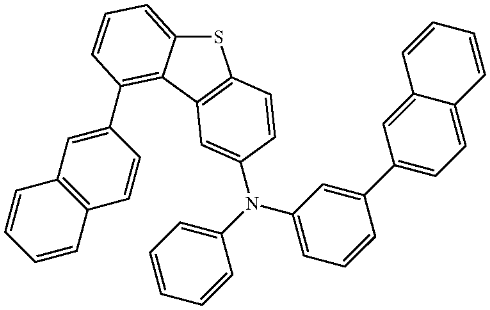
1-4
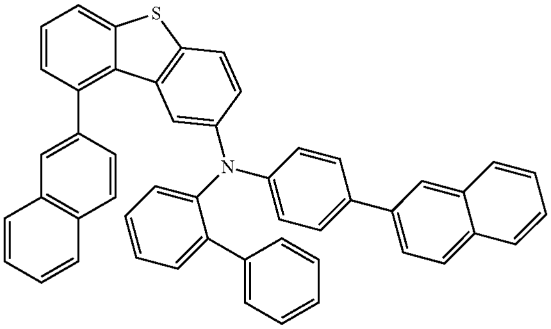
1-5
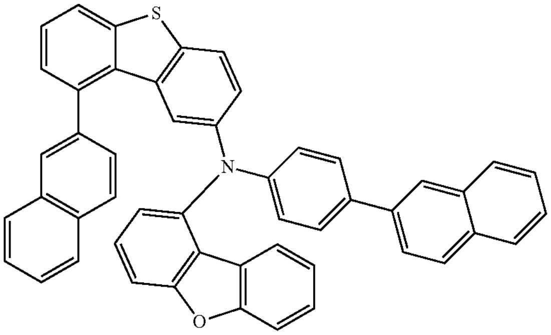
1-6
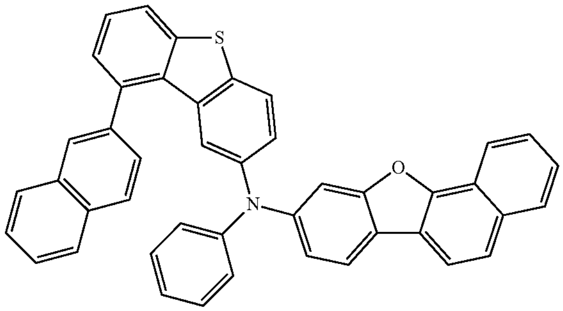
-continued
1-7
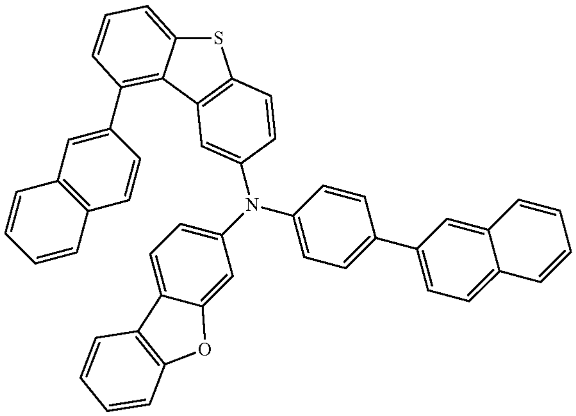
1-8
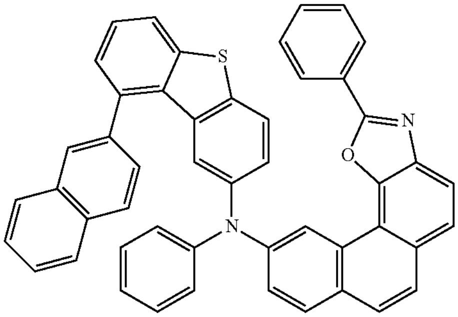
1-9
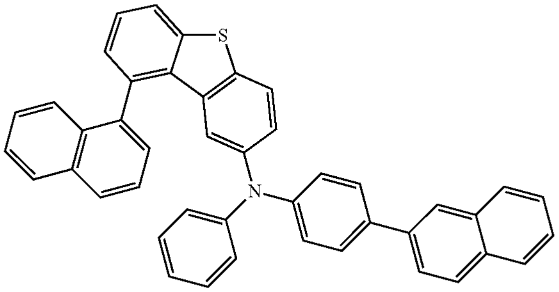
1-10
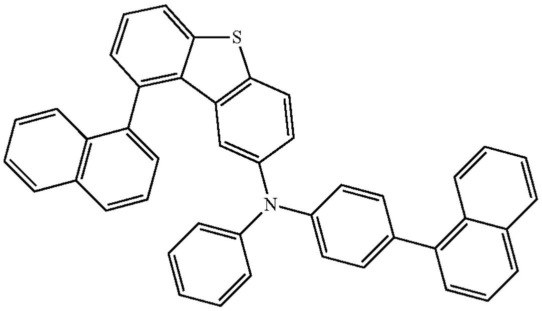

-continued
1-11
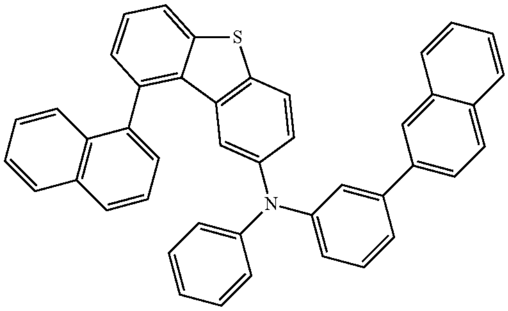
1-12
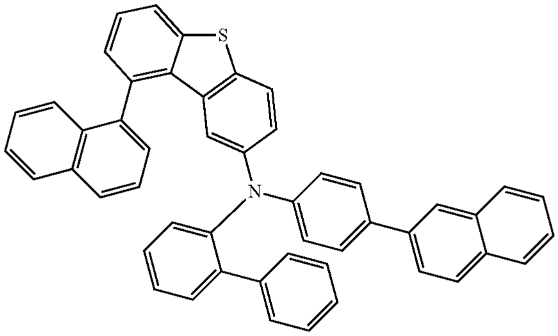
1-13
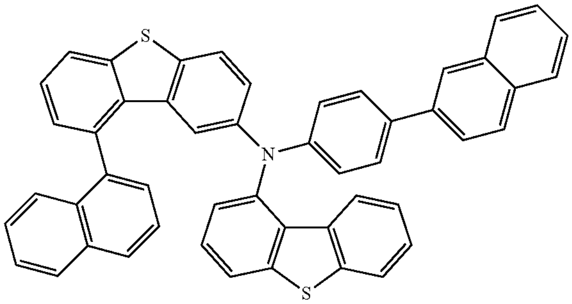
1-14
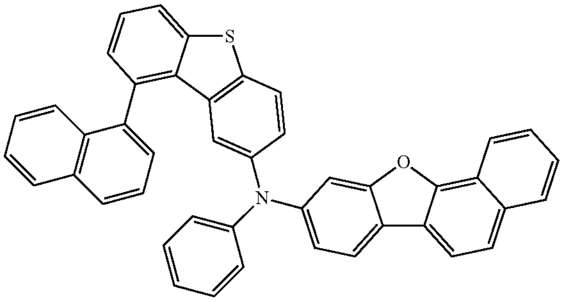
-continued
1-15
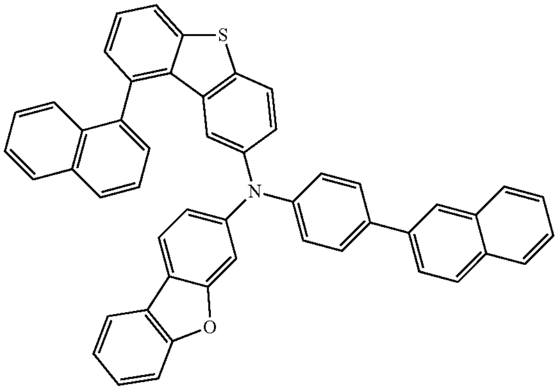
1-16
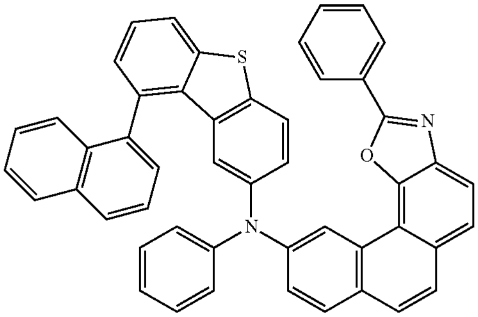
1-17
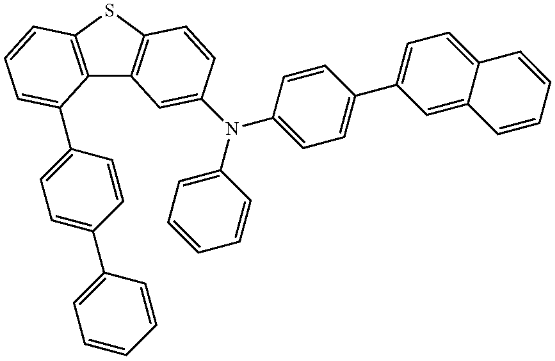
1-18
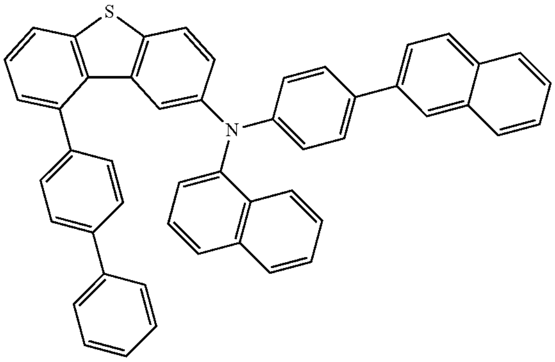

-continued
1-19
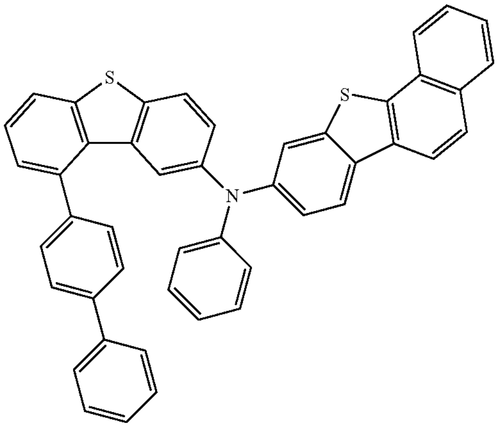
1-20
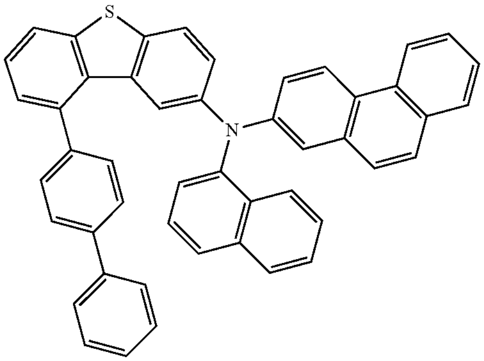
1-21
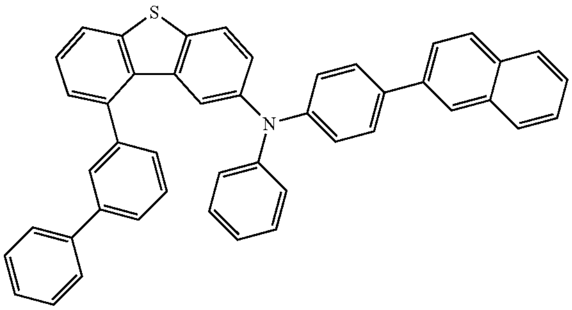
1-22
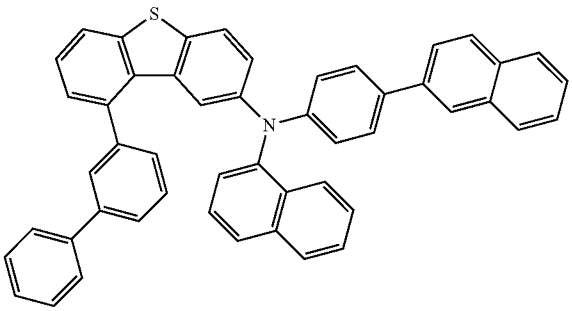
-continued
1-23
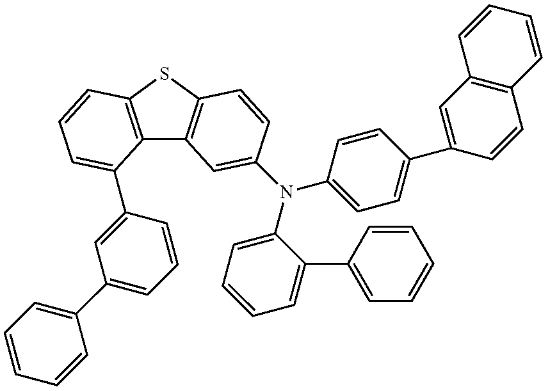
1-24
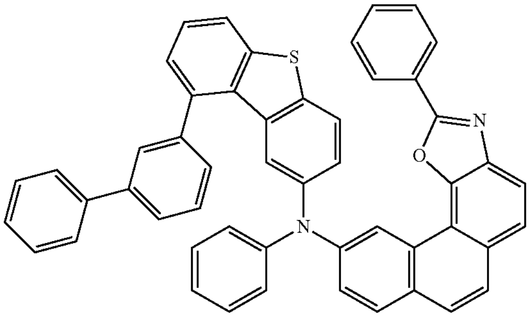
1-25
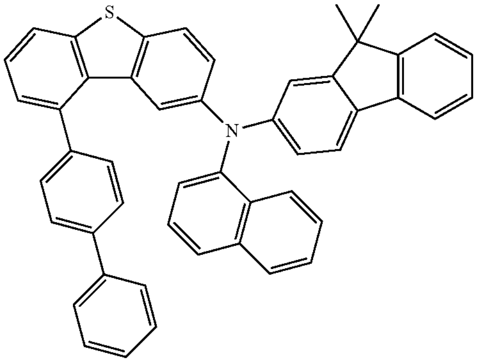
1-26
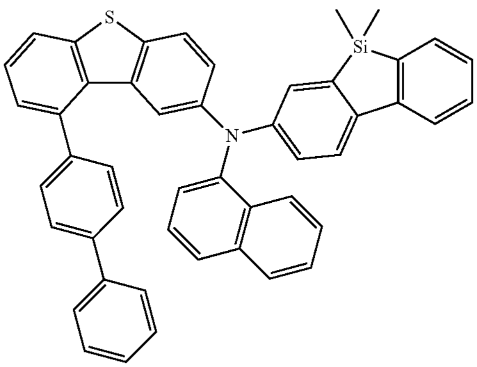

1-27
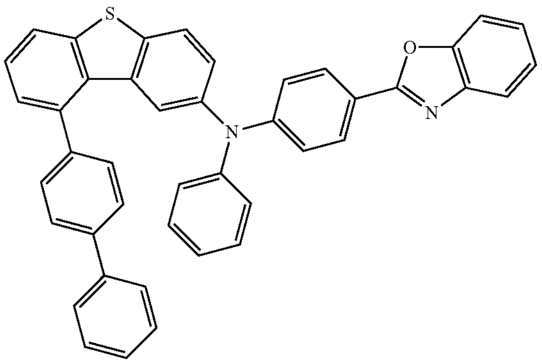
1-28
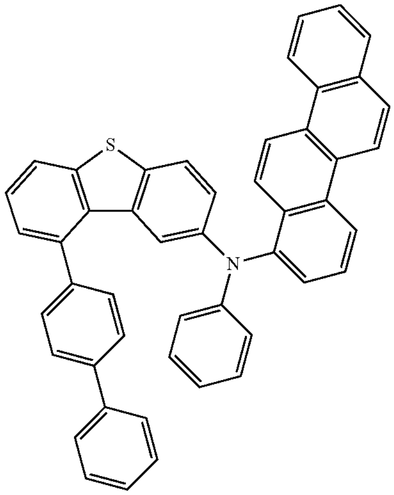
1-29
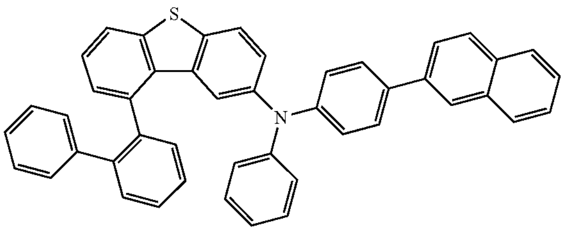
1-30
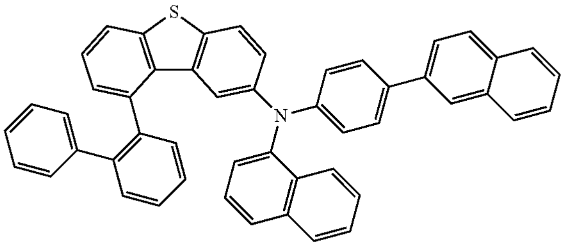
1-31
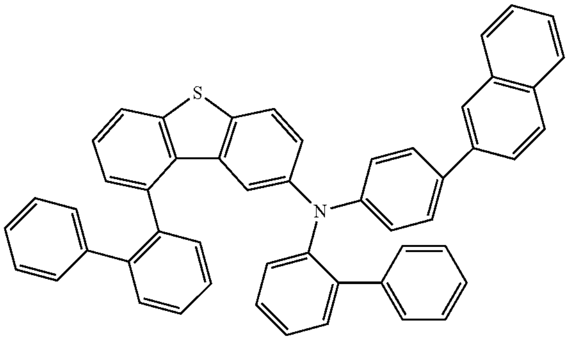
1-32
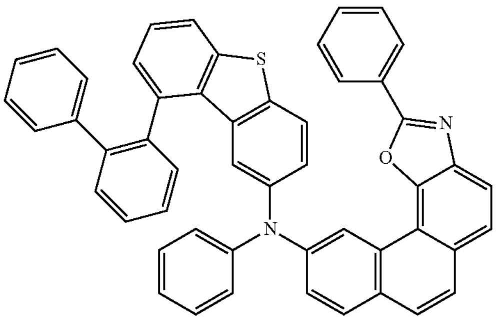
1-33
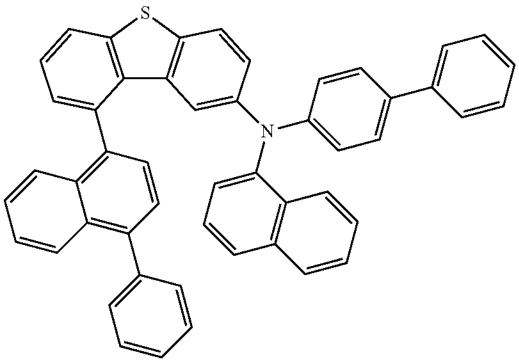
1-34
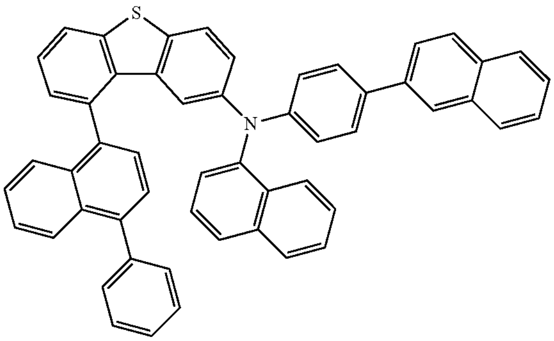

-continued
1-35
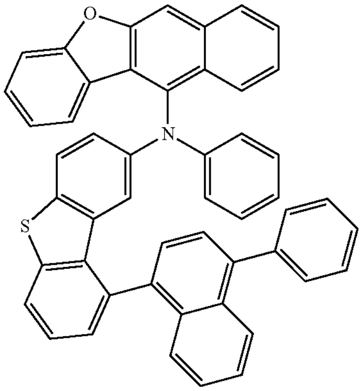
1-36
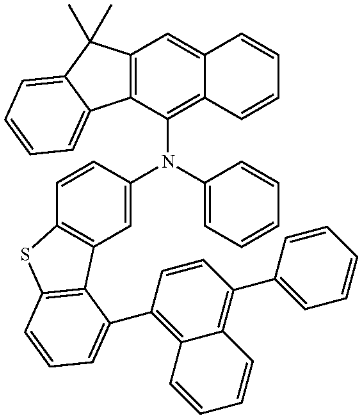
1-37
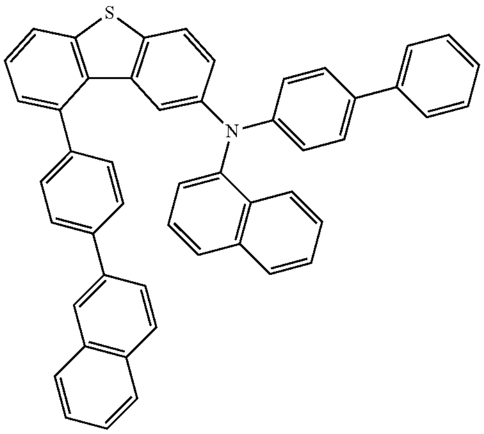
-continued
1-38
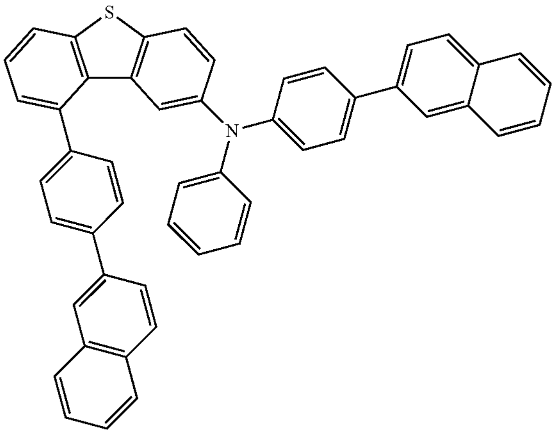
1-39
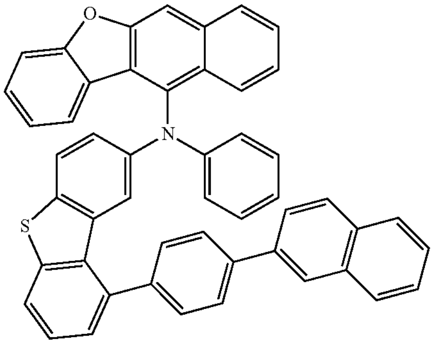
1-40
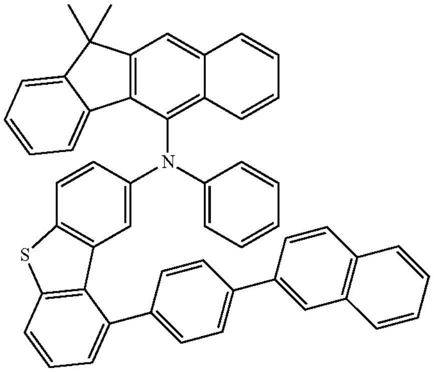
1-41
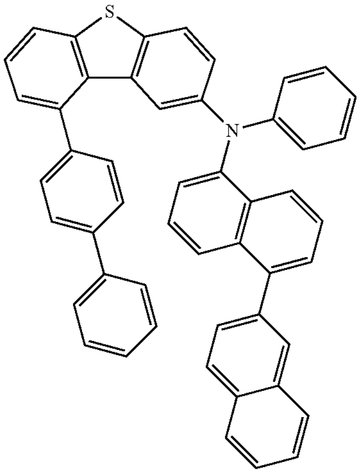

-continued
1-42
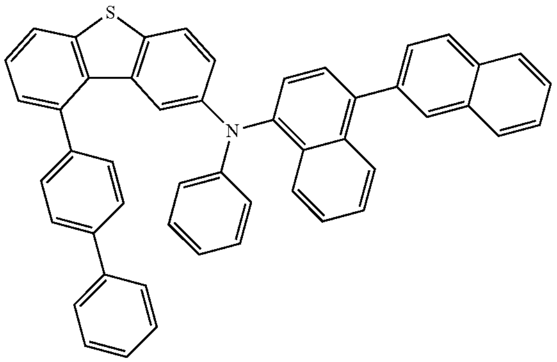
1-43
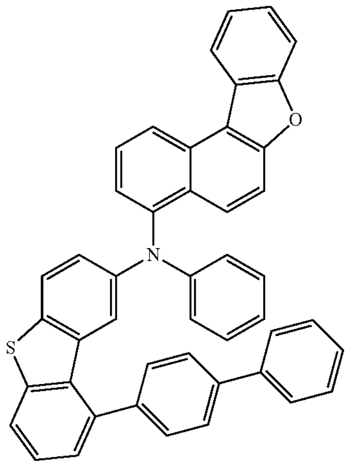
1-44
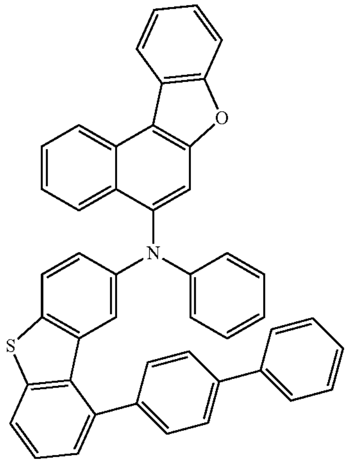
1-45
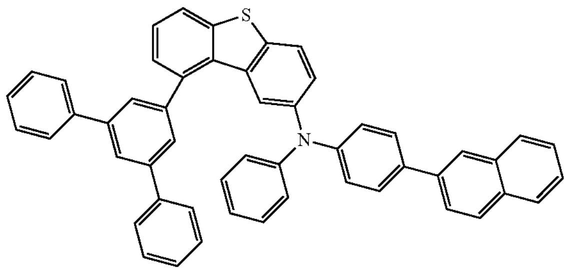
-continued
1-46
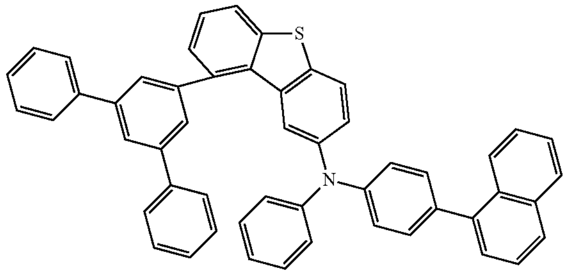
1-47
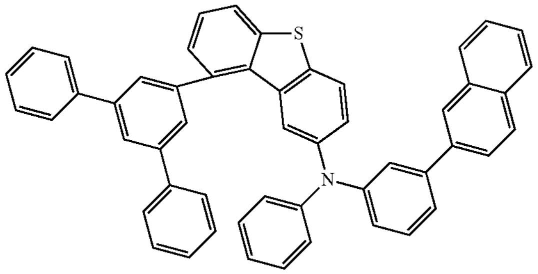
1-48
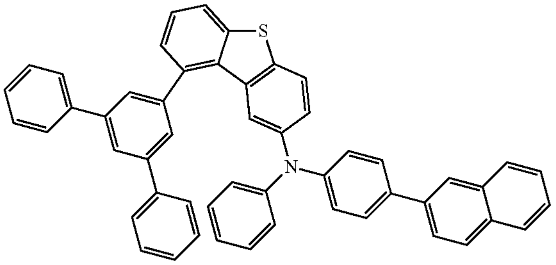
1-49
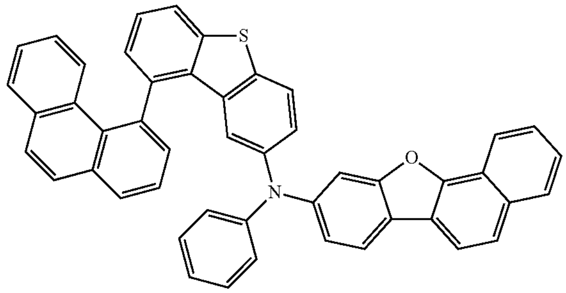
1-50
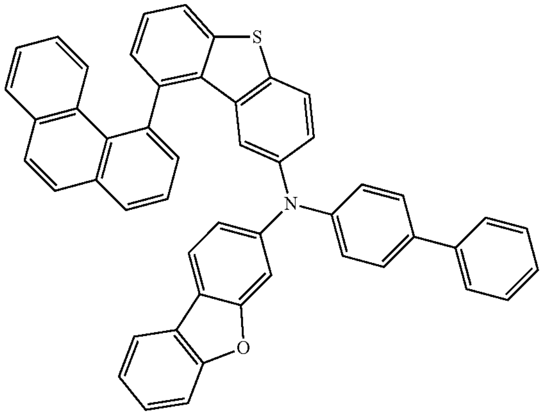

-continued
1-51
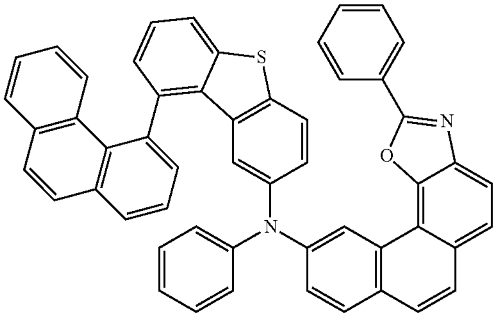
1-52
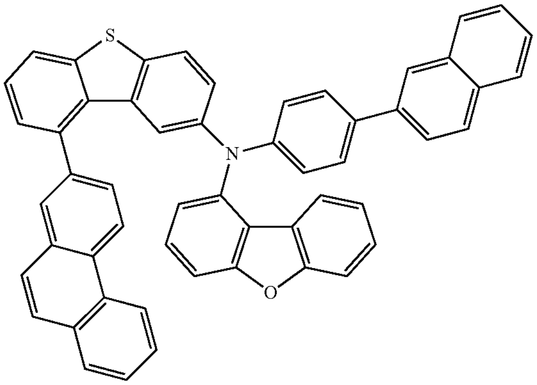
1-53
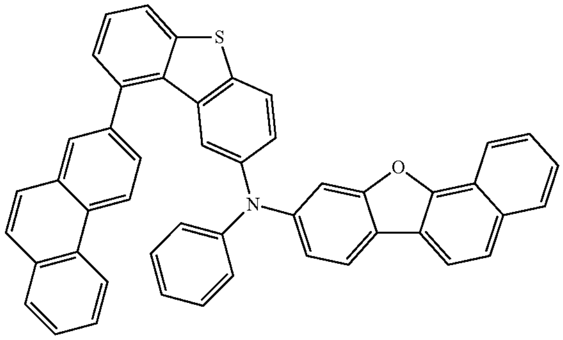
1-54
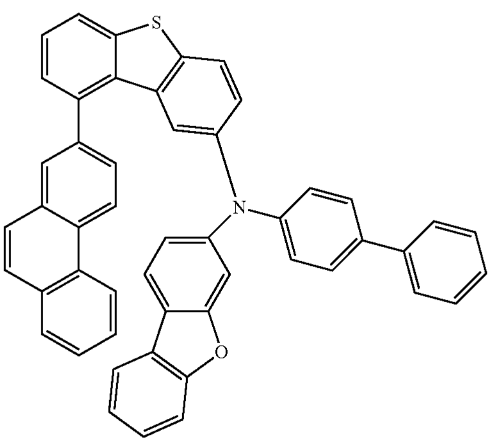
-continued
1-55
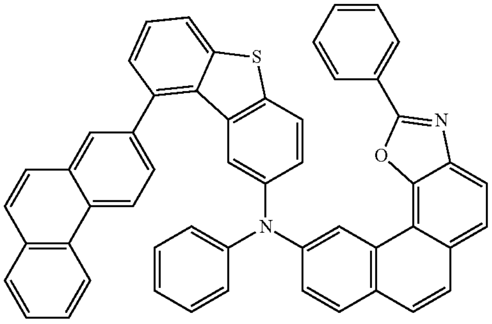
1-56
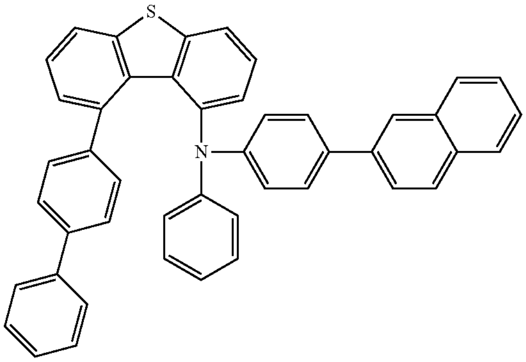
1-57
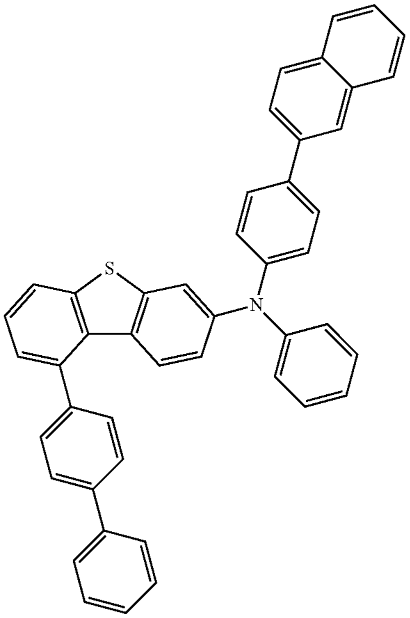

-continued
1-58
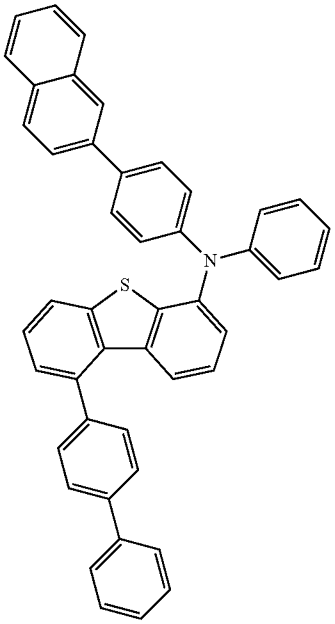
1-59
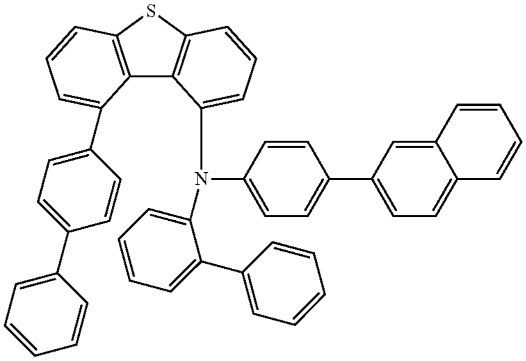
1-60
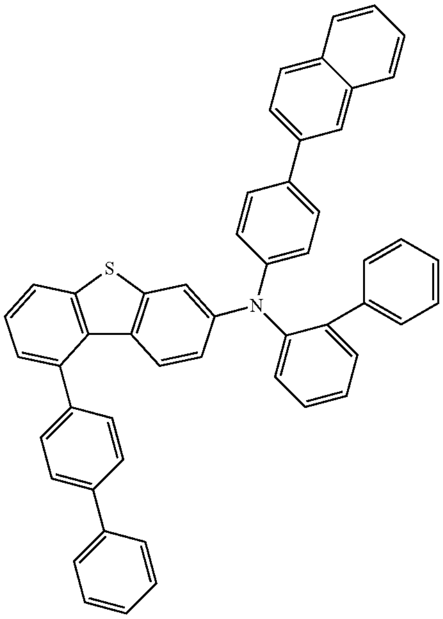
-continued
1-61
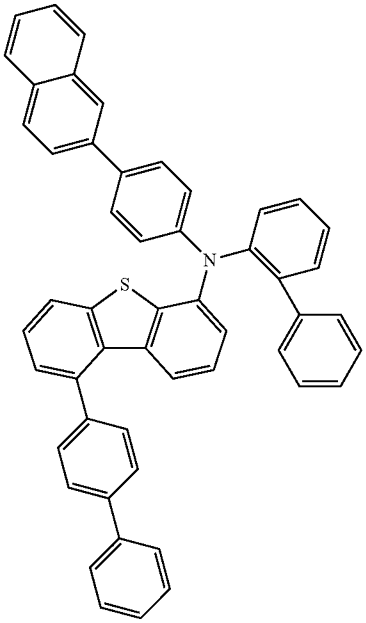
1-62
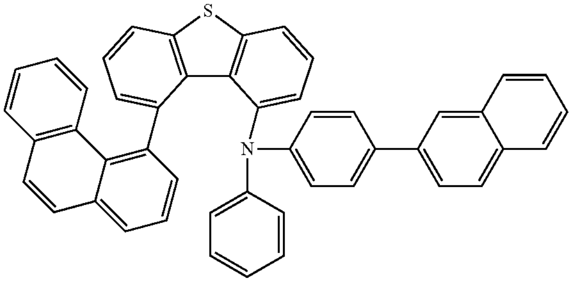
1-63
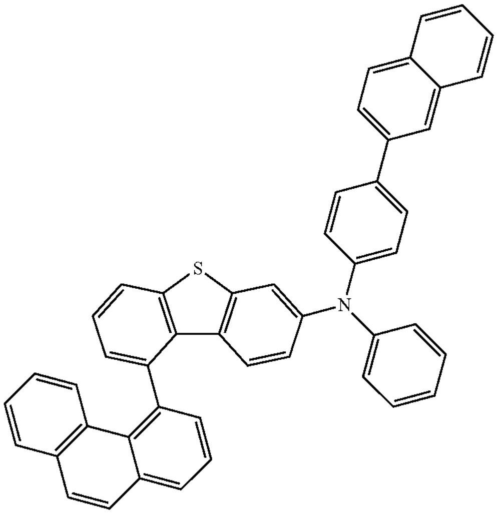

-continued
1-64
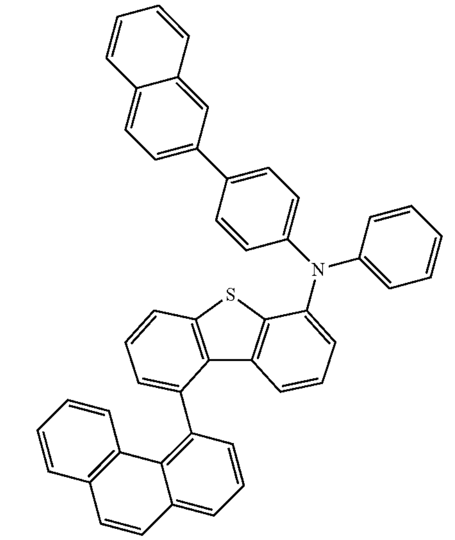
1-65
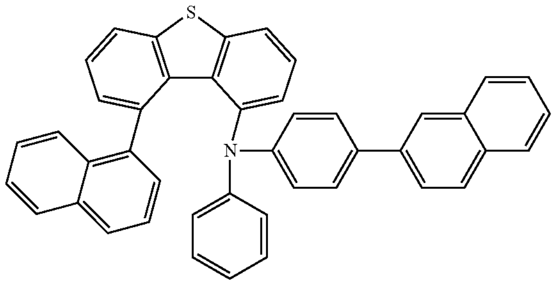
1-66
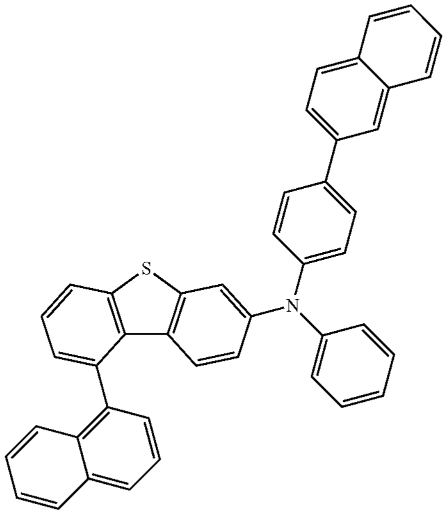
-continued
1-67
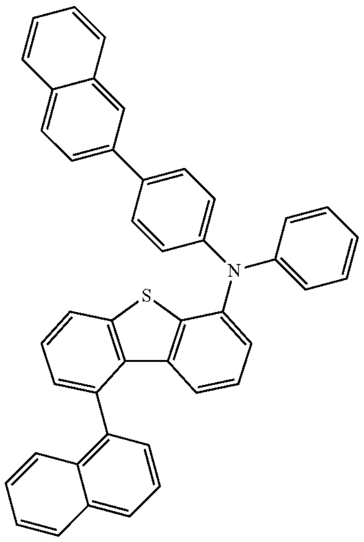
1-68
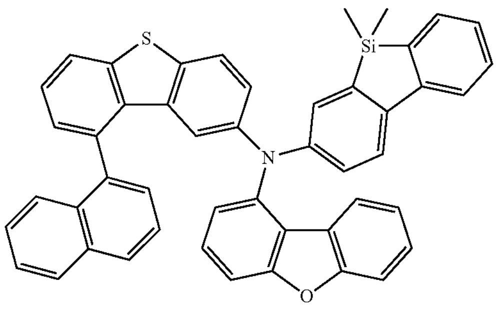
1-69
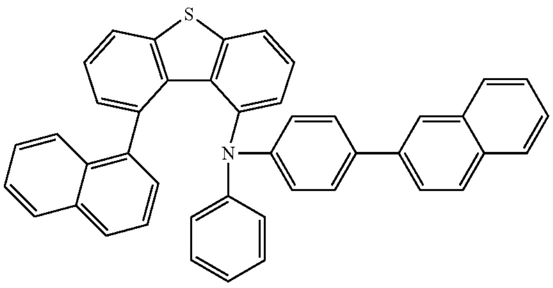

-continued
1-70
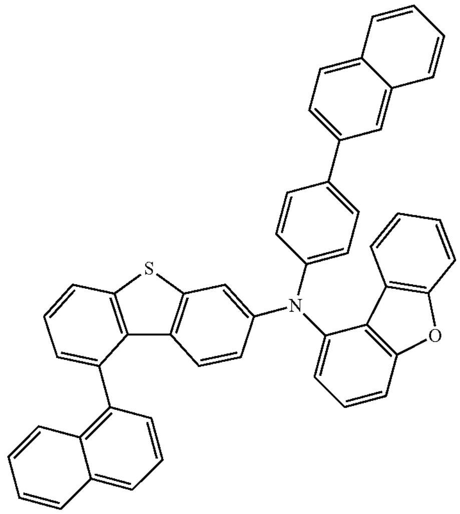
1-71
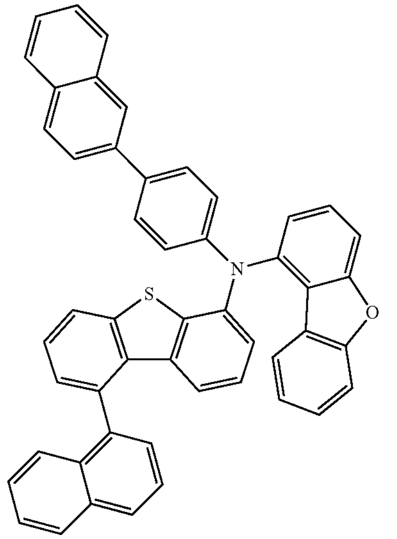
1-72
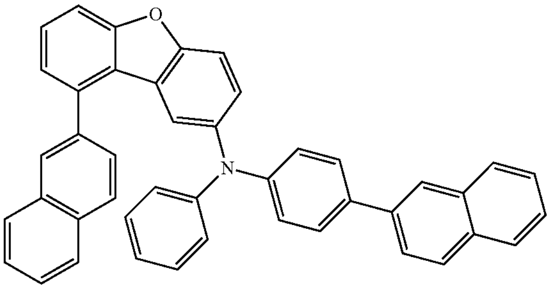
-continued
1-73
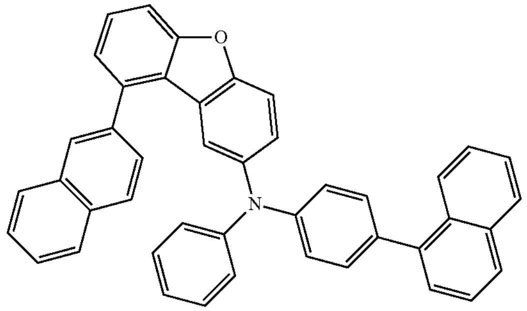
1-74
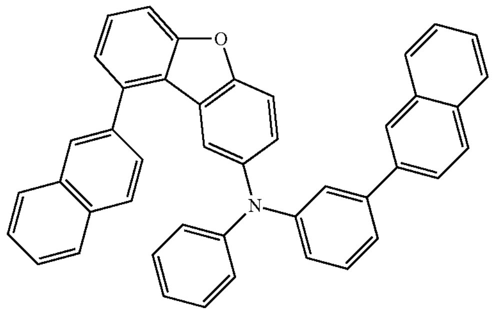
1-75
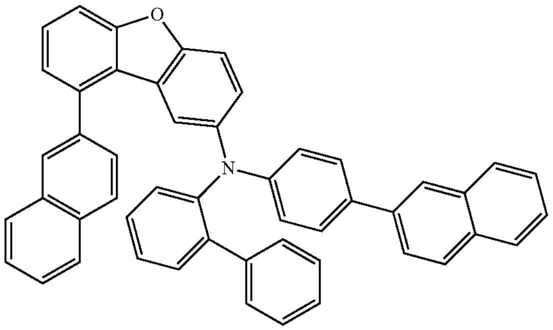
1-76
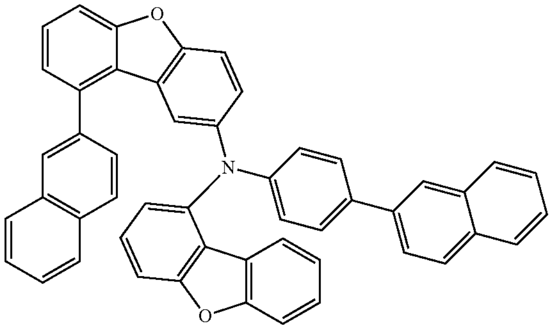

-continued
1-77
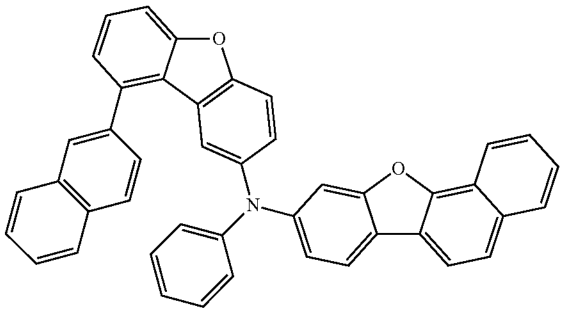
1-78
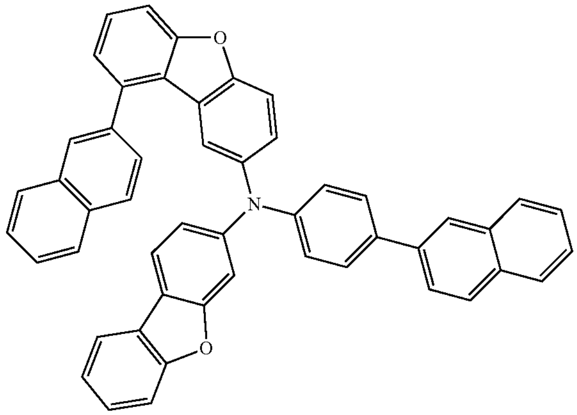
1-79
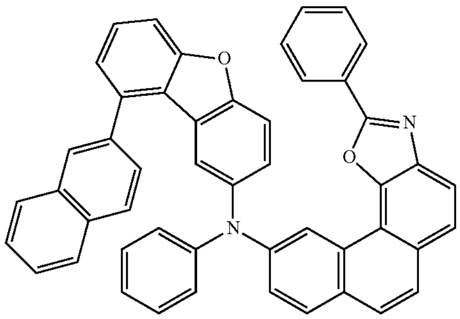
1-80
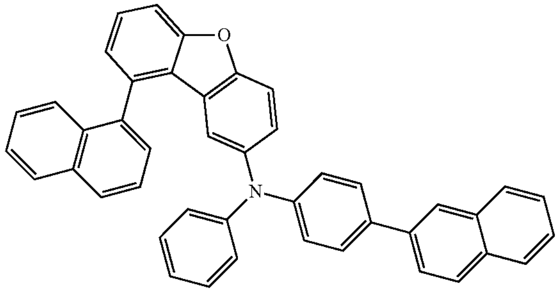
-continued
1-81
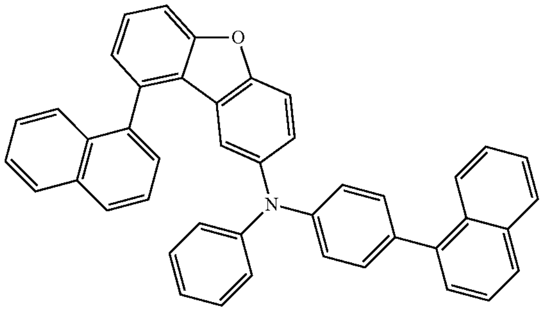
1-82
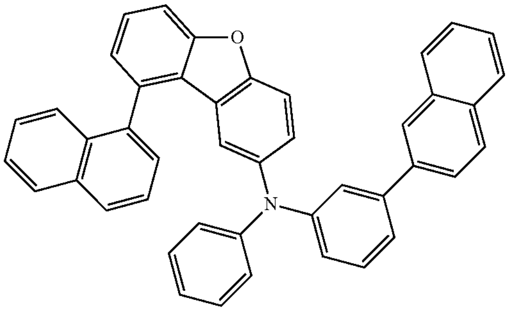
1-83
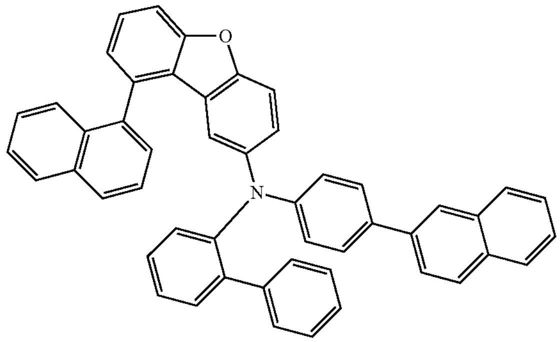
1-84
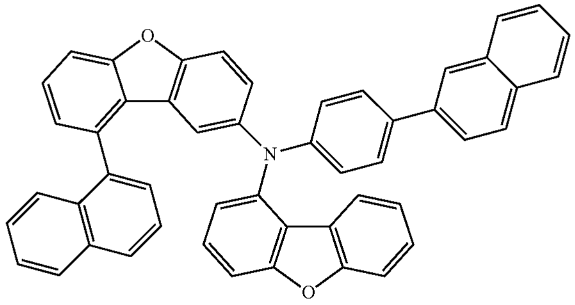

-continued
1-85
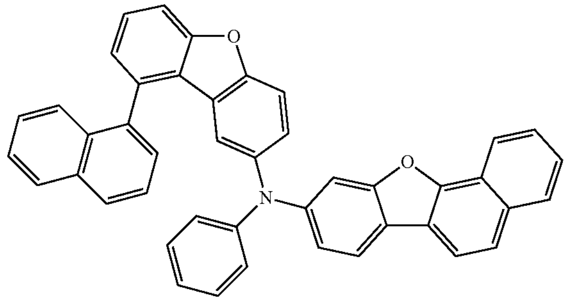
1-86
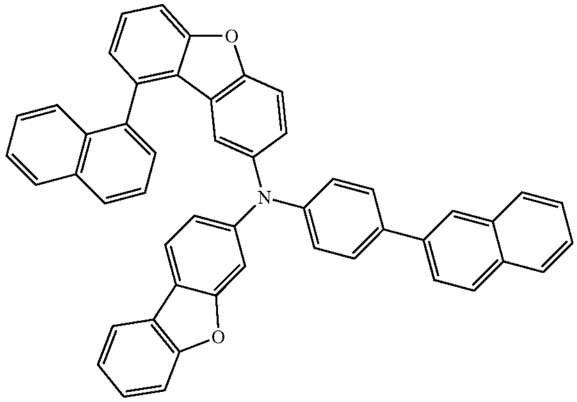
1-87
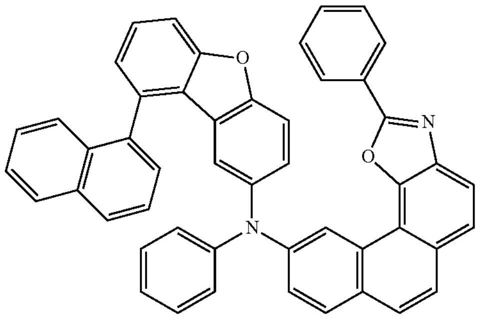
1-88
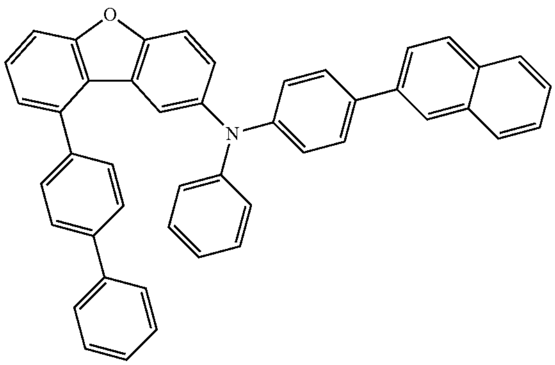
-continued
1-89
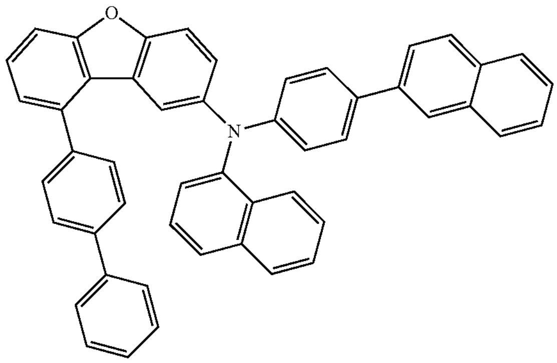
1-90
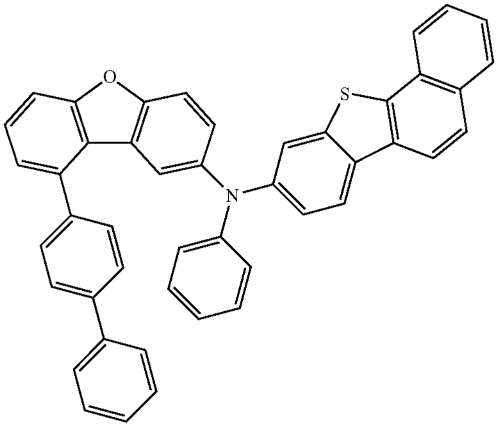
1-91
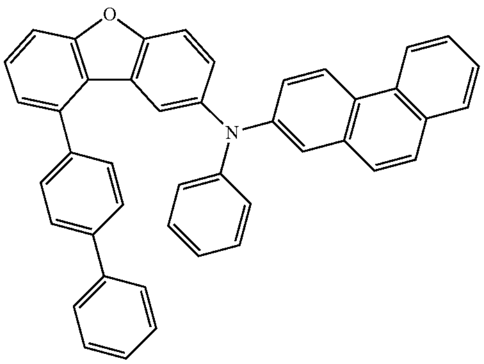
1-92
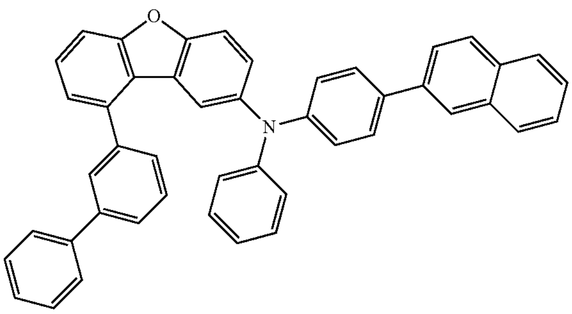

-continued
1-93
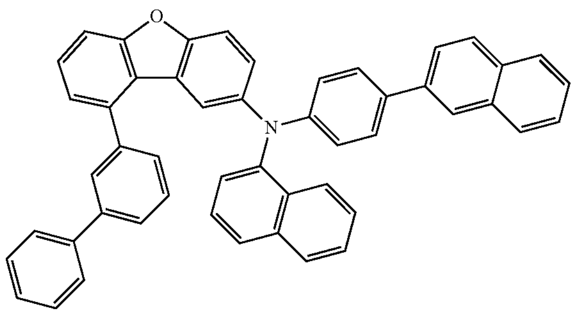
1-94
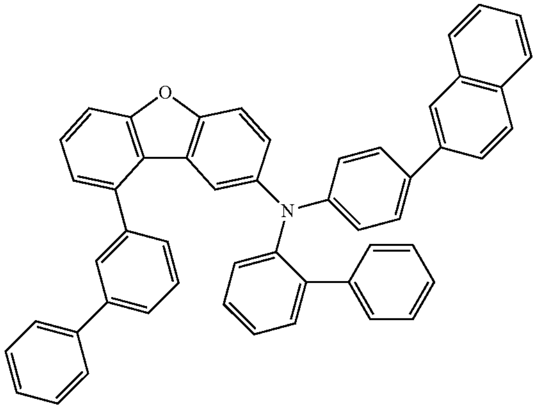
1-95
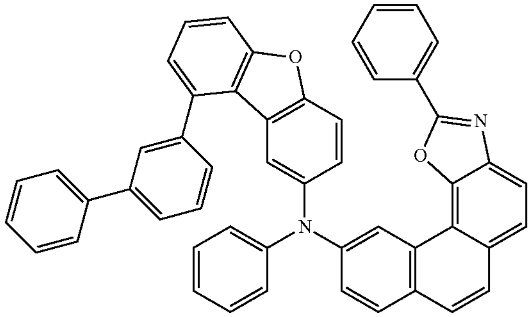
1-96
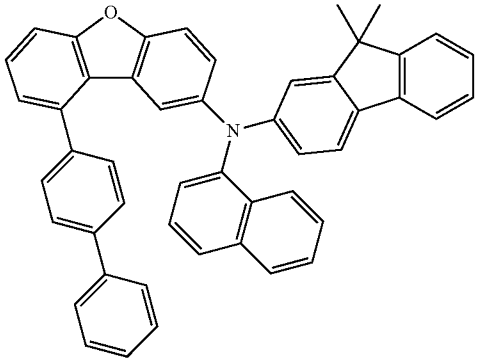
-continued
1-97
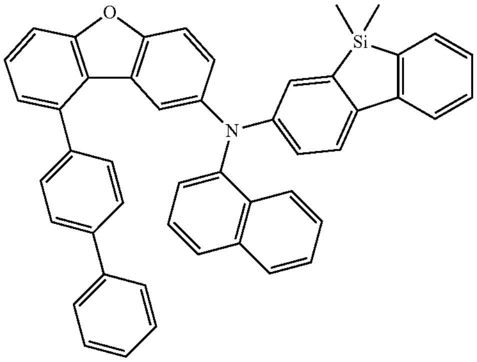
1-98
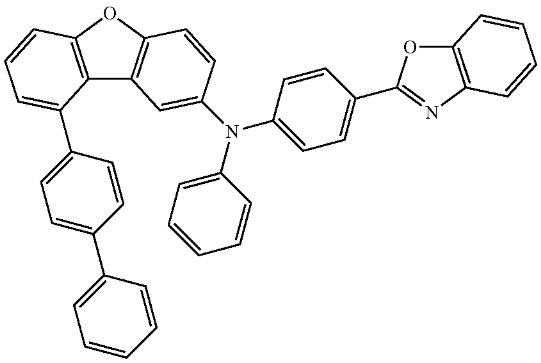
1-99
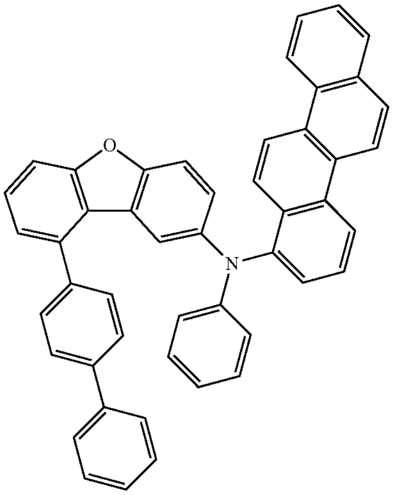
1-100
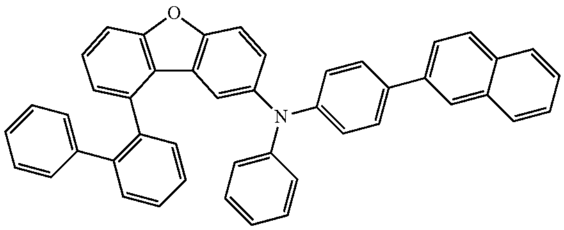

-continued
1-101
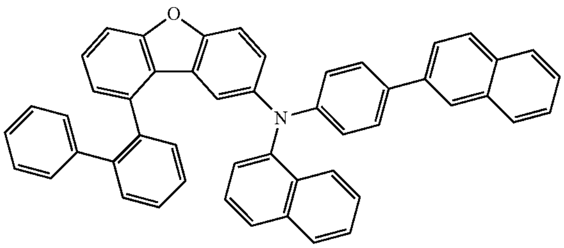
1-102
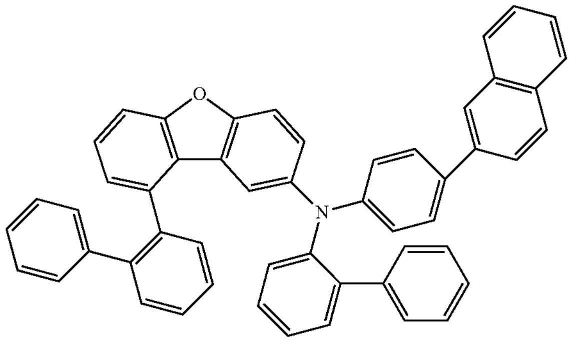
1-103
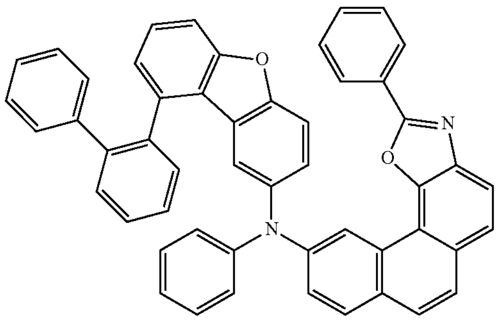
1-104
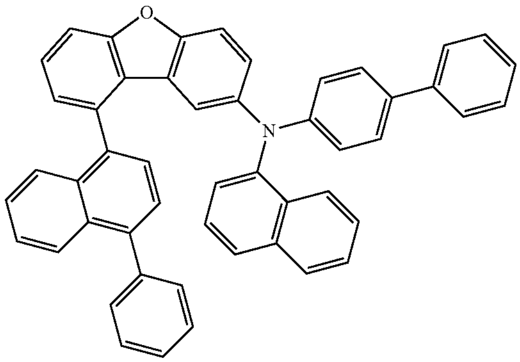
-continued
1-105
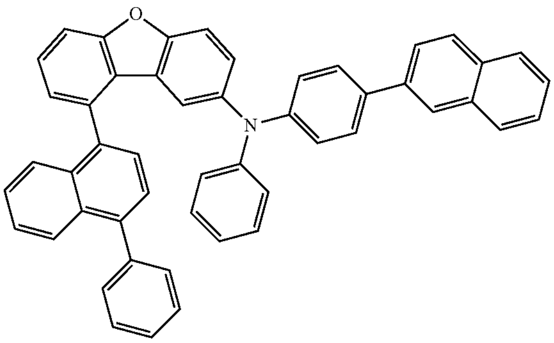
1-106
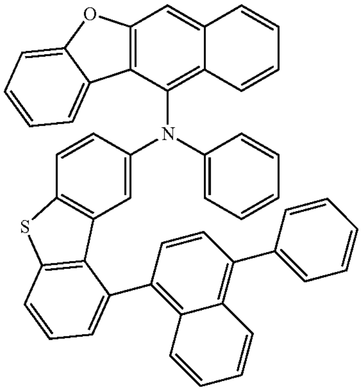
1-107
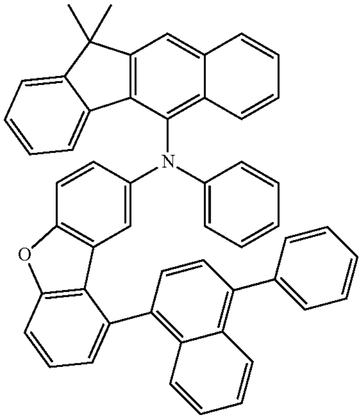
1-108
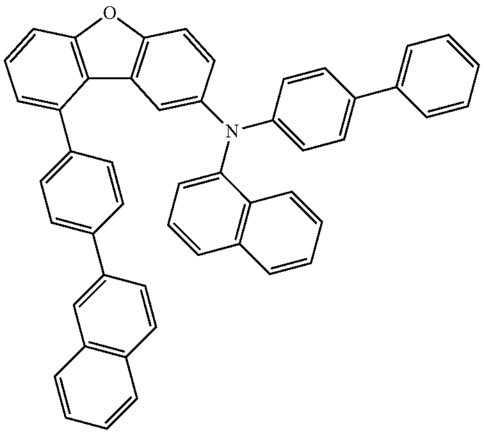

-continued
1-109
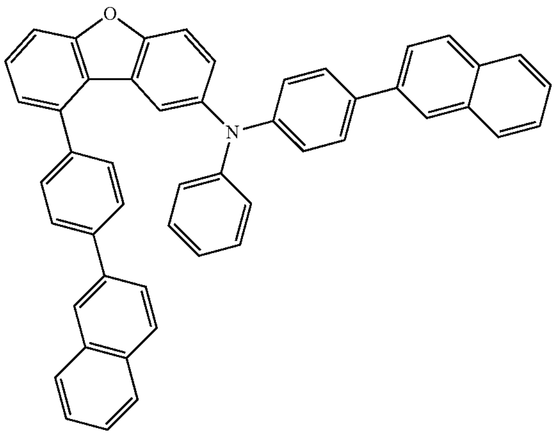
1-110
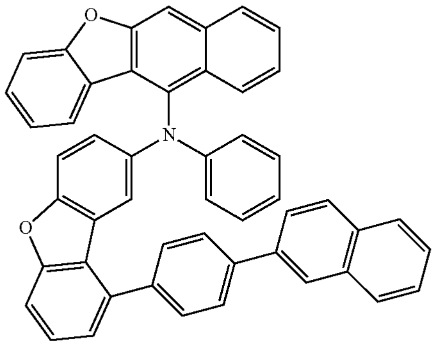
1-111
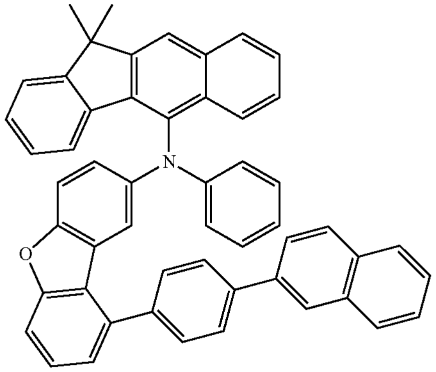
1-112
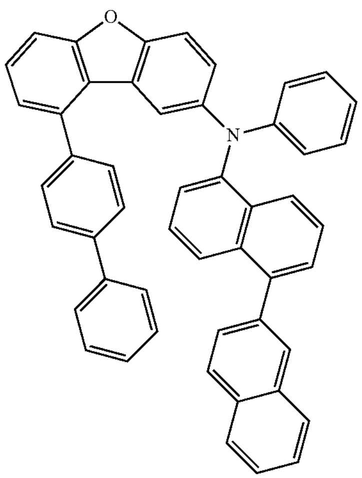
-continued
1-113
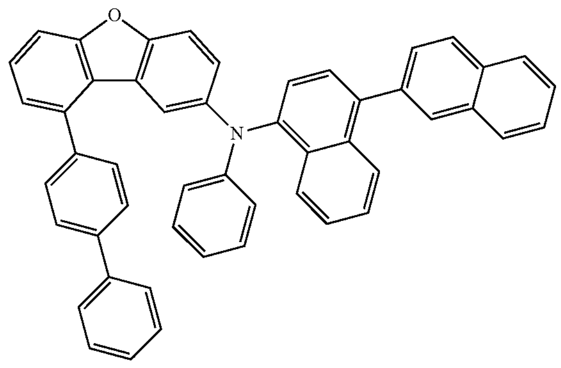
1-114
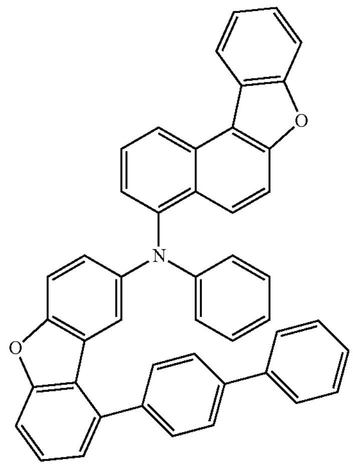
1-115
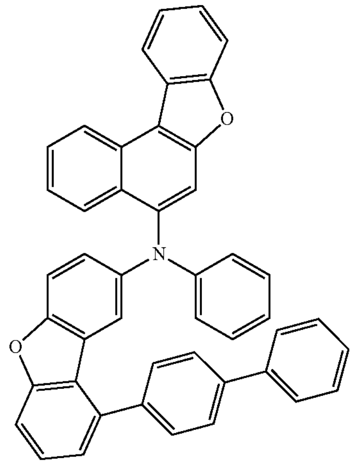
1-116
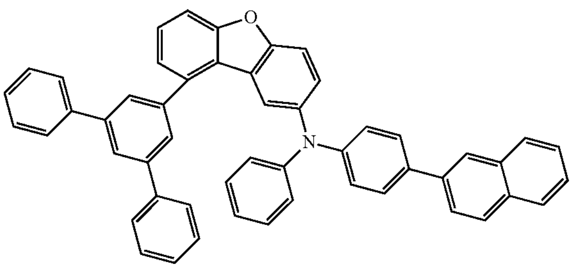

-continued
1-117
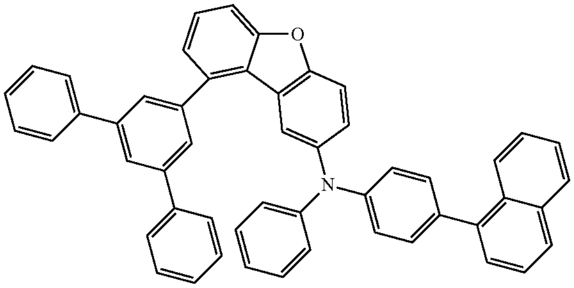
1-118
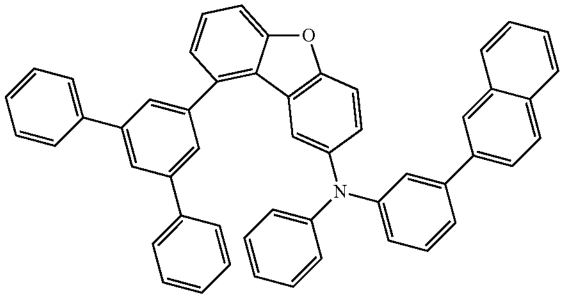
1-119
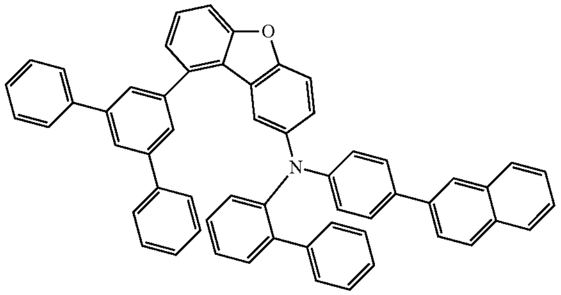
1-120
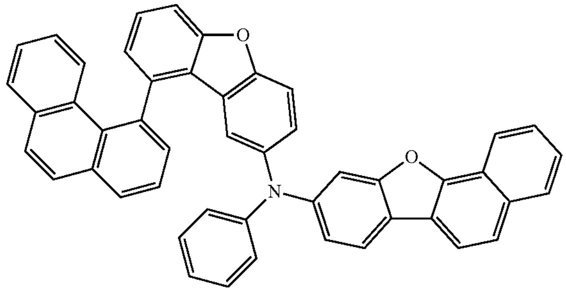
-continued
1-121
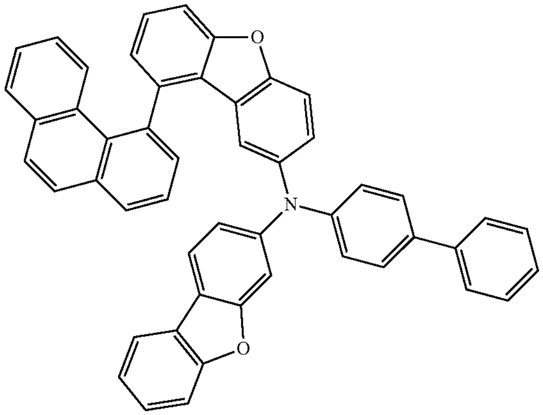
1-122
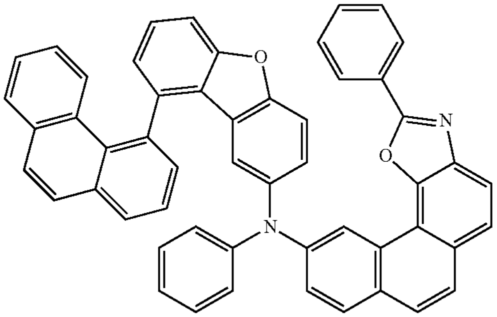
1-123
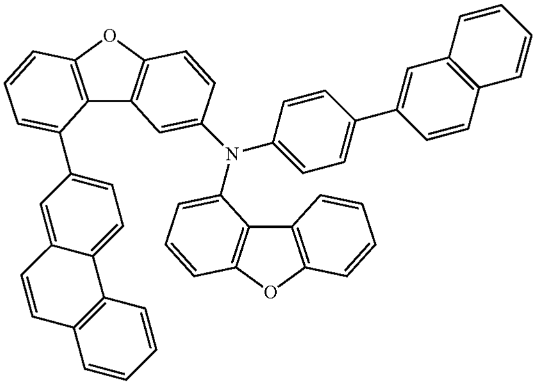
1-124
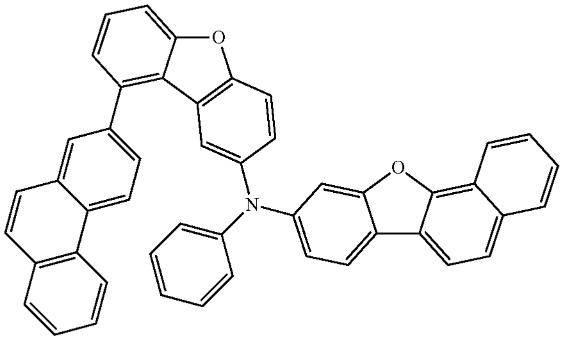

-continued
1-125
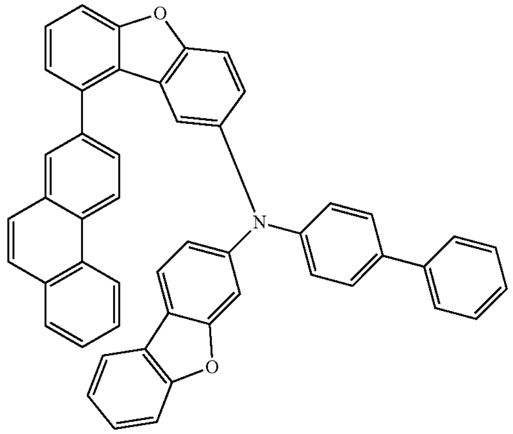
1-126
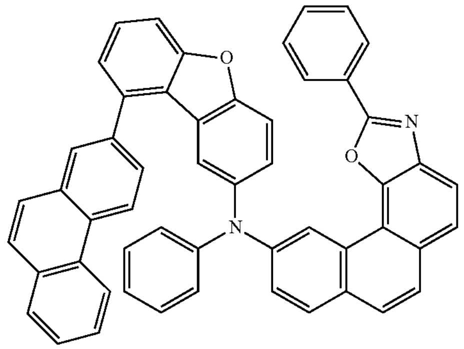
1-127
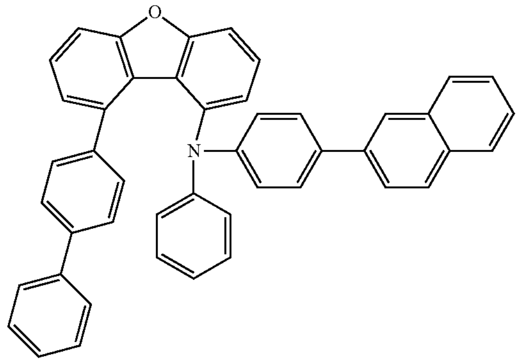
-continued
1-128
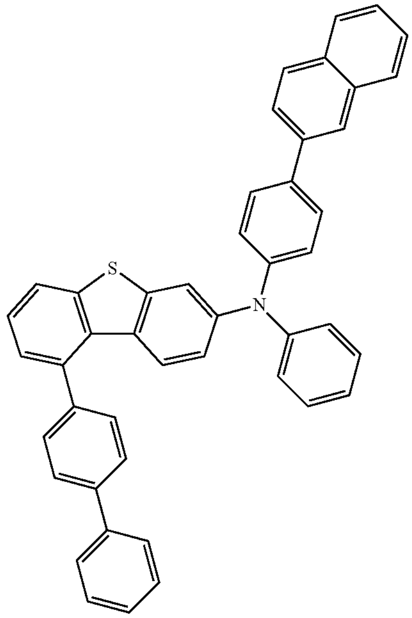
1-129
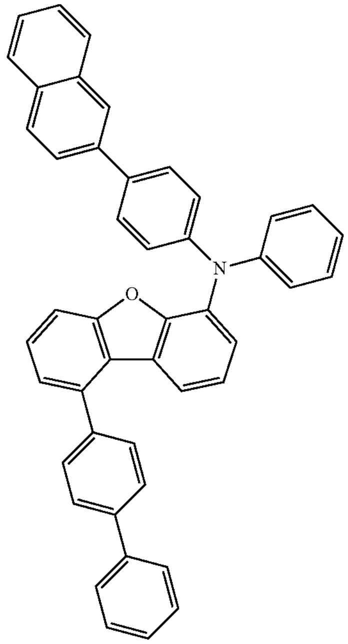
1-130
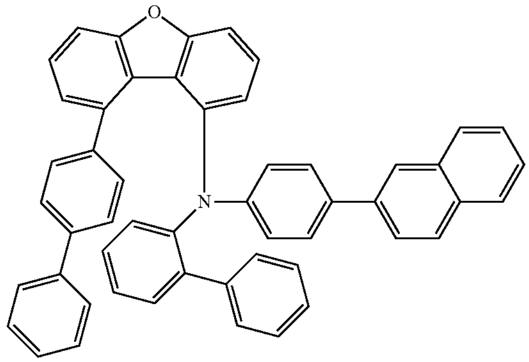

-continued
1-131
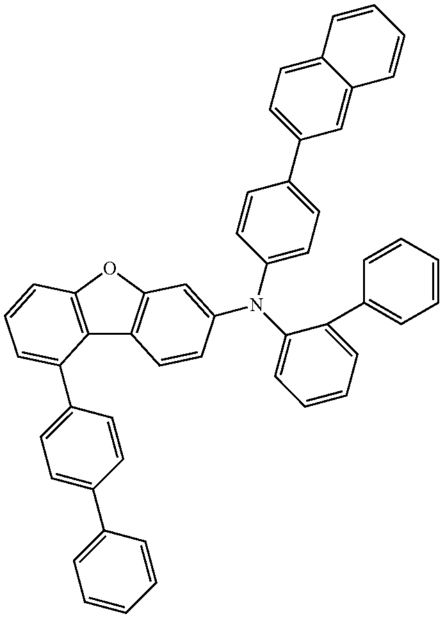
1-132
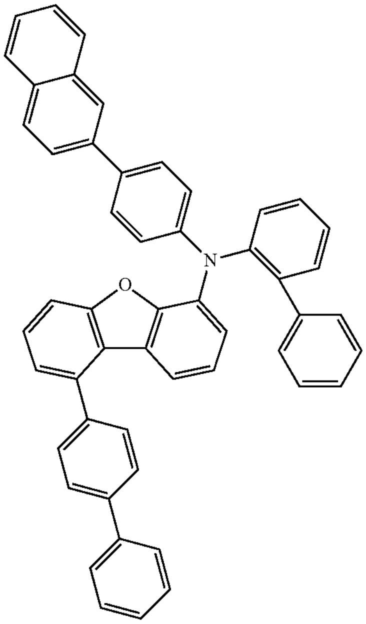
1-133
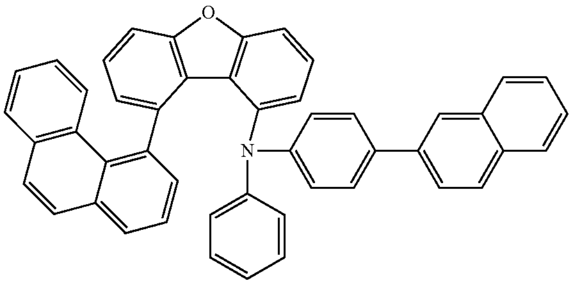
-continued
1-134
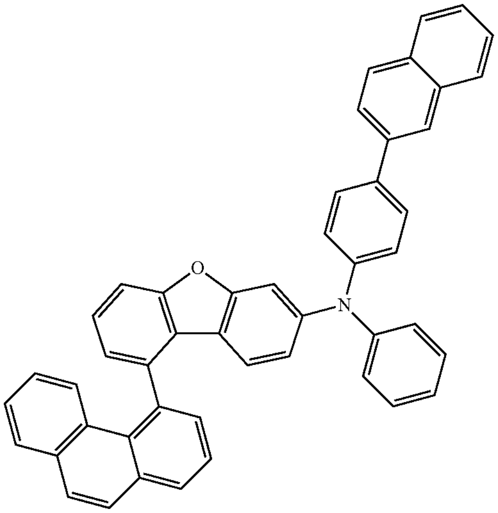
1-135
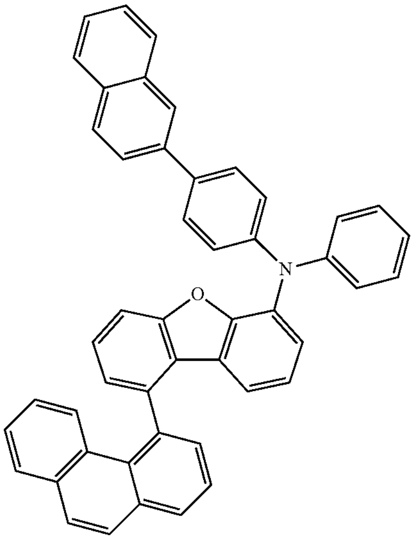
1-136
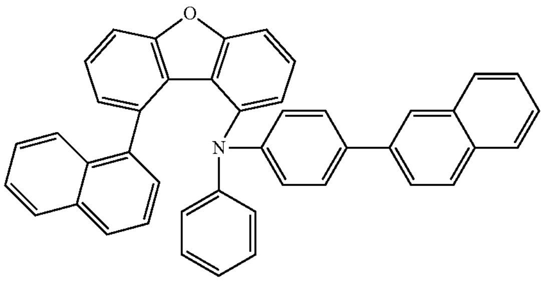

-continued
1-137
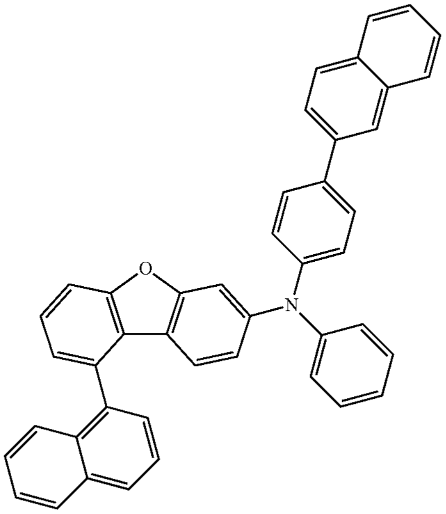
1-138
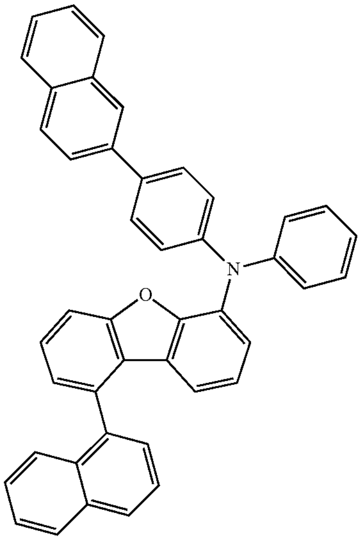
1-139
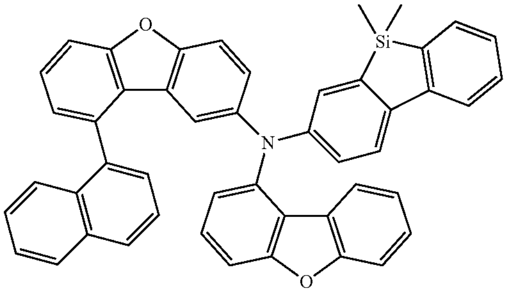
-continued
1-140
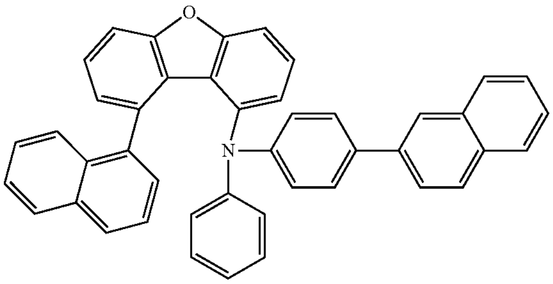
1-141
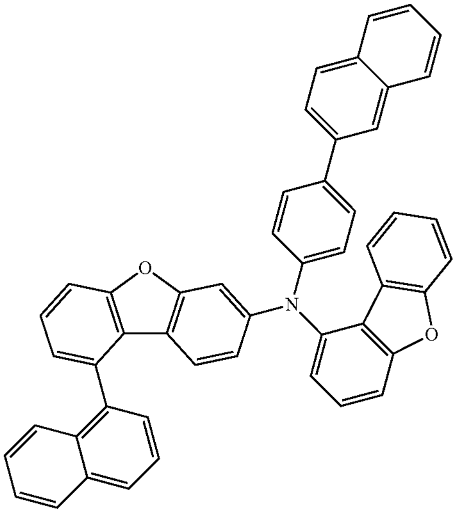
1-142
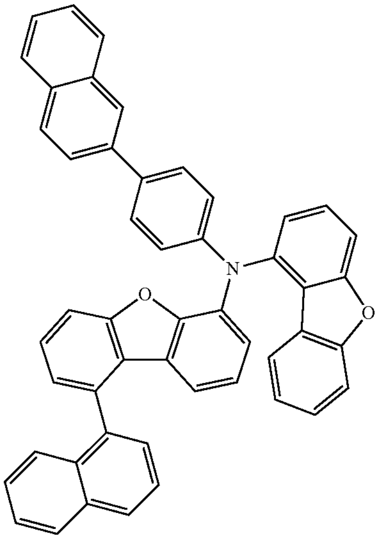

-continued
1-143
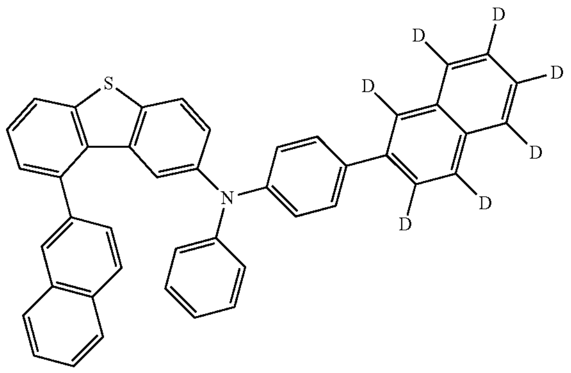
1-144
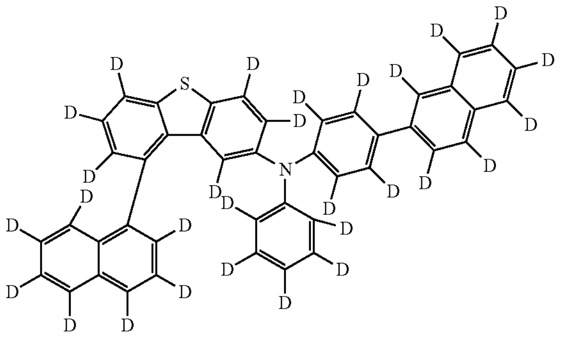
1-145
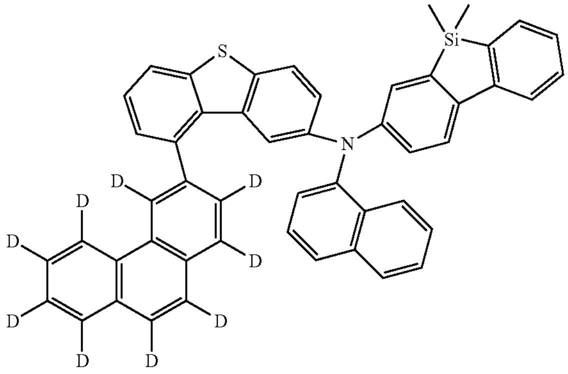
1-146
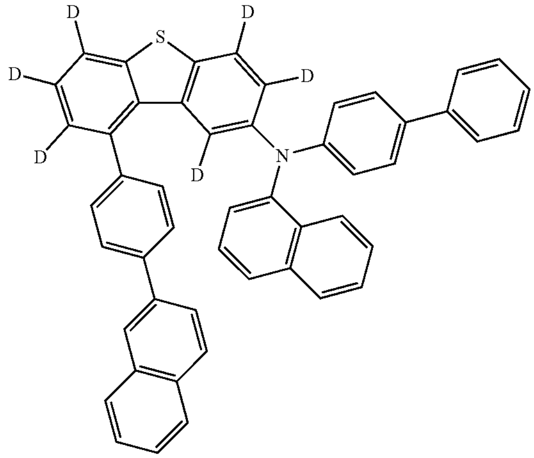
-continued
1-147
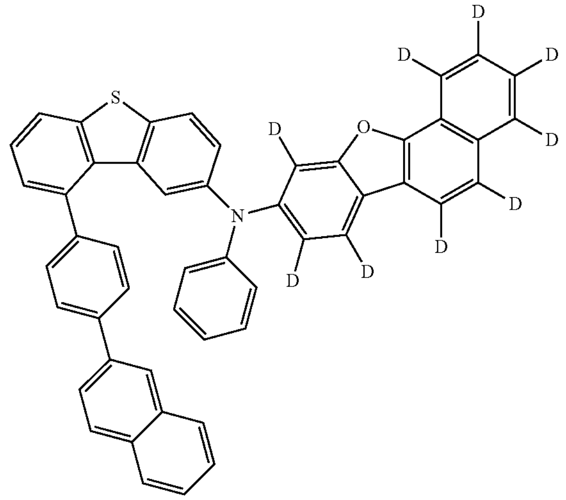
1-148
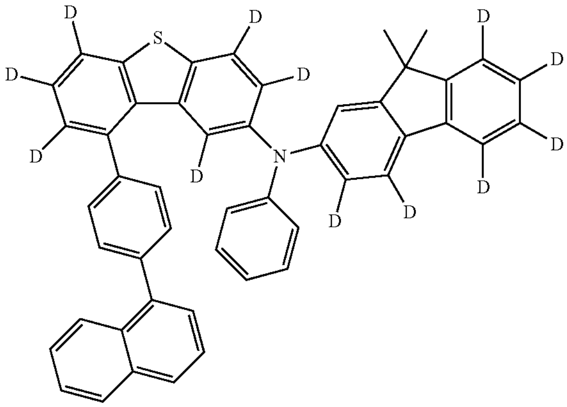
1-149
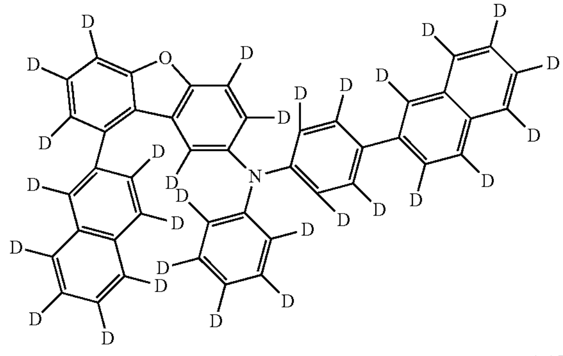
1-150
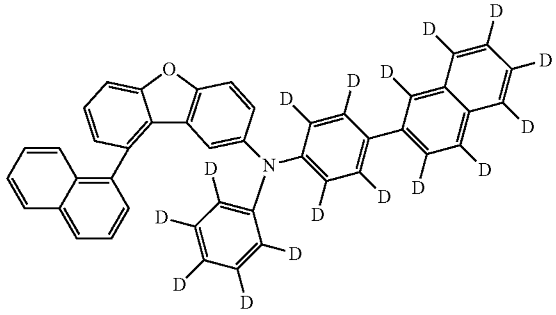

-continued 1-151

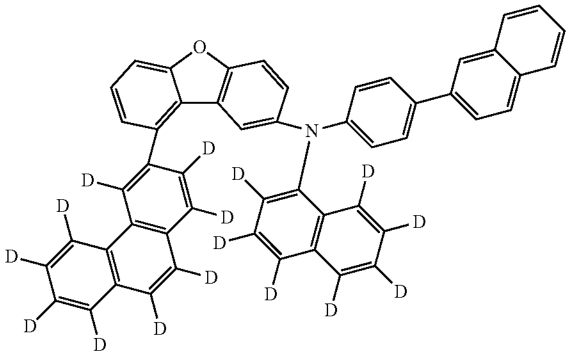

1-152

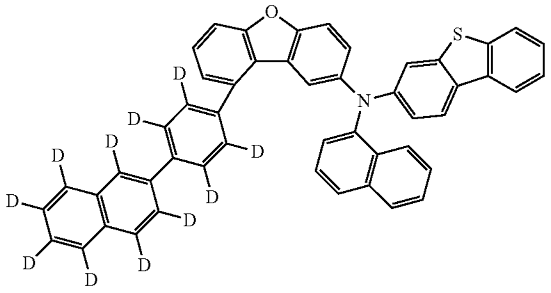

1-153

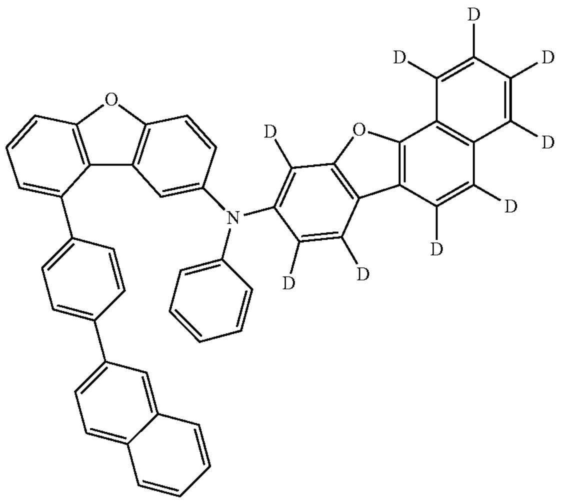

-continued 1-154

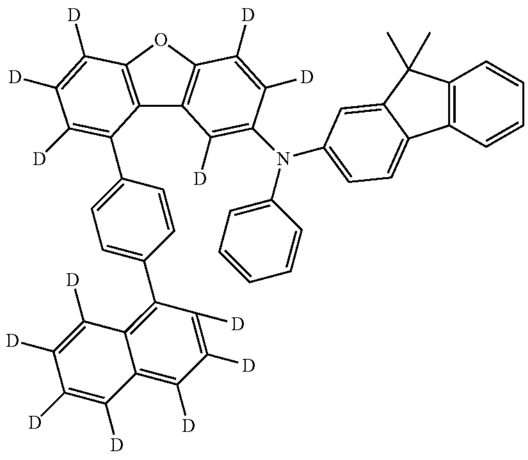

A composition for an organic optoelectronic device according to another embodiment may include a first compound and a second compound. In an implementation, the first compound may be, e.g., the aforementioned compound for an organic optoelectronic device (represented by Chemical Formula 1), and the second compound may be, e.g., a compound for an organic optoelectronic device represented by Chemical Formula 2.

[Chemical Formula 2]

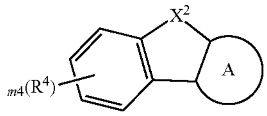

In Chemical Formula 2, $X^2$ may be, e.g., O, S, N-$L^a$-$R^a$, $CR^bR^c$, or $SiR^dR^e$.

$L^a$ may be or may include, e.g., a single bond or a substituted or unsubstituted C6 to C12 arylene group.

$R^a$, $R^b$, $R^c$, $R^d$, $R^e$, and $R^4$ may each independently be or include, e.g., hydrogen, deuterium, a substituted or unsubstituted C1 to C30 alkyl group, a substituted or unsubstituted C6 to C30 aryl group, or a substituted or unsubstituted C2 to C30 heterocyclic group.

m4 may be, e.g., an integer of 1 to 4.

A may be, e.g., a ring of Group II.

[Group II]

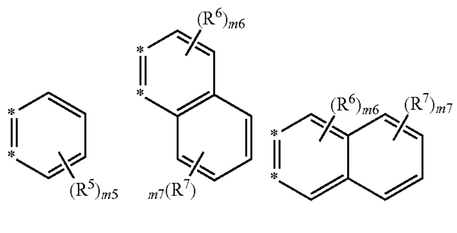

-continued

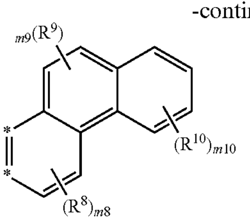

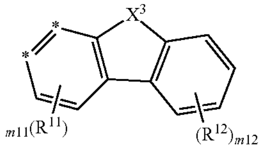

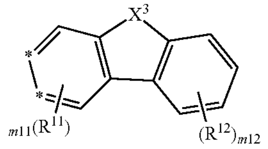

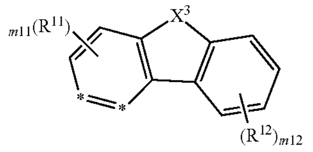

In Group II, * is a linking point.

$X^3$ may be, e.g., O or S.

$R^5$ to $R^{12}$ may each independently be or include, e.g., hydrogen, deuterium, a substituted or unsubstituted C1 to C30 alkyl group, a substituted or unsubstituted C6 to C30 aryl group, or a substituted or unsubstituted C2 to C30 heterocyclic group.

m5, m7, m10, and m12 may each independently be, e.g., an integer of 1 to 4.

m6, m8, m9, and m11 may each independently be, e.g., 1 or 2.

In an implementation, at least one of $R^a$ and $R^4$ to $R^{12}$ may be, e.g., a substituted heterocyclic group represented by Chemical Formula a.

[Chemical Formula a]

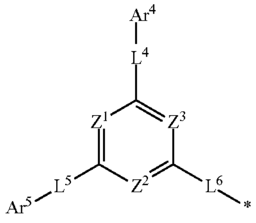

In Chemical Formula a, $Z^1$ to $Z^3$ may each independently be, e.g., N or $CR^f$. In an implementation, at least two of $Z^1$ to $Z^3$ are N.

$R^f$ may be or may include, e.g., hydrogen, deuterium, a substituted or unsubstituted C1 to C10 alkyl group, or a substituted or unsubstituted C6 to C20 aryl group.

$L^4$ to $L^6$ may each independently be or include, e.g., a single bond or a substituted or unsubstituted C6 to C30 arylene group.

$Ar^4$ and $Ar^5$ may each independently be or include, e.g., a substituted or unsubstituted C6 to C30 aryl group, or a substituted or unsubstituted C2 to C30 heterocyclic group.

* is a linking point.

The second compound may have a structure substituted including a nitrogen-containing 6-membered ring.

The second compound may effectively extend the LUMO energy band by being substituted with a nitrogen-containing 6-membered ring, and when used in the light emitting layer together with the aforementioned first compound, a balance of holes and electrons may be increased by increasing the charge mobility and stability to improve luminous efficiency and life-span characteristics of the device, and to lower a driving voltage of the device.

In an implementation, ring A of the second compound may be a ring of Group II, and the compound may be, e.g., represented by one of Chemical Formula 2-I to Chemical Formula 2-X.

[Chemical Formula 2-I]

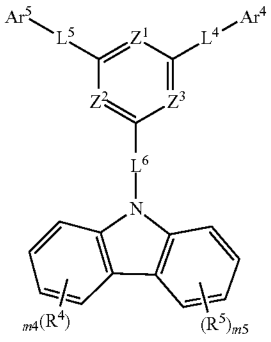

In Chemical Formula 2-I, $Z^1$ to $Z^3$, $R^4$, $R^5$, $L^4$ to $L^6$, $Ar^4$, $Ar^5$, m4, and m5 may be defined the same as those described above.

[Chemical Formula 2-II]

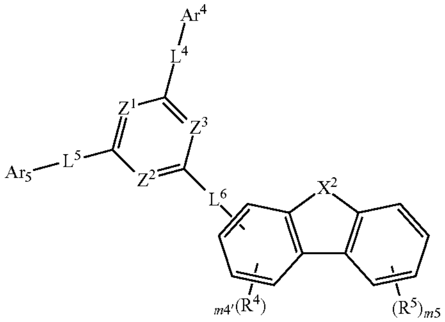

[Chemical Formula 2-III]

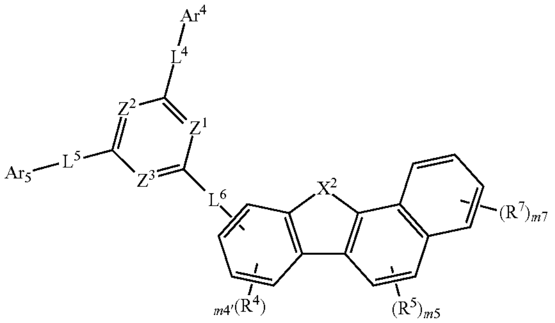

-continued

[Chemical Formula 2-IV]

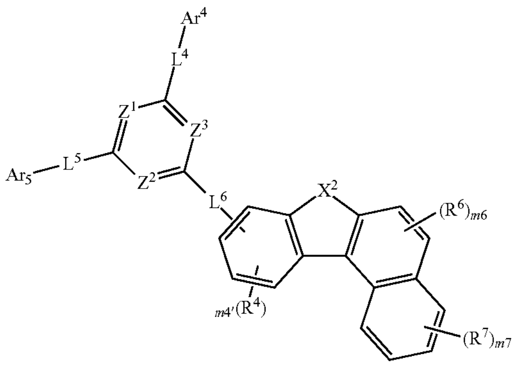

[Chemical Formula2-V]

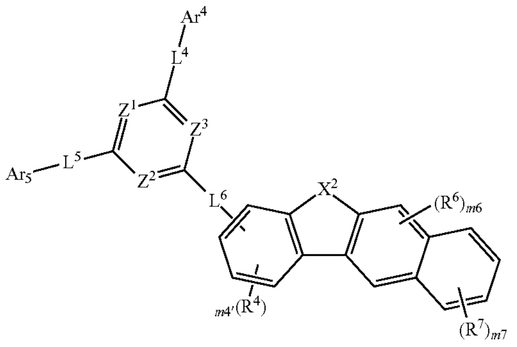

In Chemical Formula 2-II to Chemical Formula 2-V, $X^2$, $Z^1$ to $Z^3$, $R^4$ to $R^7$, $L^4$ to $L^6$, $Ar^4$, $Ar^5$, and m5 to m7 may be defined the same as those described above.

m4' may be, e.g., an integer of 1 to 3.

[Chemical Formula 2-VI]

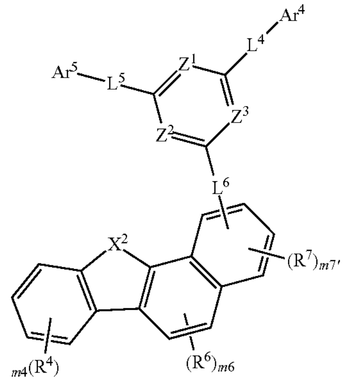

-continued

[Chemical Formula 2-VII]

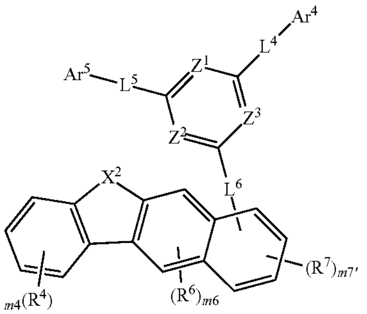

[Chemical Formula 2-VIII]

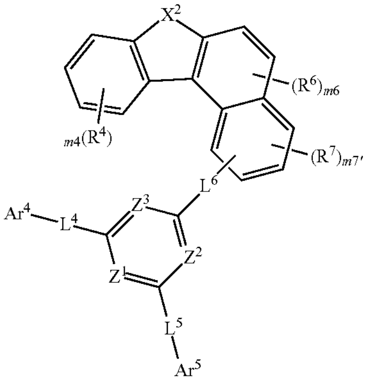

In Chemical Formula 2-VI to Chemical Formula 2-VIII, $X^2$, $Z^1$ to $Z^3$, $R^4$, $R^6$, $R^7$, $L^4$ to $L^6$, $Ar^4$, $Ar^5$, m4, and m6 may be defined the same as those described above.

m7' may be, e.g., an integer of 1 to 3.

[Chemical Formula 2-IX]

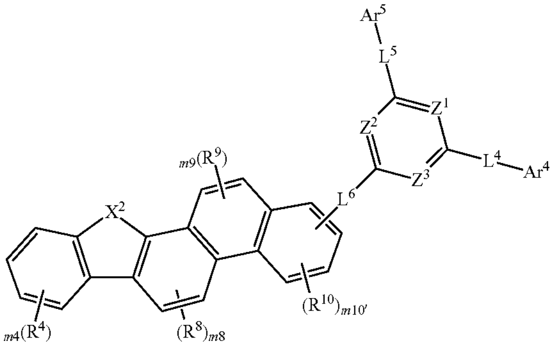

In Chemical Formula 2-IX, $X^2$, $Z^1$ to $Z^3$, $R^4$, $R^8$ to $R^{10}$, $L^4$ to $L^6$, $Ar^4$, $Ar^5$, m4, m8 and m9 may be defined the same as those described above.

m10' may be, e.g., an integer of 1 to 3.

[Chemical Formula 2-X]

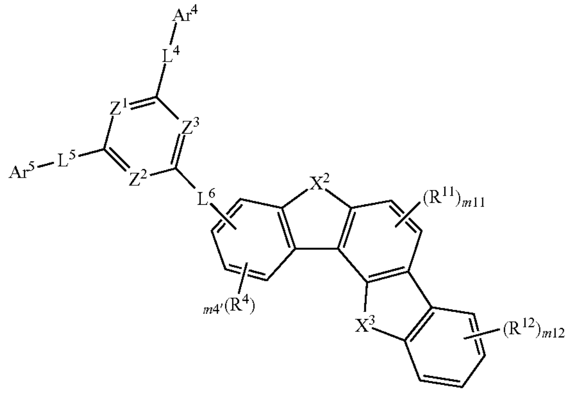

In Chemical Formula 2-X, $X^2$, $X^3$, $Z^1$ to $Z^3$, $R^4$, $R^{11}$, $R^{12}$, $L^4$ to $L^6$, $Ar^4$, $Ar^5$, m11, and m12 may be defined the same as those described above.

m4' may be, e.g., an integer of 1 to 3.

In an implementation, the second compound may be represented by, e.g., Chemical Formula 2-II, Chemical Formula 2-III, or Chemical Formula 2-VI.

In an implementation, the second compound may be represented by, e.g., Chemical Formula 2-II-3, Chemical Formula 2-III-1, Chemical Formula 2-VI-1, or Chemical Formula 2-VI-3.

[Chemical Formula 2-II-3]

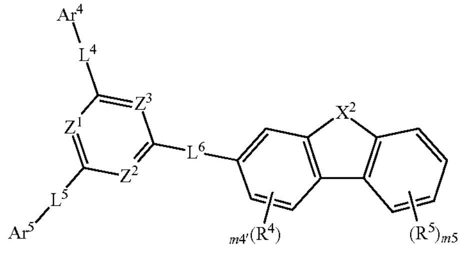

[Chemical Formula 2-III-1]

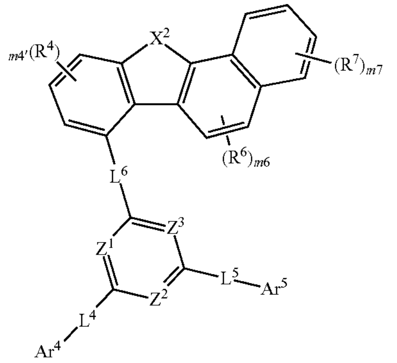

-continued

[Chemical Formula 2-VI-1]

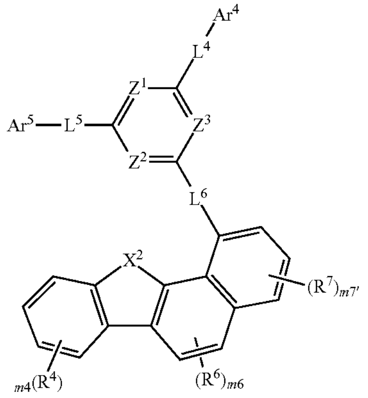

[Chemical Formula 2-VI-3]

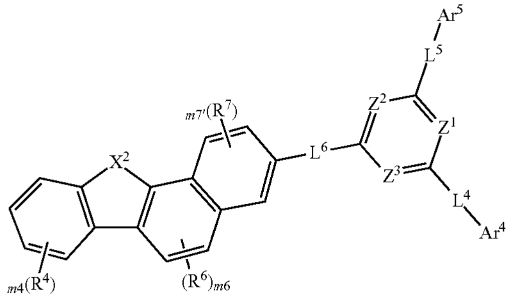

In Chemical Formula 2-II-3, Chemical Formula 2-III-1, Chemical Formula 2-VI-1, and Chemical Formula 2-VI-3, $X^2$, $Z^1$ to $Z^3$, $R^4$ to $R^7$, $L^4$ to $L^6$, $Ar^4$, $Ar^5$, m4 to m7, m4', and m7' may be defined the same as those described above.

In an implementation, $Ar^4$ and $Ar^5$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted carbazolyl group, a substituted or unsubstituted dibenzofuranyl group, a substituted or unsubstituted dibenzothiophenyl group, or a substituted or unsubstituted dibenzosilolyl group.

In an implementation, $Ar^4$ and $Ar^5$ may each independently be, e.g., a substituted or unsubstituted phenyl group, a substituted or unsubstituted biphenyl group, or a substituted or unsubstituted naphthyl group.

In an implementation, $L^4$ to $L^6$ may each independently be, e.g., a single bond, a substituted or unsubstituted phenylene group, or a substituted or unsubstituted biphenylene group.

In an implementation, $L^4$ may be, e.g., a single bond or a substituted or unsubstituted phenylene group, and $L^5$ and $L^6$ may each independently be, e.g., a single bond, a substituted or unsubstituted phenylene group, or a substituted or unsubstituted biphenylene group.

In an implementation, $L^4$ may be, e.g., a single bond, and $L^5$ and $L^6$ may each independently be, e.g., a single bond or a substituted or unsubstituted phenylene group.

In an implementation, $R^4$ to $R^7$ may each independently be, e.g., hydrogen, deuterium, a substituted or unsubstituted C1 to C10 alkyl group, a substituted or unsubstituted C6 to C12 aryl group, or a substituted or unsubstituted C2 to C18 heterocyclic group.

In an implementation, $R^4$ to $R^7$ may each independently be, e.g., hydrogen, deuterium, a substituted or unsubstituted phenyl group, or a substituted or unsubstituted naphthyl group.

In an implementation, $X^2$ may be, e.g., O, S, $CR^bR^c$, or $SiR^dR^e$, and $R^b$, $R^c$, $R^d$, and $R^e$ may each independently be, e.g., a substituted or unsubstituted C1 to C10 alkyl group or a substituted or unsubstituted C6 to C20 aryl group.

In an implementation, $R^b$, $R^c$, $R^d$, and $R^e$ may each independently be, e.g., a substituted or unsubstituted methyl group, a substituted or unsubstituted phenyl group, or a substituted or unsubstituted biphenyl group.

In an implementation, the second compound may be, e.g., a compound of Group 2.

[Group 2]

A-1

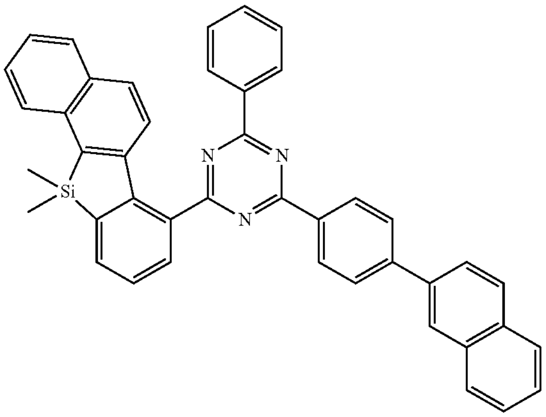

A-2

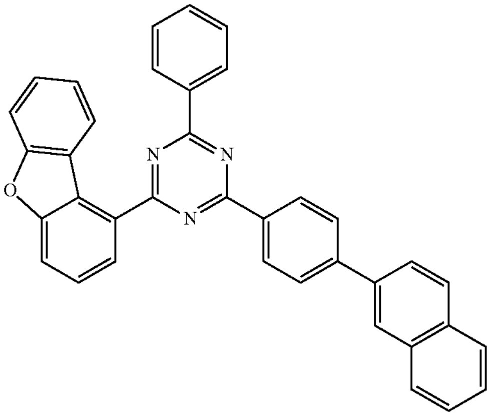

-continued

A-3

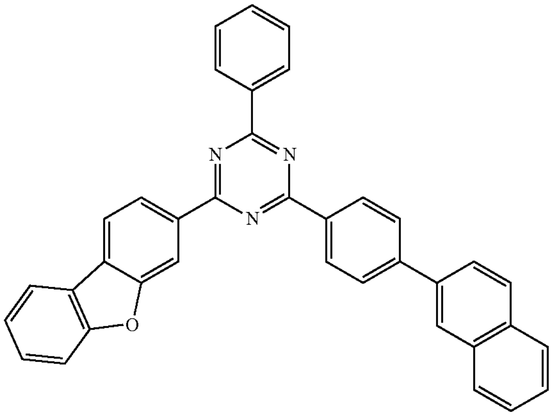

A-4

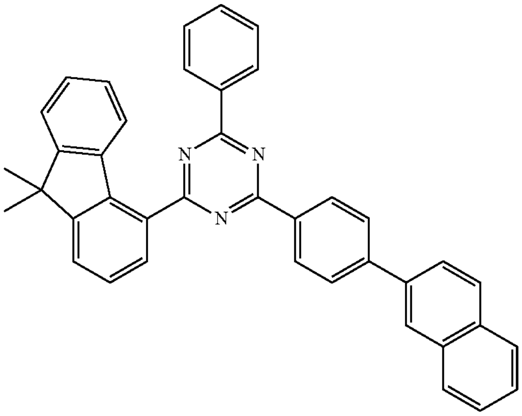

A-5

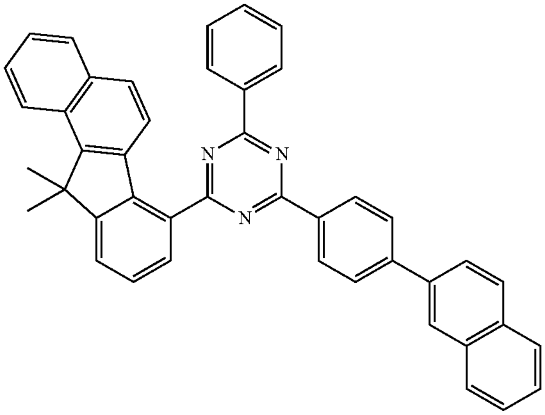

-continued
A-6
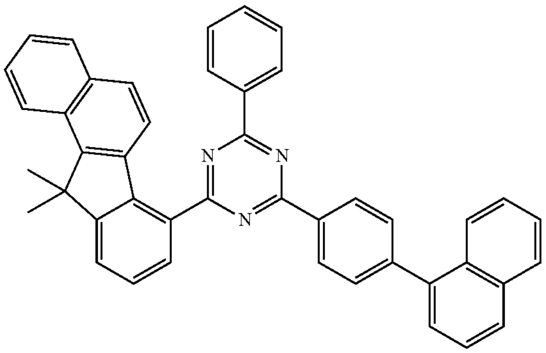
A-7
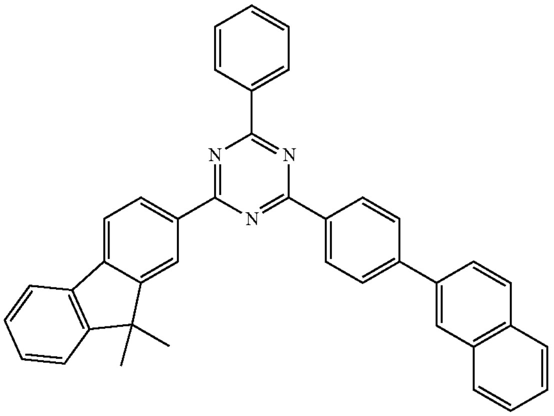
A-8
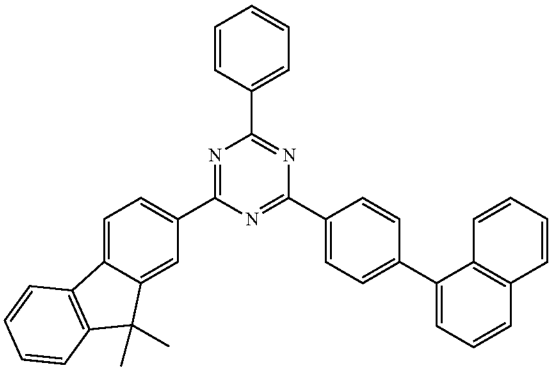
A-9
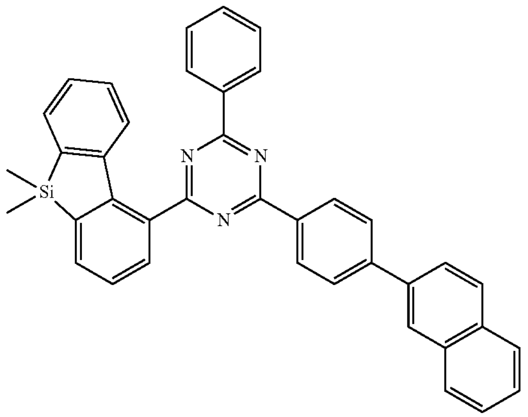
-continued
A-10
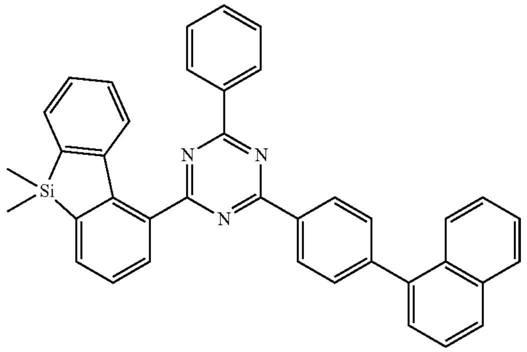
A-11
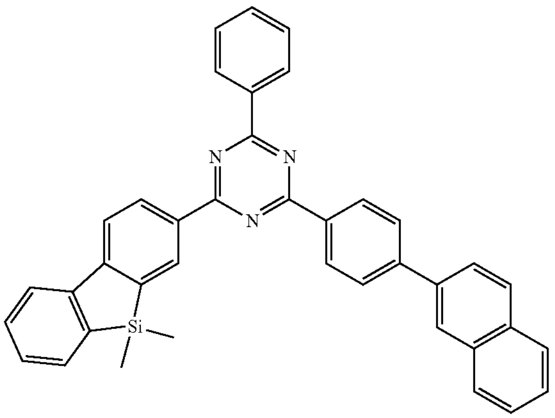
A-12
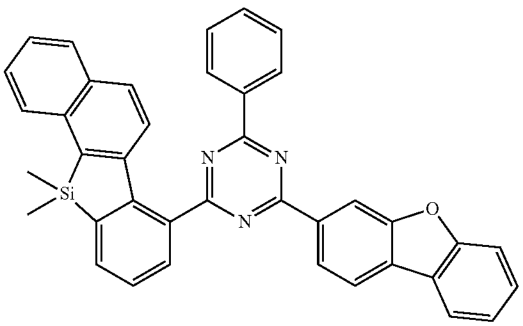
A-13
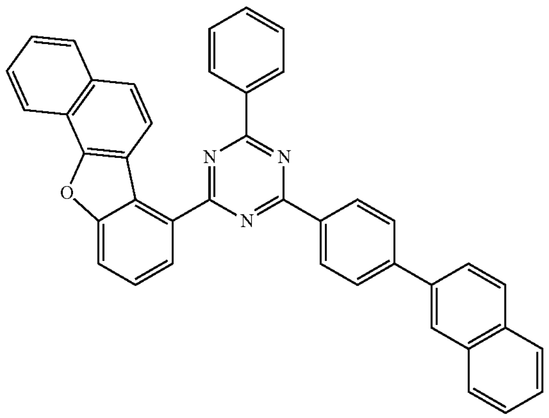

-continued
A-14
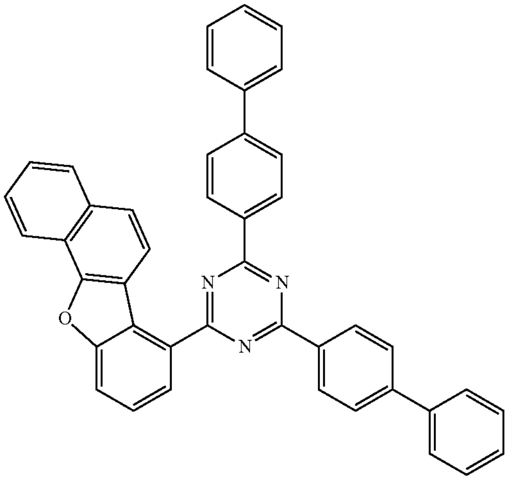
A-15
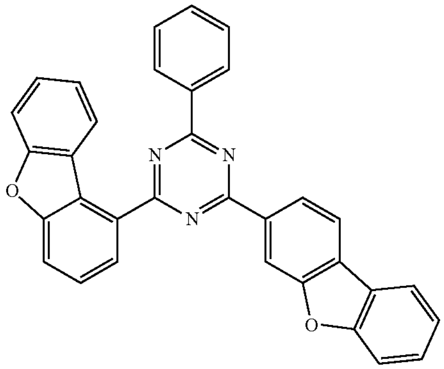
A-16
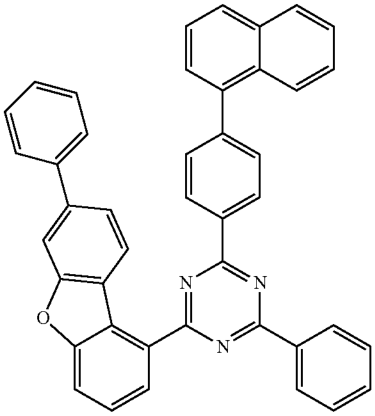
-continued
A-17
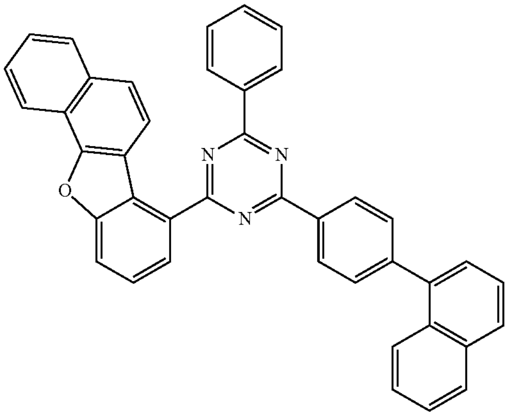
A-18
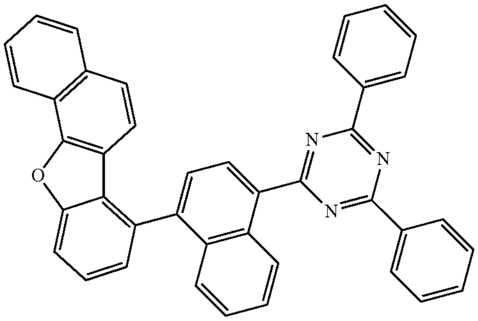
A-19
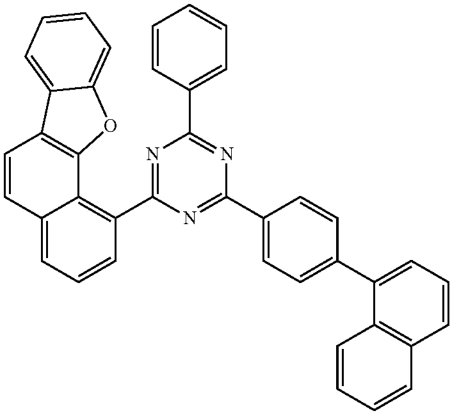
A-20
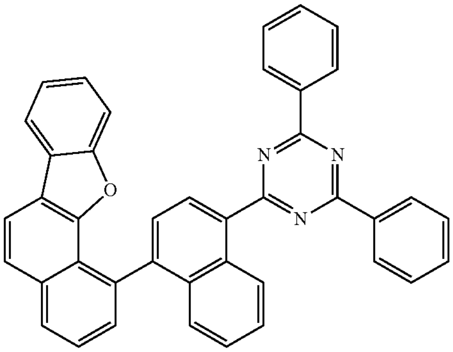

-continued
A-21
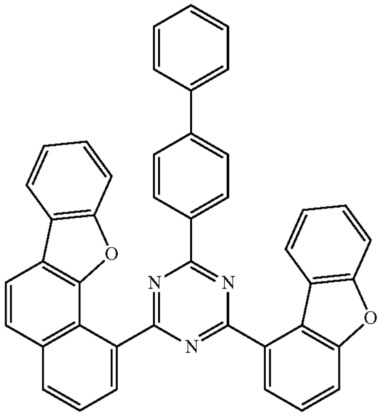
A-22
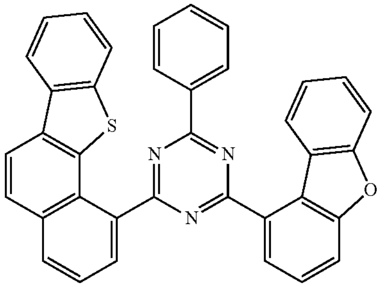
A-23
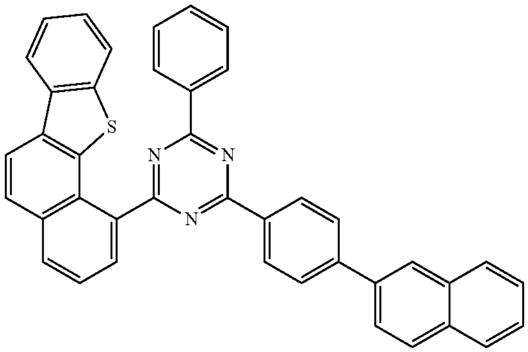
A-24
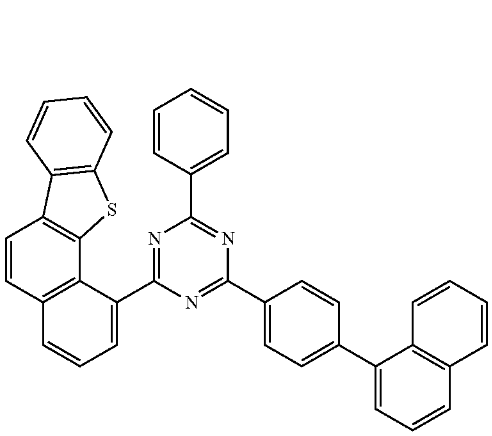
-continued
A-25
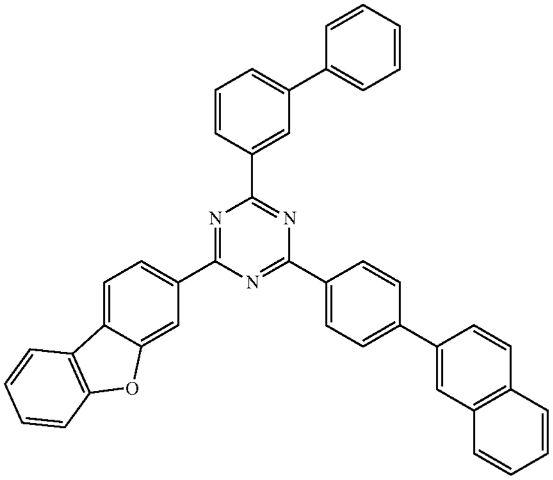
A-26
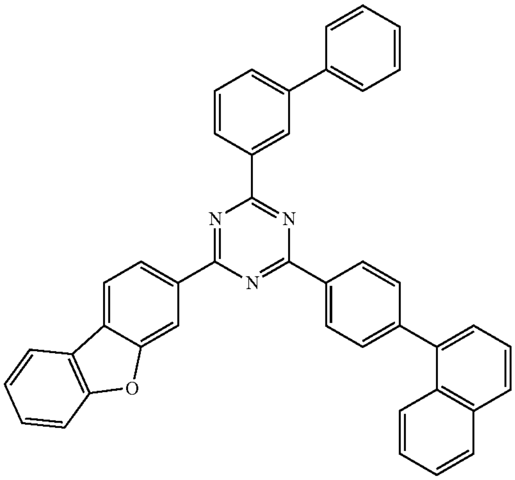
A-27
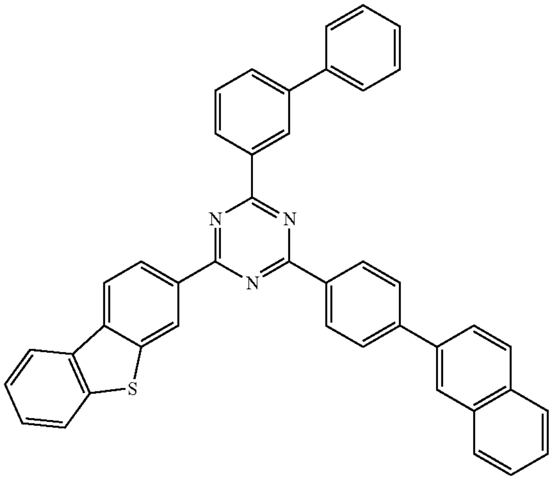

-continued
A-28
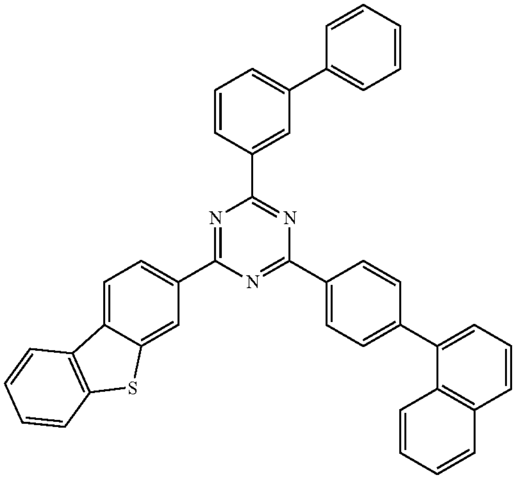
A-29
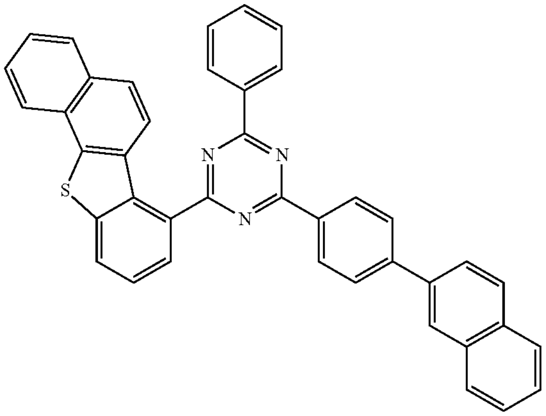
A-30
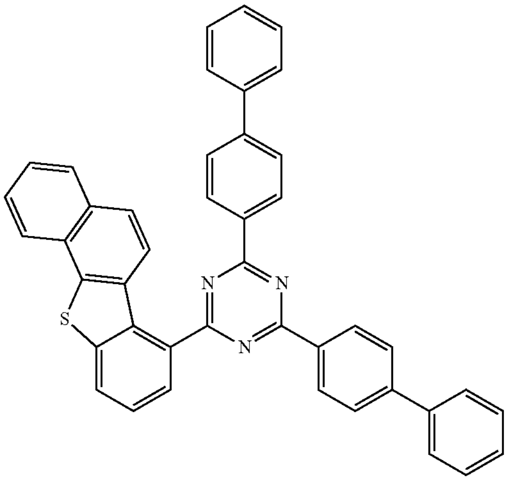
-continued
A-31
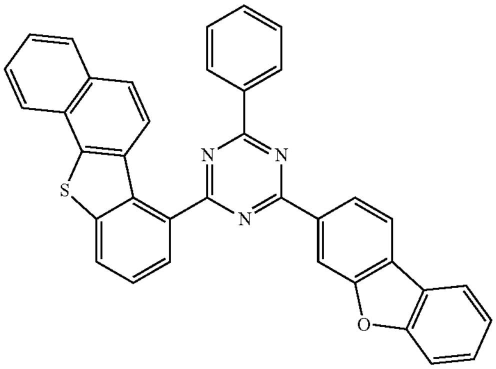
A-32
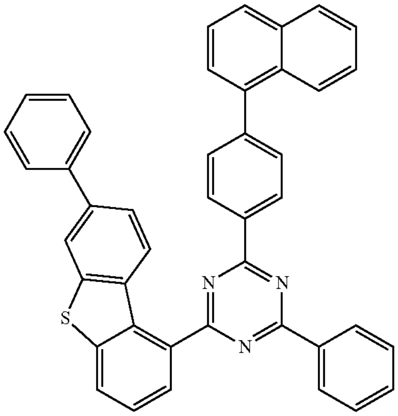
A-33
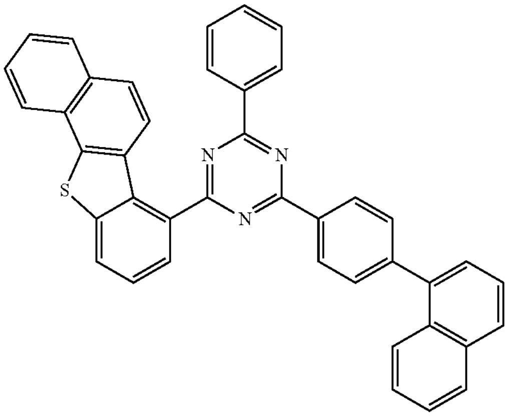
A-34
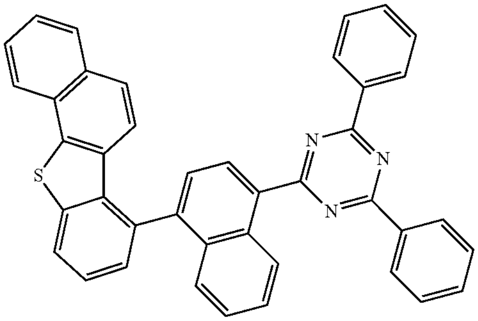

-continued
A-35
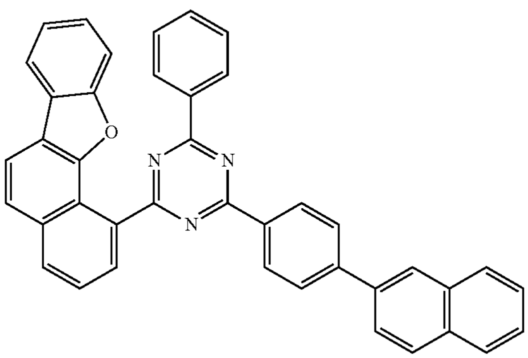
A-36
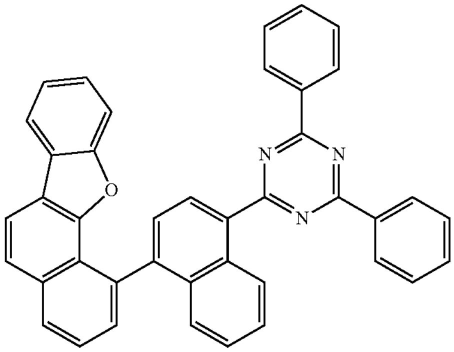
A-37
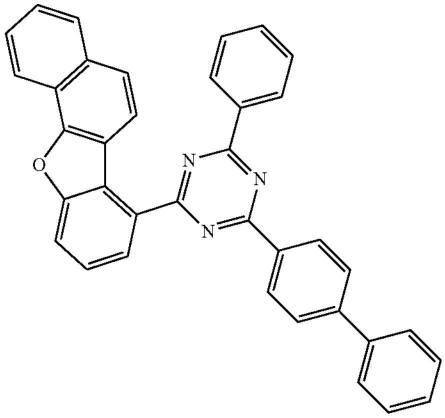
A-38
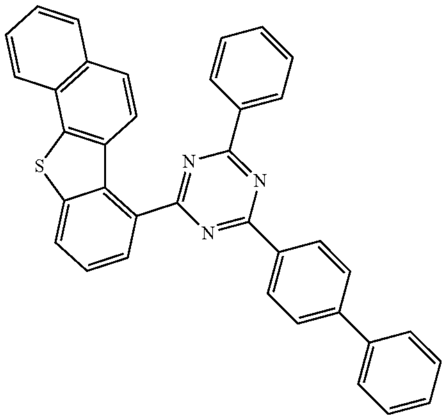
-continued
A-39
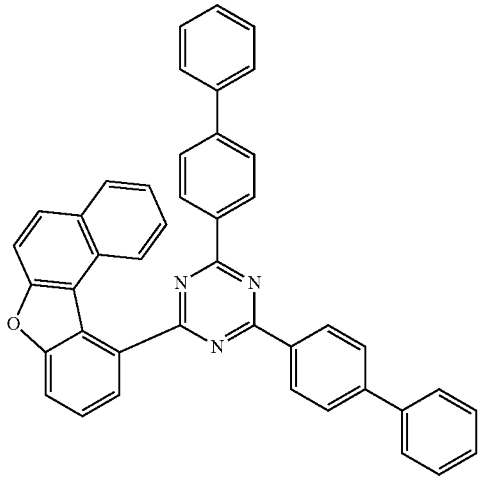
A-40
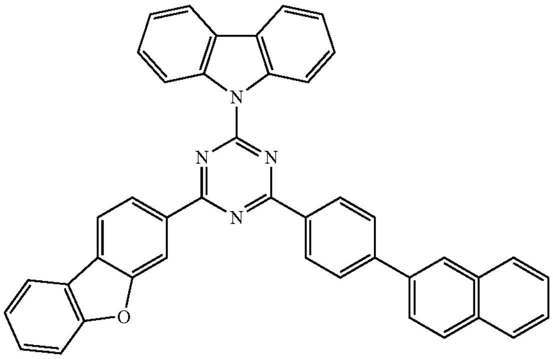
A-41
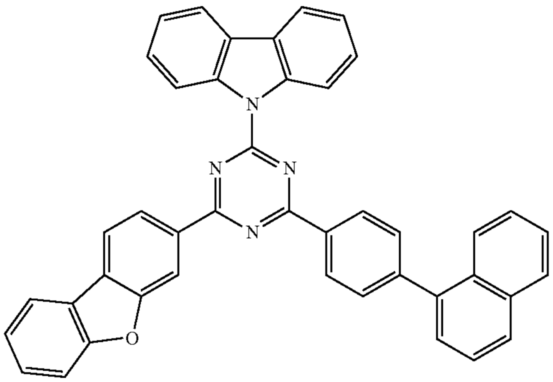

-continued
A-42
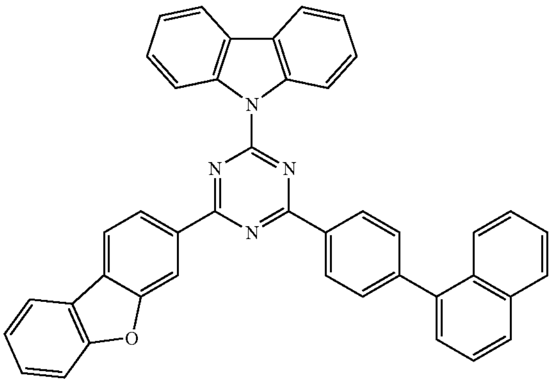
A-43
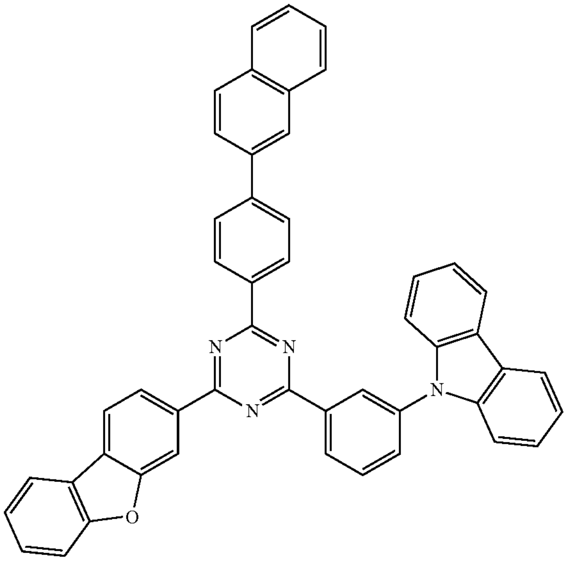
A-44
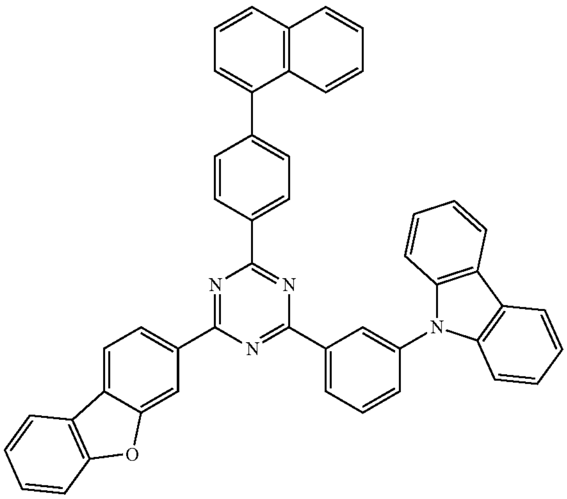
-continued
A-45
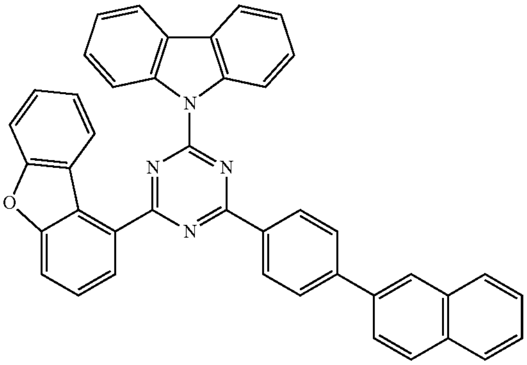
A-46
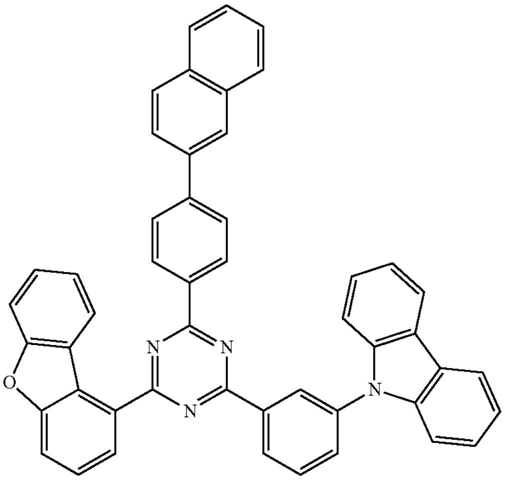
A-47
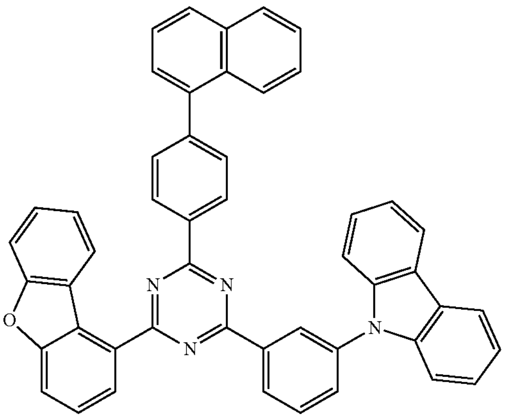

-continued
A-48
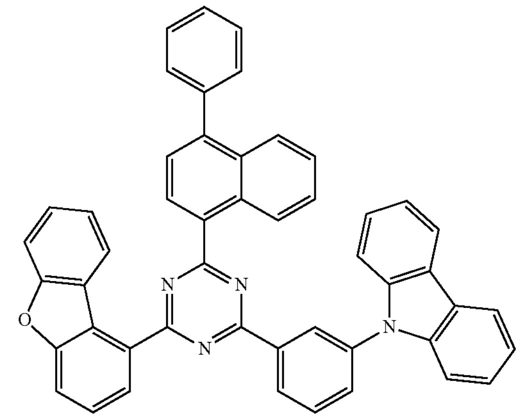
A-49
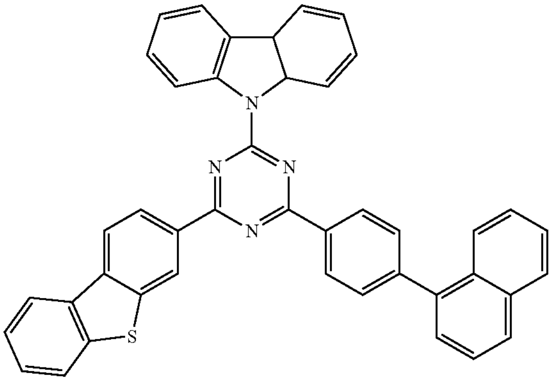
A-50
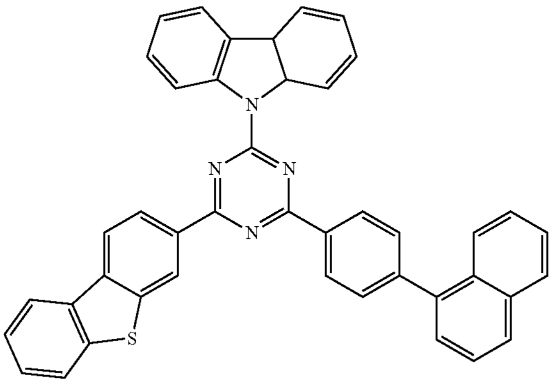
-continued
A-51
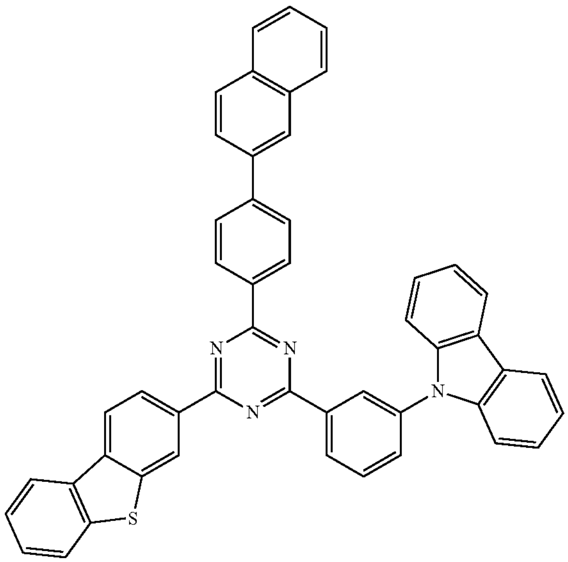
A-52
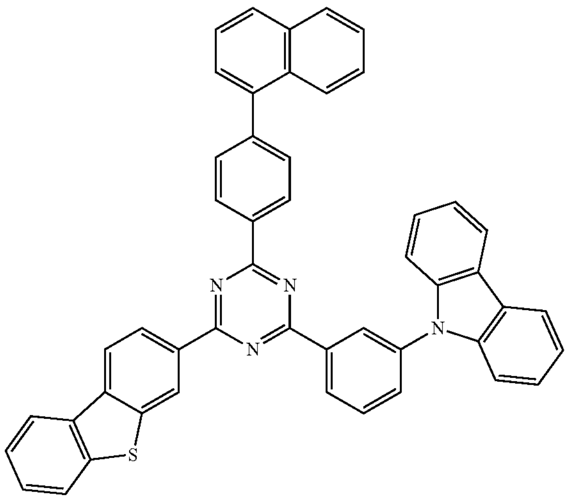
A-53
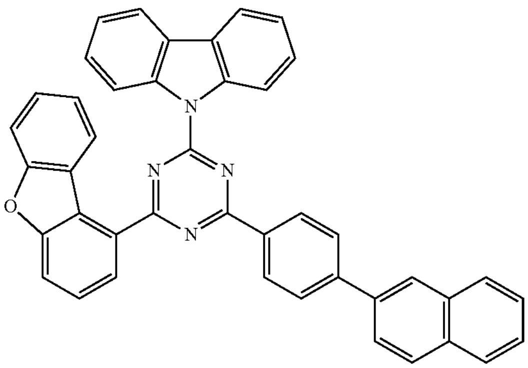

-continued
A-54
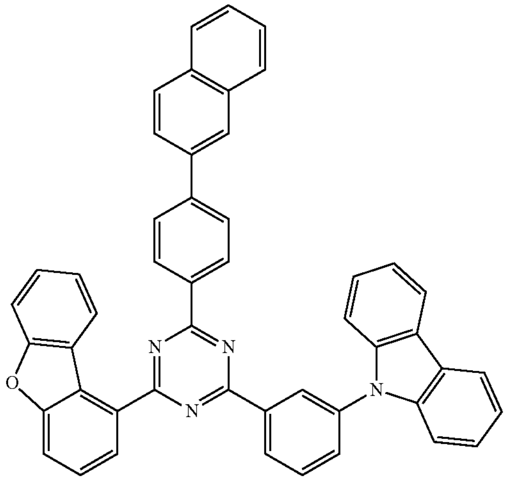
A-55
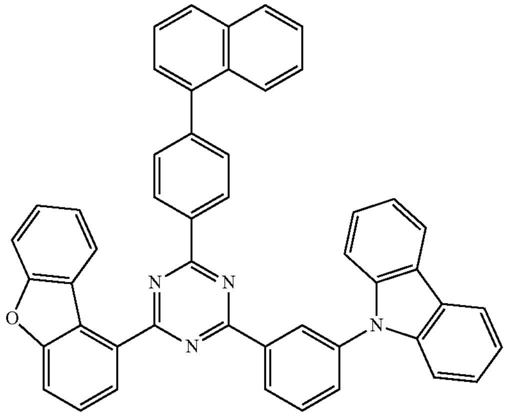
A-56
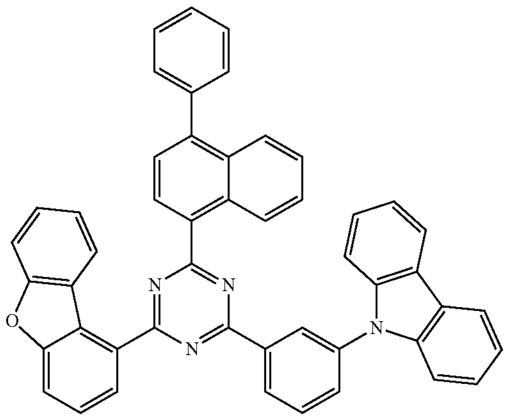
-continued
A-57
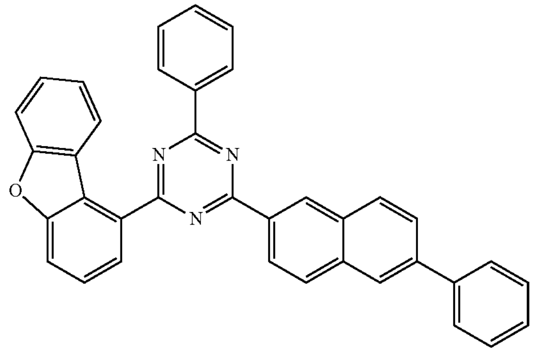
A-58
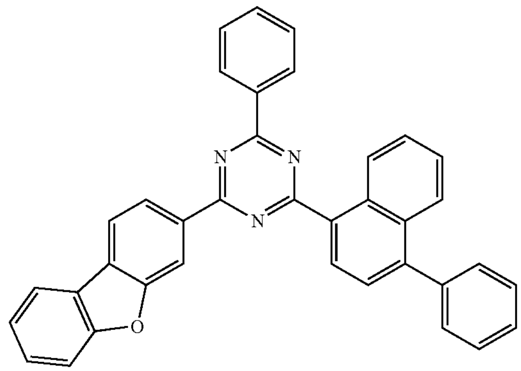
A-59
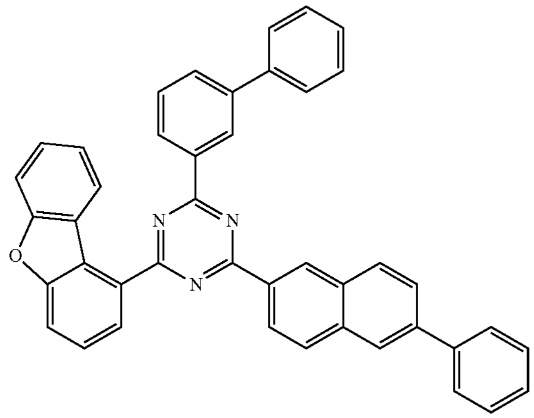

-continued
A-60
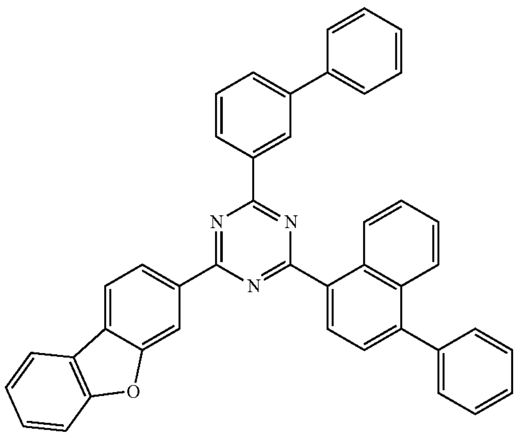
A-61
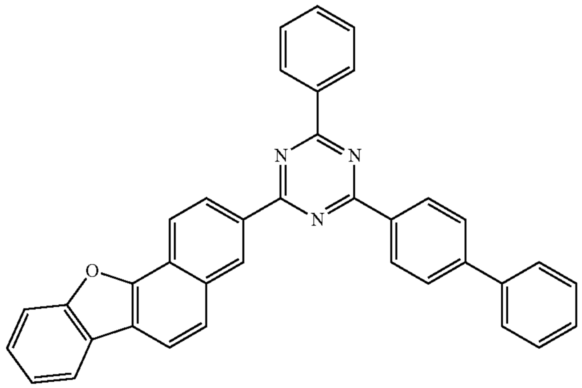
A-62
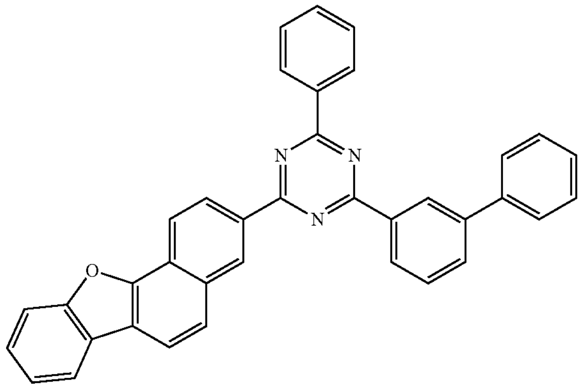
-continued
A-63
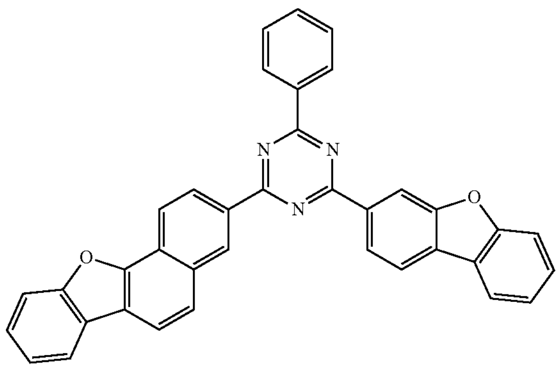
A-64
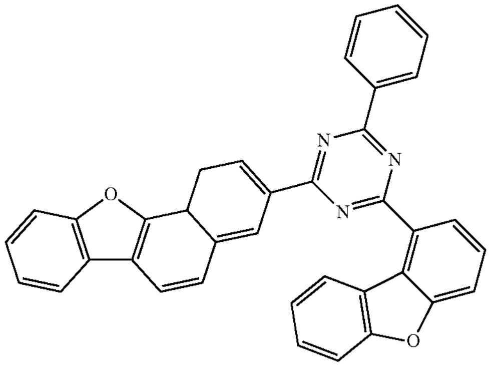
A-65
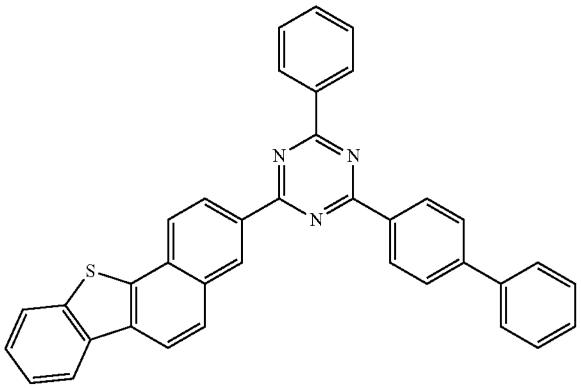
A-66
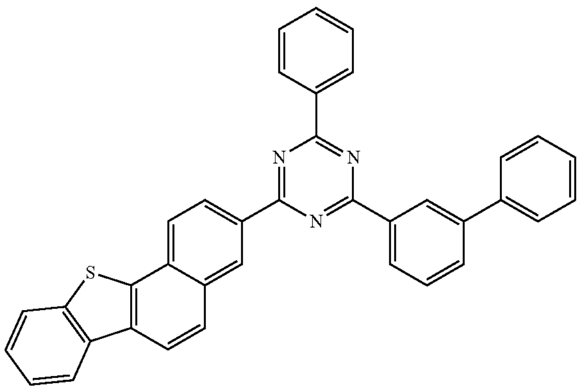

-continued
A-67
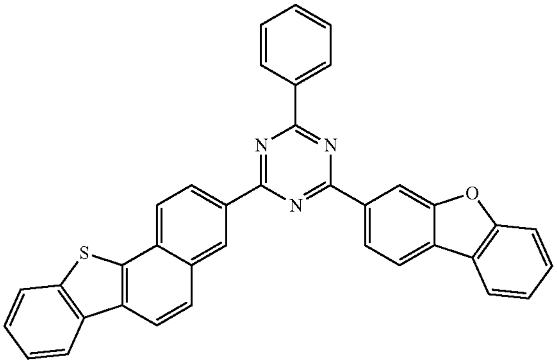
A-68
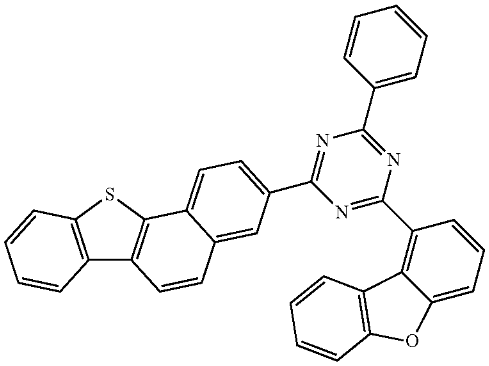
A-69
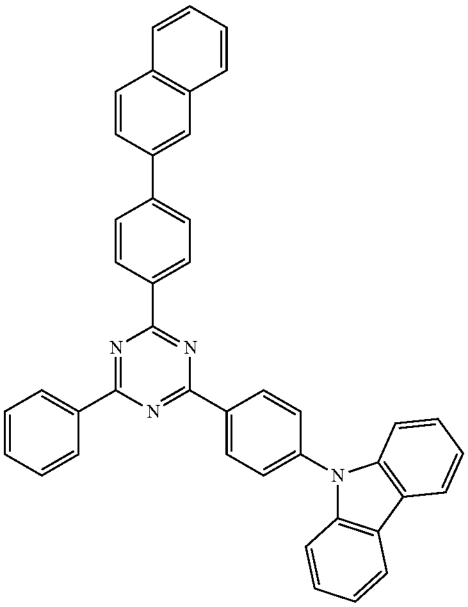
-continued
A-70
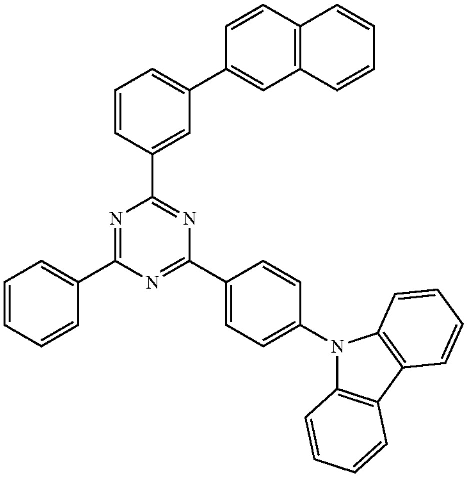
A-71
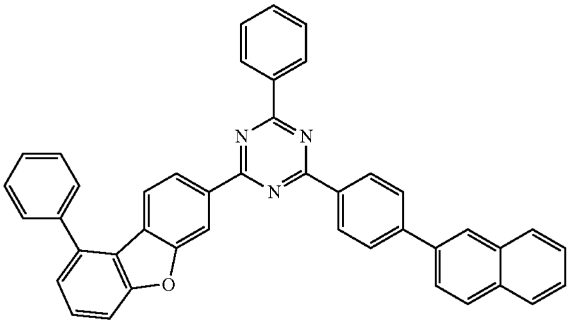
A-72
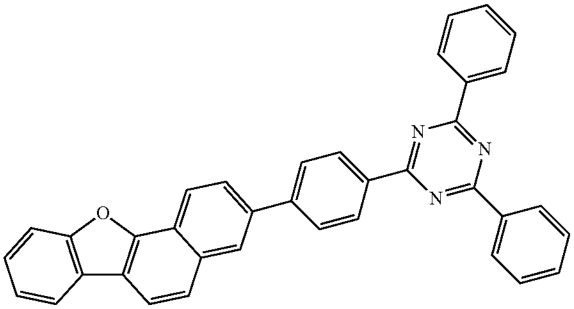
A-73
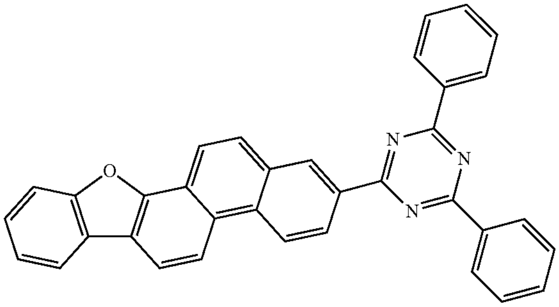

-continued
A-74
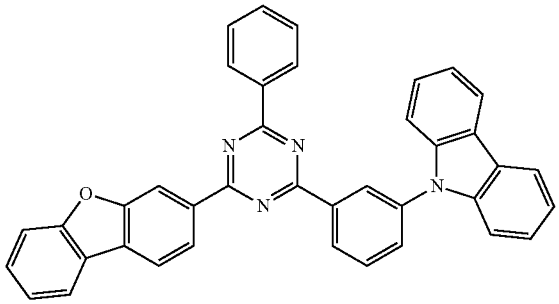
A-75
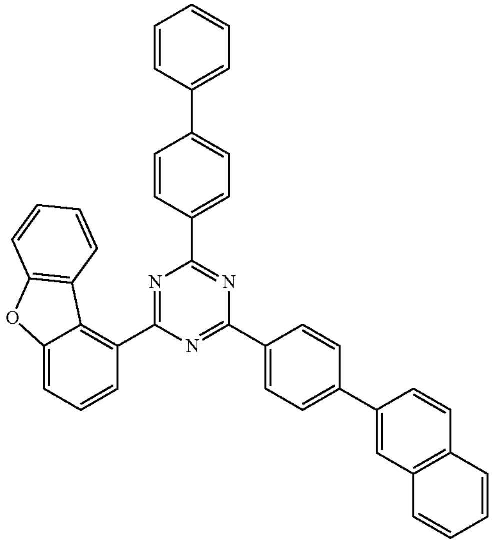
A-76
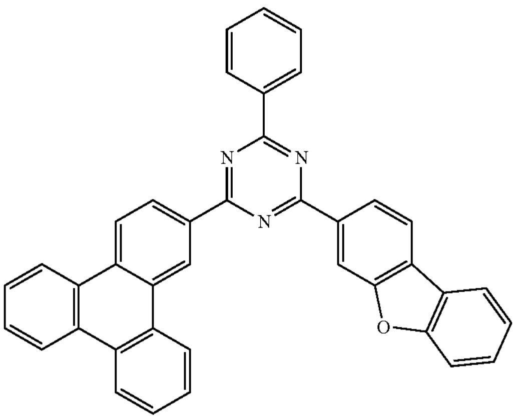
-continued
A-77
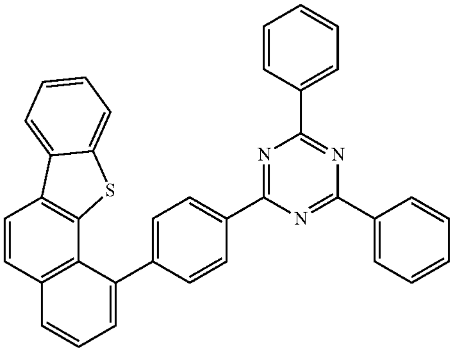
A-78
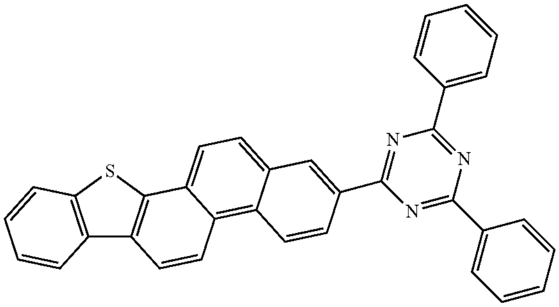
A-79
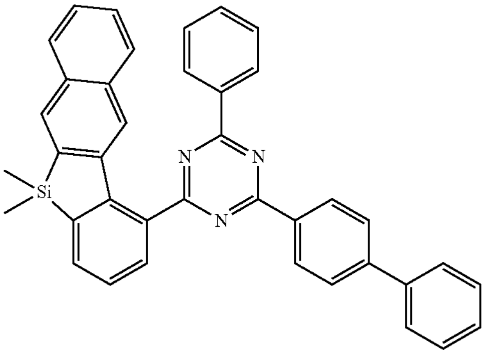
A-80
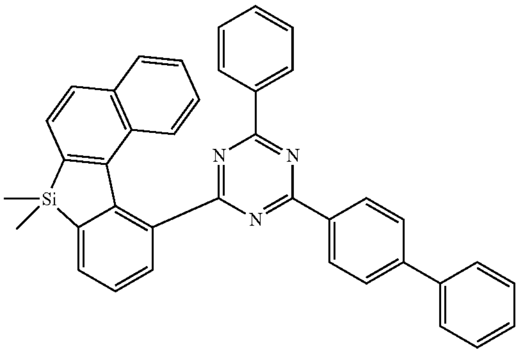

-continued
A-81
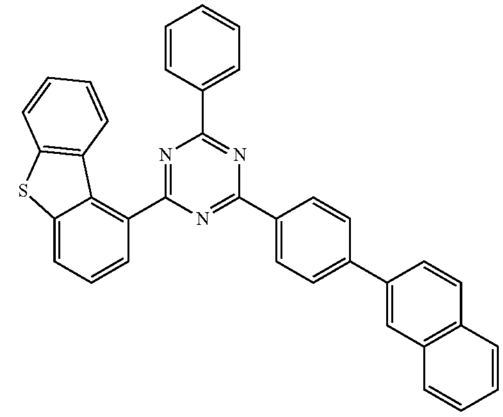
A-82
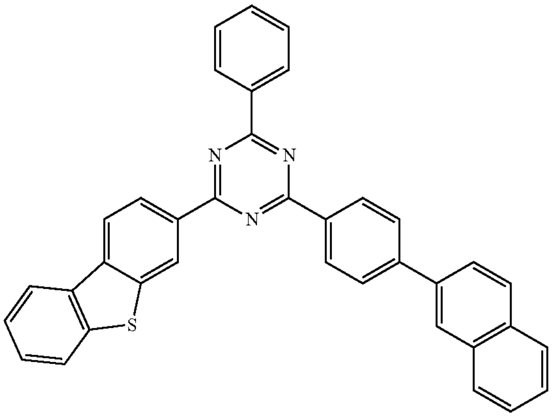
A-83
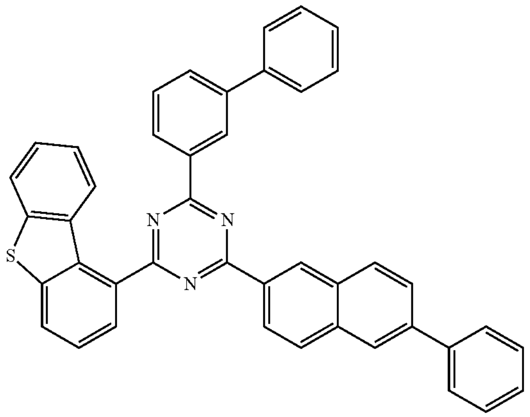
-continued
A-84
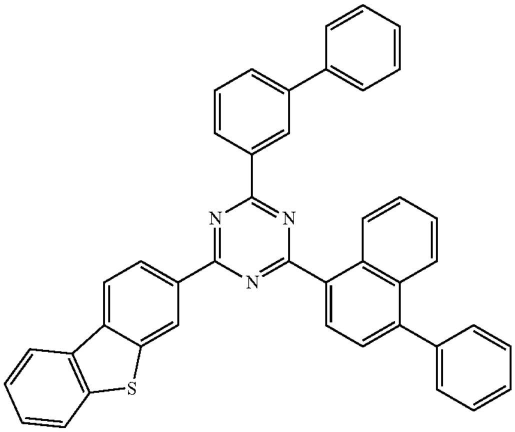
A-85
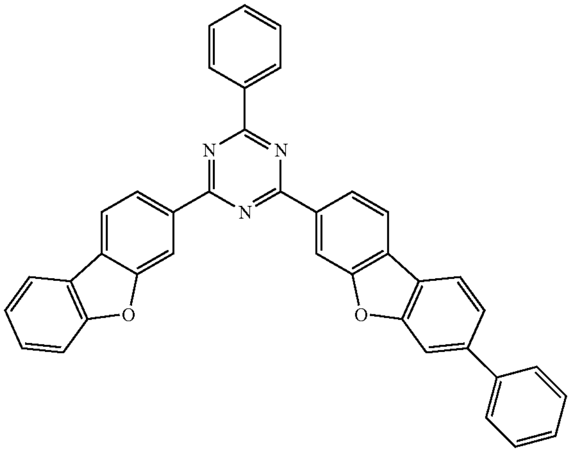
A-86
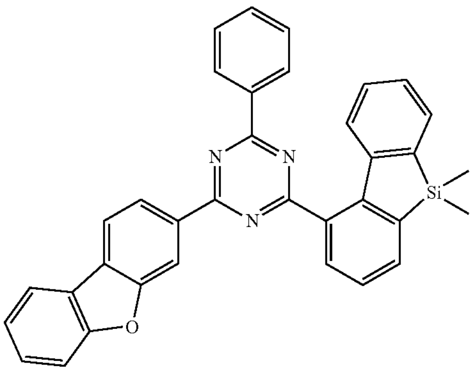

-continued
A-87
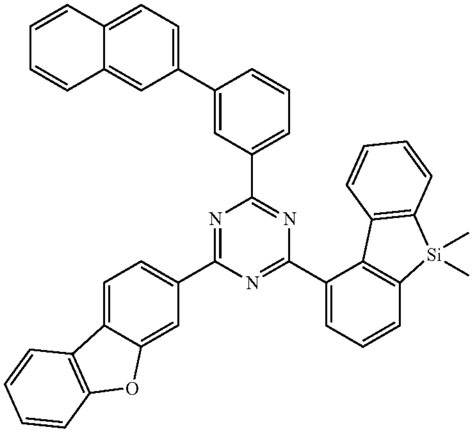
A-88
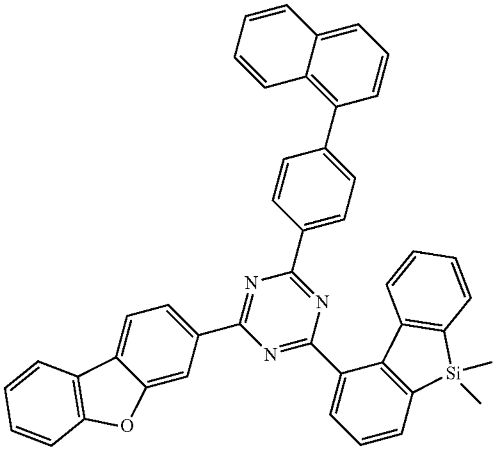
A-89
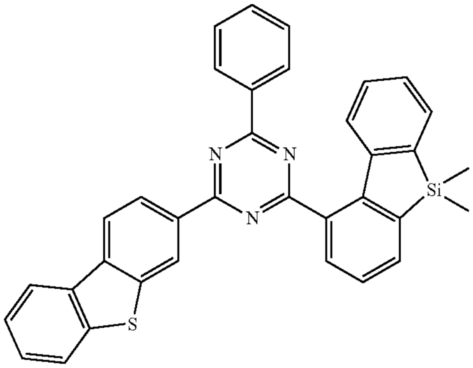
-continued
A-90
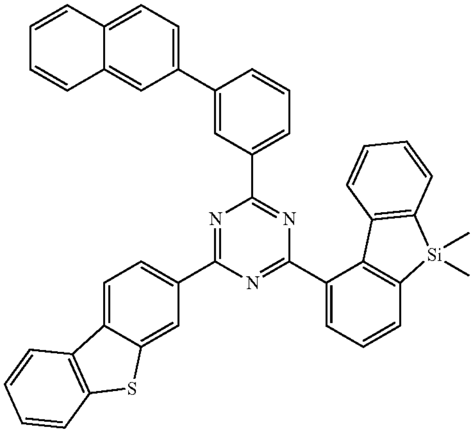
A-91
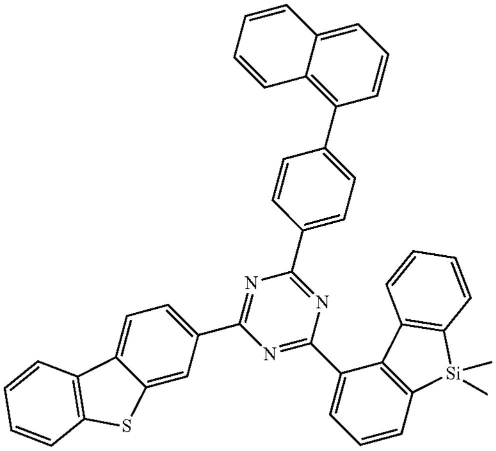
A-92
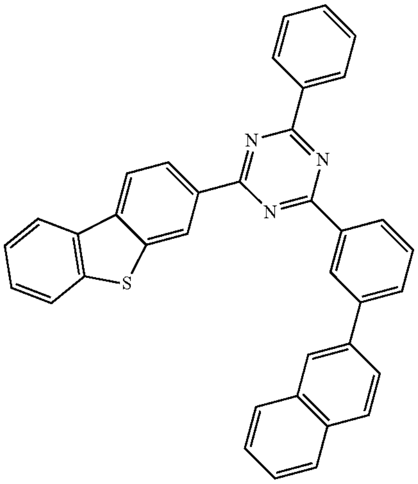

-continued
A-93
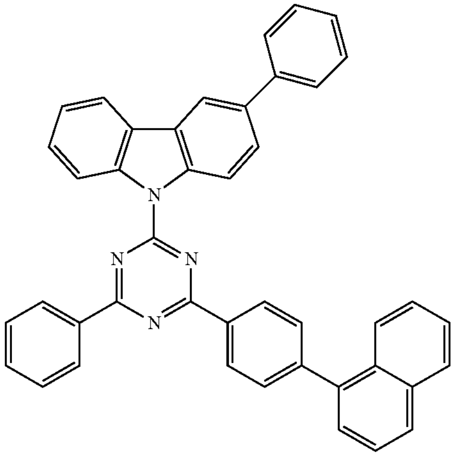
A-94
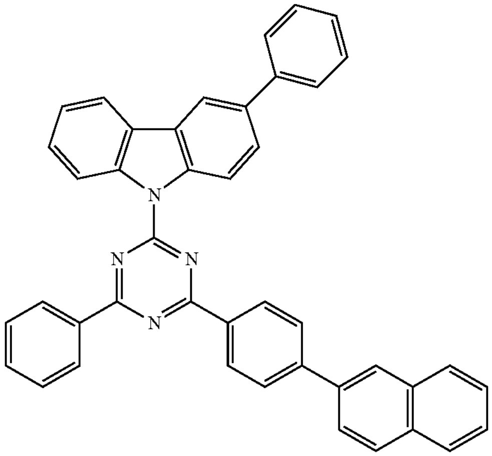
A-95
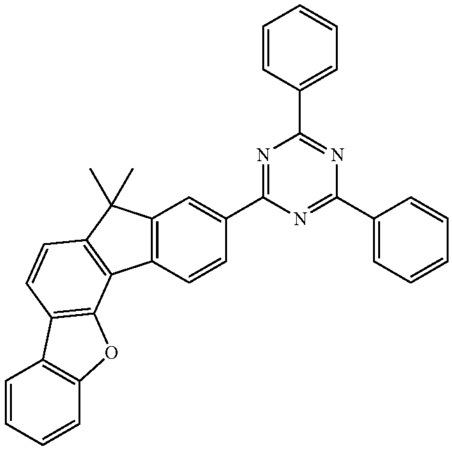
-continued
A-96
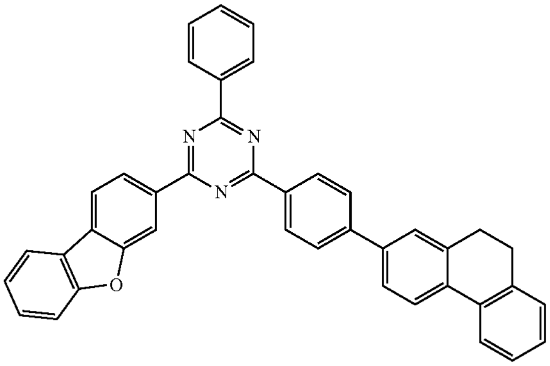
A-97
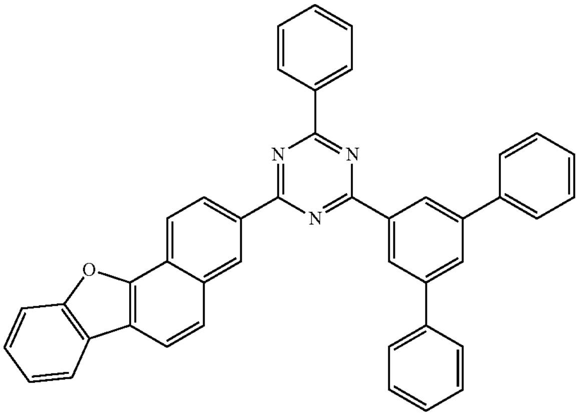
A-98
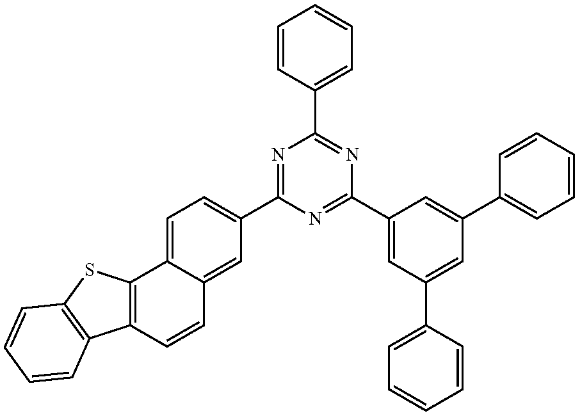

-continued
A-99
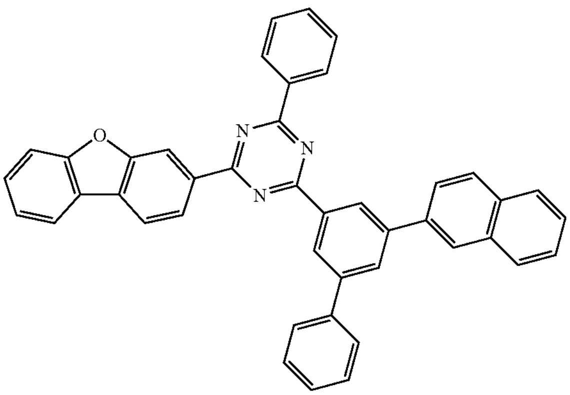
A-100
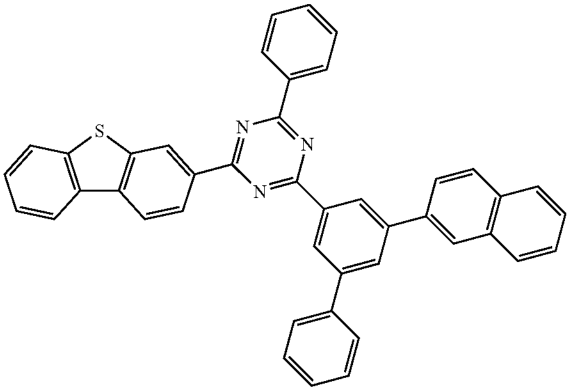
A-101
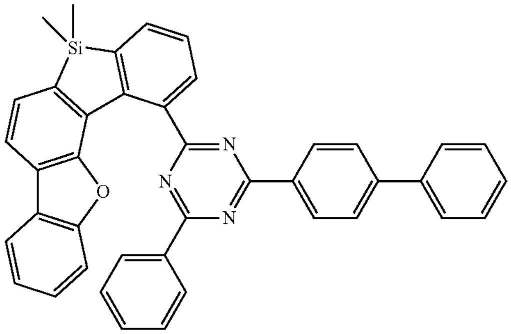
A-102
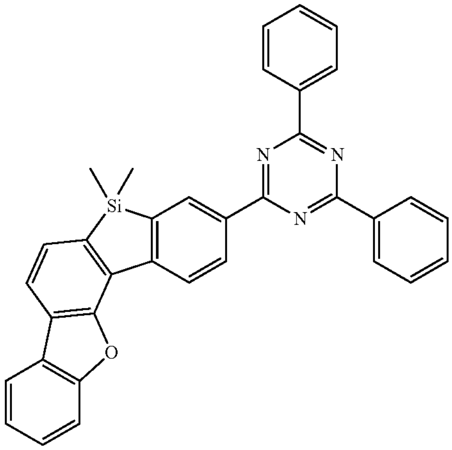
-continued
A-103
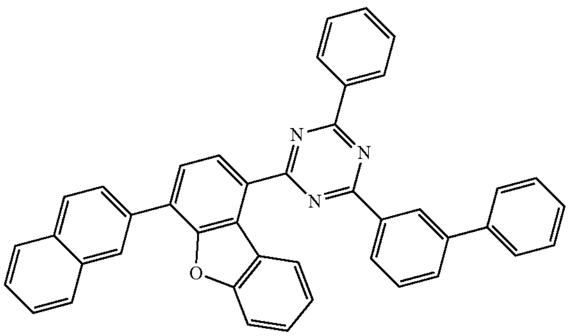
A-104
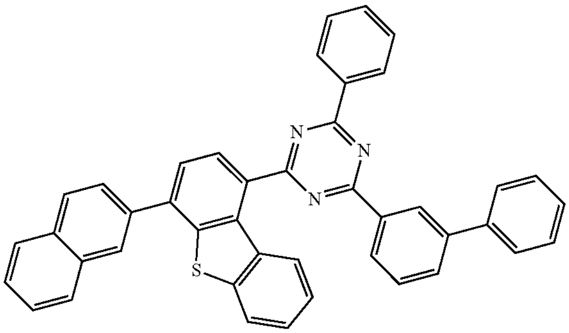
A-105
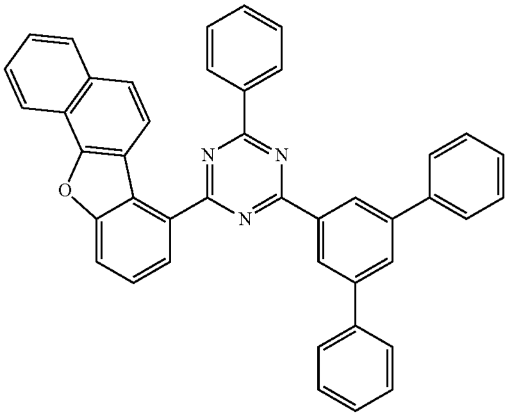
A-106
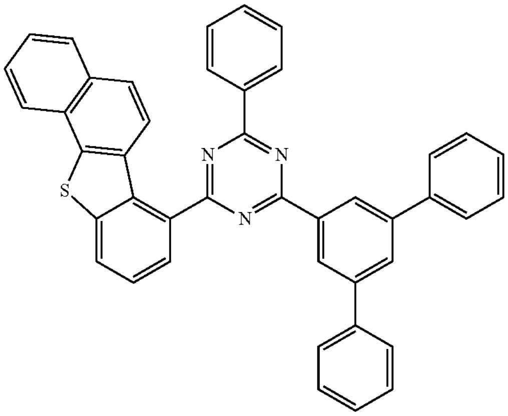

-continued
A-107
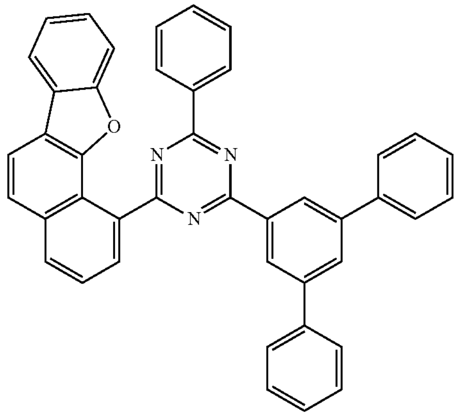
A-108
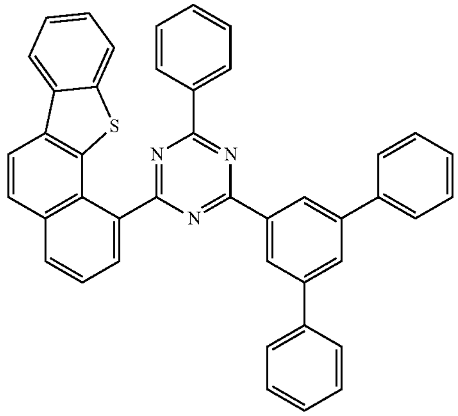
A-109
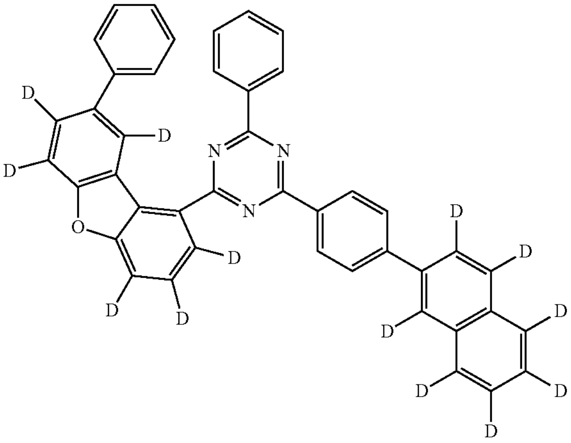
-continued
A-110
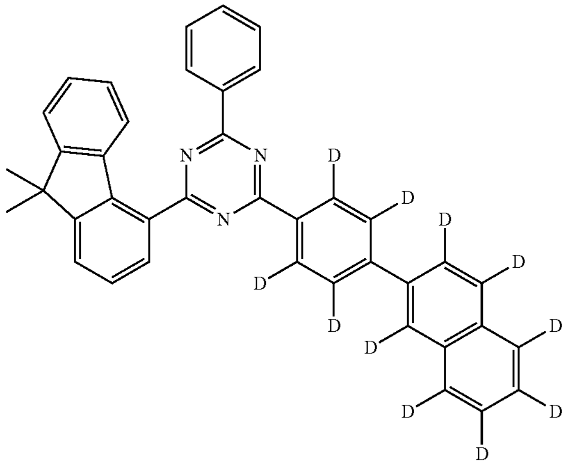
A-111
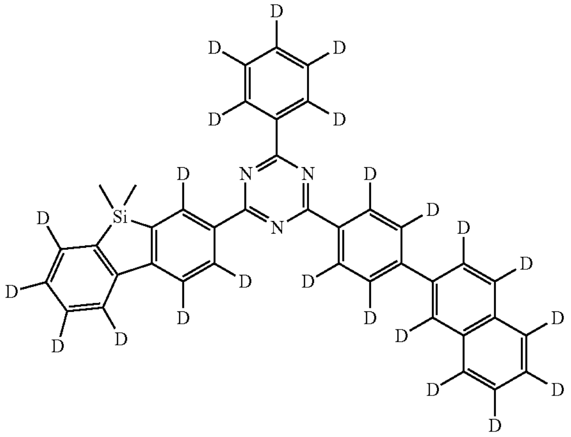
A-112
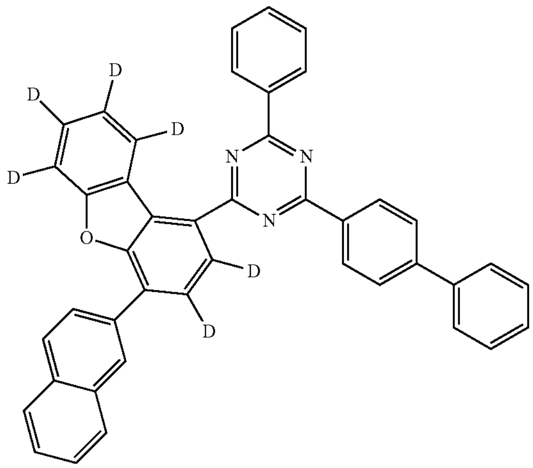

-continued
A-113
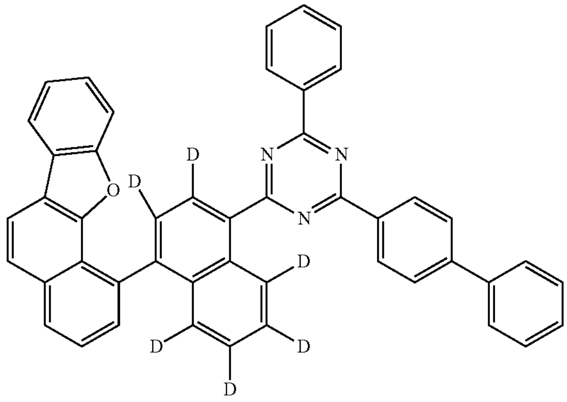
A-114
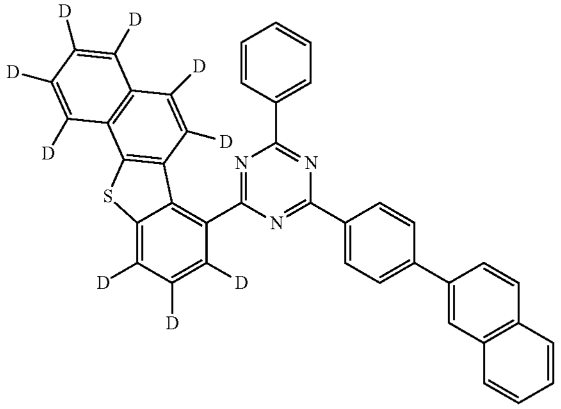
A-115
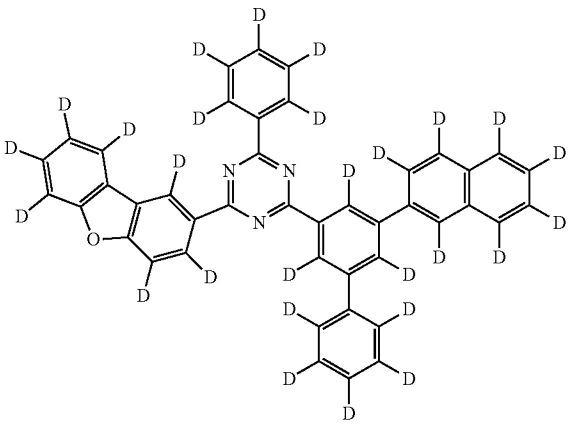
-continued
A-116
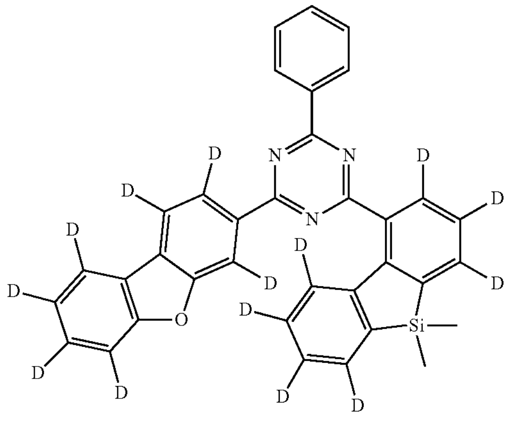
A-117
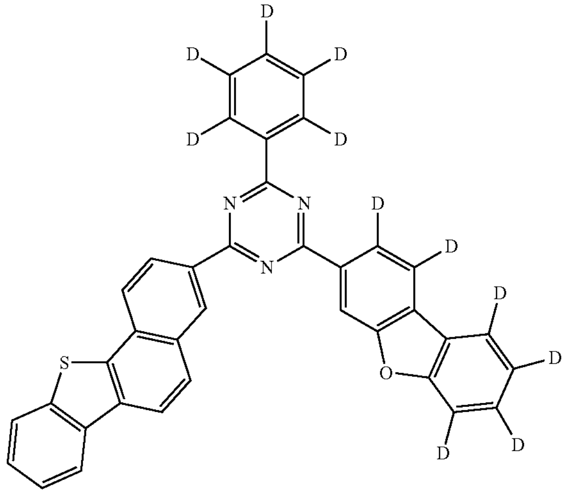
A-118
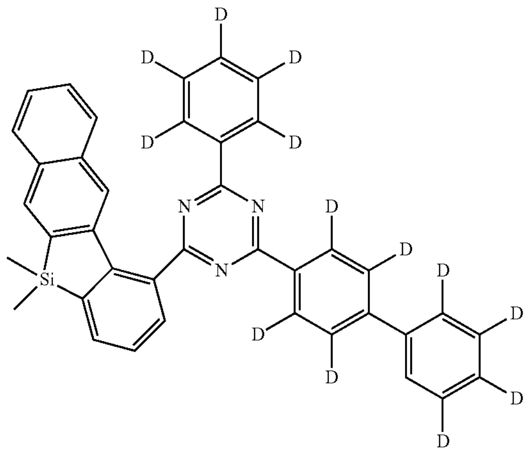

-continued

A-119

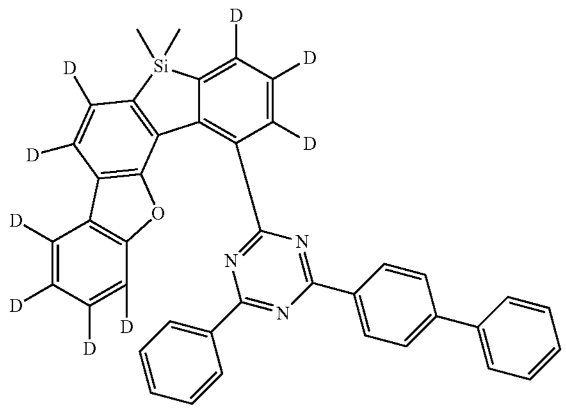

A-120

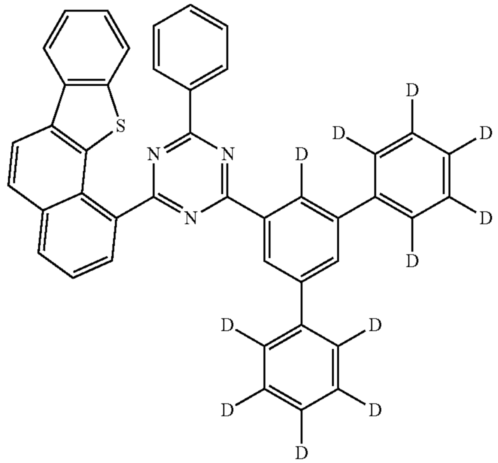

In an implementation, the composition may include, e.g., the first compound represented by Chemical Formula 1-II and the second compound represented by Chemical Formula 2-III-1 or Chemical Formula 2-VI-1.

The first compound and the second compound may be included (e.g., mixed) in a weight ratio of, e.g., about 1:99 to about 99:1. Within the above range, bipolar characteristics may be implemented by adjusting an appropriate weight ratio using the electron transport capability of the first compound and the hole transport capability of the second compound, so that efficiency and life-span may be improved. Within the above range, the first compound and the second compound may be included in a weight ratio of about 10:90 to about 90:10, about 20:80 to about 80:20, e.g., about 20:80 to about 70:30, about 20:80 to about 60:40, or about 30:70 to about 60:40. For example, they may be included in a weight ratio of about 40:60, about 50:50, or about 60:40.

One or more compounds may be further included in addition to the aforementioned first compound and second compound.

The aforementioned compound for an organic optoelectronic device or composition for an organic optoelectronic device may be a composition further including a dopant.

The dopant may be, e.g., a phosphorescent dopant, such as a red, green, or blue phosphorescent dopant. In an implementation, the dopant may be, e.g., a red or green phosphorescent dopant.

A dopant is a material that emits light by being mixed in a small amount with the compound or composition for an organic optoelectronic device. In general, the dopant may be a material such as a metal complex that emits light by multiple excitation into a triplet or more. The dopant may be, e.g., an inorganic, organic, or organic-inorganic compound, and may include one or two or more.

An example of the dopant may be a phosphorescent dopant, and examples of the phosphorescent dopant may include an organometallic compound including Ir, Pt, Os, Ti, Zr, Hf, Eu, Tb, Tm, Fe, Co, Ni, Ru, Rh, Pd, or a combination thereof. In an implementation, the phosphorescent dopant may be, e.g., a compound represented by Chemical Formula Z.

$L^7MX^4$ [Chemical Formula Z]

In Chemical Formula Z, M may be, e.g., a metal, and $L^7$ and $X^4$ may each independently be, e.g., ligands forming a complex compound with M.

The M may be, e.g., Ir, Pt, Os, Ti, Zr, Hf, Eu, Tb, Tm, Fe, Co, Ni, Ru, Rh, Pd, or a combination thereof, and $L^7$ and $X^4$ may be, e.g., a bidentate ligand.

In an implementation, the ligands represented by $L^7$ and $X^4$ may be, e.g., a ligand of Group A.

[Group A]

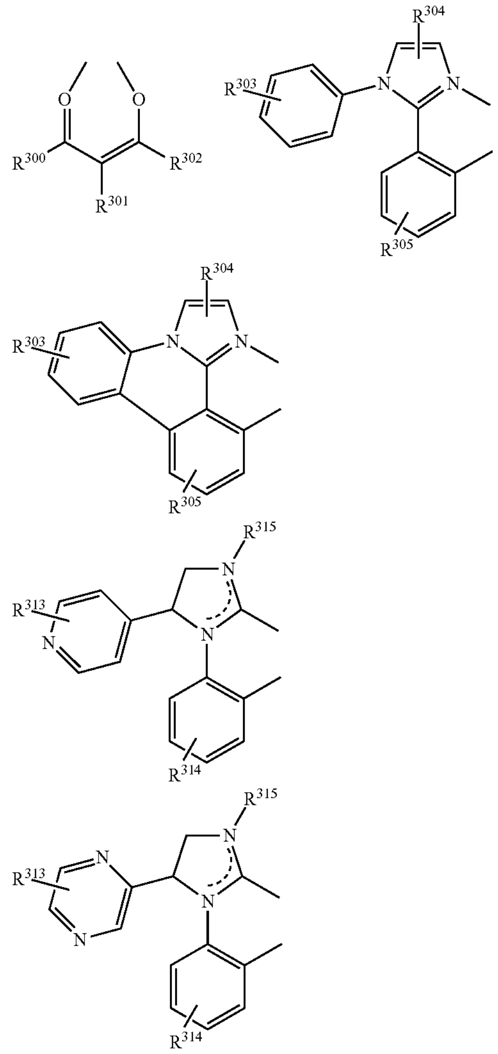

-continued
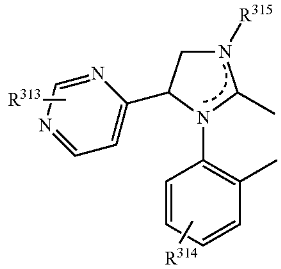
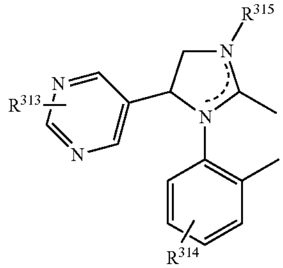
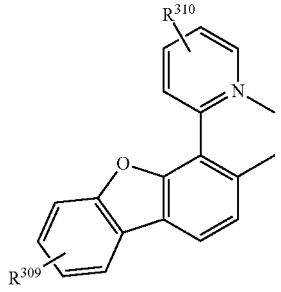
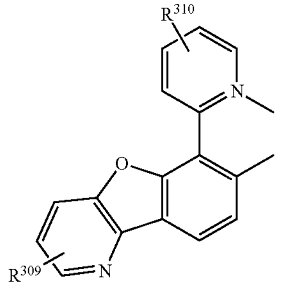
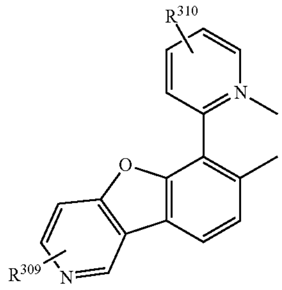
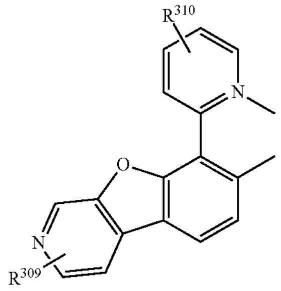
-continued
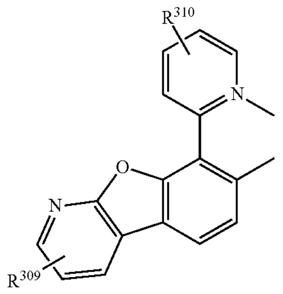
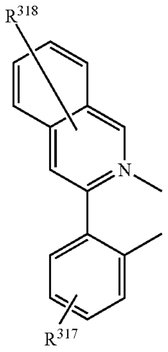
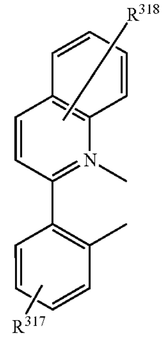
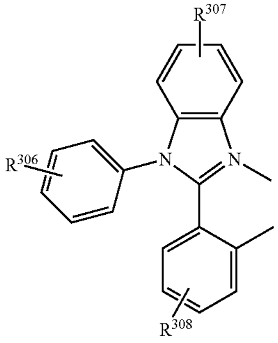
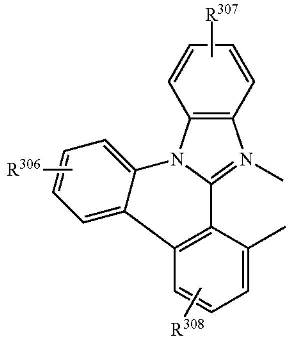
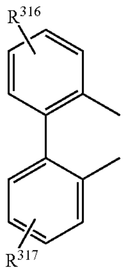
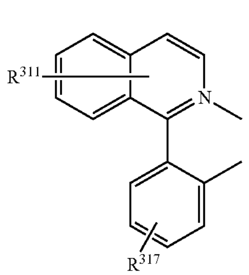
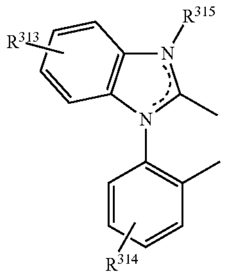
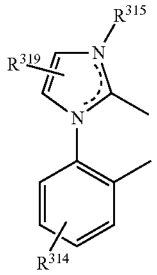
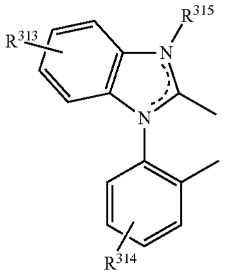

-continued

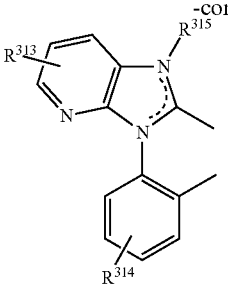

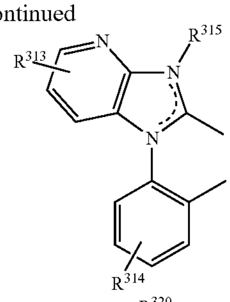

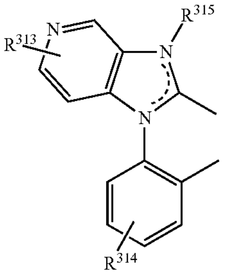

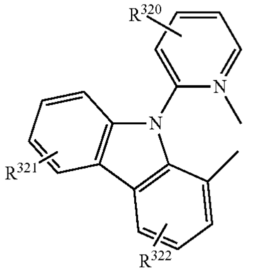

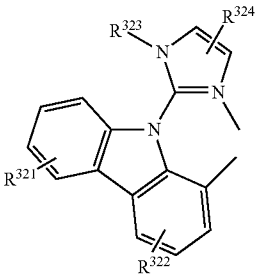

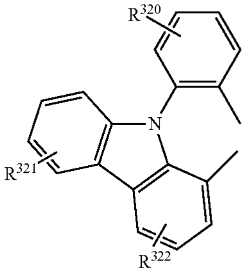

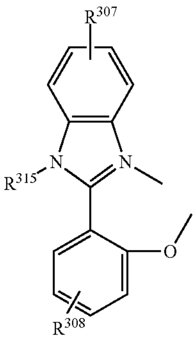

In Group A, $R^{300}$ to $R^{302}$ may each independently be, e.g., hydrogen, deuterium a C1 to C30 alkyl group that is substituted or unsubstituted with a halogen, a C6 to C30 aryl group that is substituted or unsubstituted with a C1 to C30 alkyl, or a halogen.

$R^{303}$ to $R^{324}$ may each independently be, e.g., hydrogen, deuterium, halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C2 to C30 alkenyl group, a substituted or unsubstituted C6 to C30 aryl group, a substituted or unsubstituted C1 to C30 heteroaryl group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and C6 to C30 aryl group, or a triarylsilyl group having a substituted or unsubstituted C6 to C30 aryl group.

In an implementation, a dopant represented by Chemical Formula V may be included.

[ChemicaL Formula V]

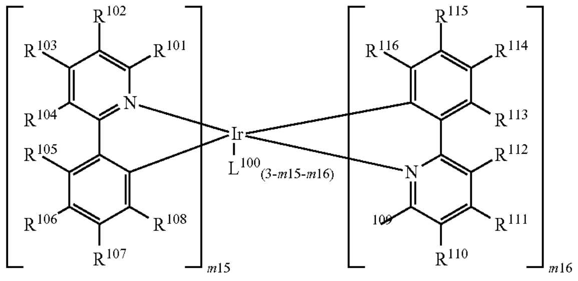

In Chemical Formula V, $R^{101}$ to $R^{116}$ may each independently be, e.g., hydrogen, deuterium, a substituted or unsubstituted C1 to C10 alkyl group, a substituted or unsubstituted C6 to C20 aryl group, or —$SiR^{132}R^{133}R^{134}$.

$R^{132}$ to $R^{134}$ may each independently be, e.g., a C1 to C6 alkyl group.

In an implementation, at least one of $R^{101}$ to $R^{116}$ may be, e.g., a functional group represented by Chemical Formula V-1.

$L^{100}$ may be, e.g., a bidentate ligand of a monovalent anion, and is a ligand that coordinates to iridium through a lone pair of carbons or heteroatoms.

m15 and m16 may each independently be, e.g., an integer of 0 to 3, and m15+m16 may be an integer of 1 to 3.

[Chemical Formula V-1]

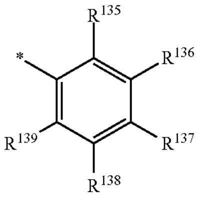

In Chemical Formula V-1, $R^{135}$ to $R^{139}$ may each independently be, e.g., hydrogen, deuterium, a substituted or unsubstituted C1 to C10 alkyl group, a substituted or unsubstituted C6 to C20 aryl group, or —$SiR^{132}R^{133}R^{134}$.

$R^{132}$ to $R^{134}$ may each independently be, e.g., a substituted or unsubstituted C1 to C6 alkyl group.

* indicates a portion linked to a carbon atom, e.g., a linking site.

In an implementation, a dopant represented by Chemical Formula Z-1 may be included.

[Chemical Formula Z-1]

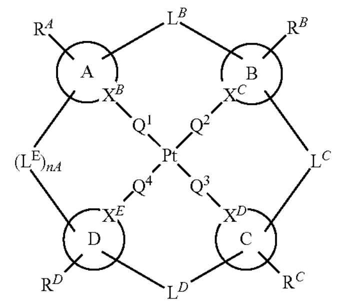

In Chemical Formula Z-1, rings A, B, C, and D may each independently represent a 5-membered or 6-membered carbocyclic or heterocyclic ring.

$R^A$, $R^B$, $R^C$, and $R^D$ may each independently represent mono-, di-, tri-, or tetra-substitution, or unsubstitution.

$L^B$, $L^C$, and $L^D$ may each independently be, e.g., a direct bond, BR, NR, PR, O, S, Se, C═O, S═O, $SO_2$, CRR', SiRR', GeRR', or a combination thereof.

when nA is 1, $L^E$ may be, e.g., a direct bond, BR, NR, PR, O, S, Se, C═O, S═O, $SO_2$, CRR', SiRR', GeRR', and a combination thereof; when nA is 0, $L^E$ does not exist.

$R^A$, $R^B$, $R^C$, and $R^D$, R, and R' may each independently be, e.g., hydrogen, deuterium, a halogen, an alkyl group, a cycloalkyl group, a heteroalkyl group, an arylalkyl group, an alkoxy group, an aryloxy group, an amino group, a silyl group, an alkenyl group, a cycloalkenyl group, a heteroalkenyl group, an alkynyl group, an aryl group, a heteroaryl group, an acyl group, a carbonyl group, a carboxylic acid group, an ester group, a nitrile group, an isonitrile group, a sulfanyl group, a sulfinyl group, a sulfonyl group, a phosphino group, or a combination thereof; any adjacent $R^A$, $R^B$, $R^C$, $R^D$, R, and R' are optionally linked to each other to provide a ring; $X^B$, $X^C$, $X^D$, and $X^E$ are each independently selected from carbon and nitrogen; and $Q^1$, $Q^2$, $Q^3$, and $Q^4$ each represent oxygen or a direct bond.

The dopant according to an embodiment may be a platinum complex, and may be, e.g., represented by Chemical Formula VI.

[Chemical Formula VI]

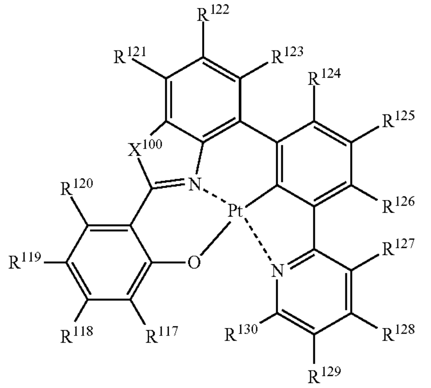

In Chemical Formula VI, $X^{100}$ may be, e.g., O, S, or $NR^{131}$.

$R^{117}$ to $R^{131}$ may each independently be, e.g., hydrogen, deuterium, a substituted or unsubstituted C1 to C10 alkyl group, a substituted or unsubstituted C6 to C20 aryl group, or $—SiR^{132}R^{133}R^{134}$.

$R^{132}$ to $R^{134}$ may each independently be, e.g., a substituted or unsubstituted C1 to C6 alkyl group.

In an implementation, at least one of $R^{117}$ to $R^{131}$ may be, e.g., $—SiR^{132}R^{133}R^{134}$ or a substituted or unsubstituted tert-butyl group.

Hereinafter, an organic optoelectronic device including the aforementioned compound for an organic optoelectronic device or composition for an organic optoelectronic device is described.

The organic optoelectronic device may be a suitable device to convert electrical energy into photoenergy and vice versa, and may be, e.g., an organic photoelectric device, an organic light emitting diode, an organic solar cell, or an organic photoconductor drum.

Herein, an organic light emitting diode as one example of an organic optoelectronic device is described referring to drawing.

The FIGURE is a cross-sectional view of an organic light emitting diode according to an embodiment.

Referring to the FIGURE, an organic light emitting diode 100 according to an embodiment may include an anode 120 and a cathode 110 facing each other and an organic layer 105 disposed between the anode 120 and cathode 110.

The anode 120 may be made of a conductor having a large work function to help hole injection, and may be, e.g., a metal, a metal oxide, or a conductive polymer. The anode 120 may be, e.g., a metal such as nickel, platinum, vanadium, chromium, copper, zinc, gold, or the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to help electron injection, and may be, e.g., a metal, a metal oxide, or a conductive polymer. The cathode 110 may be e.g., a metal such as magnesium, calcium, sodium, potassium, titanium, indium, yttrium, lithium, gadolinium, aluminum silver, tin, lead, cesium, barium, or the like, or an alloy thereof; a multi-layer structure material such as LiF/Al, $LiO_2$/Al, LiF/Ca, LiF/Al, or $BaF_2$/Ca.

The organic layer 105 may include the aforementioned compound for an organic optoelectronic device or composition for an organic optoelectronic device.

The organic layer 105 may include, e.g., the light emitting layer 130, and the light emitting layer 130 may include, e.g., the aforementioned compound for an organic optoelectronic device or composition for an organic optoelectronic device.

The composition for an organic optoelectronic device further including a dopant may be, e.g., a green light-emitting composition.

The light emitting layer 130 may include, e.g., the aforementioned compound for an organic optoelectronic device or composition for an organic optoelectronic device as a phosphorescent host, respectively.

The organic layer may further include a charge transport region in addition to the light emitting layer.

The charge transport region may be, e.g., the hole transport region 140.

The hole transport region 140 may further increase hole injection or hole mobility between the anode 120 and the light emitting layer 130 and block electrons. In an implementation, the hole transport region 140 may include a hole transport layer between the anode 120 and the light emitting layer 130 and a hole transport auxiliary layer between the light emitting layer 130 and the hole transport layer, and, e.g., a compound of Group B may be included in at least one of the hole transport layer and the hole transport auxiliary layer.

[Group B]

-continued
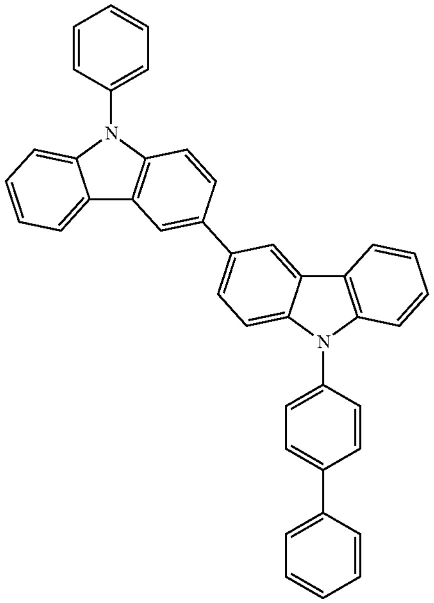
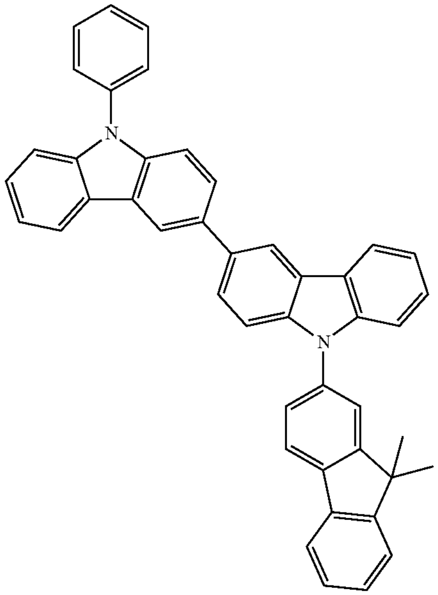
-continued
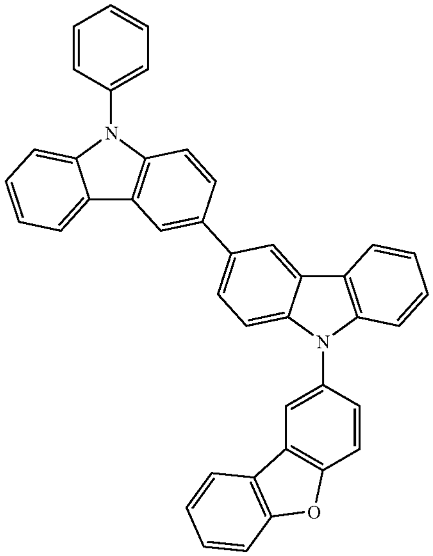
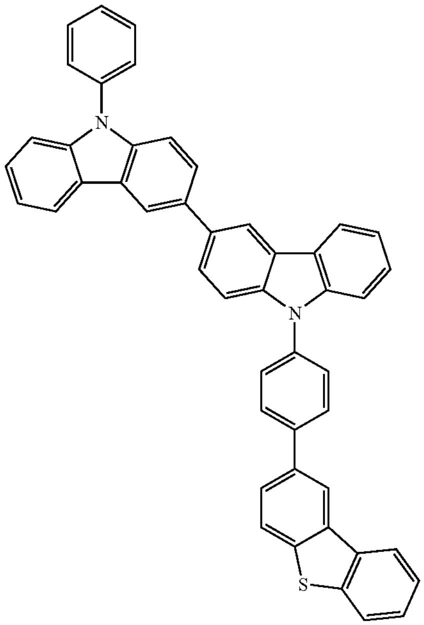

-continued
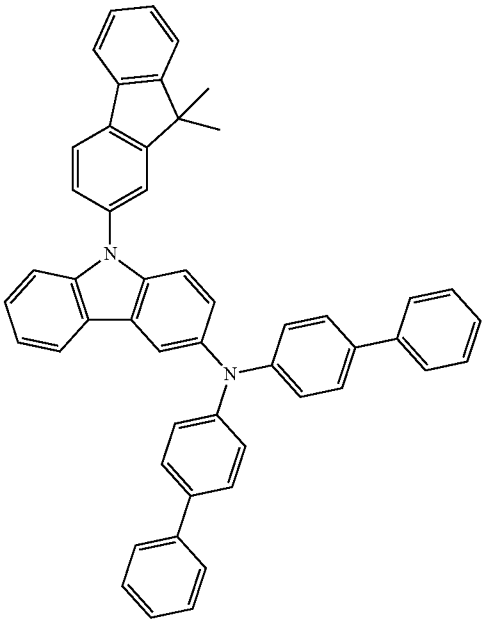
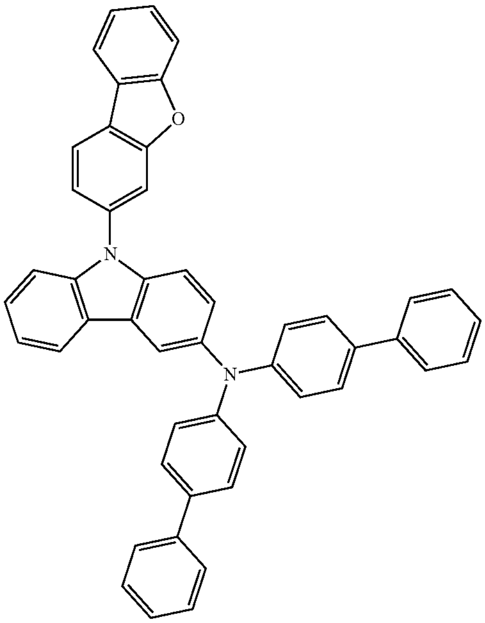
-continued
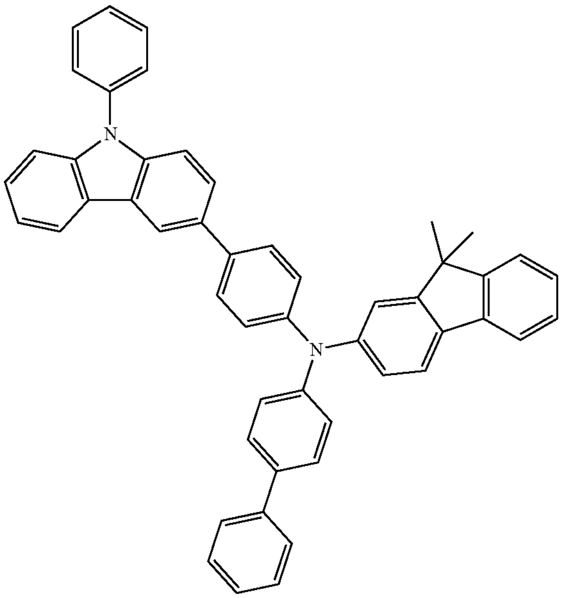
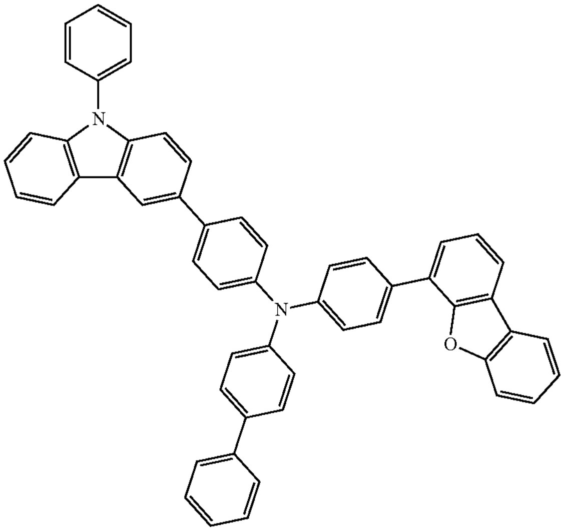
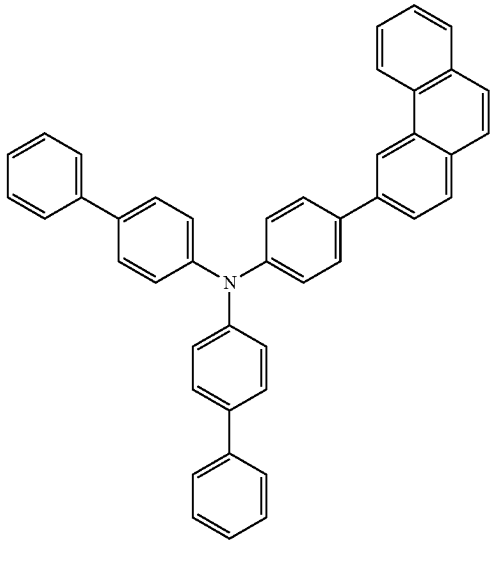

-continued
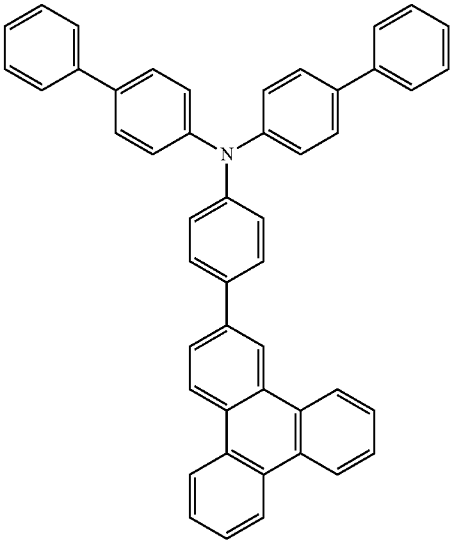
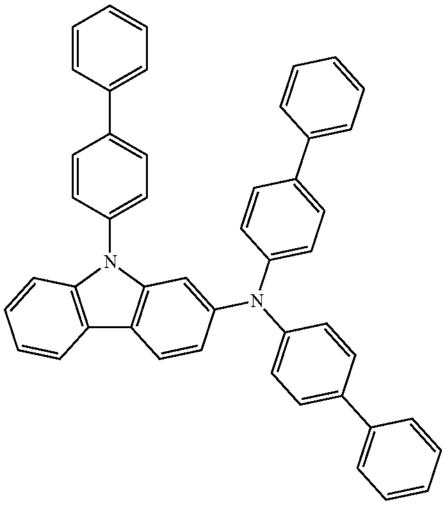
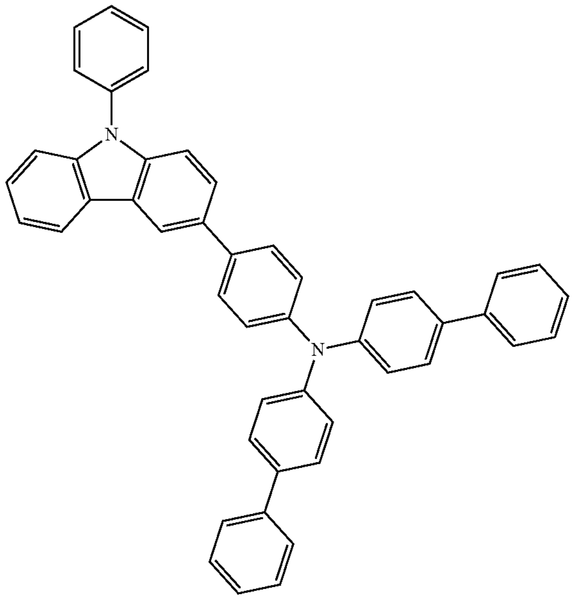
-continued
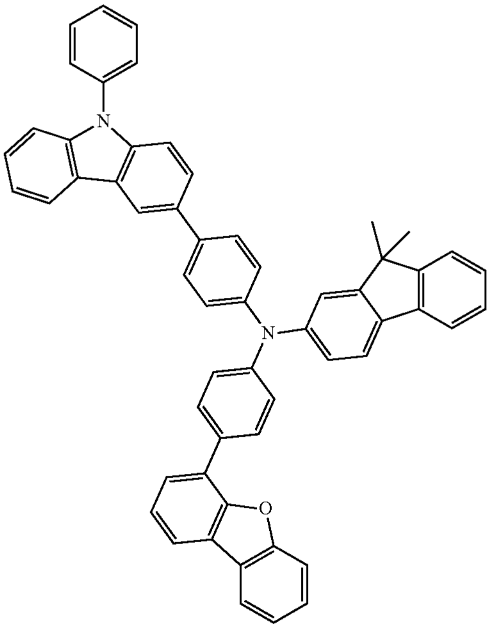
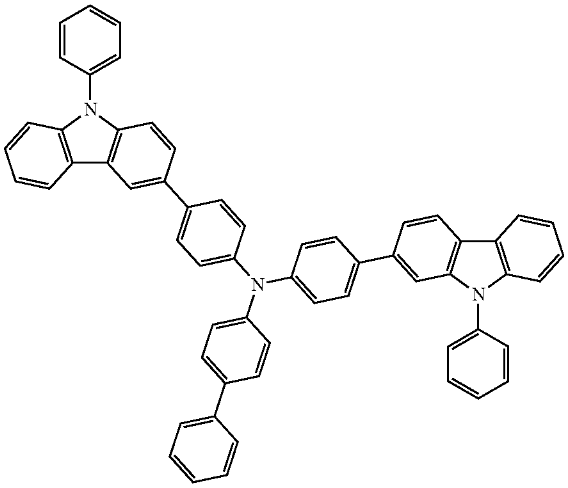
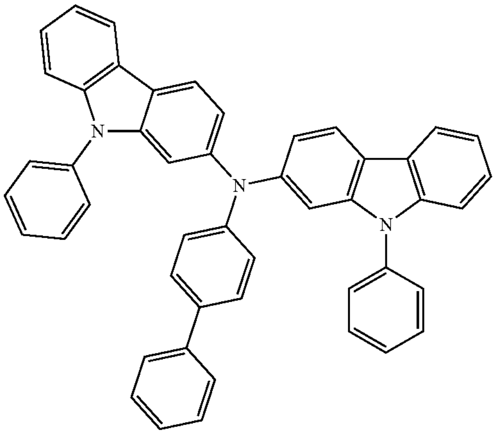

-continued
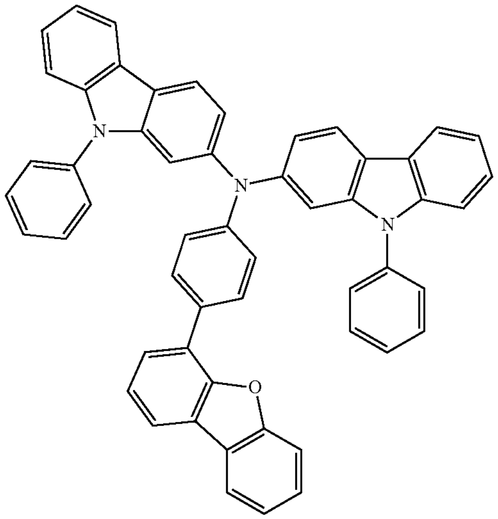
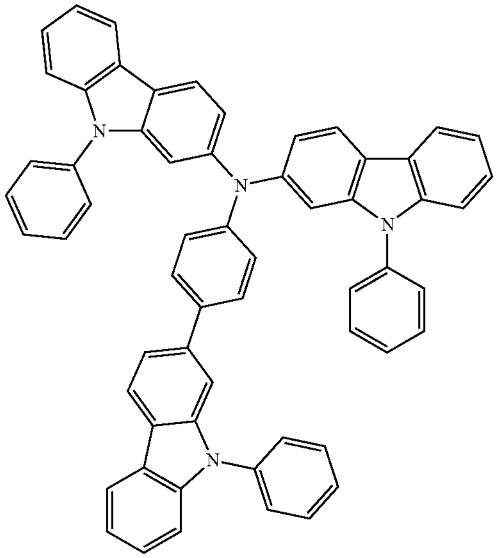
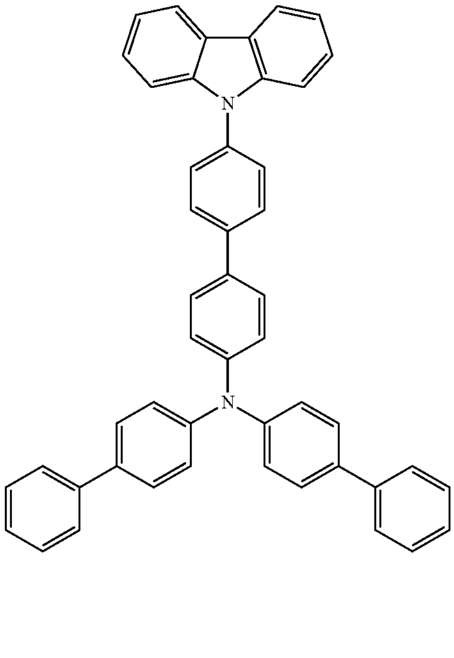
-continued
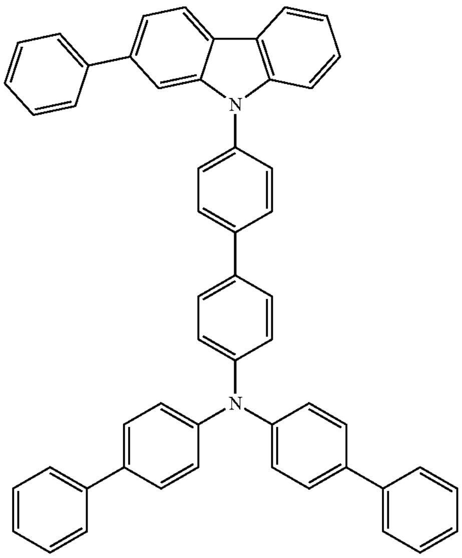
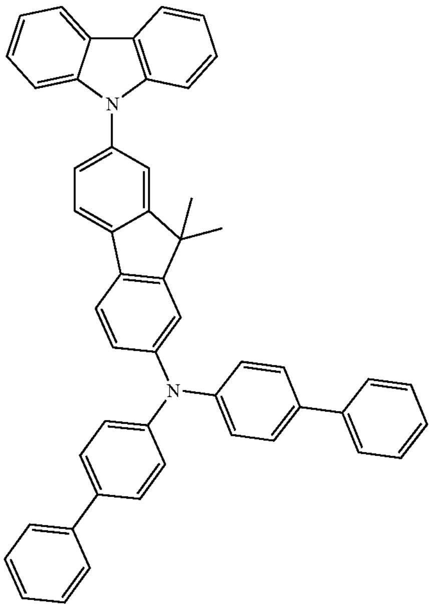
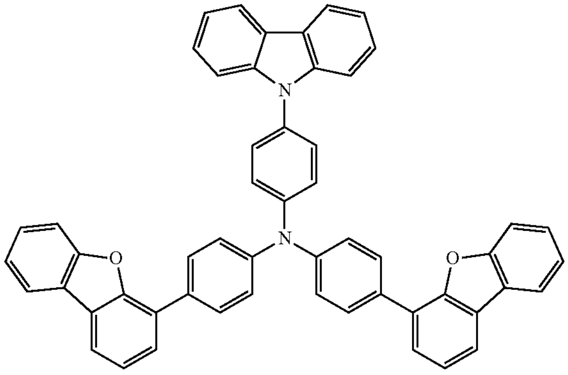

-continued
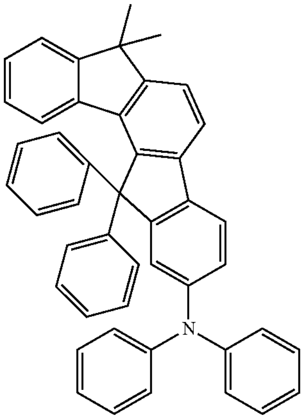
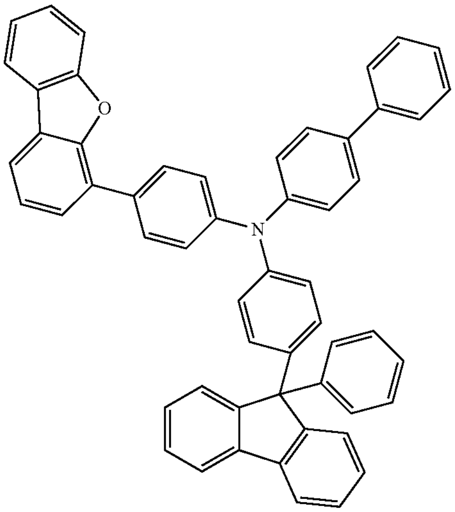
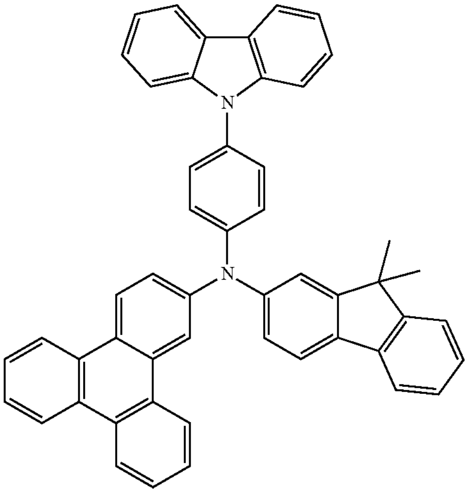
-continued
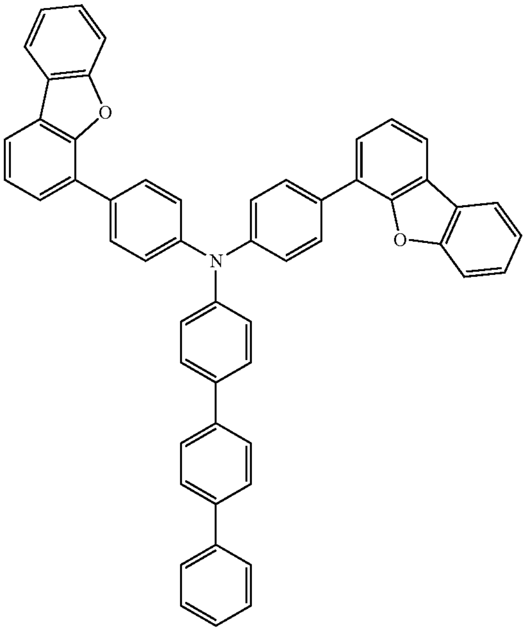
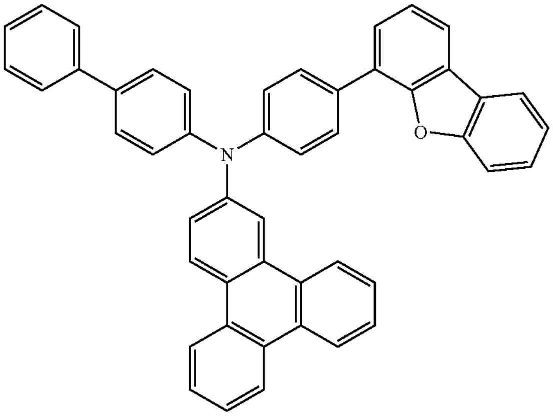
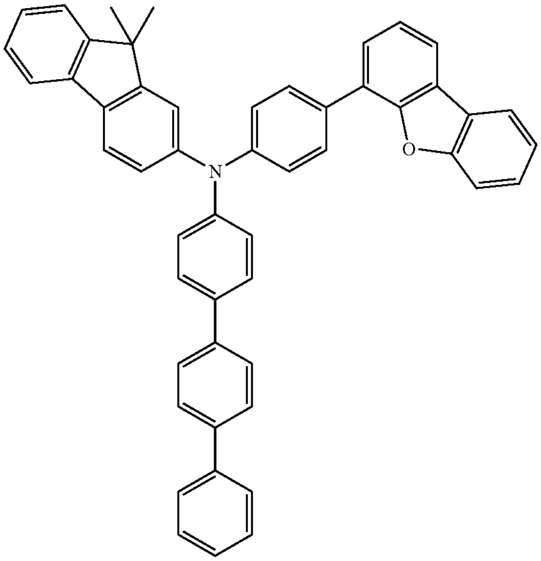

-continued
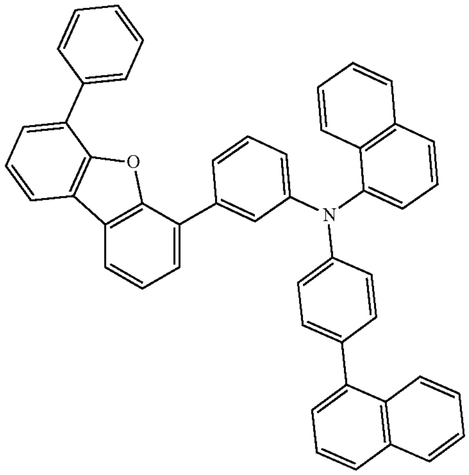
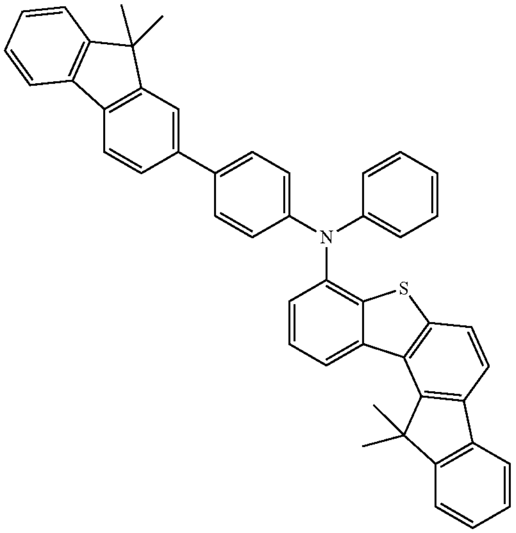
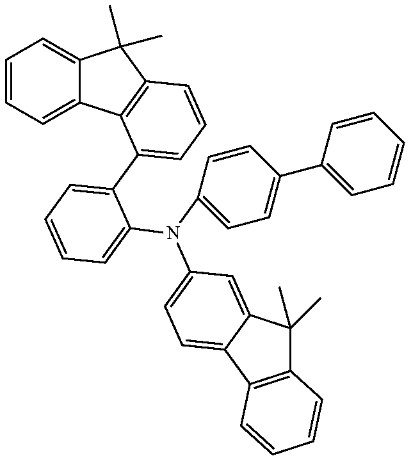
-continued
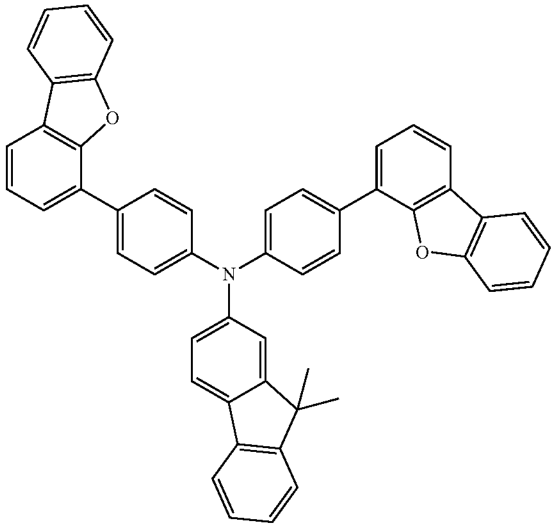
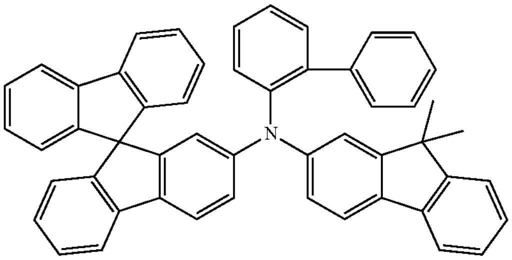
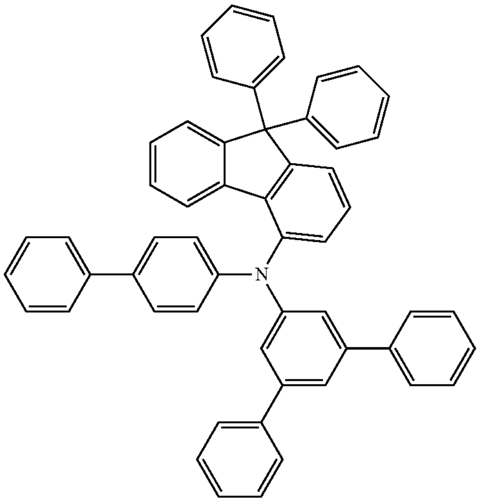
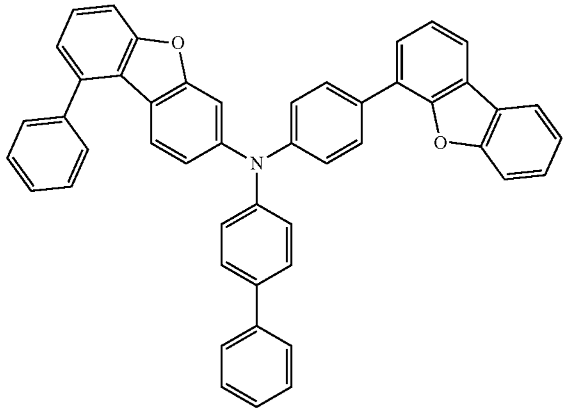

-continued
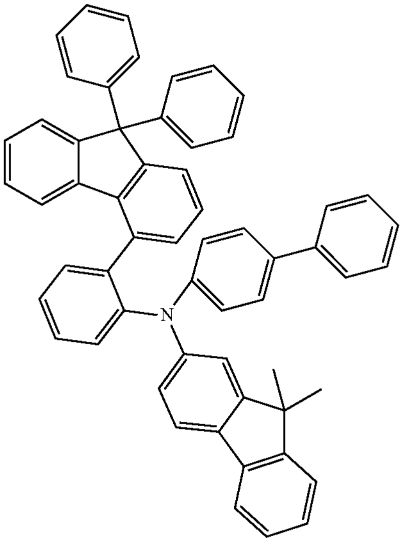
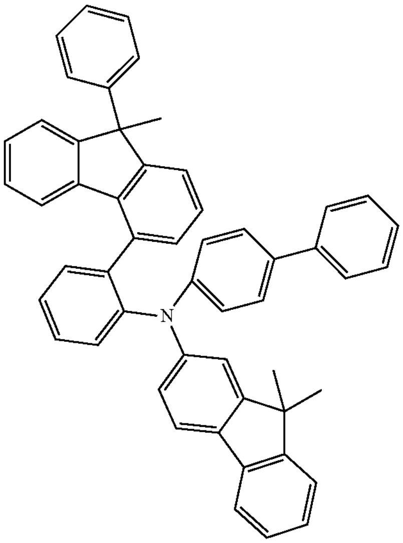
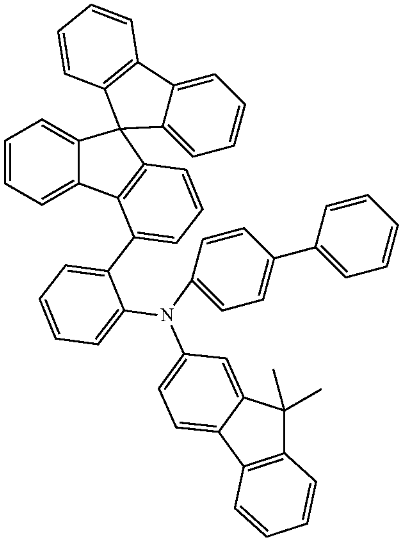
-continued
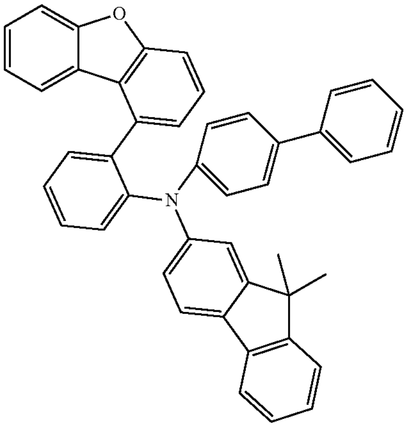
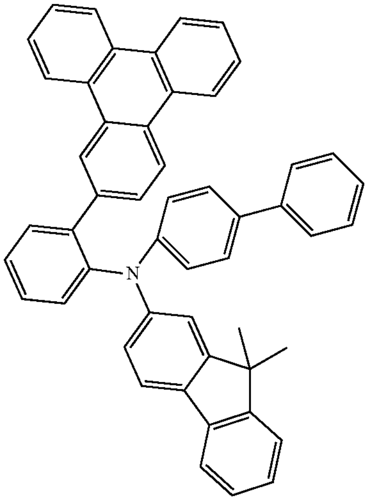 [SMILES: CC1(C)c2ccccc2-c2ccc(N(c3ccc(-c4ccccc4)cc3)c3ccccc3-c3ccc4c5ccccc5c5ccccc5c4c3)cc21]
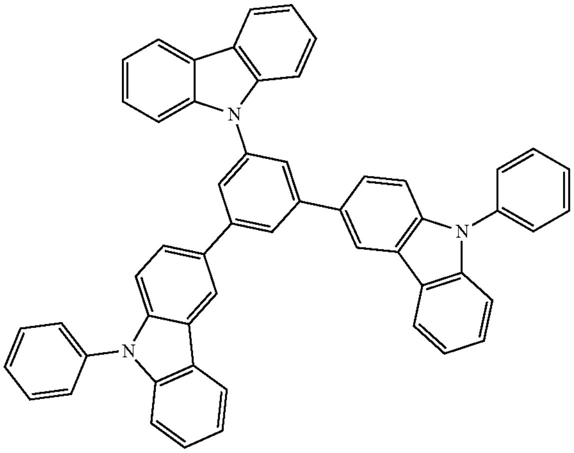
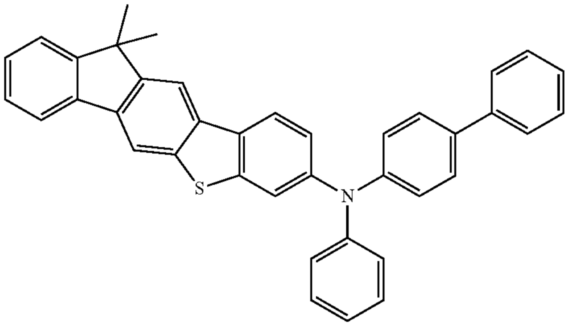

-continued
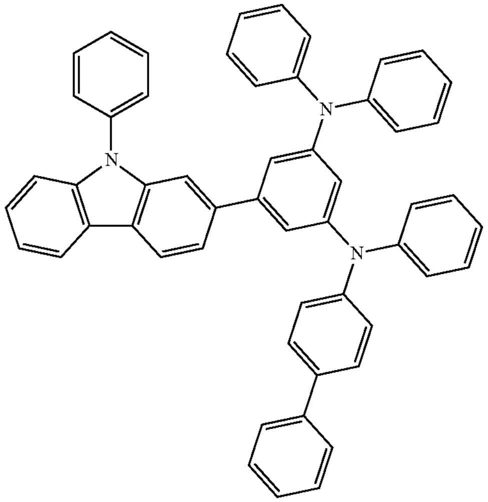
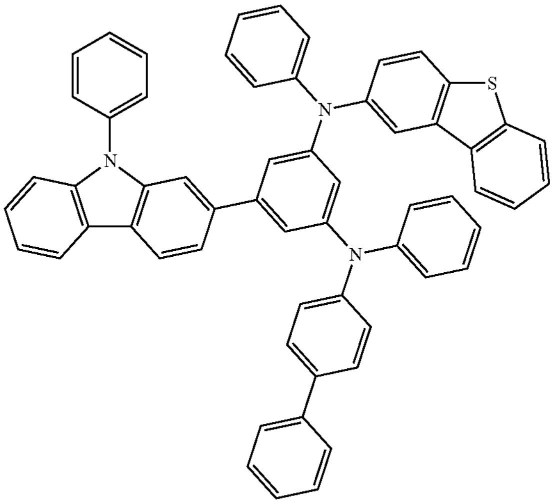
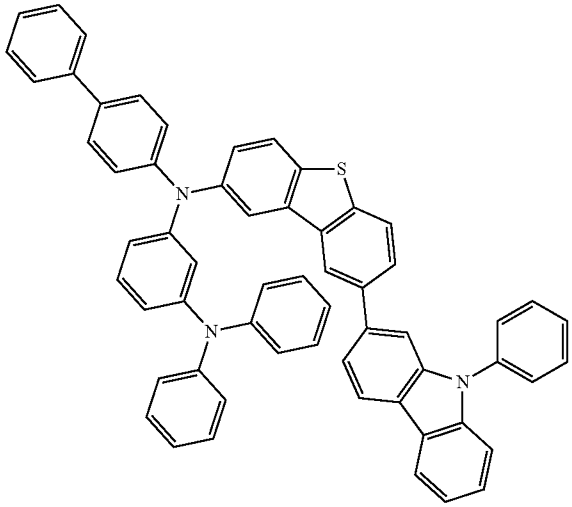
-continued
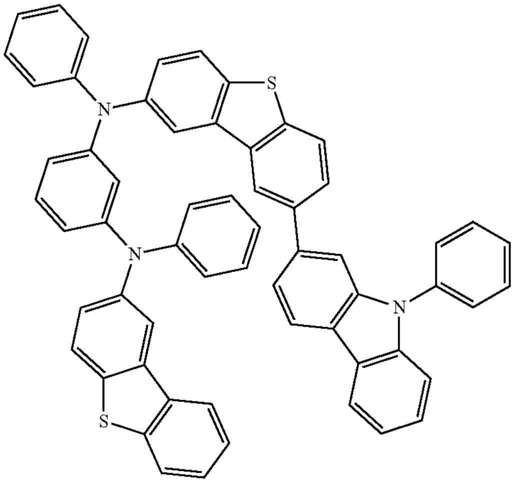
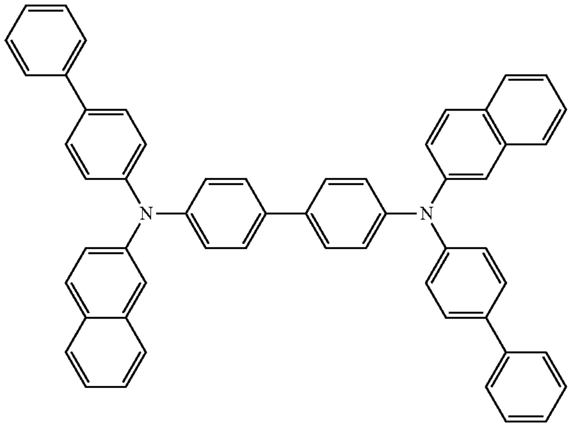
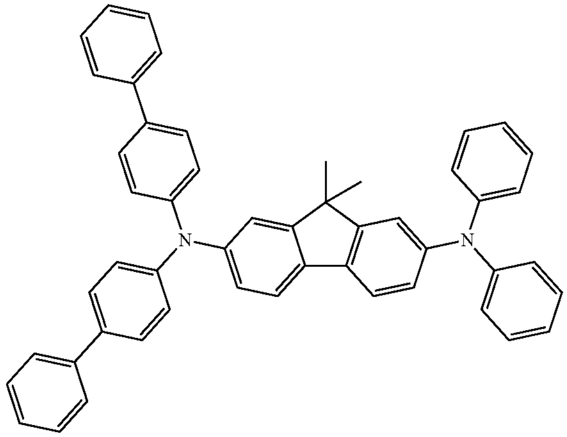

-continued
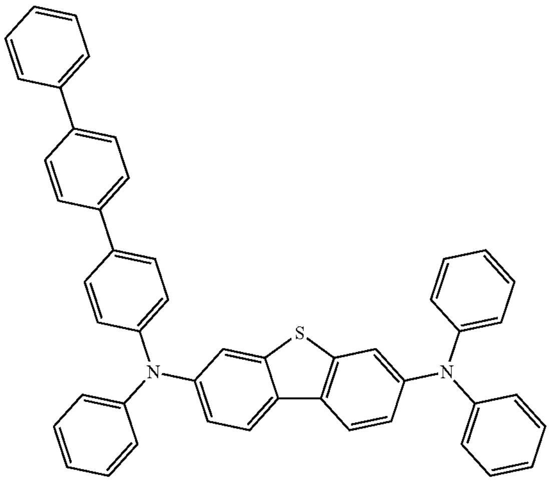
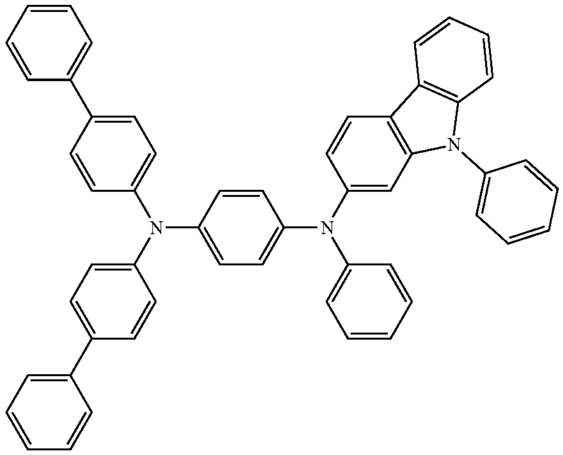
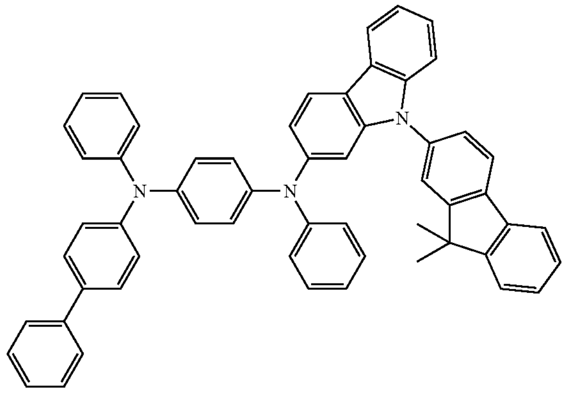
-continued
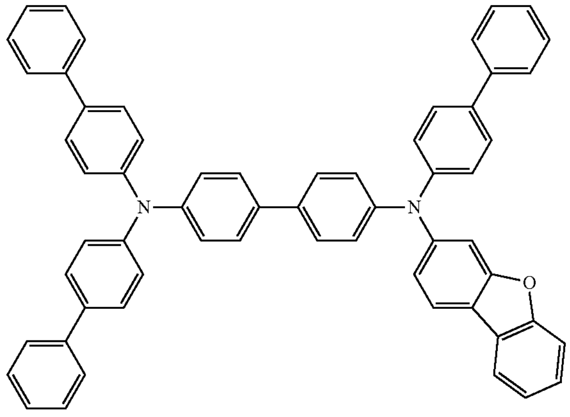
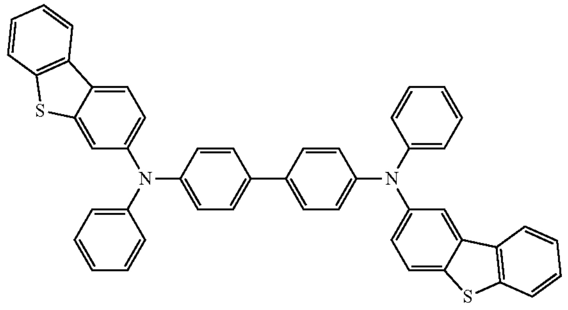
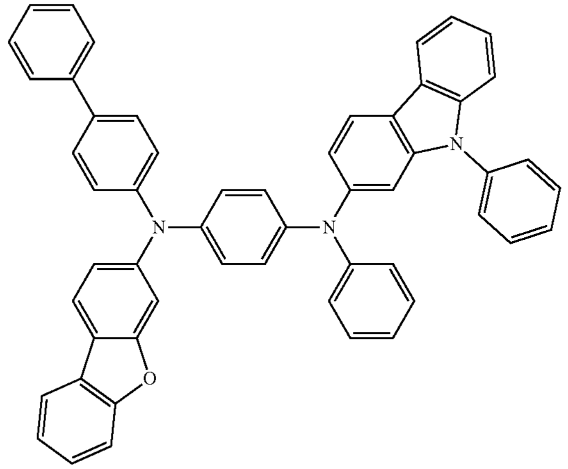
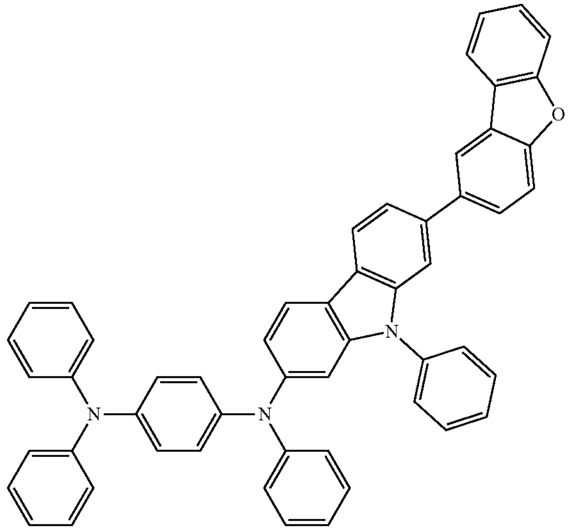

-continued
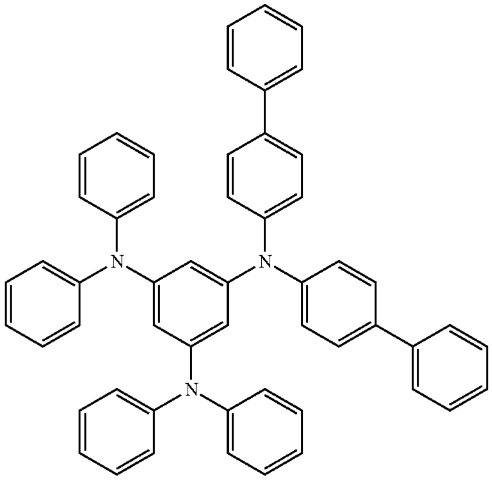
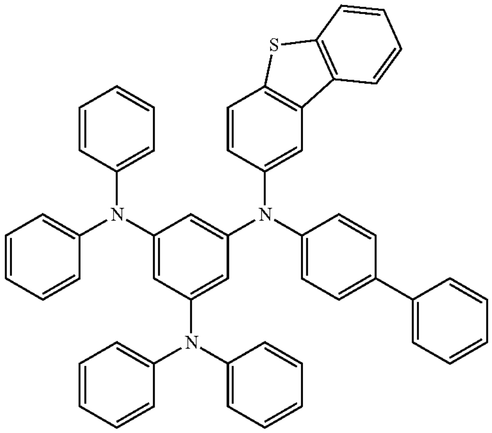
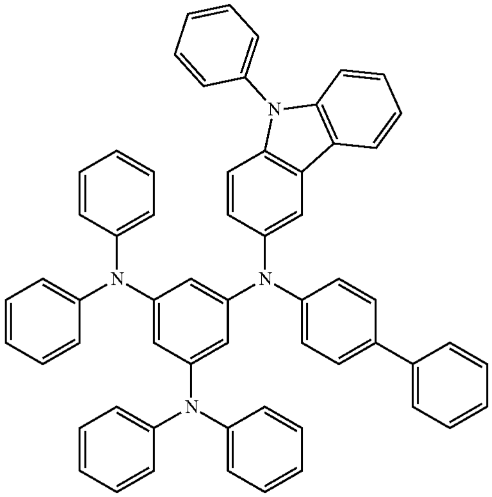
-continued
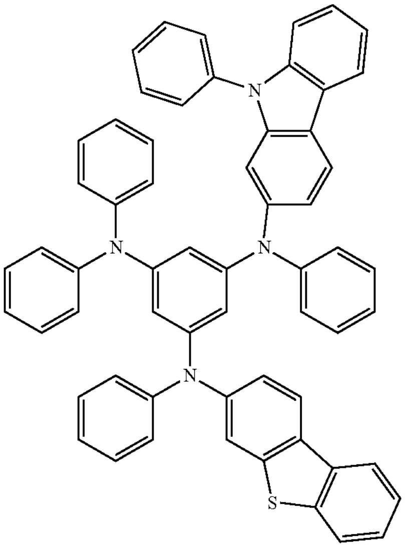
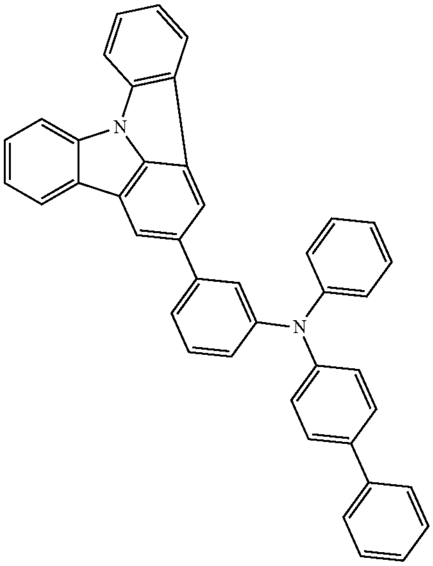
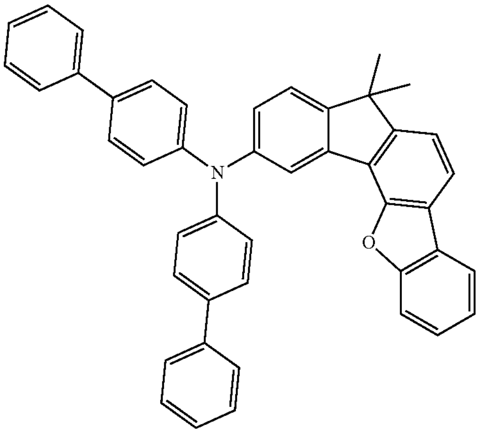

-continued
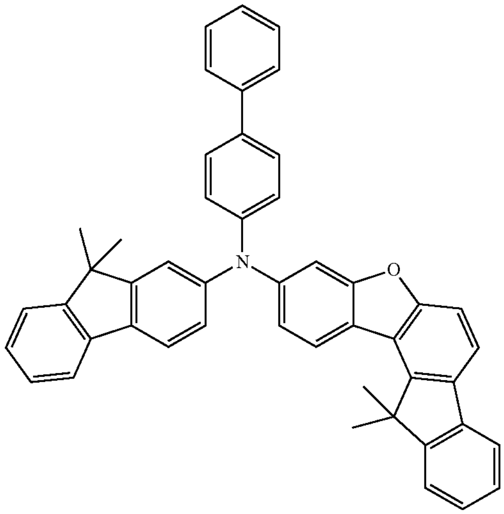
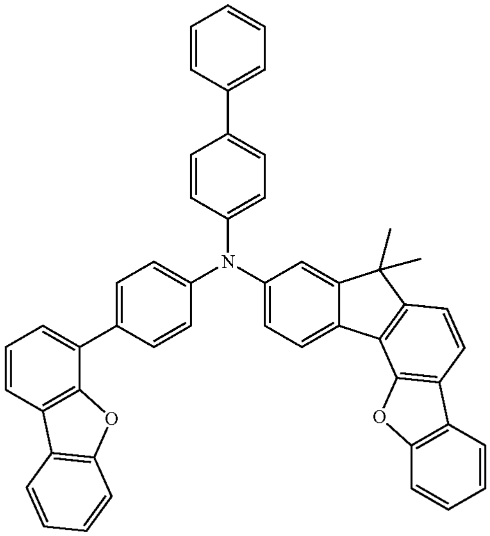
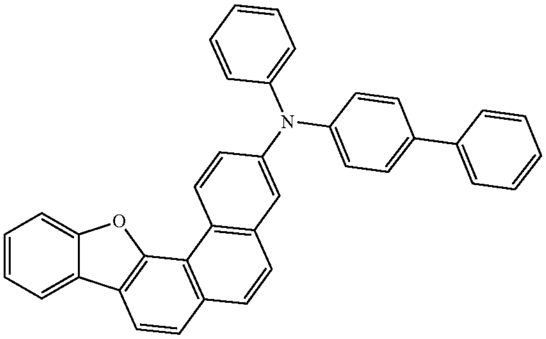
-continued
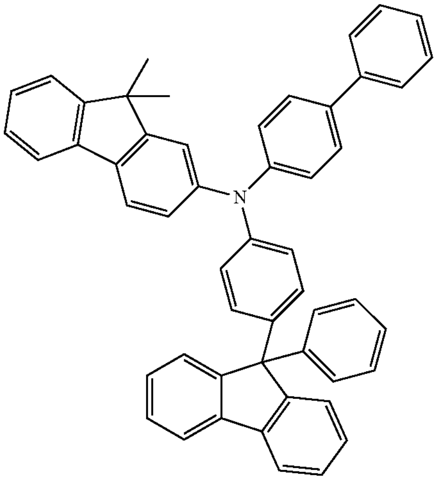
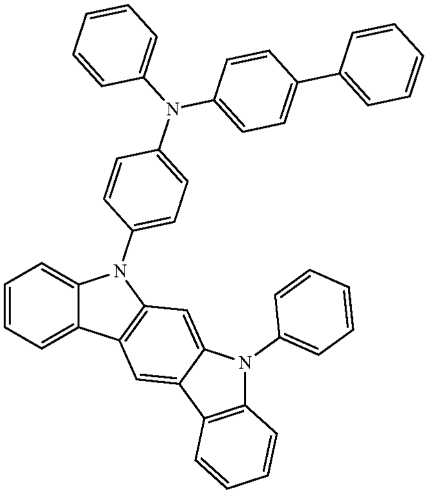
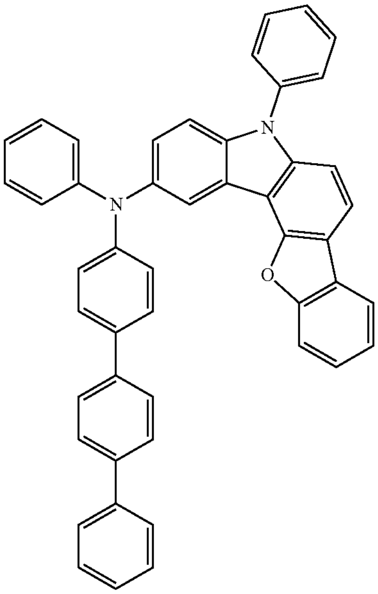

-continued
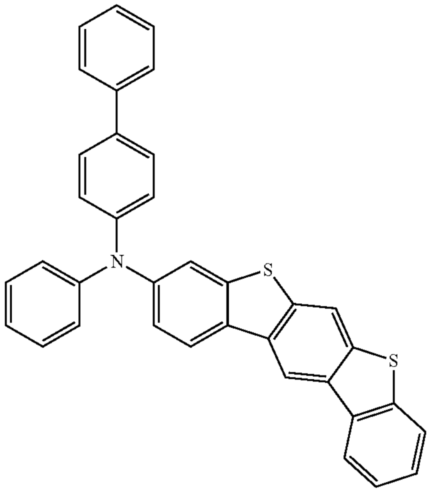
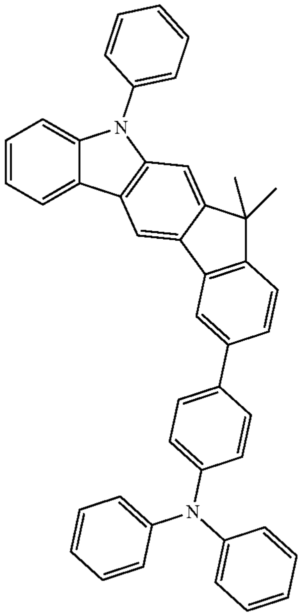
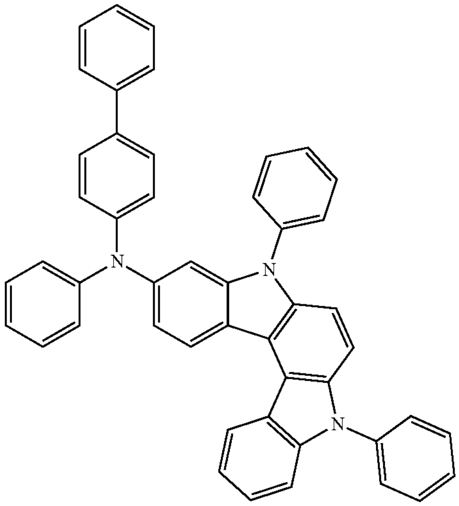
-continued
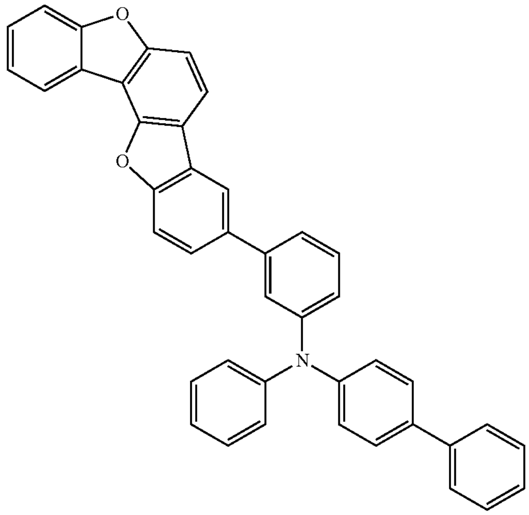
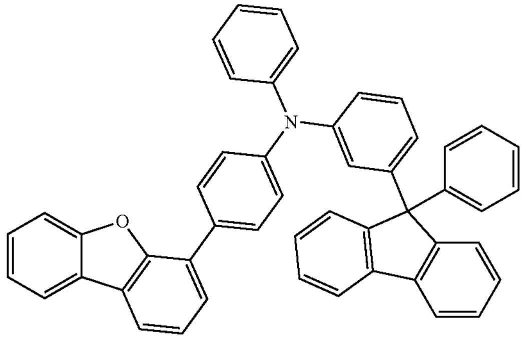
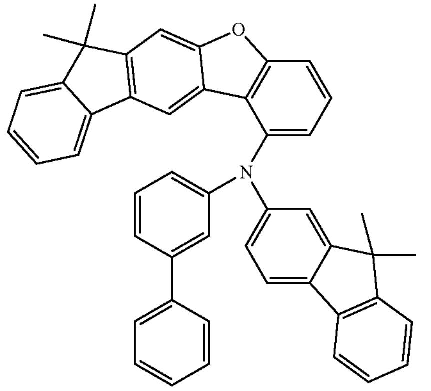
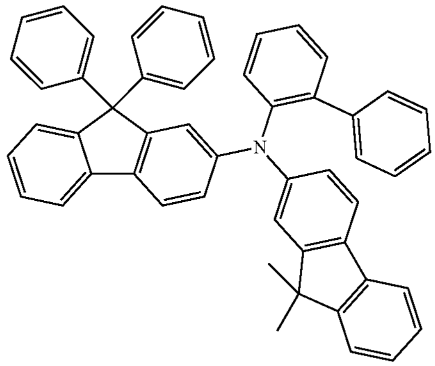

-continued
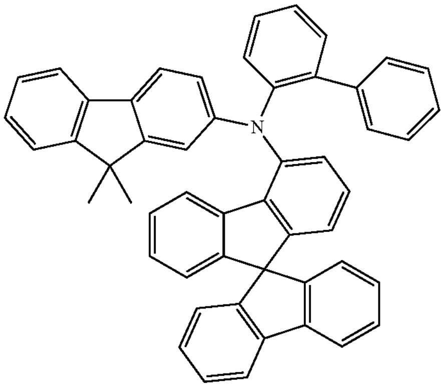
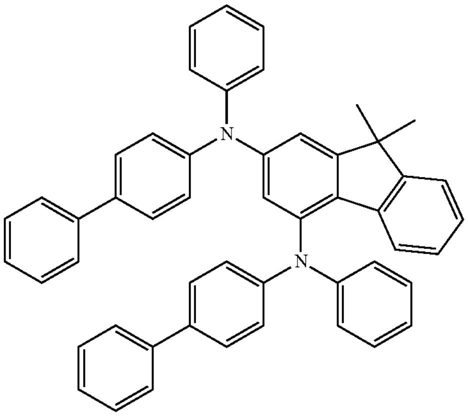
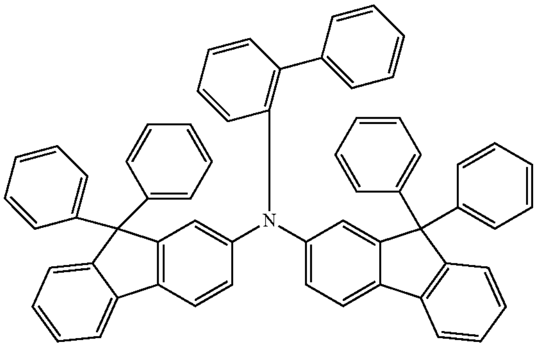
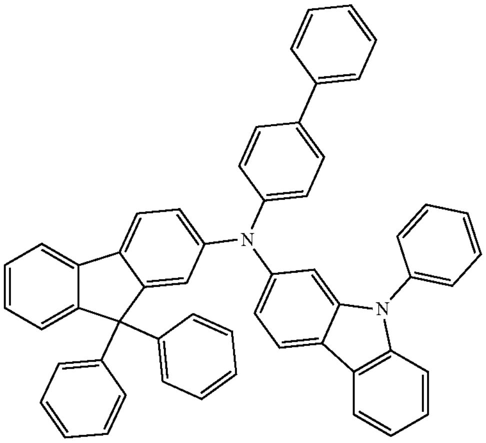
-continued
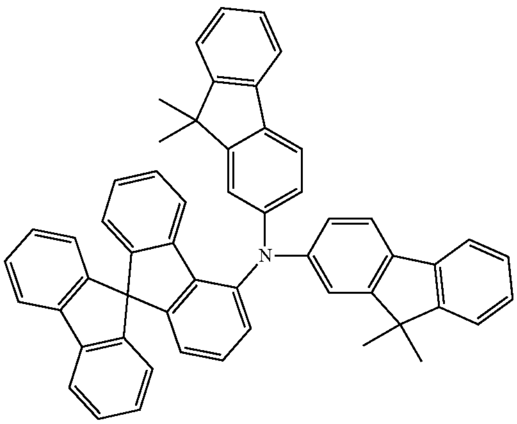
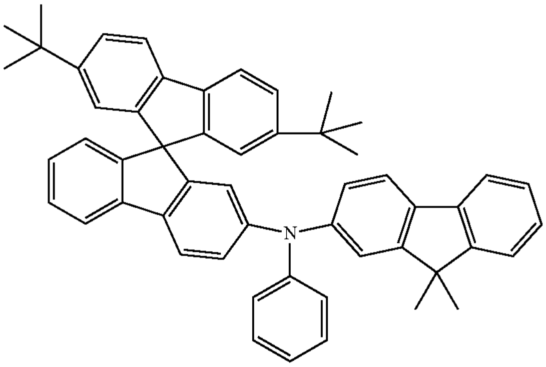
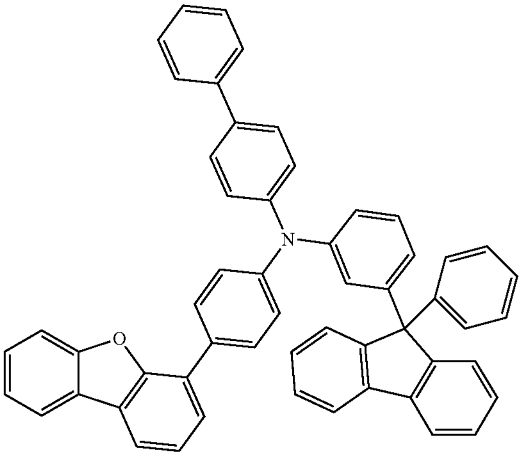
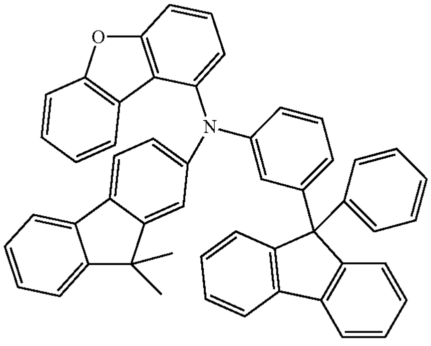

-continued
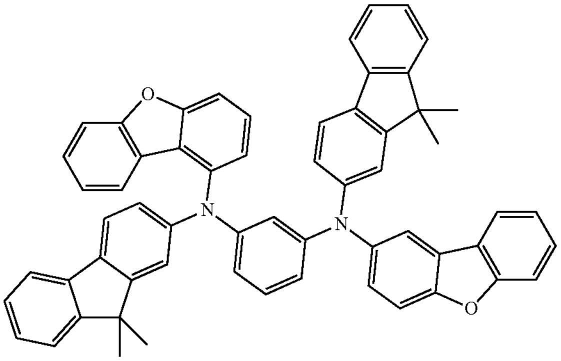
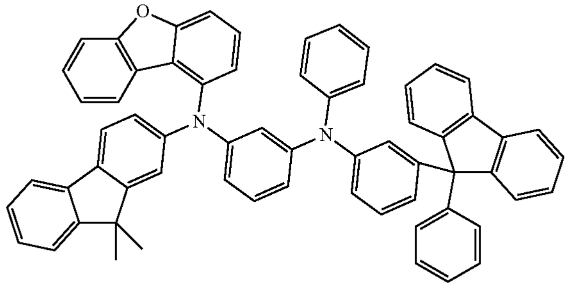
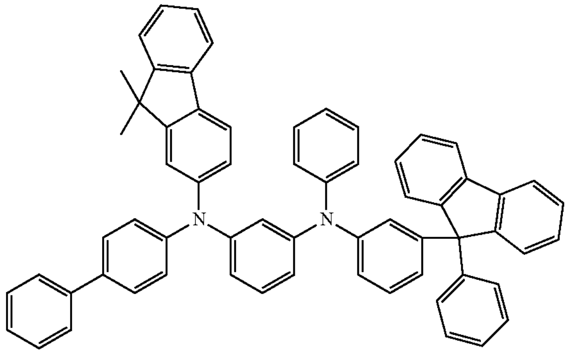
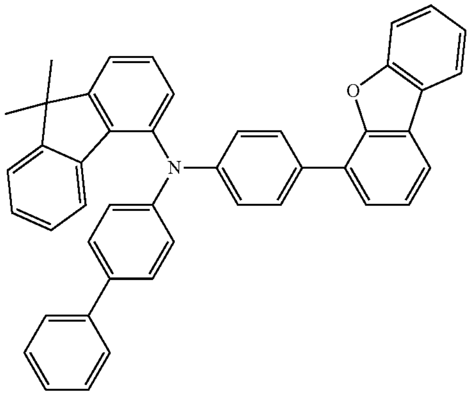
-continued
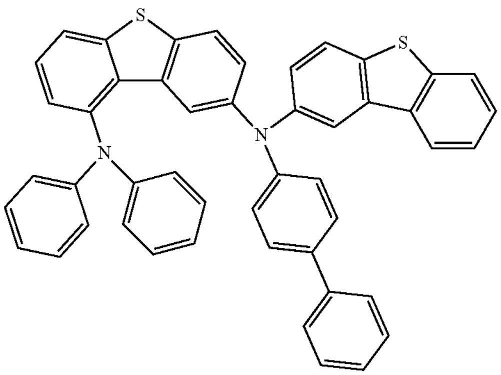
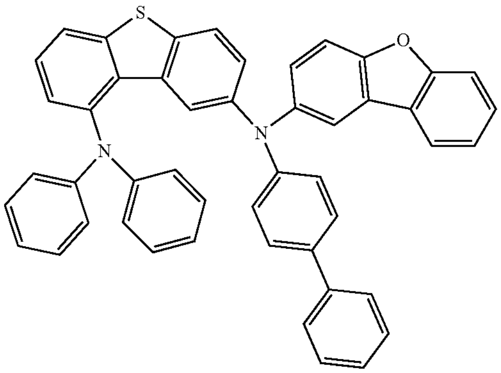
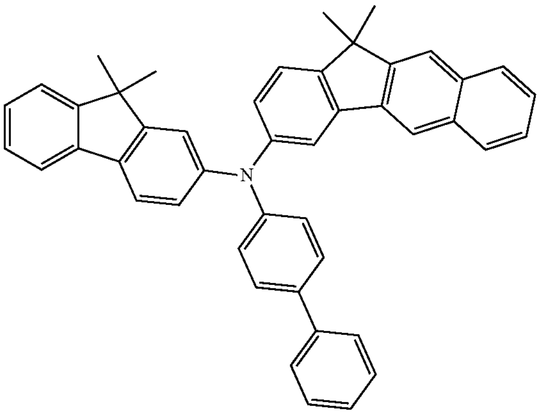
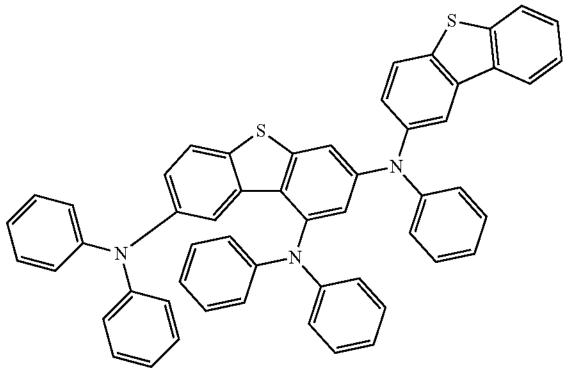

-continued

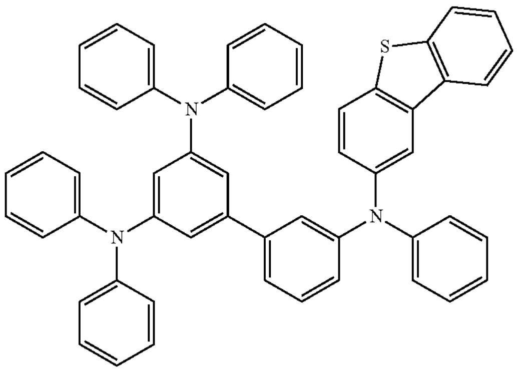

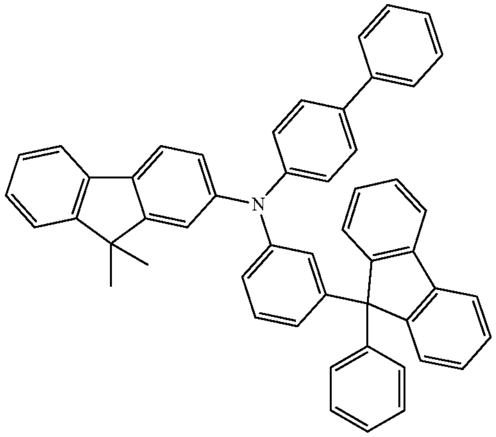

In the hole transport region, other suitable compounds may be used in addition to the compound.

Also, the charge transport region may be, e.g., the electron transport region 150.

The electron transport region 150 may help further increase electron injection and/or electron mobility between the cathode 110 and the light emitting layer 130 and block holes.

In an implementation, the electron transport region 150 may include an electron transport layer between the cathode 110 and the light emitting layer 130, and an electron transport auxiliary layer between the light emitting layer 130 and the electron transport layer and, e.g., a compound of Group C may be included in at least one of the electron transport layer and the electron transport auxiliary layer.

[Group C]

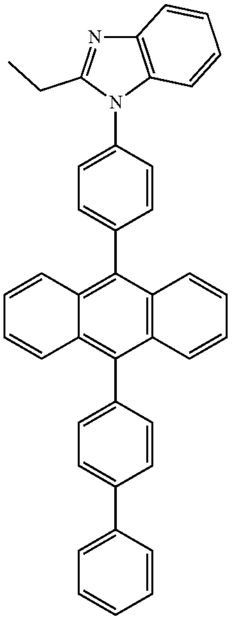

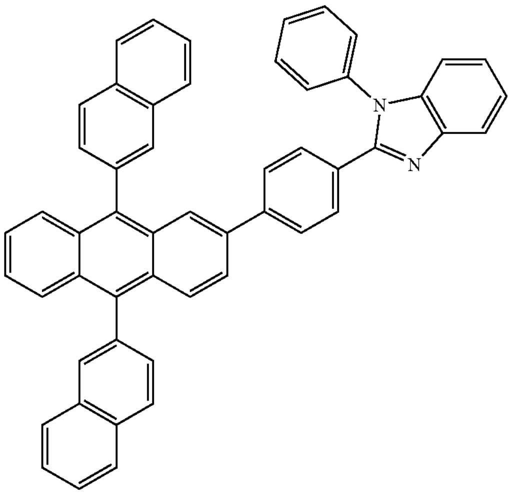

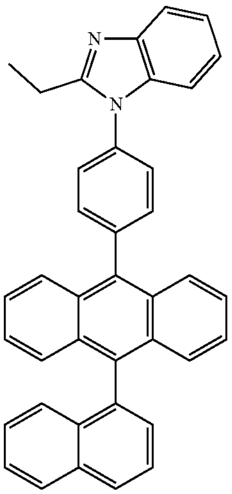

-continued
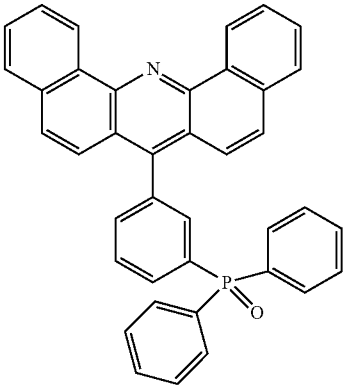
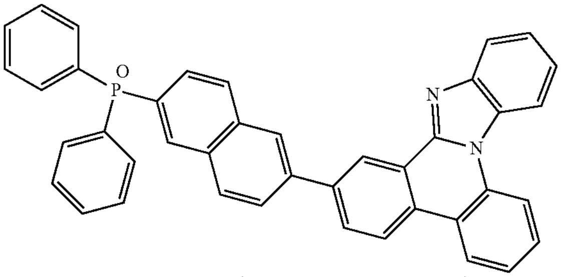
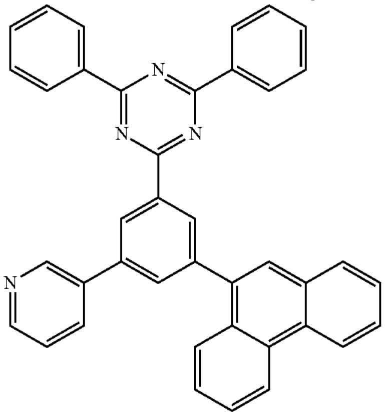
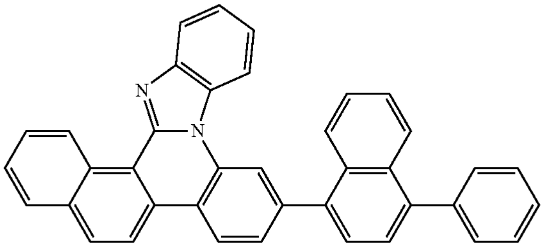
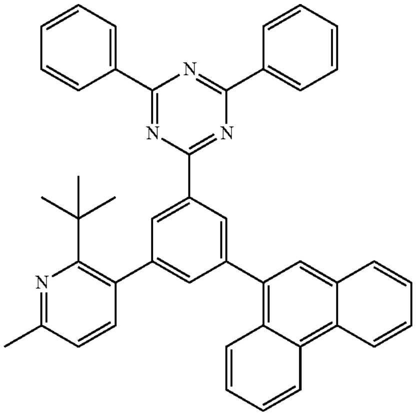
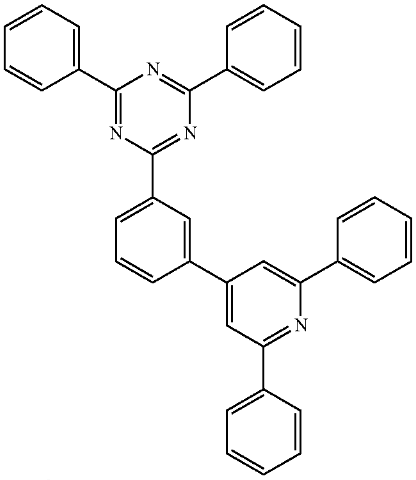
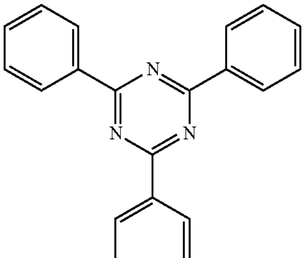
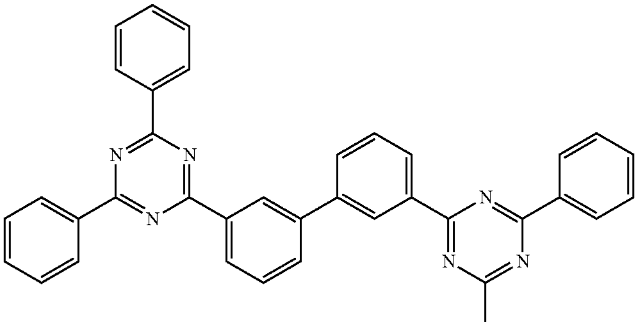

One embodiment may provide an organic light emitting diode including a light emitting layer as an organic layer.

Another embodiment may provide an organic light emitting diode including a light emitting layer and a hole transport region as an organic layer.

Another embodiment may provide an organic light emitting diode including a light emitting layer and an electron transport region as an organic layer.

The organic light emitting diode according to an embodiment may include a hole transport region 140 and an electron transport region 150 in addition to the light emitting layer 130 as the organic layer 105, as shown in FIG. 1.

In an implementation, the organic light emitting diode may further include an electron injection layer, a hole injection layer, or the like, in addition to the light emitting layer as the aforementioned organic layer.

The organic light emitting diode 100 may be produced by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in examples and synthesis examples were purchased from Sigma-Aldrich Co. Ltd., TCI Inc., or Tokyo Chemical Industry, and as far as there is no particular comment or were synthesized by suitable methods.

(Preparation of Compound for Organic Optoelectronic Device)

Synthesis Example 1: Synthesis of Int-6

[Reaction Scheme 1]

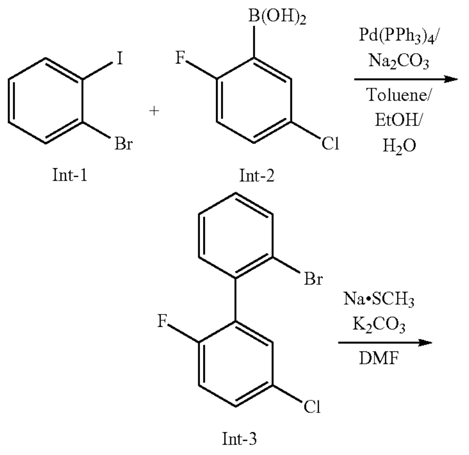

-continued

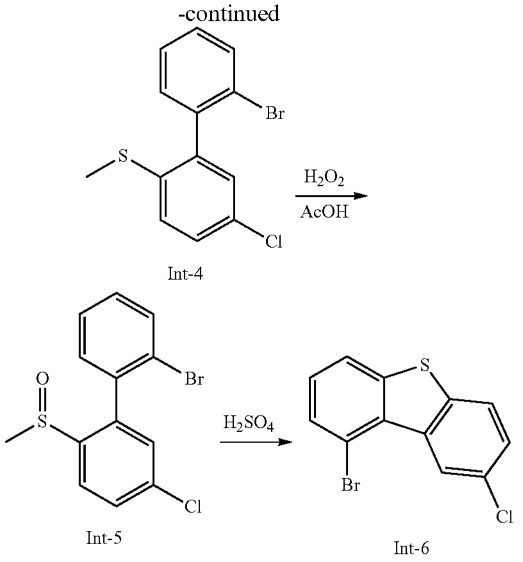

1st Step: Synthesis of Int-3

Int-1 (100 g, 353 mmol) was dissolved in 400 mL of toluene/200 mL of EtOH, and Int-2 (62 g, 353 mmol) and tetrakis(triphenylphosphine)palladium (12.3 g, 10.6 mmol) were added thereto and then, stirred. Subsequently, sodium carbonate (94 g, 884 mmol) saturated in water was added thereto and then, heated under reflux at 100° C. for 48 hours. When a reaction was completed, water was added thereto, and the mixture was extracted with dichloromethane (DCM) and then, treated with anhydrous magnesium sulfate to remove moisture, filtered, and concentrated under a reduced pressure. The obtained residue was separated and purified through flash column chromatography, obtaining 78.2 g (78%) of Int-3.

2nd Step: Synthesis of Int-4

In a 1,000 mL round-bottomed flask, 78 g (273 mmol) of Int-3 was added to 550 mL of N,N-dimethylformamide, and an internal temperature thereof was set at 0° C. Subsequently, 21.1 g (286.6 mmol) of sodium thiomethoxide (CAS No.: 5188-07-8) and 56.5 g (409.39 mmol) of potassium carbonate were slowly added thereto. Herein, the internal temperature thereof was maintained at 0° C. The mixture was heated at 80° C. under a nitrogen atmosphere. After 12 hours, the reaction solution was cooled, ethyl acetate and an aqueous layer were added thereto and then, stirred, and an organic layer therefrom was treated under a reduced pressure and then, through column chromatography, obtaining 73 g (Yield: 85%) of Int-4.

3rd Step: Synthesis of Int-5

73 g (233 mmol) of Int-4 was added to 500 mL of acetic acid, and an internal temperature thereof was set at 0° C. Subsequently, 50 ml of hydrogen peroxide was slowly added thereto. Herein, the internal temperature was maintained at 0° C. After stirring the mixture at ambient temperature for 12 hours, the reaction solution was placed in ice water and then, extracted with dichloromethane (DCM), treated with anhydrous magnesium sulfate to remove moisture, filtered, and concentrated under a reduced pressure, obtaining Int-5 74 g (Yield: 96%).

4th Step: Synthesis of Int-6

74 g (224 mmol) of Int-5 was added to 500 mL of sulfuric acid and then, stirred at ambient temperature for 20 hours, and then, the reaction solution was placed in ice water and then, adjusted to pH 9 by using a NaOH aqueous solution.

The resultant was extracted with dichloromethane (DCM) and then, treated with anhydrous magnesium sulfate to remove moisture, filtered, and concentrated under a reduced pressure, obtaining 52 g (Yield: 78%) of Int-6.

Synthesis Example 2: Synthesis of Int-12

[Reaction Scheme 2]

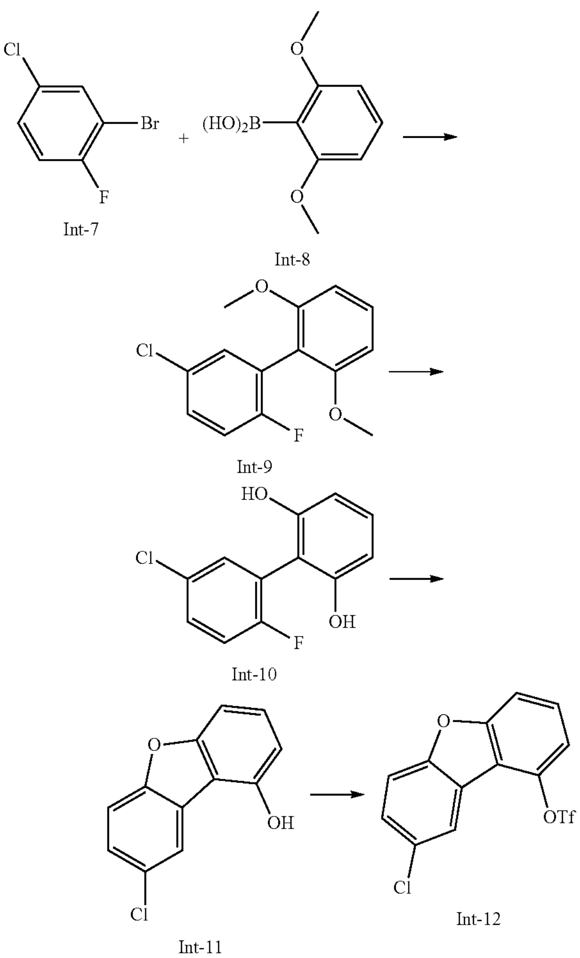

1st Step: Synthesis of Int-9

Int-7 (61 g, 291 mmol), Int-8 (50.4 g, 277 mmol), $K_2CO_3$ (60.4 g, 437 mmol), and $Pd(PPh_3)_4$ (10.1 g, 8.7 mmol) were put in a round-bottomed flask and dissolved in 500 ml of THF and 200 ml of distilled water and then, stirred under reflux at 60° C. for 12 hours. When a reaction was completed, after removing an aqueous layer therefrom, the residue was treated through column chromatography (hexane:DCM (20%)), obtaining 38 g (51%) of Int-9.

2nd Step: Synthesis of Int-10

Int-9 (38 g, 142 mmol) and pyridine hydrochloride (165 g, 1425 mmol) were put in a round-bottomed flask and stirred under reflux at 200° C. for 24 hours. When a reaction was completed, the resultant was cooled to ambient temperature and slowly poured into distilled water and then, stirred for 1 hour. A solid therein was filtered, obtaining 23 g (68%) of Int-10.

3rd Step: Synthesis of Int-11

Int-10 (23 g, 96 mmol) and $K_2CO_3$ (20 g, 144 mmol) were put in a round-bottomed flask and dissolved in 100 ml of NMP and then, stirred under reflux at 180° C. for 12 hours. When a reaction was completed, the mixture was poured into distilled water. A solid therein was filtered, dissolved in ethyl acetate, and dried with $MgSO_4$, and an organic layer was removed therefrom under a reduced pressure. The residue was treated through column chromatography (hexane:EA (30%)), obtaining 16 g (76%) of Int-11.

4th Step: Synthesis of Int-12

Int-11 (16 g, 73 mmol) and pyridine (12 ml, 146 mmol) were put in a round-bottomed flask and dissolved in 200 ml of DCM. After decreasing a temperature to 0° C., trifluoromethanesulfonic anhydride (14.7 ml, 88 mmol) was slowly added thereto in a dropwise fashion. After stirring the mixture for 6 hours, when a reaction was completed, an excess of distilled water was added thereto and then, stirred for 30 minutes and extracted with DCM. After removing an organic solvent therefrom under a reduced pressure, the residue was vacuum-dried, obtaining 22.5 g (88%) of Int-12.

Synthesis Example 3: Synthesis of Int-14 to Int-20

[Reaction Scheme 3]

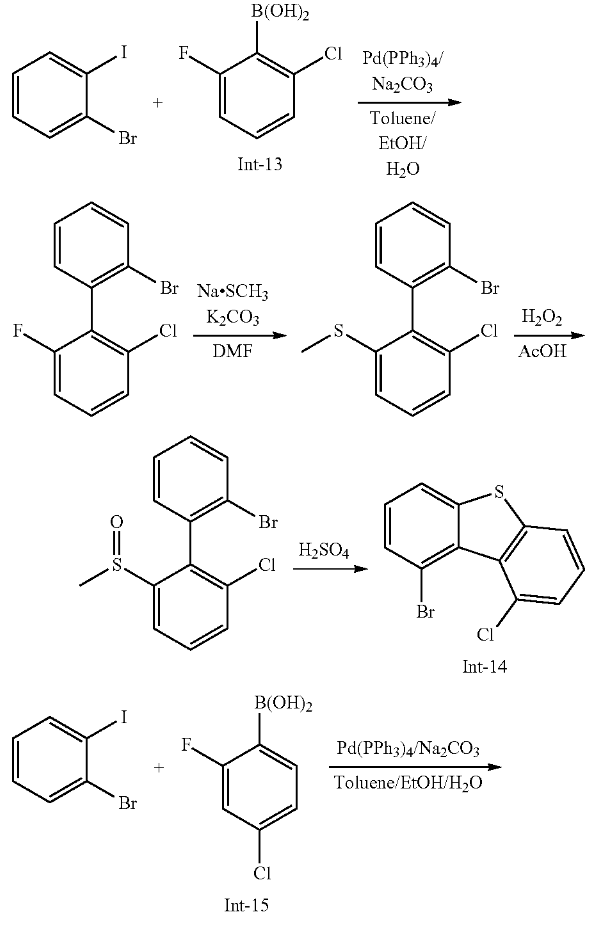

-continued
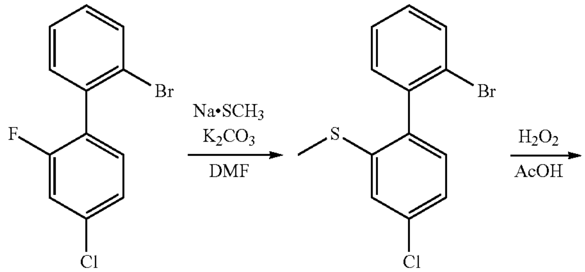
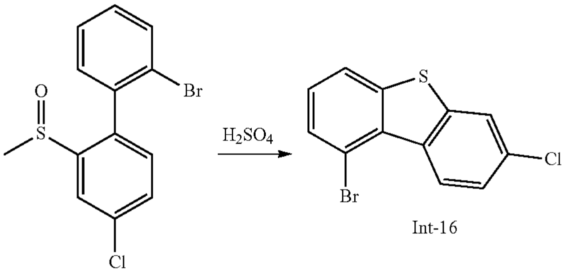
Int-16
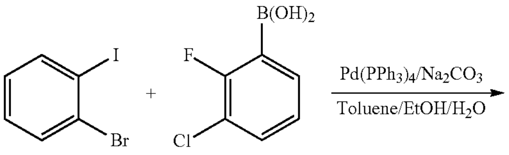
Int-17
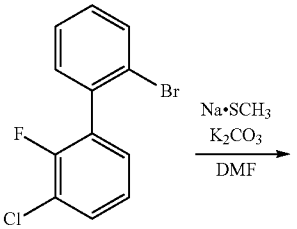
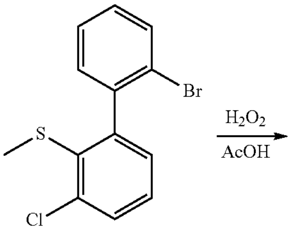
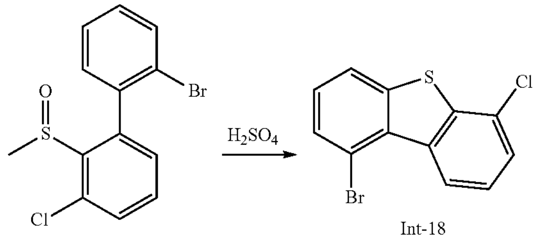
Int-18
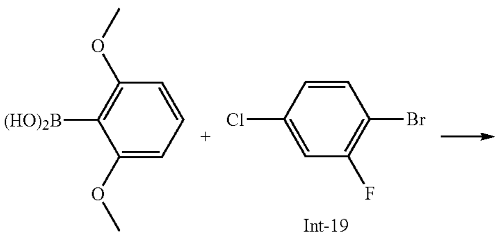
Int-19
-continued
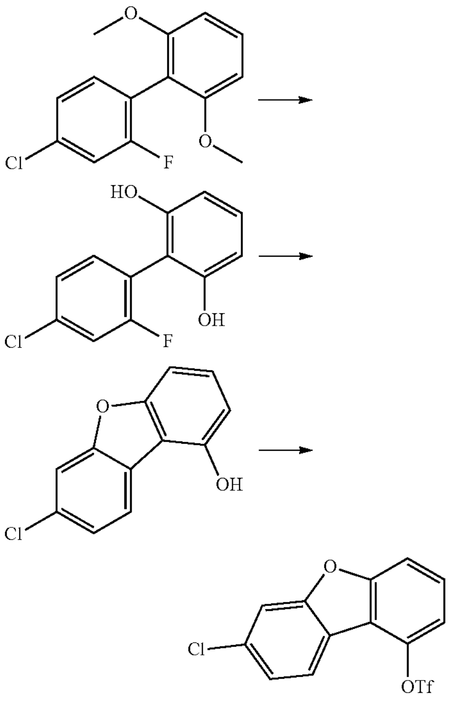
Int-20
Int-14, Int-16, Int-19, and Int-20 were respectively synthesized in the same manner as Synthesis Examples 1 and 2 except that Int-13, Int-15, and Int-17 were respectively used instead of Int-2 of Synthesis Example 1, and Int-19 was used instead of Int-7 of Synthesis Example 2.
Synthesis Example 4: Synthesis of Compound 1-1
[Reaction Scheme 4]
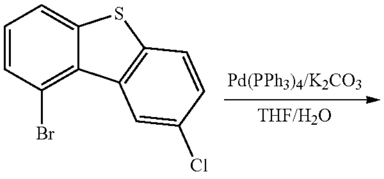
Int-6
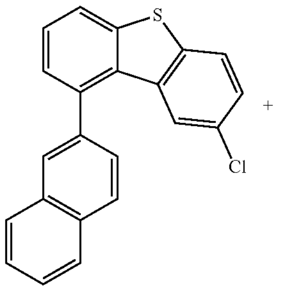
Int-21

-continued

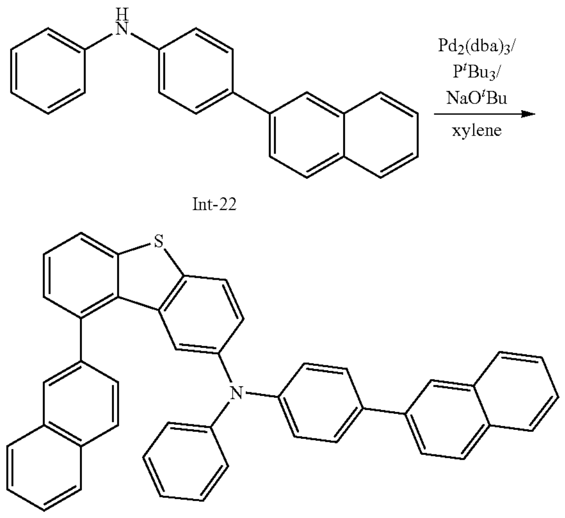

Int-22

1-1

1st Step: Synthesis of Int-21

3.0 g (10.1 mmol) of Int-6 was added to 30 mL of tetrahydrofuran and 15 mL of distilled water in a round-bottomed flask, and 1.84 g (10.6 mmol) of naphthalene-2-boronic acid, 0.03 equivalent of tetrakis(triphenylphosphine)palladium, and 2 equivalents of potassium carbonate were added thereto and then, stirred under reflux under a nitrogen atmosphere. After 12 hours, the reaction solution was cooled, and after removing an aqueous layer, an organic layer therefrom was dried under a reduced pressure. A solid obtained therefrom was washed with water and hexane and recrystallized with 20 mL of toluene, obtaining 2.7 g (Yield: 78%) of Int-21.

2nd Step: Synthesis of Compound 1-1

2.7 g (7.83 mmol) of Int-21, 2.41 g (8.22 mmol) of Int-22, 2.26 g (23.49 mmol) of sodium t-butoxide, and 0.32 g (0.78 mmol) of tri-tert-butylphosphine were dissolved in 50 ml of xylene, and 0.36 g (0.39 mmol) of $Pd_2(dba)_3$ were added thereto and then, stirred for reflux for 12 hours under a nitrogen atmosphere. When a reaction was completed, after extracting with xylene and distilled water, an organic layer therefrom was dried with anhydrous magnesium sulfate and filtered, and a filtrate therefrom was concentrated under a reduced pressure. A product therefrom was purified with normal hexane/dichloromethane (a volume ratio of 2:1) through silica gel column chromatography, obtaining 3.78 g (Yield: 80%) of Compound 1-1.

calcd. C44H29NS: C, 87.53; H, 4.84; N, 2.32; S, 5.31. found: C, 87.54; H, 4.84; N, 2.32; S, 5.30.

Synthesis Examples 5 to 18

Each compound was synthesized in the same manner as in Synthesis Example 4 except that Int A of Table 1 was used instead of Int-21 of Synthesis Example 4, and Int B of Table 1 was used instead of Int-22.

TABLE 1

| Synthesis Example | Int A | Int B | Final product | Amount (yield) | Property data of Final product |
|---|---|---|---|---|---|
| Synthesis Example 5 | Int-23 | Int-22 | Compound 1-9 | 3.77 g (71%) | calcd. C44H29NS: C, 87.53; H, 4.84; N, 2.32; S, 5.31 found: C, 87.53; H, 4.84; N, 2.32; S, 5.31 |
| Synthesis Example 6 | Int-24 | Int-22 | Compound 1-17 | 4.812 g (71%) | calcd. C46H31NS: C, 87.72; H, 4.96; N, 2.22; S, 5.09 found: C, 87.73; H, 4.96; N, 2.22; S, 5.08 |
| Synthesis Example 7 | Int-24 | Int-35 | Compound 1-18 | 5.72 g (73%) | calcd. C50H33NS: C, 88.33; H, 4.89; N, 2.06; S, 4.72 found: C, 88.33; H, 4.89; N, 2.06; S, 4.72 |
| Synthesis Example 8 | Int-24 | Int-36 | Compound 1-26 | 6.94 g (65%) | calcd. C48H35NSSi: C, 84.05; H, 5.14; N, 2.04; S, 4.67; Si, 4.09 found: C, 84.06; H, 5.14; N, 2.03; S, 4.67; Si, 4.09 |
| Synthesis Example 9 | Int-25 | Int-37 | Compound 1-37 | 4.63 g (73%) | calcd. C50H33NS: C, 88.33; H, 4.89; N, 2.06; S, 4.72 found: C, 88.33; H, 4.89; N, 2.06; S, 4.72 |
| Synthesis Example 10 | Int-26 | Int-38 | Compound 1-49 | 5.49 g (71%) | calcd. C48H29NOS: C, 86.33; H, 4.38; N, 2.10; O, 2.40; S, 4.80 found: C, 86.33; H, 4.38; N, 2.10; O, 2.40; S, 4.80 |
| Synthesis Example 11 | Int-27 | Int-22 | Compound 1-65 | 7.28 g (72%) | calcd. C44H29NS: C, 87.53; H, 4.84; N, 2.32; S, 5.31 found: C, 87.54; H, 4.84; N, 2.31; S, 5.31 |
| Synthesis Example 12 | Int-28 | Int-22 | Compound 1-66 | 3.74 g (73%) | calcd. C44H29NS: C, 87.53; H, 4.84; N, 2.32; S, 5.31 found: C, 87.53; H, 4.84; N, 2.32; S, 5.31 |
| Synthesis Example 13 | Int-29 | Int-22 | Compound 1-67 | 4.38 g (67%) | calcd. C44H29NS: C, 87.53; H, 4.84; N, 2.32; S, 5.31 found: C, 87.54; H, 4.83; N, 2.32; S, 5.31 |
| Synthesis Example 14 | Int-30 | Int-22 | Compound 1-72 | 5.92 g (73%) | calcd. C44H29NO: C, 89.92; H, 4.97; N, 2.38; O, 2.72 found: C, 89.92; H, 4.97; N, 2.38; O, 2.72 |
| Synthesis Example 15 | Int-31 | Int-22 | Compound 1-80 | 4.02 g (78%) | calcd. C44H29NO: C, 89.92; H, 4.97; N, 2.38; O, 2.72 found: C, 89.93; H, 4.96; N, 2.38; O, 2.72 |
| Synthesis Example 16 | Int-32 | Int-35 | Compound 1-89 | 6.13 g (64%) | calcd. C50H33NO: C, 90.47; H, 5.01; N, 2.11; O, 2.41; found: C, 90.47; H, 5.01; N, 2.11; O, 2.41 |
| Synthesis Example 17 | Int-33 | Int-38 | Compound 1-120 | 4.37 g (70%) | calcd. C48H29NO2: C, 88.46; H, 4.49; N, 2.15; O, 4.91; found: C, 88.48; H, 4.48; N, 2.14; O, 4.91 |
| Synthesis Example 18 | Int-34 | Int-22 | Compound 1-137 | 4.48 g (67%) | calcd. C44H29NO: C, 89.92; H, 4.97; N, 2.38; O, 2.72; found: C, 89.92; H, 4.97; N, 2.38; O, 2.72 |

Int A

TABLE 1-continued
| Synthesis Example | Int A | Int B | Final product | Amount (yield) | Property data of Final product |
|---|---|---|---|---|---|
| 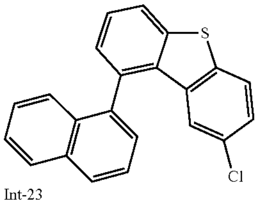 Int-23 | | | | | |
| 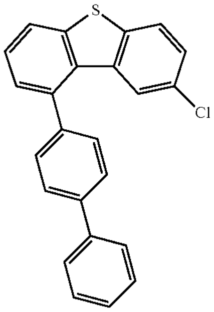 [SMILES: Clc1ccc2sc3cccc(-c4ccc(-c5ccccc5)cc4)c3c2c1] Int-24 | | | | | |
| 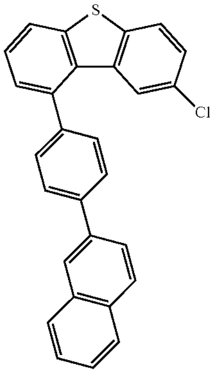 [SMILES: Clc1ccc2sc3cccc(-c4ccc(-c5ccc6ccccc6c5)cc4)c3c2c1] Int-25 | | | | | |
| 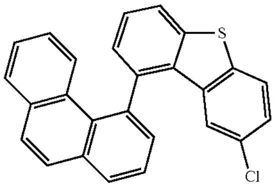 [SMILES: Clc1ccc2sc3cccc(-c4cccc5ccc6ccccc6c45)c3c2c1] Int-26 | | | | | |
| 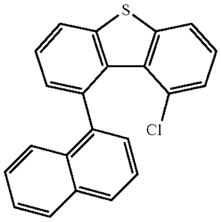 [SMILES: Clc1cccc2sc3cccc(-c4cccc5ccccc45)c3c12] Int-27 | | | | | |
| 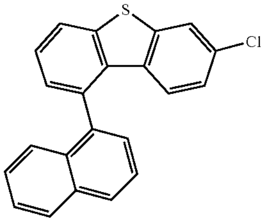 [SMILES: Clc1ccc2c(c1)sc1cccc(-c3cccc4ccccc34)c12] Int-28 | | | | | |
| 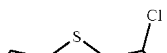 | | | | | |

Synthesis Example 19: Synthesis of Compound A-3

[Reaction Scheme 5]

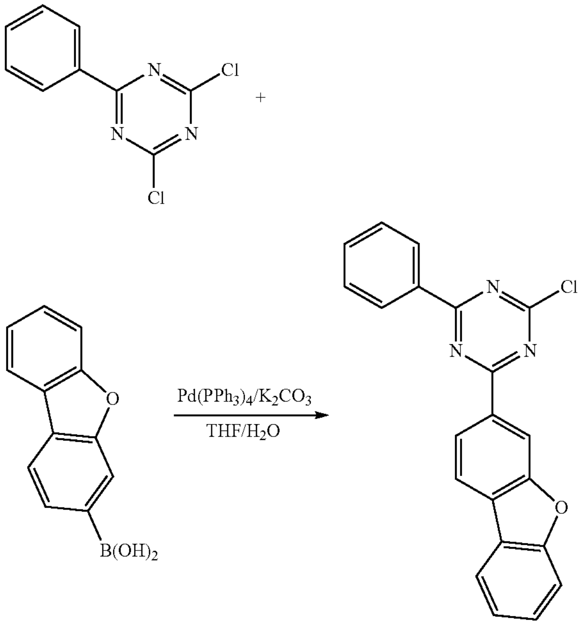

Int-39

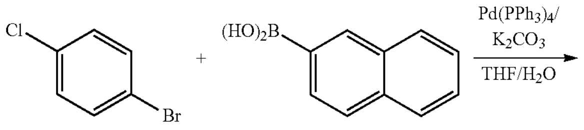

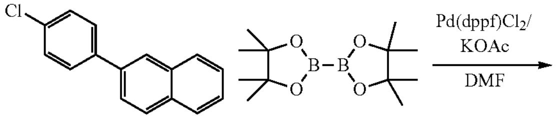

Int-40

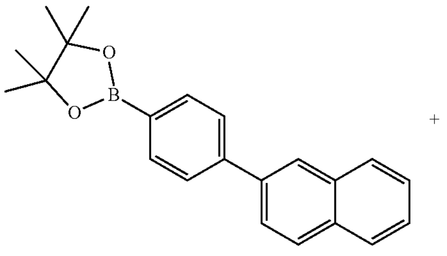

Int-41

-continued

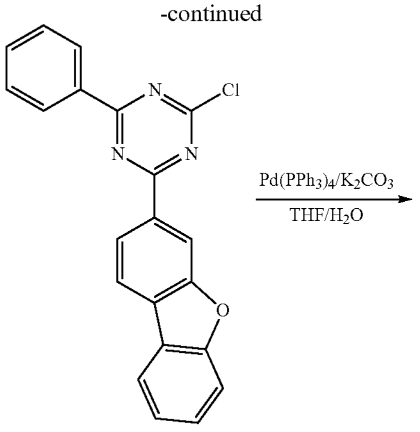

Int-39

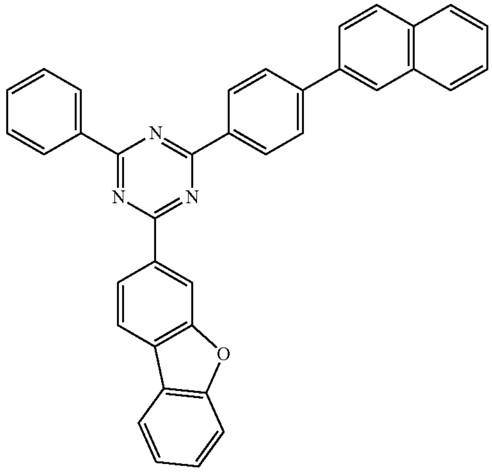

A-3

1st Step: Synthesis of Int-39

22.6 g (100 mmol) of 2,4-dichloro-6-phenyl-1,3,5-triazine was added to 200 mL of tetrahydrofuran and 100 mL of distilled water in a round-bottomed flask, and 0.9 equivalent of dibenzofuran-3-boronic acid (CAS No.: 395087-89-5), 0.03 equivalent of tetrakis(triphenylphosphine)palladium, and 2 equivalents of potassium carbonate were added thereto and then, stirred under reflux under a nitrogen atmosphere. After 6 hours, the reaction solution was cooled, after removing an aqueous layer, an organic layer therefrom was dried under a reduced pressure. The obtained solid was washed with water and hexane and then, recrystallized with 200 mL of toluene, obtaining 21.4 g (Yield: 60%) of Int-39.

2nd Step: Synthesis of Int-40

In a round-bottomed flask, 50.0 g (261.16 mmol) of 1-bromo-4-chloro-benzene, 44.9 g (261.16 mmol) of 2-naphthalene boronic acid, 9.1 g (7.83 mmol) of tetrakis (triphenylphosphine)palladium, and 71.2 g (522.33 mmol) of potassium carbonate were dissolved in 1,000 mL of tetrahydrofuran and 500 mL of distilled water and then, heated under reflux under a nitrogen atmosphere. After 6 hours, the reaction solution was cooled, and after removing an aqueous layer, an organic layer therefrom was dried under a reduced pressure. The obtained solid was washed with water and hexane and then, recrystallized with 200 mL of toluene, obtaining 55.0 g (Yield: 88%) of Int-40.

3rd Step: Synthesis of Int-41

In a round-bottomed flask, 100.0 g (418.92 mmol) of Int-40 was added to 1,000 mL of DMF, and 17.1 g (20.95 mmol) of dichlorodiphenylphosphinoferrocene palladium, 127.7 g (502.70 mmol) of bis(pinacolato)diboron, and 123.3 g (1256.76 mmol) of potassium acetate were added thereto and then, heated under reflux for 12 hours under a nitrogen atmosphere. The reaction solution was cooled and then, added dropwise to 2 L of water to catch a solid. The solid was dissolved in boiling toluene and then, filtered through silica gel, and a filtrate therefrom was concentrated. The concentrated solid was stirred with a small amount of hexane and then, filtered, obtaining 28.5 g (Yield: 70%) of Int-41.

4th Step: Synthesis of Compound A-3

In a round-bottomed flask, 10.0 g (27.95 mmol) of Int-41, 11.1 g (33.54 mmol) of Int-39, 1.0 g (0.84 mmol) of tetrakis(triphenylphosphine)palladium, and 7.7 g (55.90 mmol) of potassium carbonate were dissolved in 150 mL of tetrahydrofuran and 75 mL of distilled water and then, heated under reflux under a nitrogen atmosphere. After 12 hours, the reaction solution was cooled, and after removing an aqueous layer, an organic layer therefrom was dried under a reduced pressure. The obtained solid was washed with water and methanol and recrystallized with 200 mL of toluene, obtaining 13.4 g (Yield: 91%) of Compound A-3.

calcd. C37H23N3O: C, 84.55; H, 4.41; N, 7.99; O, 3.04. found: C, 84.55; H, 4.41; N, 8.00; O, 3.03.

Synthesis Example 20: Synthesis of Compound A-71

[Reaction Scheme 6]

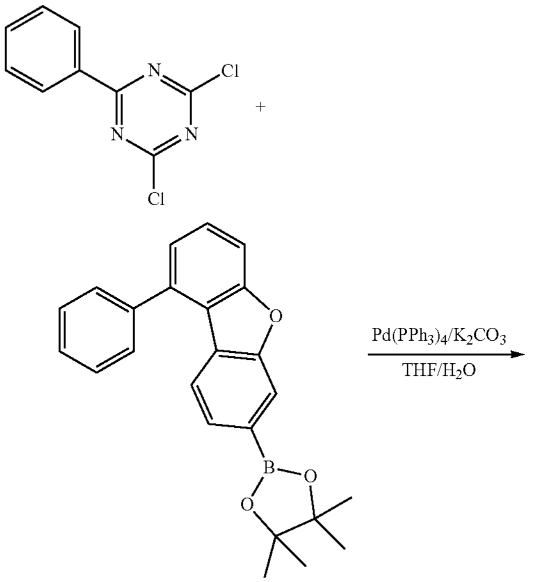

-continued

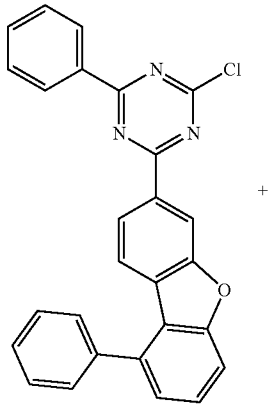

Int-42

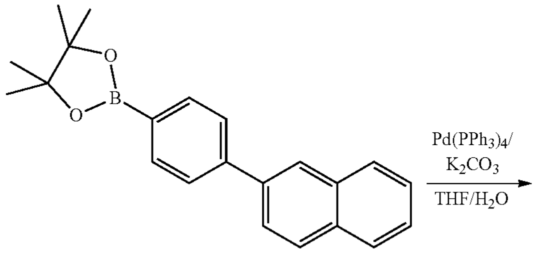

Int-41

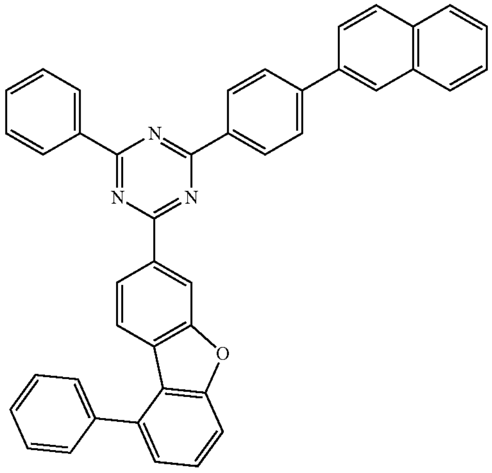

A-71

1st Step: Synthesis of Int-42

Int-42 was synthesized in the same manner as in the 1st step of Synthesis Example 19 by using 2,4-dichloro-6-phenyl-1,3,5-triazine and 1-phenyl-7-(4,4,5,5-tetramethyl-[1,3,2]dioxaborolan-2-yl)-dibenzofuran respectively by 1.0 equivalent.

2nd Step: Synthesis of Compound A-71

Compound A-71 was synthesized in the same manner as in the 4th step of Example 19 by using Int-42 and Int-41 respectively by 1.0 equivalent.

calcd. C43H27N3O: C, 85.83; H, 4.52; N, 6.98; O, 2.66. found: C, 85.83; H, 4.52; N, 6.98; O, 2.66.

Synthesis Example 21: Synthesis of Compound A-61

[Reaction Scheme 7]

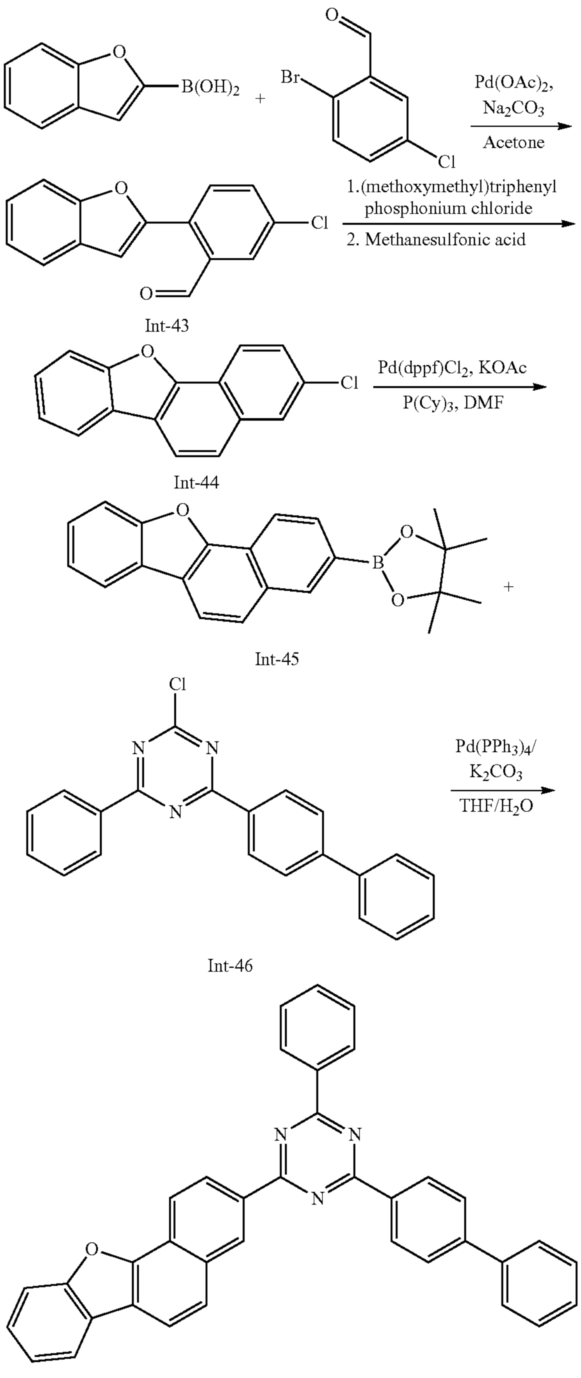

Int-43

Int-44

Int-45

Int-46

A-61

1st Step: Synthesis of Int-43

In a round-bottomed flask, 21.95 g (135.53 mmol) of 2-benzofuranylboronic acid, 26.77 g (121.98 mmol) of 2-bromo-5-chlorobenzaldehyde, 2.74 g (12.20 mmol) of $Pd(OAc)_2$, and 25.86 g (243.96 mmol) of $Na_2CO_3$ were suspended in 200 mL of acetone/220 mL of distilled water and then, stirred for 12 hours at ambient temperature. When a reaction was completed, the resultant was concentrated and extracted with DCM, and an organic layer therefrom was silica gel-columned, obtaining 21.4 g (Yield: 68%) of Int-43.

2nd Step: Synthesis of Int-44

20.4 g (79.47 mmol) of Int-43 and 29.97 g (87.42 mmol) of (methoxymethyl)triphenyl phosphonium chloride were suspended in 400 ml of THF, and 10.70 g (95.37 mmol) of potassium tert-butoxide was added thereto and then, stirred for 12 hours at ambient temperature. When a reaction was completed, 400 ml of distilled water was added thereto and then, extracted, an organic layer therefrom was concentrated and reextracted with DCM, magnesium sulfate was added thereto and then, stirred for 30 minutes and filtered, and a filtrate therefrom was concentrated. Subsequently, 100 ml of DCM was added again to the concentrated filtrate, and 10 ml of methane sulfonic acid was added thereto and then, stirred for 1 hour.

When a reaction was completed, a solid produced therein was filtered and dried with distilled water and methyl alcohol, obtaining 21.4 g (Yield: 65%) of Int-44.

3rd Step: Synthesis of Int-45

12.55 g (49.66 mmol) of Int-44, 2.43 g (2.98 mmol) of $Pd(dppf)Cl_2$, 15.13 g (59.60 mmol) of bis(pinacolato)diboron, 14.62 g (148.99 mmol) of KOAc, and 3.34 g (11.92 mmol) of $P(Cy)_3$ were suspended in 200 ml of DMF and then, stirred under reflux for 12 hours. When a reaction was completed, 200 ml of distilled water was added thereto, and a solid produced therein was filtered and extracted with DCM, and an organic layer therefrom was columned with hexane:EA=4:1 (v/v), obtaining 13 g (Yield: 76%) of Int-45.

4th Step: Synthesis of Compound A-61

Compound A-61 was synthesized in the same manner as in the $4^{th}$ step of Synthesis Example 19 by using Int-45 and Int-46 respectively by 1.0 equivalent.

calcd. C37H23N3O: C, 84.55; H, 4.41; N, 7.99; O, 3.04. found: C, 84.55; H, 4.41; N, 7.99; O, 3.04.

Synthesis Example 22: Synthesis of Compound A-17

[Reaction Scheme 8]

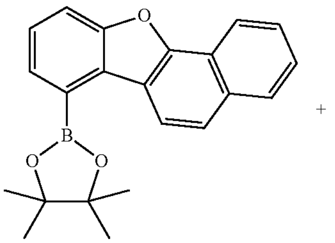

Int-47

-continued

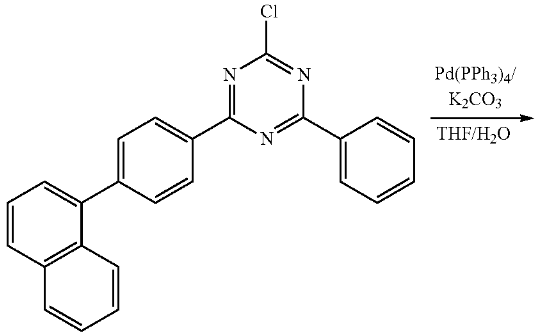

Int-48

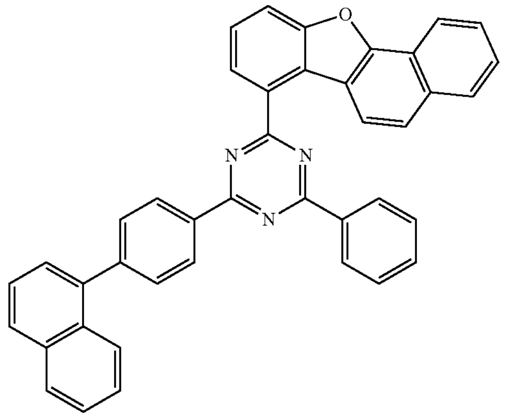

A-17

Compound A-17 was synthesized in the same manner as in the 4$^{th}$ step of Synthesis Example 19 by using Int-47 and Int-48 respectively by 1.0 equivalent.

calcd. C41H25N3O: C, 85.54; H, 4.38; N, 7.30; O, 2.78. found: C, 85.53; H, 4.38; N, 7.30; O, 2.77.

Synthesis Example 23: Synthesis of Compound A-37

[Reaction Scheme 9]

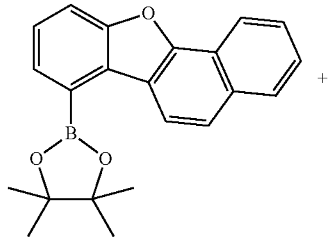

Int-47

-continued

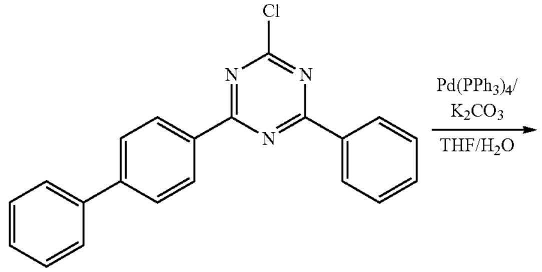

Int-46

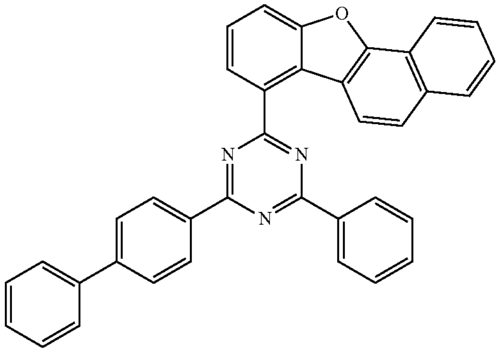

A-37

Compound A-37 was synthesized in the same manner as in the 4$^{th}$ step of Synthesis Example 19 by using Int-47 and Int-46 respectively by 1.0 equivalent.

calcd. C37H23N3O: C, 84.55; H, 4.41; N, 7.99; O, 3.04. found: C, 84.57; H, 4.40; N, 7.99; O, 3.03.

Synthesis of Synthesis Examples 24 to 26

Each compound was synthesized in the same manner as in the 4$^{th}$ step of Synthesis Example 19 except that Int C of Table 2 was used instead of Int-41 of Synthesis Example 19, and Int D of Table 2 was used instead of Int-39.

TABLE 2

| Synthesis Example | Int C | Int D | Final product | Amount (yield) | Property data of Final product |
|---|---|---|---|---|---|
| Synthesis Example 24 | Int-49 | Int-48 | Compound A-24 | 8.33 g (74%) | calcd. C41H25N3S: C, 83.22; H, 4.26; N, 7.10; S, 5.42 found: C, 83.22; H, 4.26; N, 7.10; S, 5.42 |
| Synthesis Example 25 | Int-50 | Int-52 | Compound A-77 | 6.29 g (71%) | calcd. C37H23N3S: C, 82.04; H, 4.28; N, 7.76; S, 5.92 found: C, 82.04; H, 4.28; N, 7.76; S, 5.92 |
| Synthesis Example 26 | Int-51 | Int-53 | Compound A-35 | 7.67 g (71%) | calcd. C41H25N3O: C, 85.54; H, 4.38; N, 7.30; O, 2.78 found: C, 85.55; H, 4.38; N, 7.29; O, 2.7 |

Int C

TABLE 2-continued

| Synthesis Example | Int C | Int D | Final product | Amount (yield) | Property data of Final product |
|---|---|---|---|---|---|

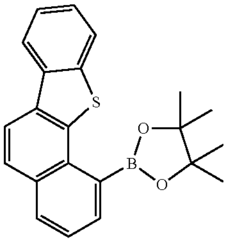 [SMILES: CC1(C)OB(c2cccc3ccc4c5ccccc5sc4c23)OC1(C)C]

Int-49

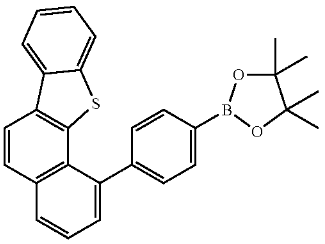 [SMILES: CC1(C)OB(c2ccc(-c3cccc4ccc5c6ccccc6sc5c34)cc2)OC1(C)C]

Int-50

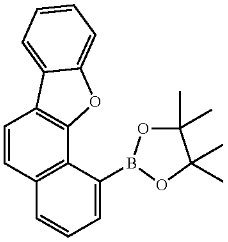 [SMILES: CC1(C)OB(c2cccc3ccc4c5ccccc5oc4c23)OC1(C)C]

Int-51

Int D

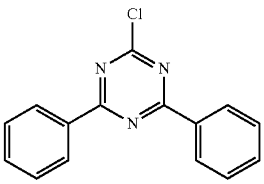 [SMILES: Clc1nc(-c2ccccc2)nc(-c2ccccc2)n1]

Int-52

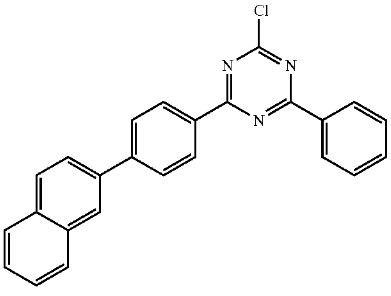 [SMILES: Clc1nc(-c2ccccc2)nc(-c2ccc(-c3ccc4ccccc4c3)cc2)n1]

Int-53

Comparative Synthesis Example 1: Synthesis of Comparative Compound 1

[Reaction Scheme 10]

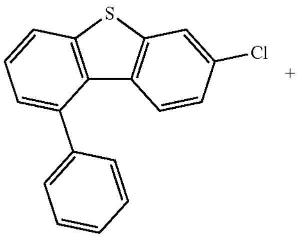

Int-54

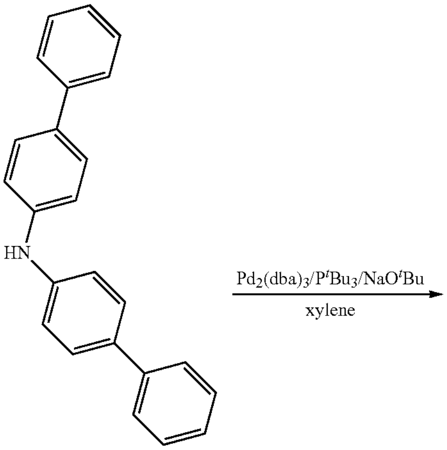

Int-55

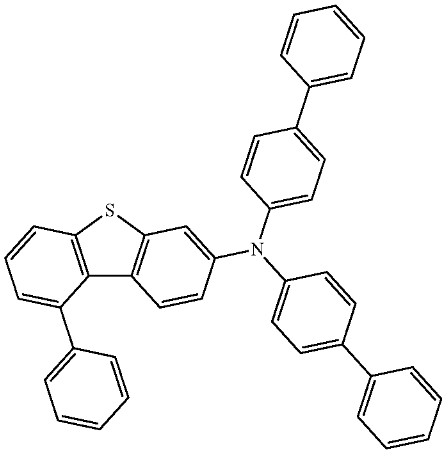

Comparative Compound 1

Comparative Compound 1 was synthesized in the same manner as in the 2$^{nd}$ step of Synthesis Example 4 except that Int-54 was used instead of Int-21 of Synthesis Example 4, and Int-55 was used instead of Int-22.

calcd. C42H29NS: C, 87.01; H, 5.04; N, 2.42; S, 5.53. found: C, 87.01; H, 5.04; N, 2.42; S, 5.53.

Comparative Synthesis Example 2: Synthesis of Comparative Compound 2

[Reaction Scheme 11]

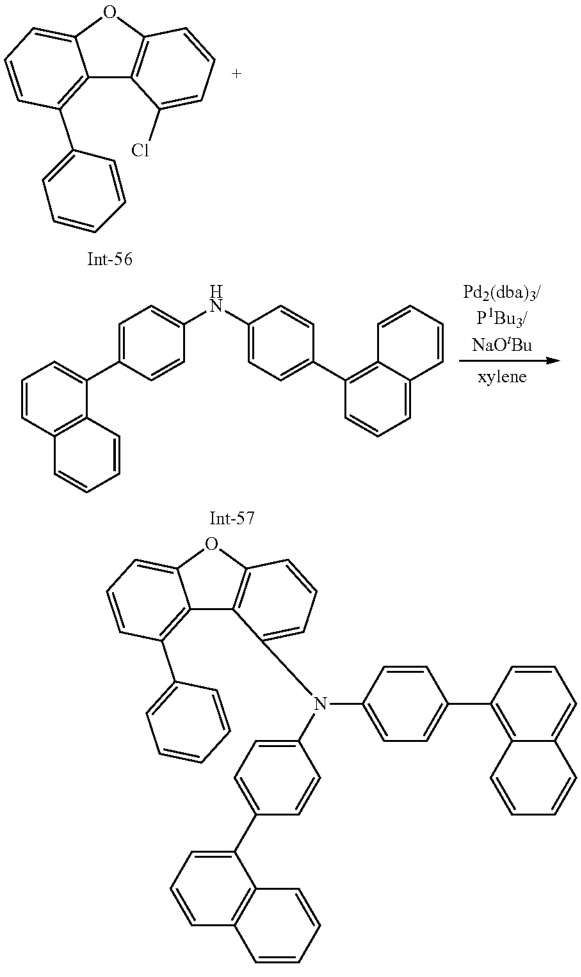

Int-56

Int-57

Comparative Compound 2

Comparative Compound 2 was synthesized in the same manner as in the 2$^{nd}$ step of Synthesis Example 4 except that Int-56 was used instead of Int-21 of Synthesis Example 4, and Int-57 was used instead of Int-22.

calcd. C50H33NO: C, 90.47; H, 5.01; N, 2.11; O, 2.41. found: C, 90.47; H, 5.02; N, 2.11; O, 2.40.

(Manufacture of Organic Light Emitting Diode)

Example 1

A glass substrate coated with ITO (Indium tin oxide) at a thickness of 1,500 Å was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 3% NDP-9 (commercially available from Novaled) was vacuum-deposited on the ITO substrate to form a 100 Å-thick hole injection layer, and then Compound A was deposited to be 1,300 Å-thick to form a hole transport layer. Compound B was deposited on the hole transport layer to a 700 Å-thick hole transport auxiliary layer. On the hole transport auxiliary layer, a 400 Å-thick light emitting layer was vacuum-deposited by using Compound 1-1 obtained in Synthesis Example 1 as a host and 2 wt % of $[Ir(piq)_2acac]$ as a dopant. Subsequently, on the light emitting layer, Compound C was deposited to a thickness of 50 Å to form an electron transport auxiliary layer, and a 300 Å-thick electron transport layer was formed by simultaneously vacuum-depositing Compound D and LiQ in a weight ratio of 1:1. On the electron transport layer, LiQ and Al were sequentially vacuum-deposited to be 15 Å thick and 1,200 Å thick, manufacturing an organic light emitting diode.

A structure of ITO/Compound A (3% NDP-9 doping, 100 Å)/Compound A (1,300 Å)/Compound B (700 Å)/EML [Compound 1-1 (98 wt %),$[Ir(piq)_2acac]$(2 wt %)](400 Å)/Compound C (50 Å)/Compound D: Liq (300 Å)/LiQ (15 Å)/Al (1,200 Å)

Compound A: N-(biphenyl-4-yl)-9,9-dimethyl-N-(4-(9-phenyl-9H-carbazol-3-yl)phenyl)-9H-fluoren-2-amine Compound B: N,N-di([1,1'-biphenyl]-4-yl)-7,7-dimethyl-7H-fluoreno[4,3-b]benzofuran-10-amine Compound C: 2-(3-(3-(9,9-dimethyl-9H-fluoren-2-yl)phenyl)phenyl)-4,6-diphenyl-1,3,5-triazine Compound D: 8-(4-(4,6-di(naphthalen-2-yl)-1,3,5-triazin-2-yl)phenyl)quinoline Example 2

A glass substrate coated with ITO (Indium tin oxide) at a thickness of 1,500 Å was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 3% NDP-9 (commercially available from Novaled) was vacuum-deposited on the ITO substrate to form a 100 Å-thick hole injection layer, and then Compound A was deposited to be 1,300 Å-thick to form a hole transport layer. Compound B was deposited on the hole transport layer to a 700 Å-thick hole transport auxiliary layer. A 400 Å-thick light emitting layer was formed by using Compound 1-1 obtained in Synthesis Example 1 and Compound A-17 obtained in Synthesis Example 22 as a host simultaneously, and 2 wt % of $[Ir(piq)_2acac]$ as a dopant by vacuum deposition on the hole transport auxiliary layer. Herein, Compound 1-1 and Compound A-17 were used in a weight ratio of 5:5. Subsequently, on the light emitting layer, Compound C was deposited to form a 50 Å-thick electron transport auxiliary layer, and a 300 Å-thick electron transport layer was formed by simultaneously vacuum-depositing Compound D and LiQ in a weight ratio of 1:1. On the electron transport layer, LiQ and Al were sequentially vacuum-deposited to be 15 Å-thick and 1,200 Å-thick, manufacturing an organic light emitting diode.

A structure of ITO/Compound A (3% NDP-9 doping, 100 Å)/Compound A (1,300 Å)/Compound B (700 Å)/EML [98 wt % of host (Compound 1-1:Compound A-17=5:5 (w/w)): 2 wt % of $[Ir(piq)_2acac]$](400 Å)/Compound C (50 Å)/Compound D: Liq (300 Å)/LiQ (15 Å)/Al (1,200 Å)

Examples 3 to 16 and Comparative Examples 1 and 2

Diodes of Examples 3 to 16 and Comparative Examples 1 and 2 were manufactured in the same manner as in Example 1, except that the host was changed as shown in Table 3.

Examples 17 to 31 and Comparative Examples 3 and 4

Diodes of Examples 17 to 31 and Comparative Examples 3 and 4 were manufactured in the same manner as in Example 2, except that the host was changed as shown in Table 4.

Evaluation

Luminous efficiency and life-span characteristics of the organic light emitting diodes of Examples 1 to 31 and Comparative Examples 1 to 4 were evaluated.

Specific measurement methods are as follows, and the results are shown in Tables 3 and 4.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Luminous efficiency (cd/A) at the same current density (10 $mA/cm^2$) were calculated by using the luminance and current density from the items (1) and (2) and voltage.

The relative values based on the luminous efficiency of Comparative Example 2 were calculated and shown in Table 3.

The relative values based on the luminous efficiency of Comparative Example 4 were calculated and shown in Table 4.

(4) Measurement of Life-Span

The organic light emitting diodes of Examples 1 to 31, and Comparative Examples 1 to 4 were measured with respect to T95 life-spans by emitting light at initial luminance ($cd/m^2$) of 6,000 $cd/m^2$ and measuring luminance decreases over time to obtain when the luminance decreased down to 95% of the initial luminance as T95 life-span.

The relative values based on the T95 life-span of Comparative Example 2 were calculated and shown in Table 3.

The relative values based on the T95 life-span of Comparative Example 4 were calculated and shown in Table 4.

TABLE 3

| | Host | T95 life-span (%) | Efficiency (%) |
|---|---|---|---|
| Example 1 | 1-1 | 124% | 115% |
| Example 3 | 1-9 | 120% | 117% |
| Example 4 | 1-17 | 115% | 113% |
| Example 5 | 1-18 | 119% | 115% |
| Example 6 | 1-26 | 117% | 114% |
| Example 7 | 1-37 | 121% | 114% |
| Example 8 | 1-49 | 125% | 119% |
| Example 9 | 1-65 | 108% | 109% |
| Example 10 | 1-66 | 114% | 112% |
| Example 11 | 1-67 | 112% | 110% |
| Example 12 | 1-72 | 118% | 112% |
| Example 13 | 1-80 | 121% | 113% |
| Example 14 | 1-89 | 117% | 114% |
| Example 15 | 1-120 | 123% | 116% |
| Example 16 | 1-137 | 112% | 111% |
| Comparative Example 1 | Comparative Compound 1 | 83% | 94% |
| Comparative Example 2 | Comparative Compound 2 | 100% | 100% |

TABLE 4

| | Host | | T95 life-span | Efficiency |
|---|---|---|---|---|
| | First host | Second host | (%) | (%) |
| Example 2 | 1-1 | A-17 | 120% | 121% |
| Example 17 | 1-9 | | 125% | 123% |
| Example 18 | 1-18 | | 124% | 118% |
| Example 19 | 1-37 | | 126% | 119% |
| Example 20 | 1-49 | | 134% | 125% |
| Example 21 | 1-80 | | 125% | 117% |
| Example 22 | 1-120 | | 128% | 119% |
| Example 23 | 1-9 | A-24 | 125% | 123% |
| Example 24 | 1-49 | | 135% | 124% |
| Example 25 | 1-120 | | 128% | 121% |
| Example 26 | 1-9 | A-35 | 128% | 125% |
| Example 27 | 1-49 | | 136% | 126% |
| Example 28 | 1-120 | | 132% | 123% |
| Example 29 | 1-9 | A-37 | 131% | 126% |
| Example 30 | 1-49 | | 138% | 128% |
| Example 31 | 1-120 | | 134% | 123% |
| Comparative Example 3 | Comparative Compound 1 | A-17 | 78% | 90% |
| Comparative Example 4 | Comparative Compound 2 | | 100% | 100% |

Referring to Table 3, when the compound according to the Examples was applied as a host, compared with the Comparative Compounds, efficiency and a life-span were improved. In addition, referring to Table 4, when a mixture thereof with a second host was applied, overall efficiency and life-span were greatly improved.

One or more embodiments may provide a compound for an organic optoelectronic device capable of implementing an organic optoelectronic device having high efficiency and a long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device represented by Chemical Formula 1:

[Chemical Formula 1]

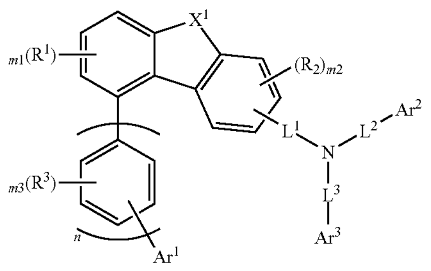

wherein, in Chemical Formula 1, $X^1$ is O or S, $L^1$ to $L^3$ are each independently a single bond, a substituted or unsubstituted C6 to C20 arylene group, or a substituted or unsubstituted C2 to C30 heterocyclic group, $Ar^1$ is a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted chrysenyl group, or a substituted or unsubstituted triphenylene group, $Ar^2$ and $Ar^3$ are each independently a substituted or unsubstituted C6 to C20 aryl group or a substituted or unsubstituted C2 to C30 heterocyclic group, $R^1$ to $R^3$ are each independently hydrogen, deuterium, a halogen, a substituted or unsubstituted C1 to C10 alkyl group, or a substituted or unsubstituted C6 to C12 aryl group, m1 and m2 are each independently an integer of 1 to 3, m3 is an integer of 1 to 4, n is 0 or 1, and "substituted" refers to replacement of at least one hydrogen of a substituent or a compound by deuterium, a halogen, a hydroxyl group, an amino group, a C1 to C30 amine group, a nitro group, a C1 to C40 silyl group, a C1 to C30 alkyl group, a C1 to C10 alkylsilyl group, a C6 to C30 arylsilyl group, a C3 to C30 heterocycloalkyl group, a C6 to C30 aryl group, a C2 to C30 heteroaryl group, a C1 to C20 alkoxy group, a C1 to C10 trifluoroalkyl group, or a combination thereof, and wherein moieties $*-L^2-Ar^2$ and $*-L^3-Ar^3$ of Chemical Formula 1 do not include a thiophene group.

2. The compound as claimed in claim 1, wherein $Ar^1$ is a biphenyl group that is unsubstituted or substituted with deuterium or a C6 to C12 aryl group, a terphenyl group that is unsubstituted or substituted with deuterium or a C6 to C12 aryl group, a naphthyl group that is unsubstituted or substituted with deuterium or a C6 to C12 aryl group, or a phenanthrenyl group that is unsubstituted or substituted with deuterium or a C6 to C12 aryl group.

3. The compound as claimed in claim 1, wherein $Ar^2$ and $Ar^3$ are each independently a substituted or unsubstituted phenyl group, a substituted or unsubstituted biphenyl group, a substituted or unsubstituted naphthyl group, a substituted or unsubstituted phenanthrenyl group, a substituted or unsubstituted chrysenyl group, a substituted or unsubstituted fluorenyl group, a substituted or unsubstituted benzofluorenyl group, a substituted or unsubstituted benzophenanthrenyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuranyl group, a substituted or unsubstituted benzonaphthothiophenyl group, a substituted or unsubstituted benzooxazolyl group, or a substituted or unsubstituted phenanthrooxazolyl group.

4. The compound as claimed in claim 1, wherein:

moieties $L^2-Ar^2$ and $L^3-Ar^3$ of Chemical Formula 1 are each independently a moiety of Group I:

[Group I]

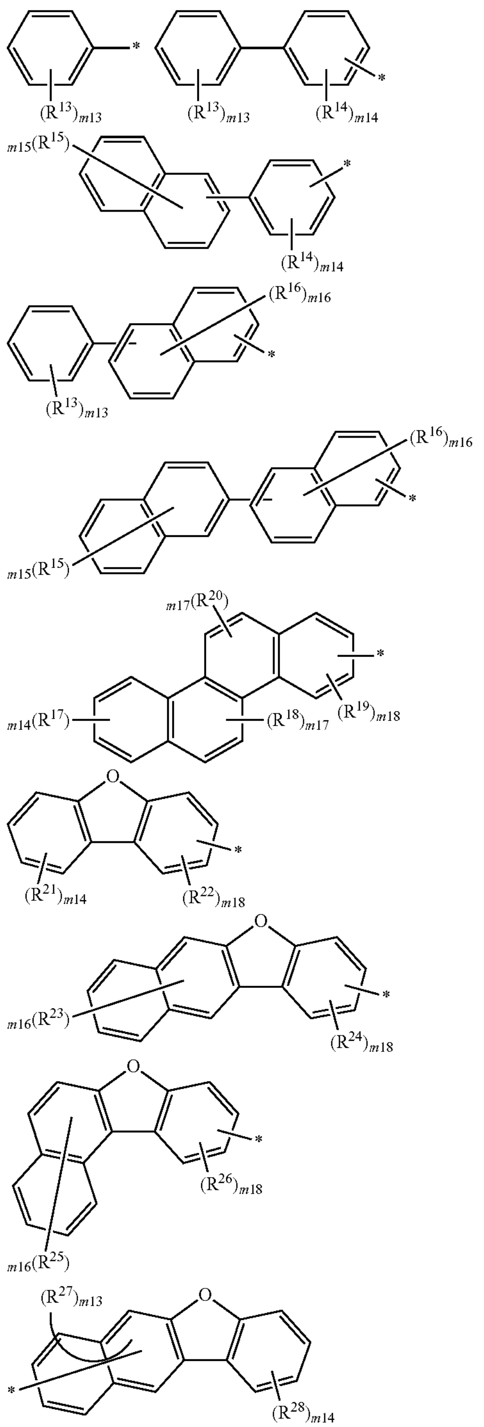

-continued
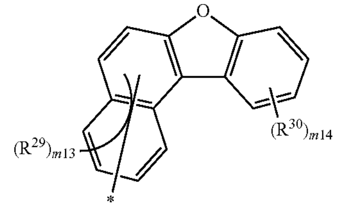
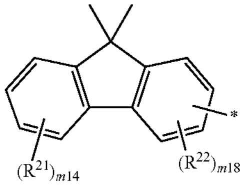
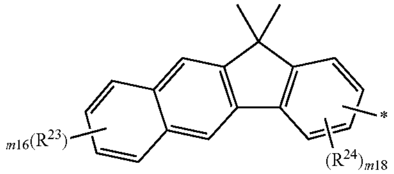
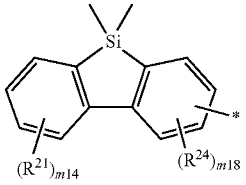
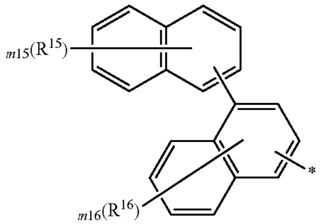
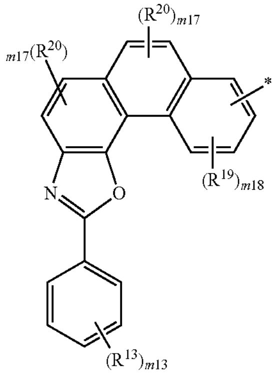
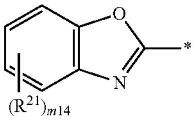
in Group I,
$R^{13}$ to $R^{30}$ are each independently hydrogen, deuterium, a halogen, a C1 to C10 alkyl group, or a C6 to C12 aryl group,
m13 is an integer of 1 to 5,
m14 is an integer of 1 to 4,
m15 is an integer of 1 to 7,
m16 is an integer of 1 to 6,
m17 is an integer of 1 or 2,
m18 is an integer of 1 to 3, and
* is a linking point.
5. The compound as claimed in claim 1, wherein the compound is a compound of Group 1:
[Group 1]
1-1
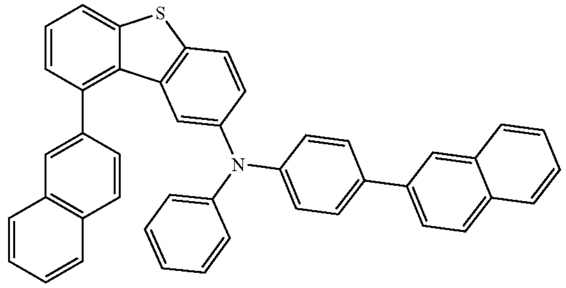
1-2
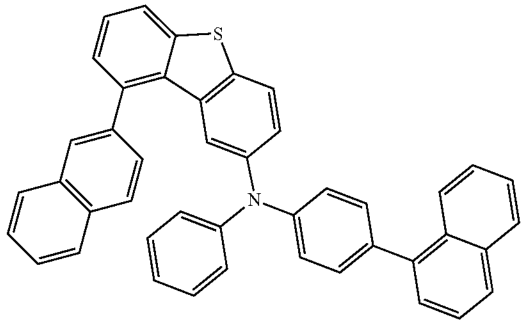
1-3
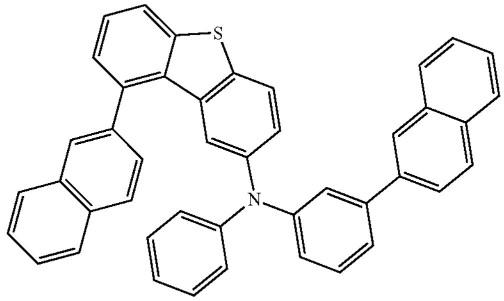
1-4
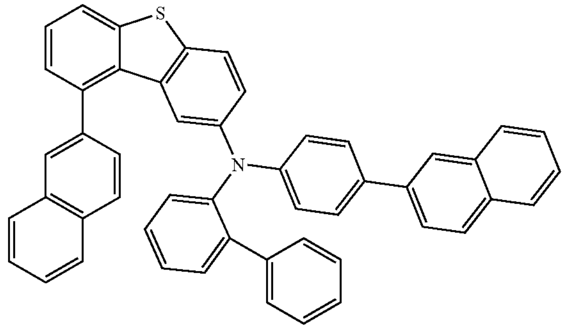

-continued
1-5
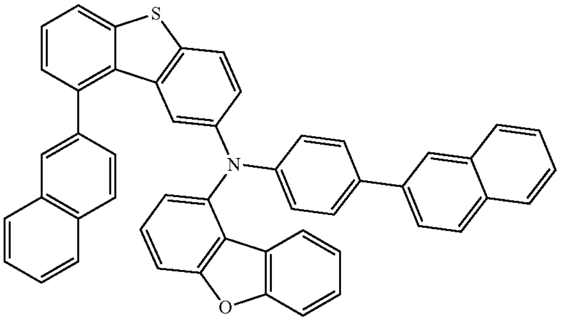
1-6
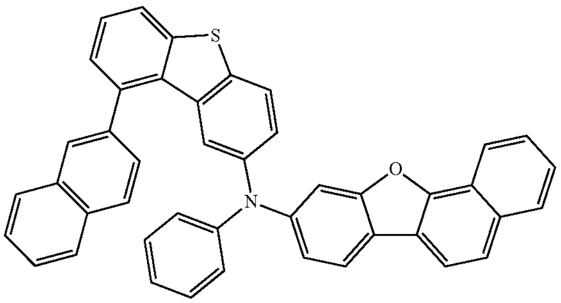
1-7
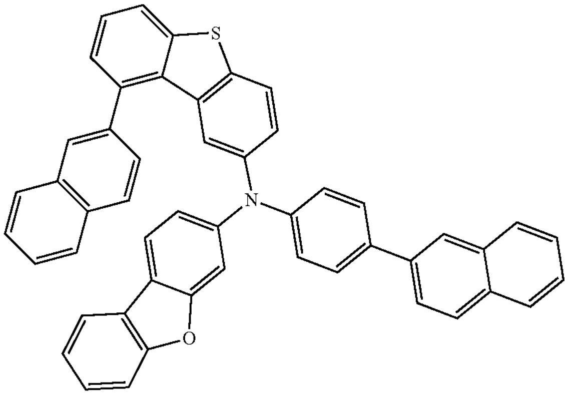
1-8
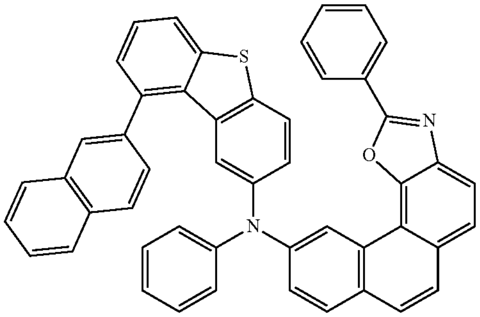
-continued
1-9
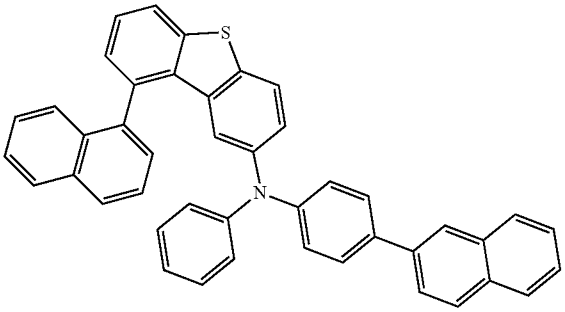
1-10
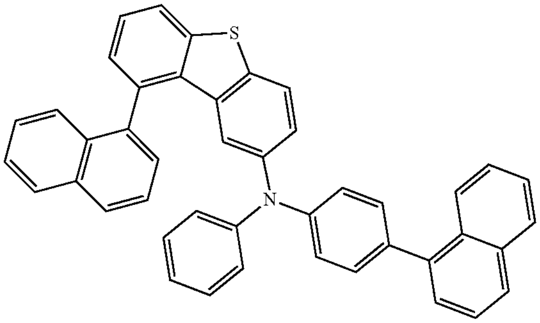
1-11
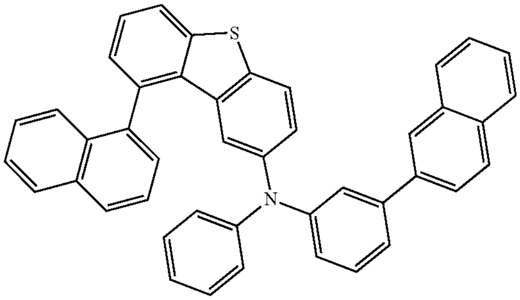
1-12
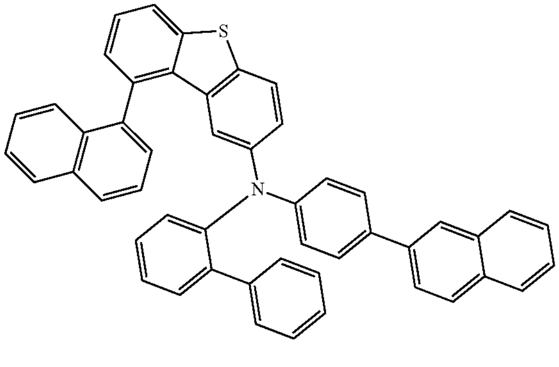

-continued
1-13
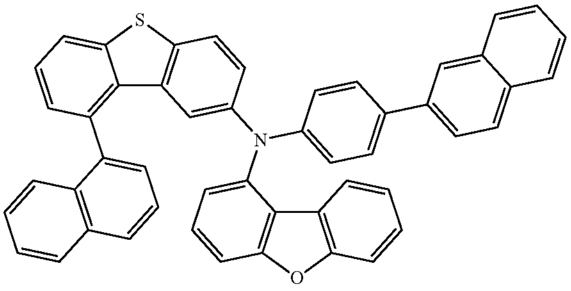
1-14
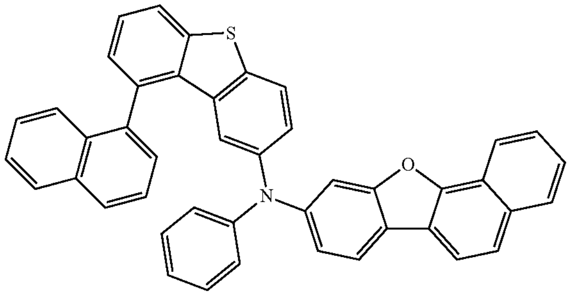
1-15
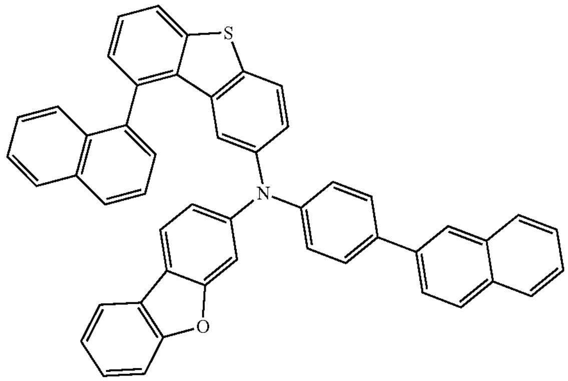
1-16
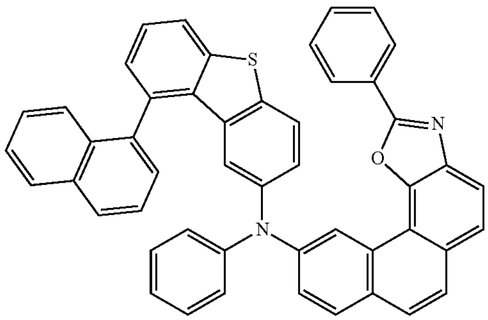
-continued
1-17
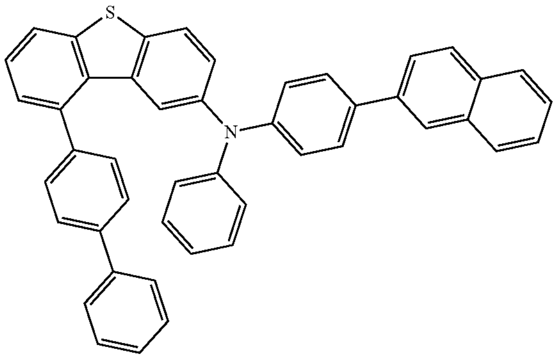
1-18
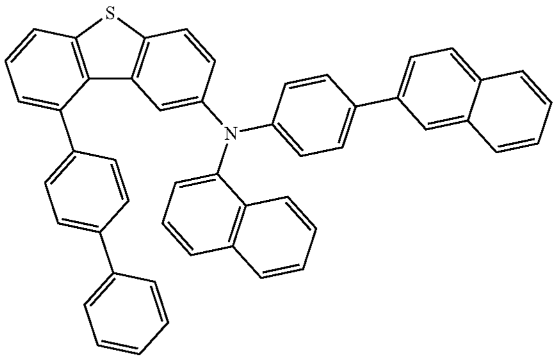
1-19
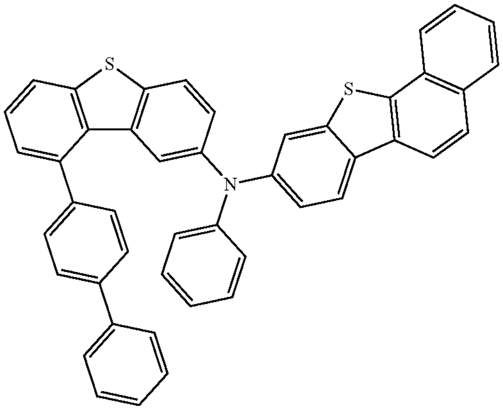
1-20
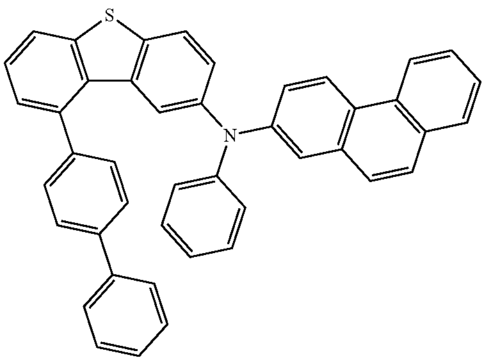

-continued
1-21
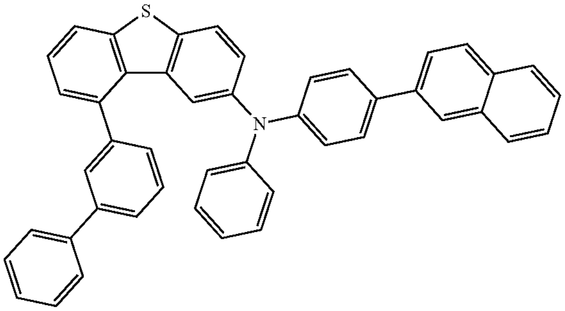
1-22
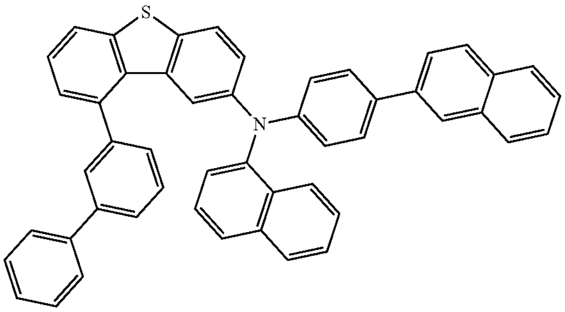
1-23
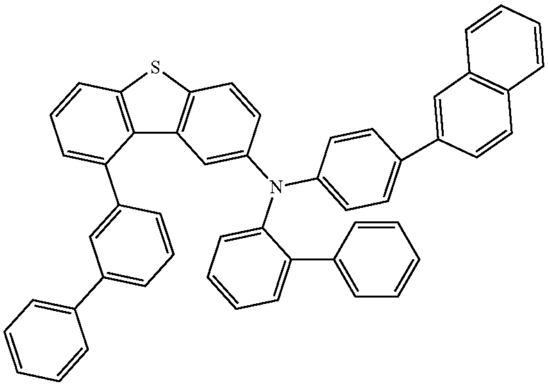
1-24
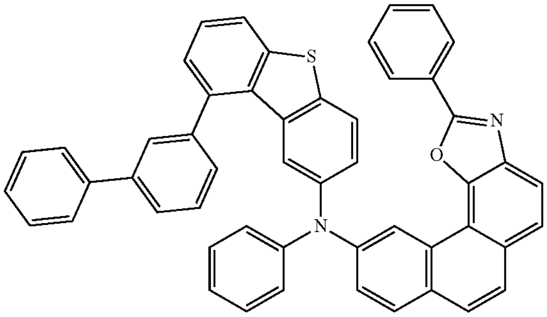
-continued
1-25
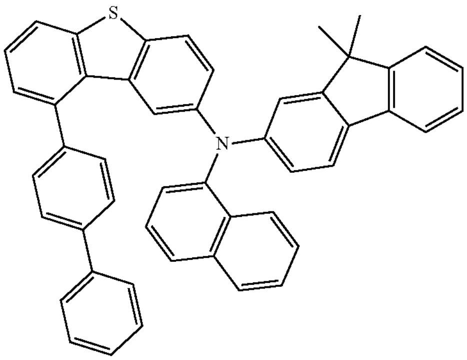
1-26
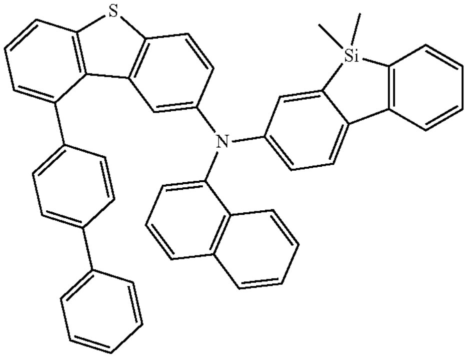
1-27
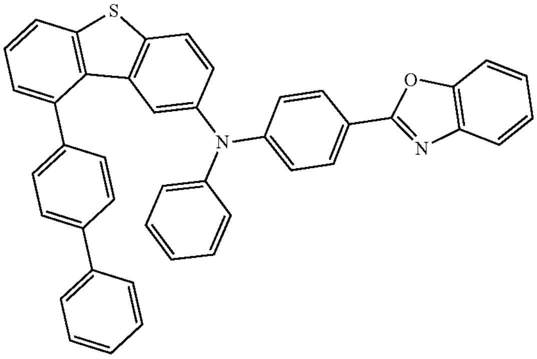
1-28
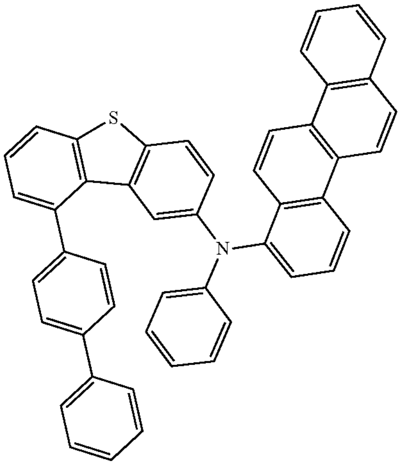

-continued
1-29
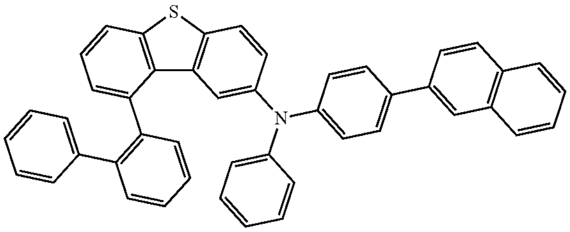
1-30
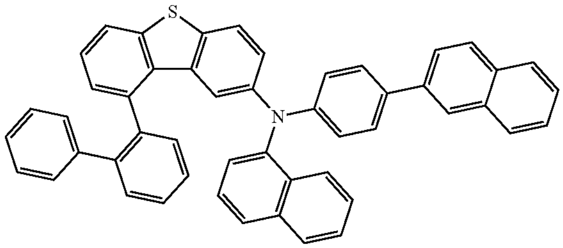
1-31
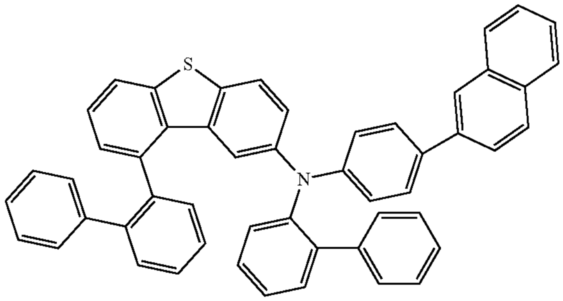
1-32
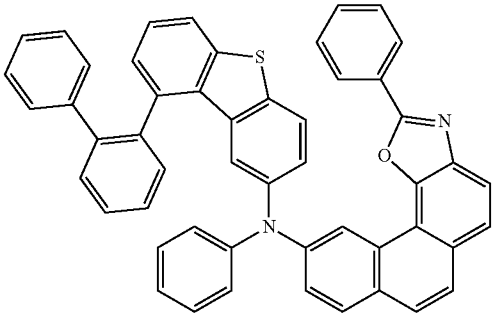
1-33
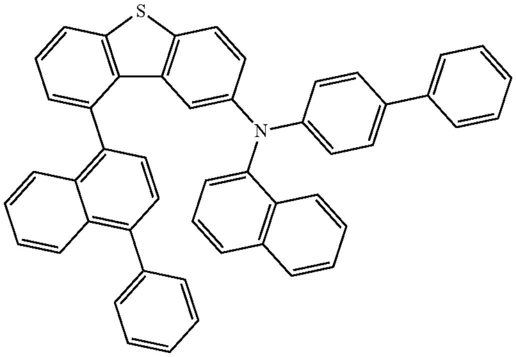
-continued
1-34
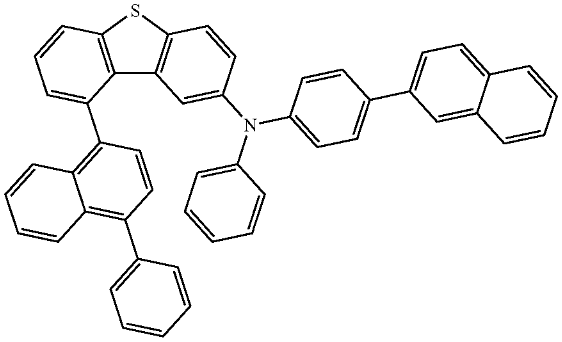
1-35
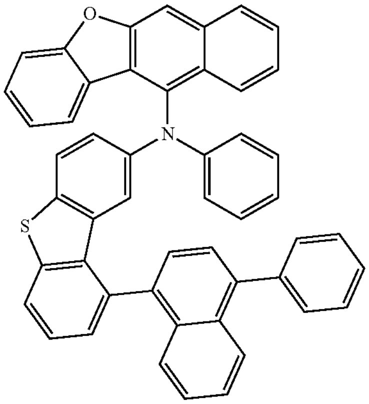
1-36
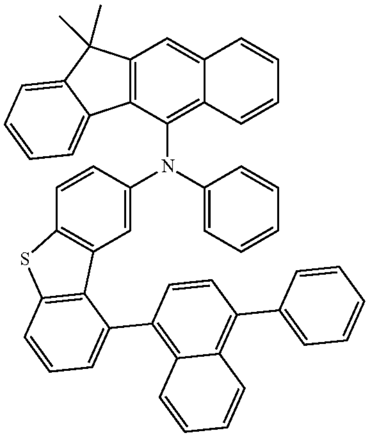

-continued
1-37
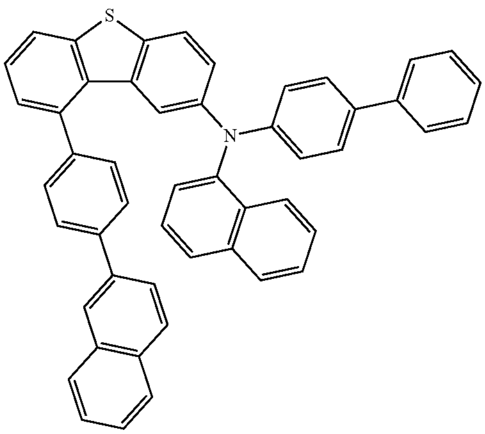
1-38
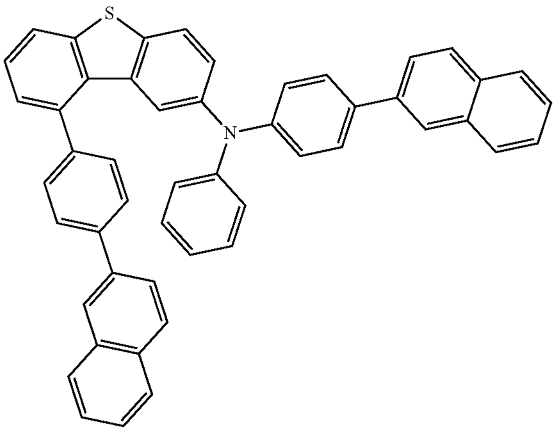
1-39
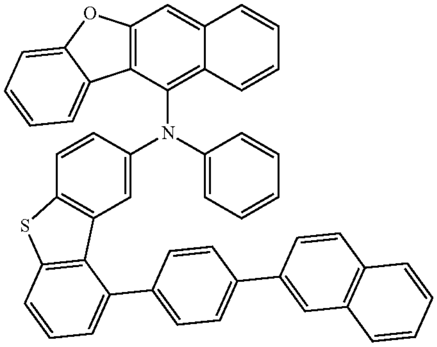
1-40
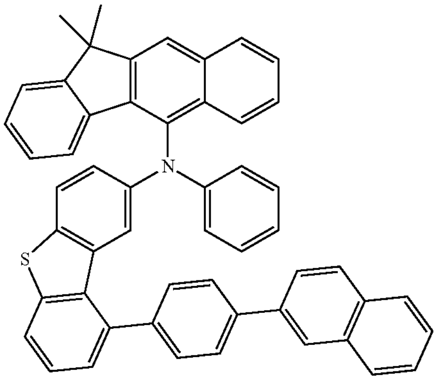
-continued
1-41
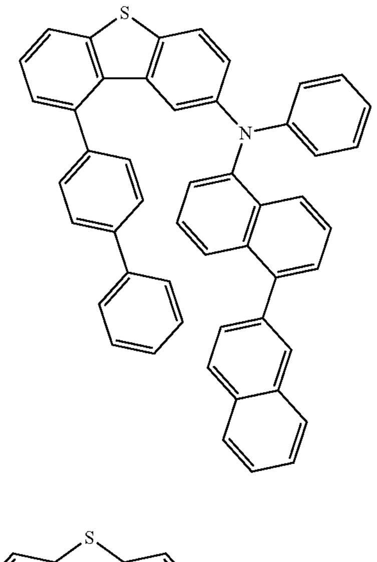
1-42
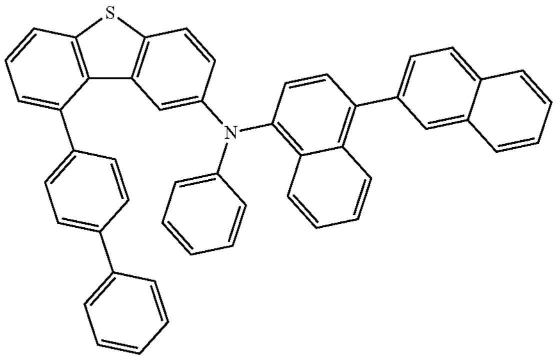
1-43
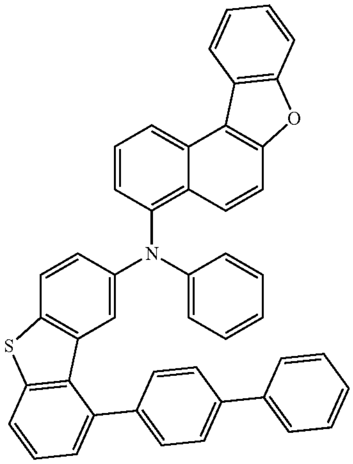

1-44
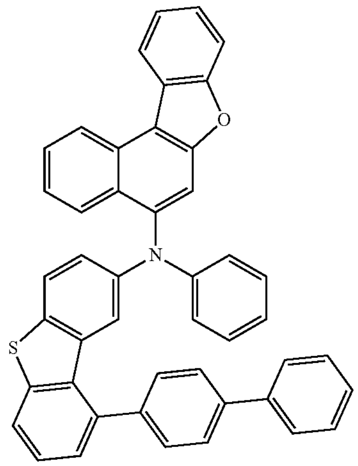
1-45
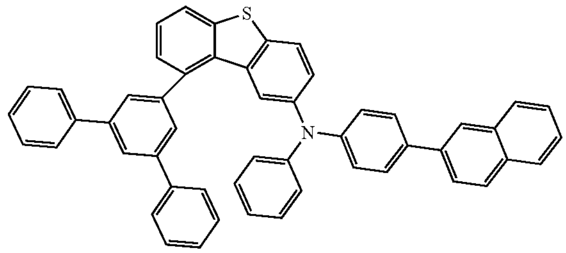
1-46
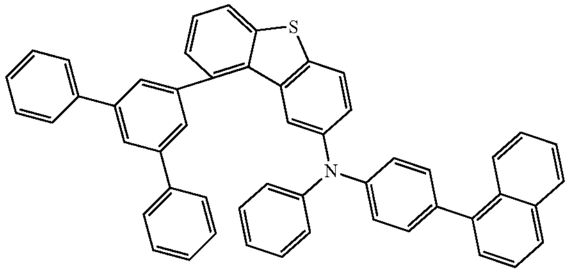
1-47
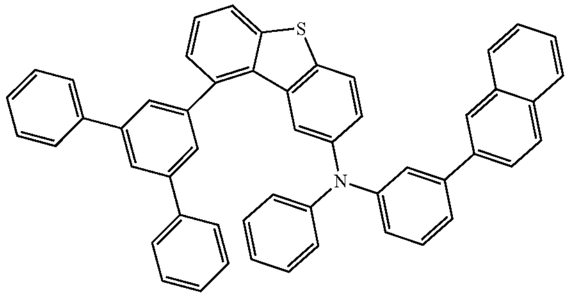
1-48
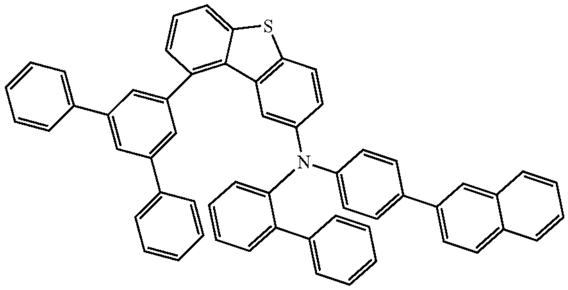
1-49
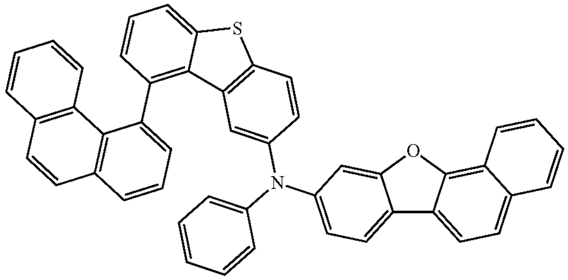
1-50
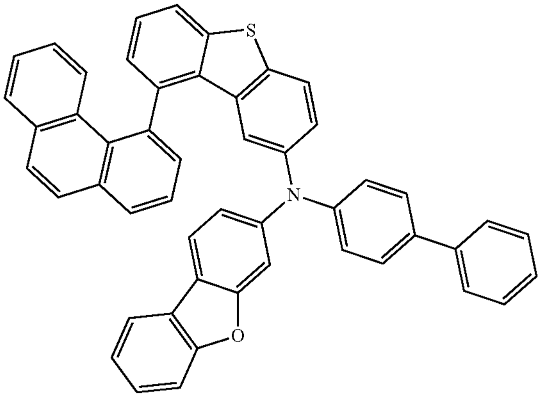
1-51
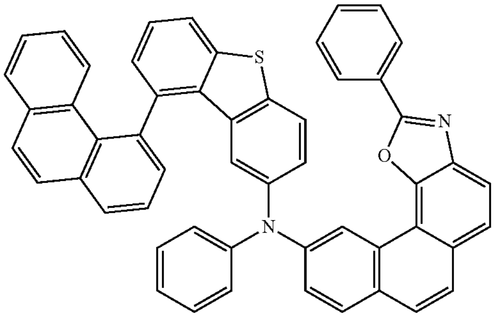

-continued
1-52
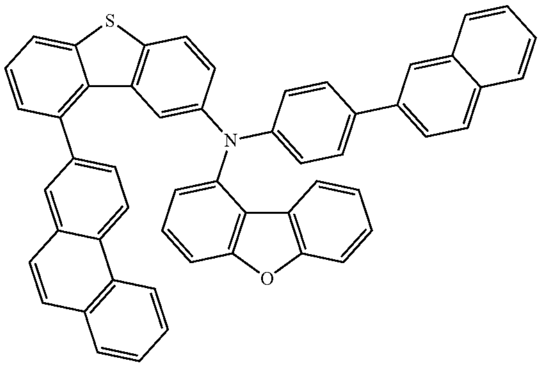
1-53
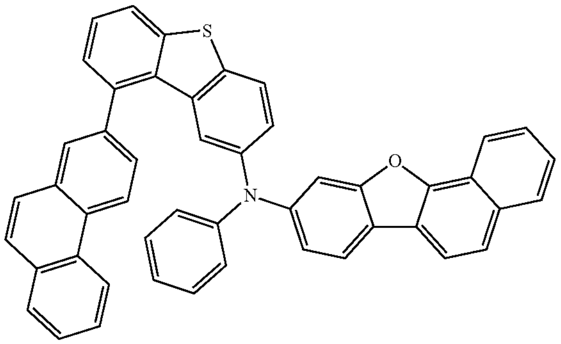
1-54
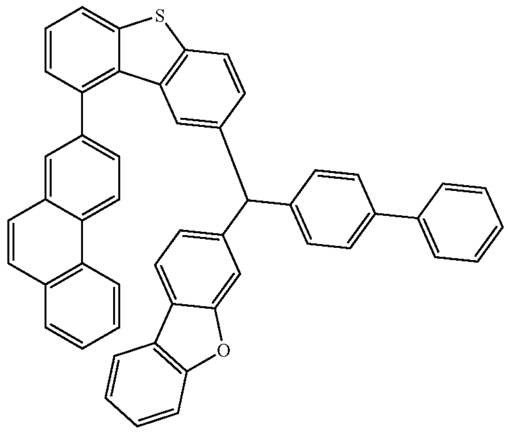
1-55
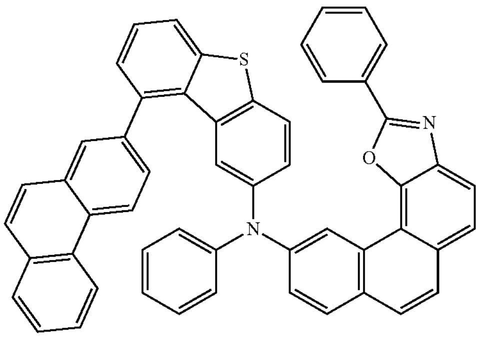
-continued
1-56
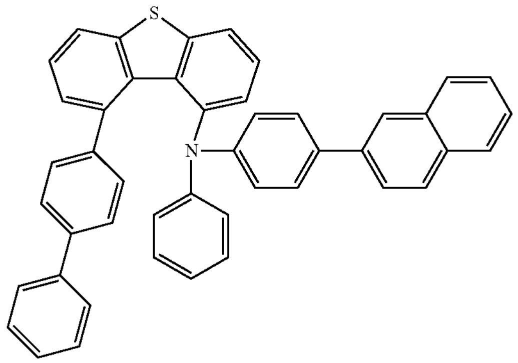
1-57
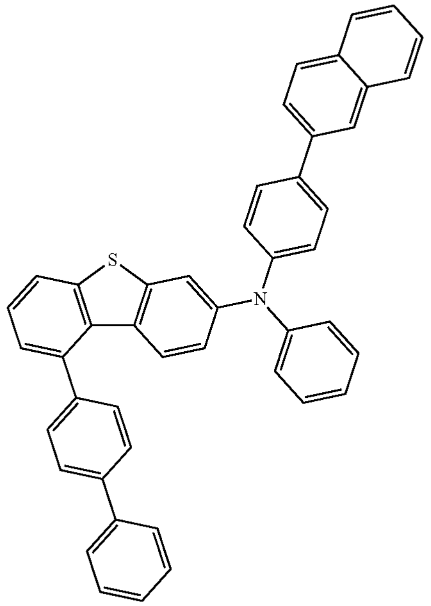
1-58
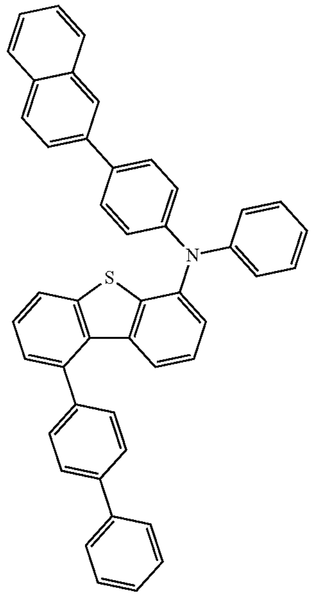

-continued
1-59
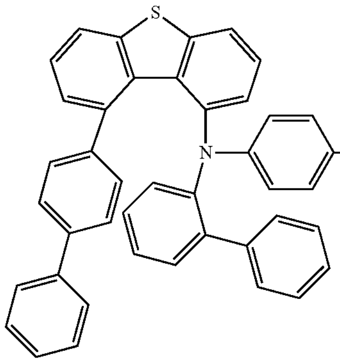
1-60
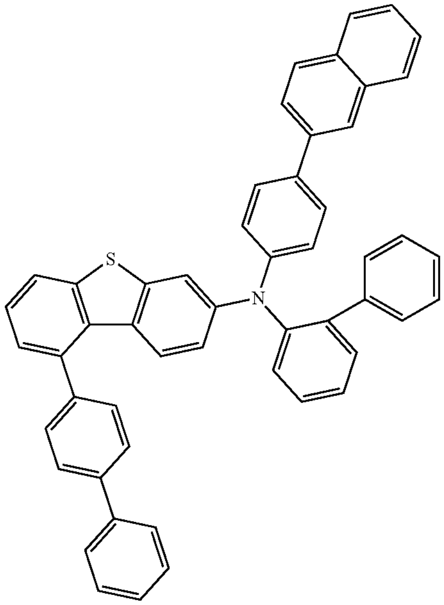
1-61
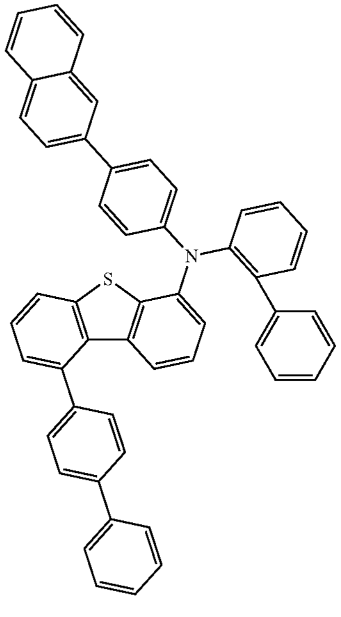
-continued
1-62
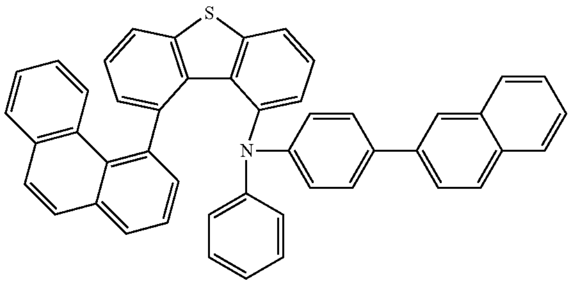
1-63
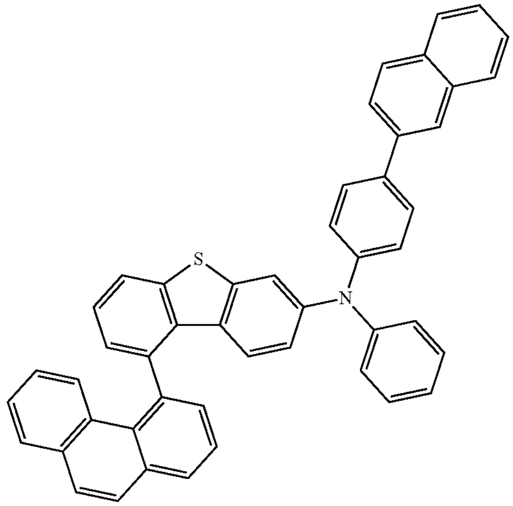
1-64
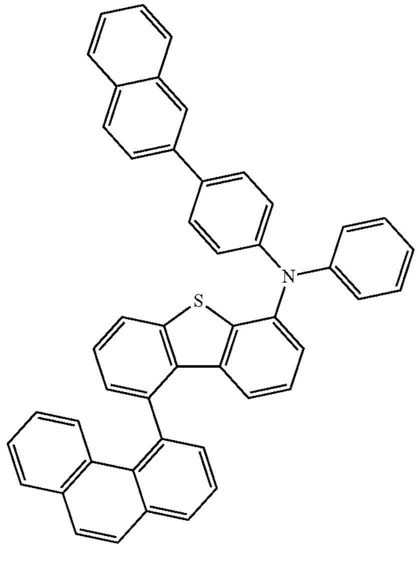

-continued
1-65
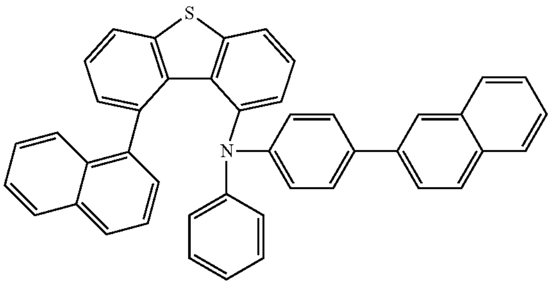
1-66
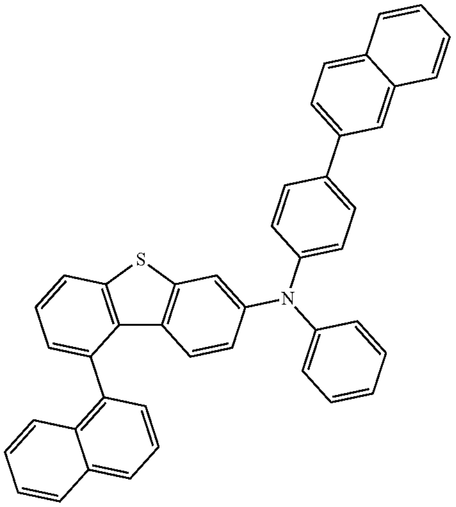
1-67
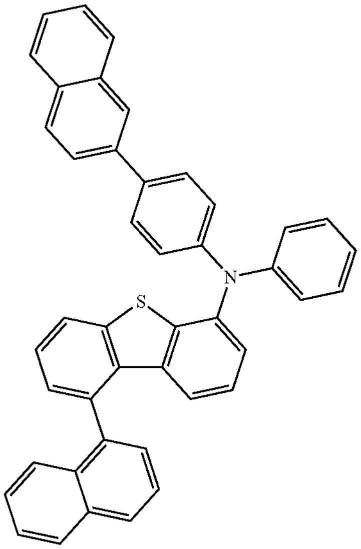
-continued
1-68
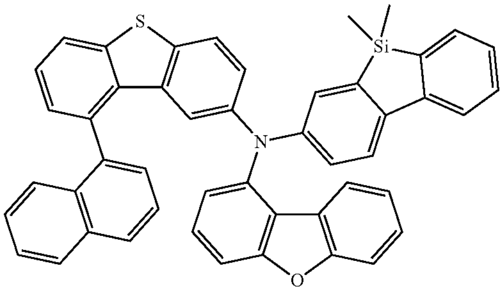
1-69
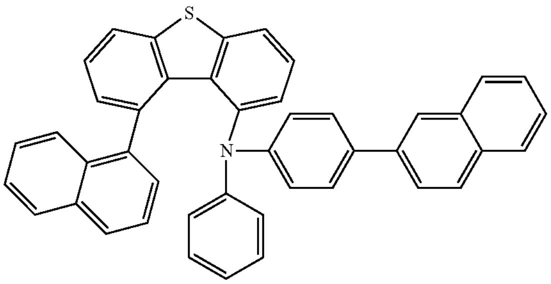
1-70
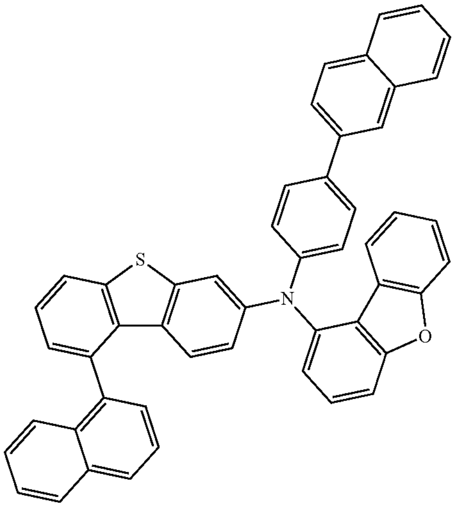

-continued
1-71
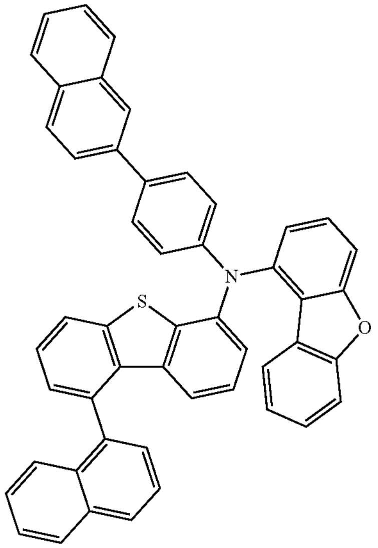
1-72
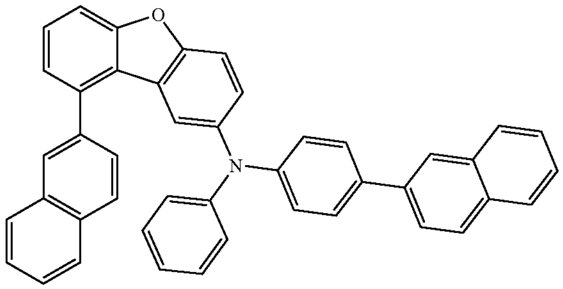
1-73
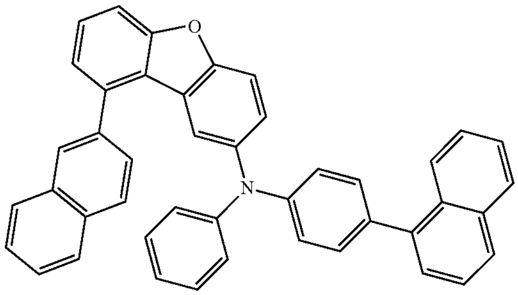
1-74
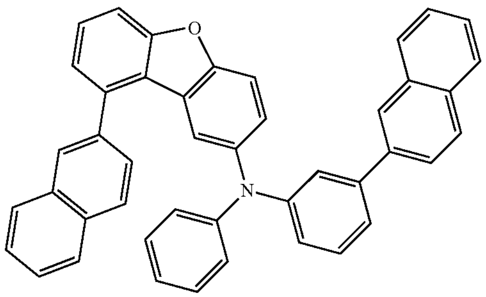
-continued
1-75
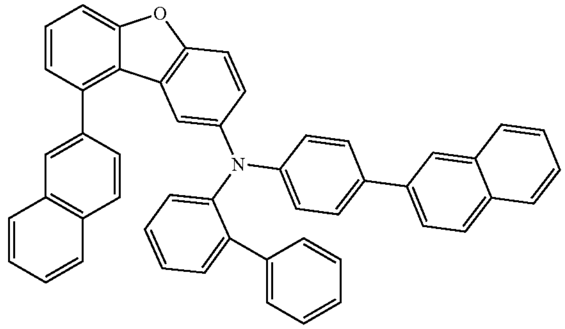
1-76
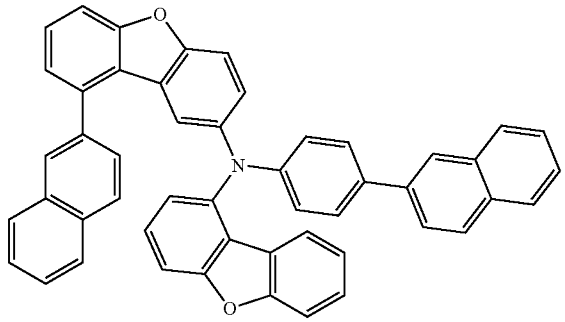
1-77
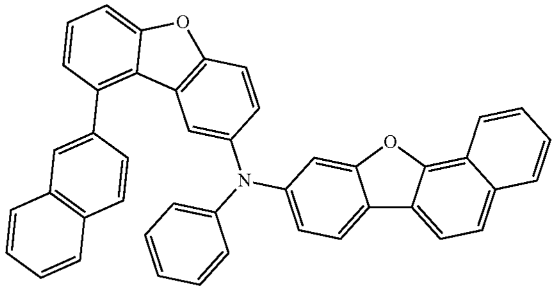
1-78
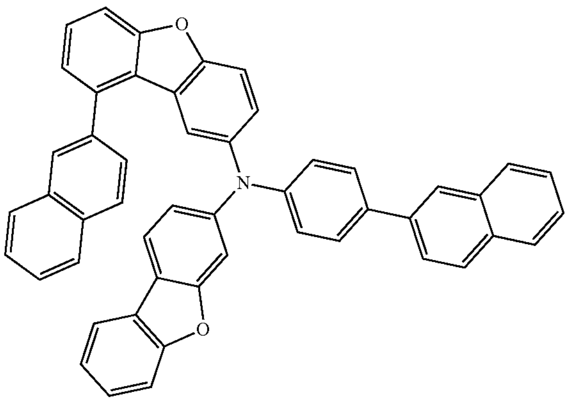

-continued
1-79
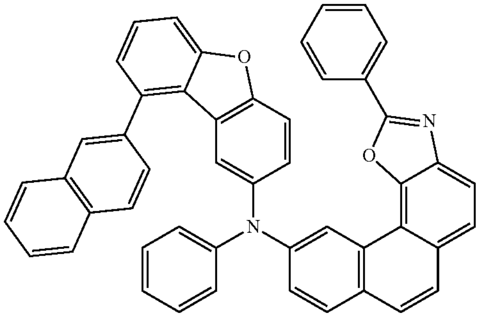
1-80
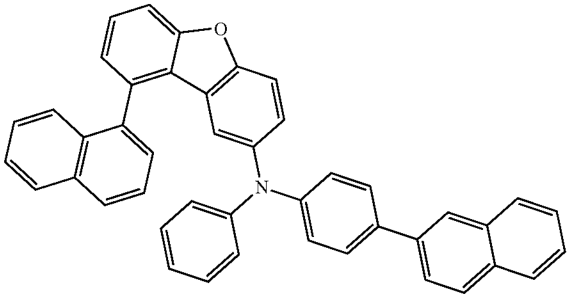
1-81
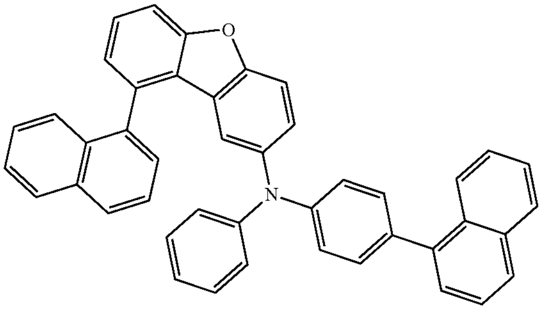
1-82
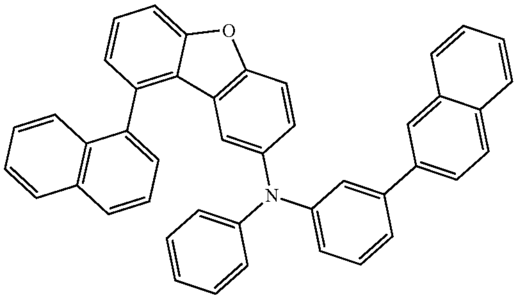
-continued
1-83
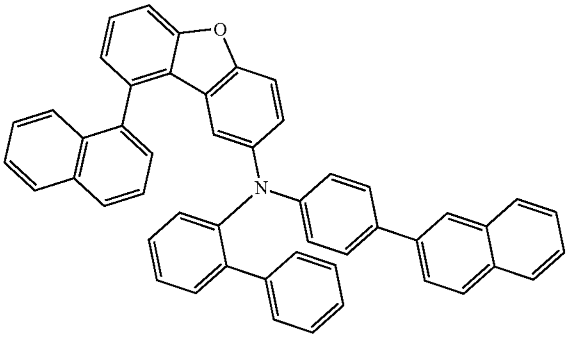
1-84
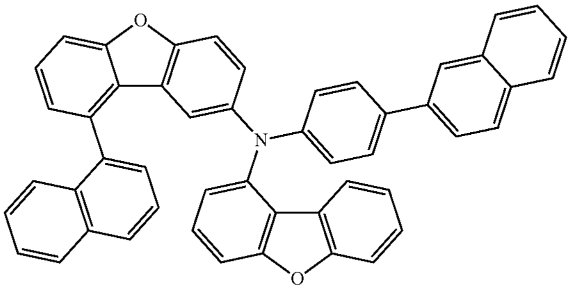
1-85
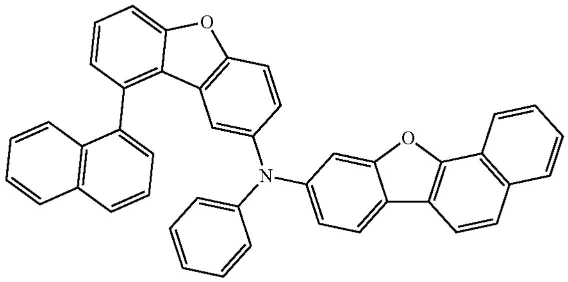
1-86
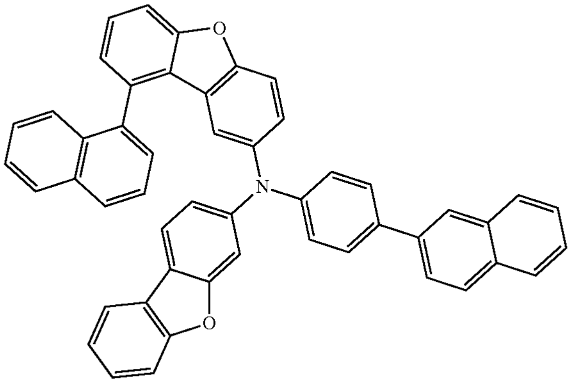

-continued
1-87
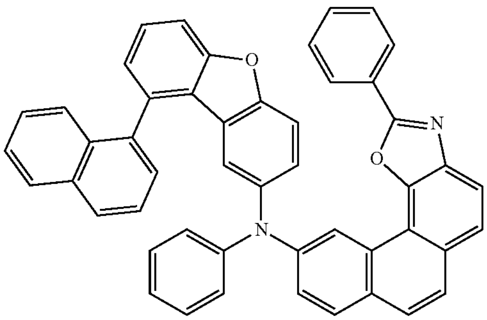
1-88
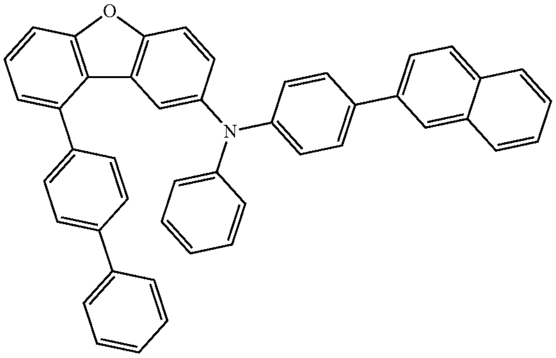
1-89
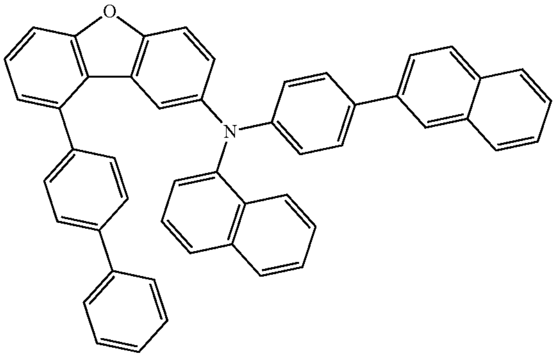
1-91
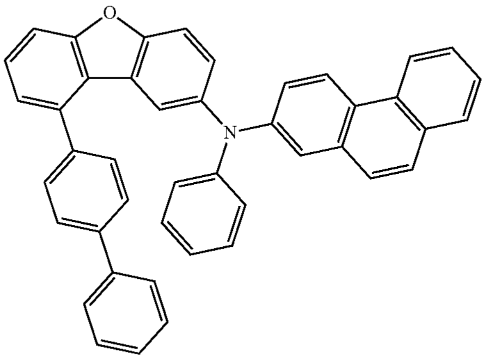
-continued
1-92
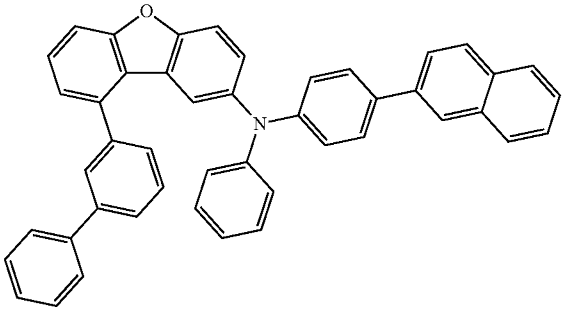
1-93
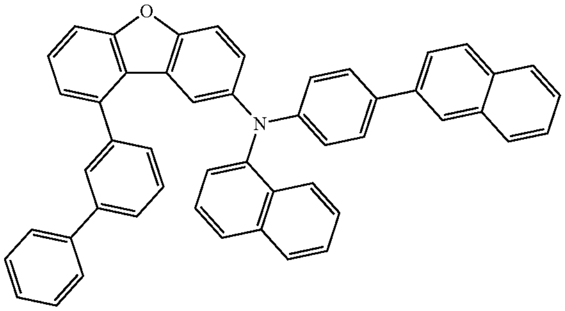
1-94
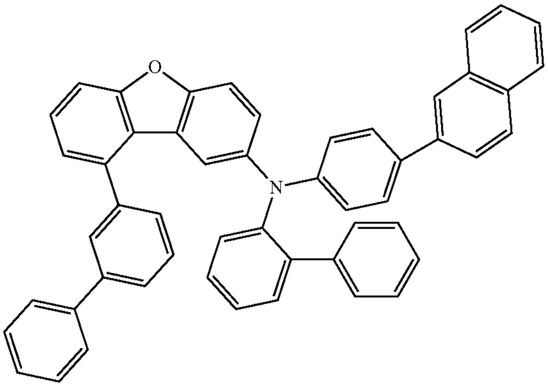
1-95
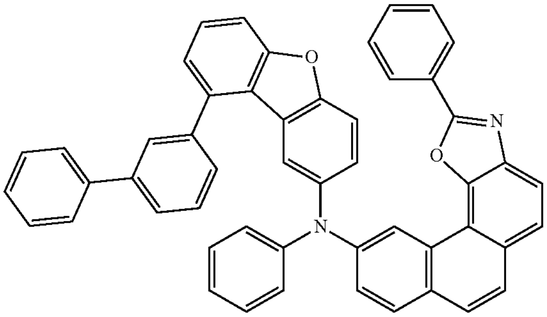

-continued
1-96
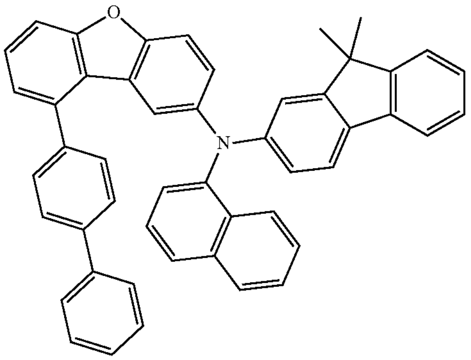
1-97
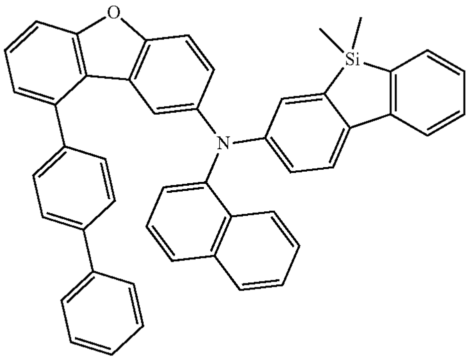
1-98
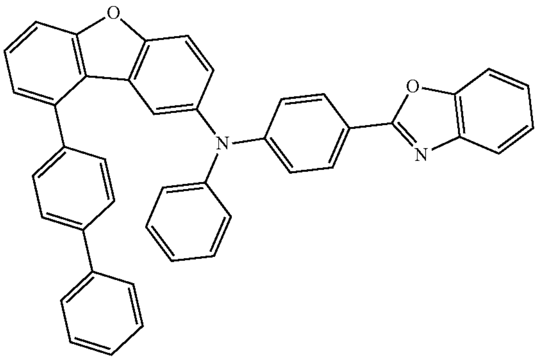
1-99
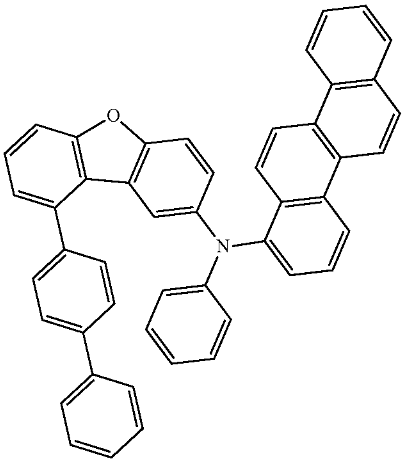
-continued
1-100
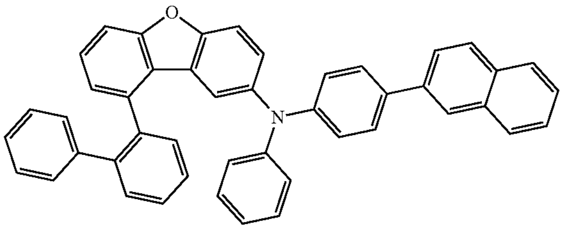
1-101
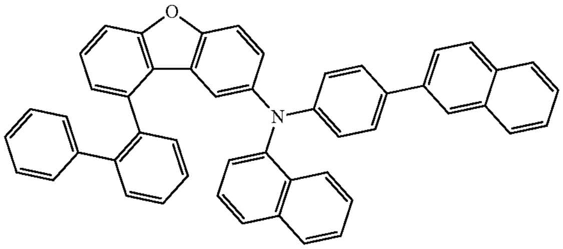
1-102
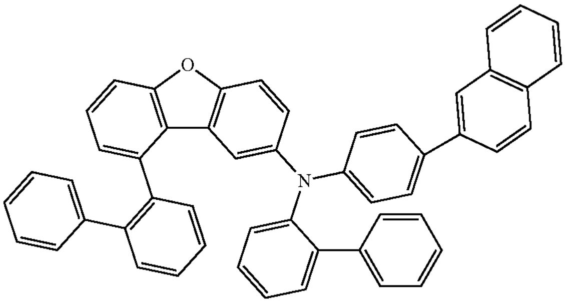
1-103
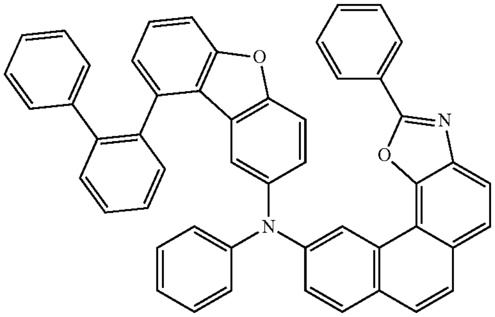
1-104
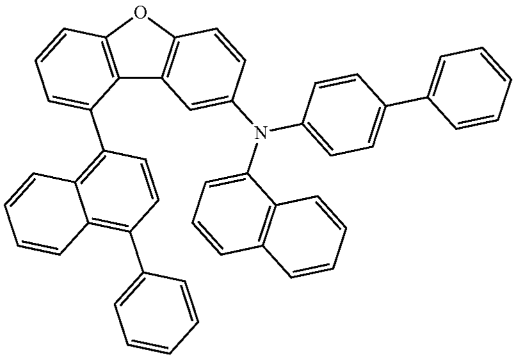

-continued
1-105
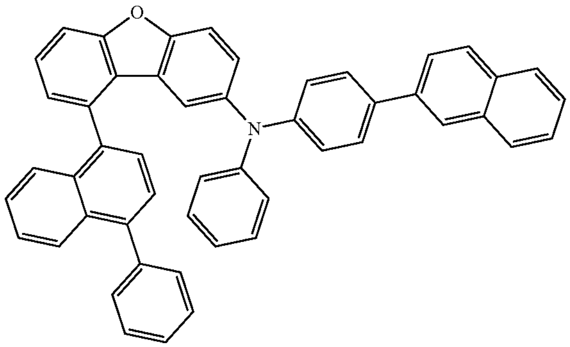
1-106
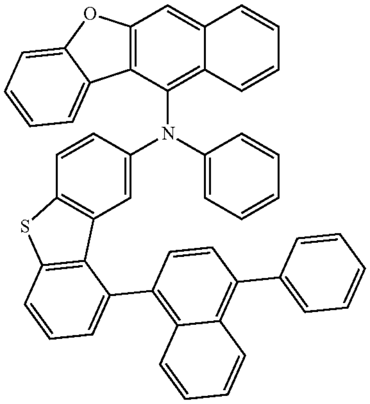
1-107
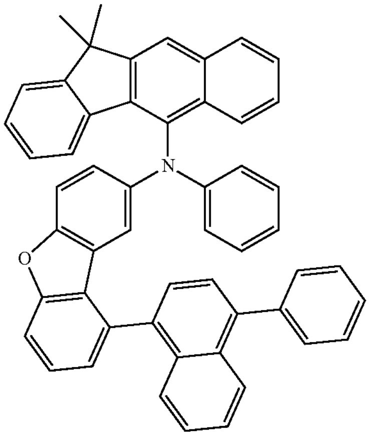
-continued
1-108
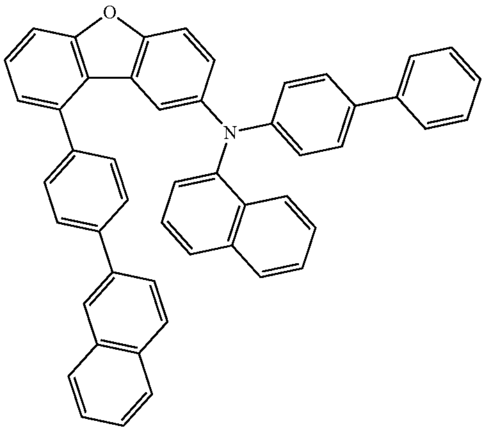
1-109
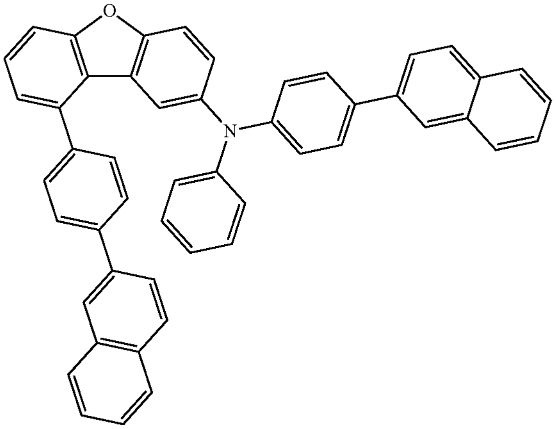
1-110
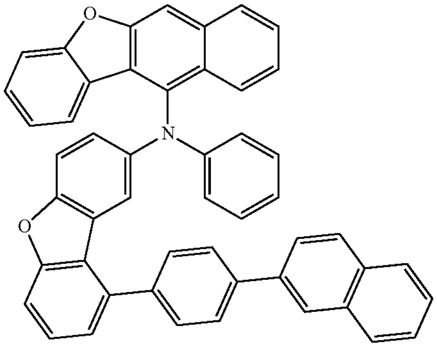
1-111
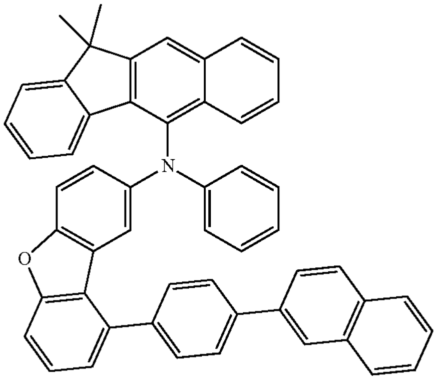

-continued
1-112
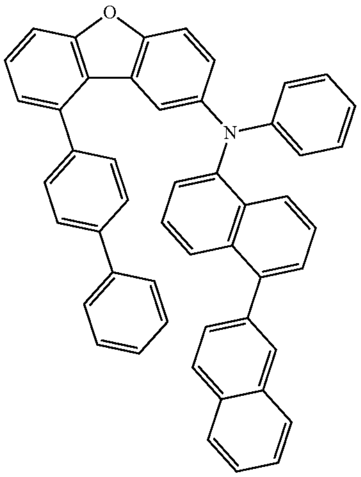
1-113
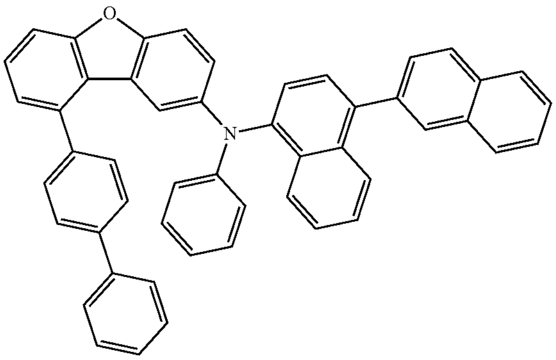
1-114
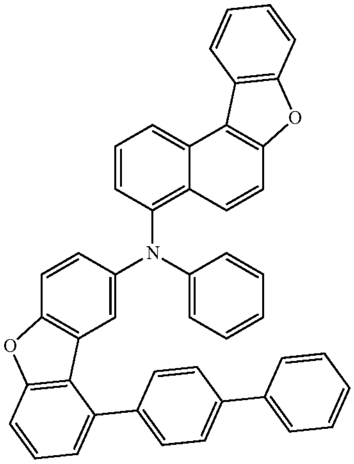
-continued
1-115
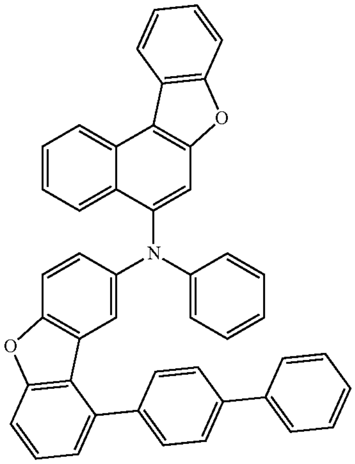
1-116
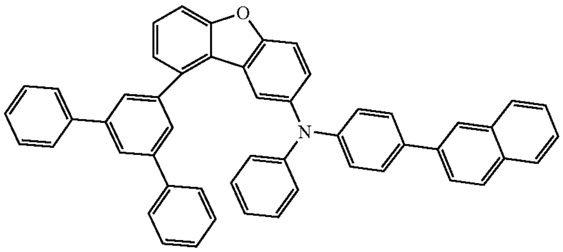
1-117
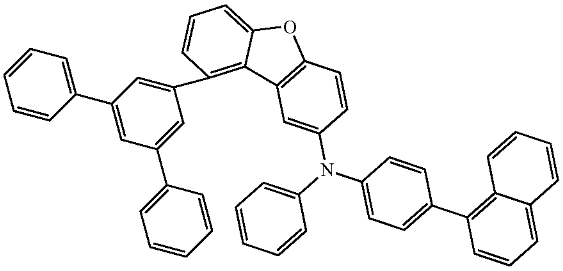
1-118
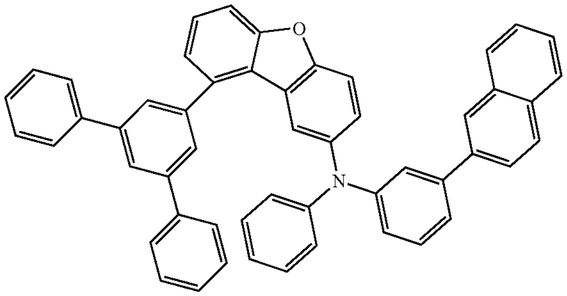

-continued
1-119
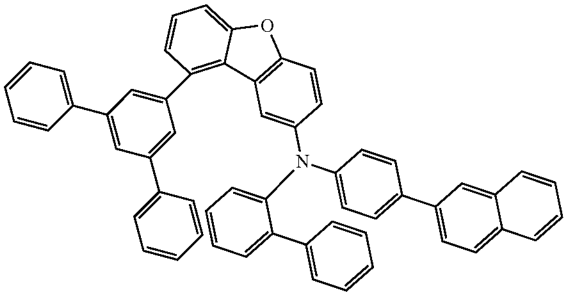
1-120
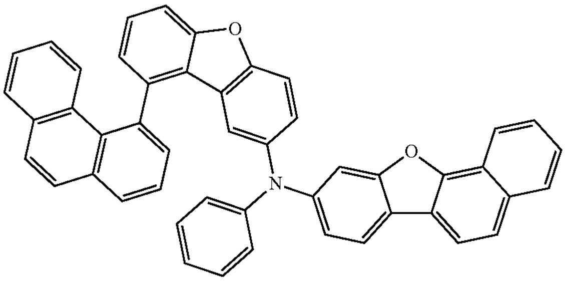
1-121
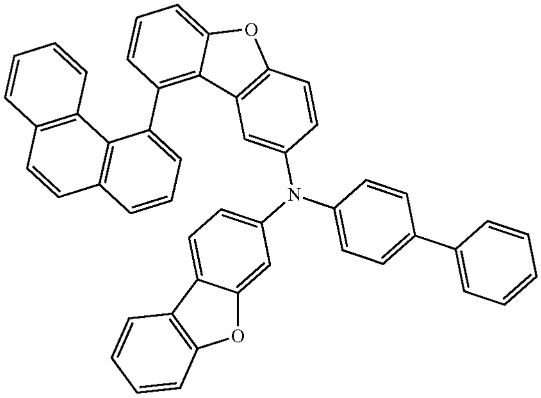
1-122
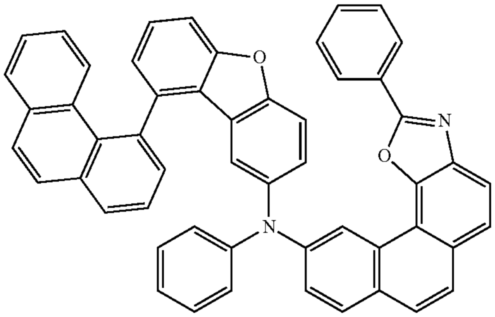
-continued
1-123
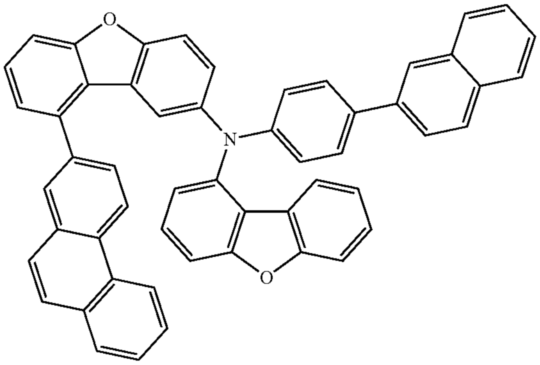
1-124
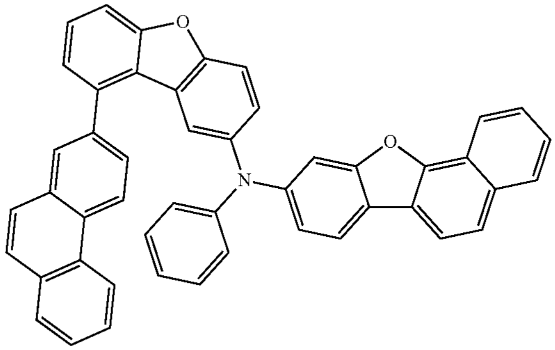
1-125
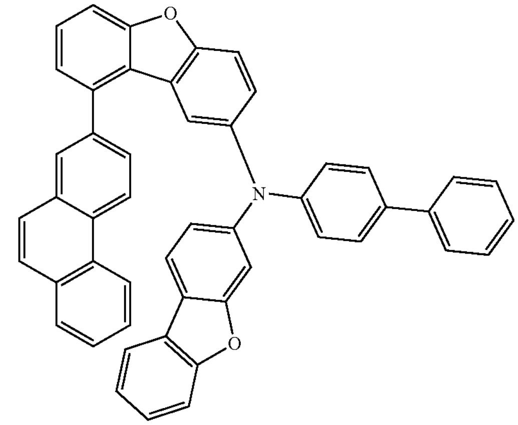
1-126
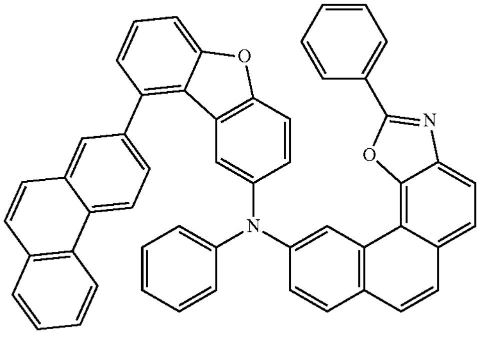

-continued
1-127
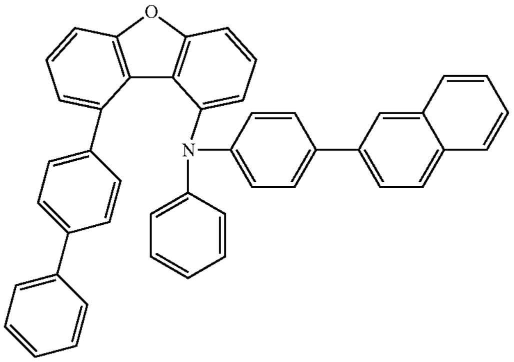
1-128
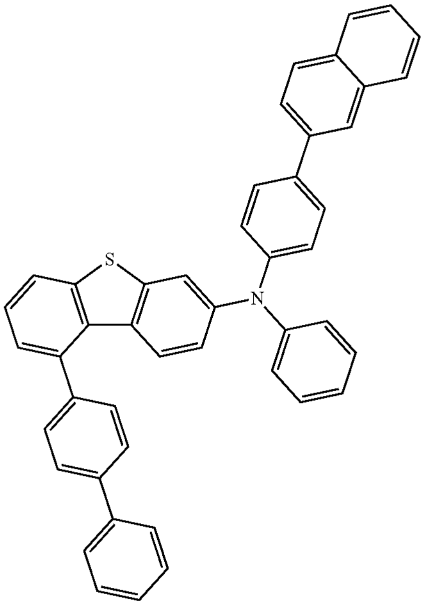
1-129
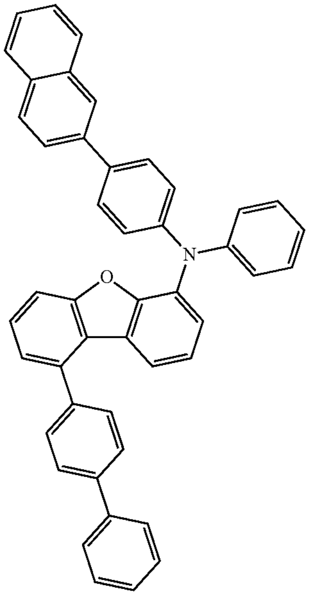
-continued
1-130
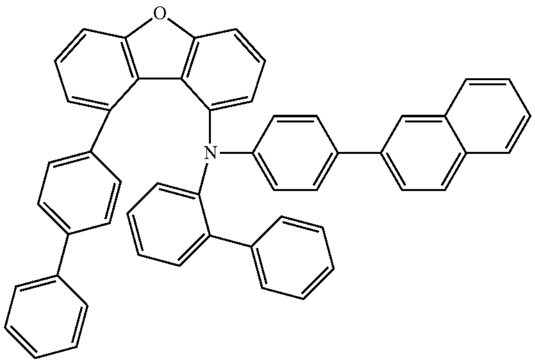
1-131
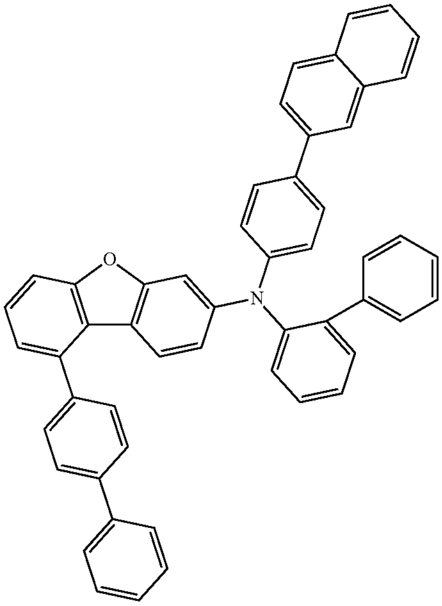
1-132
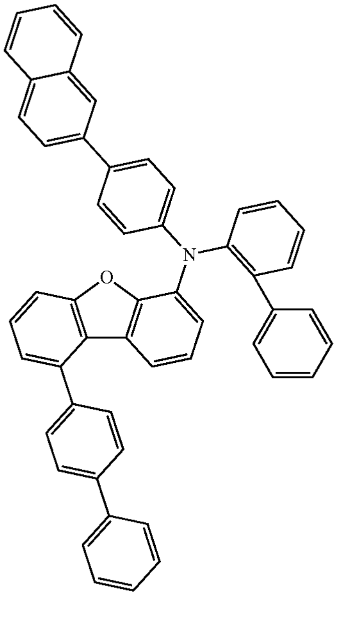

-continued
1-133
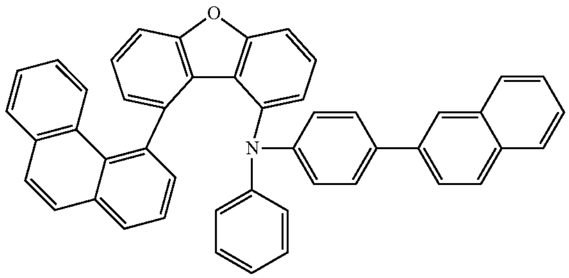
1-134
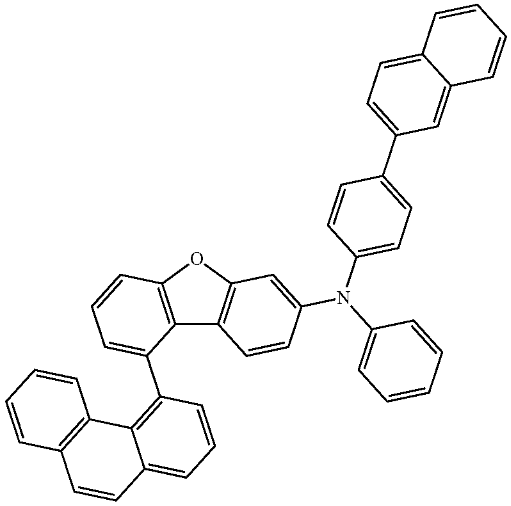
1-135
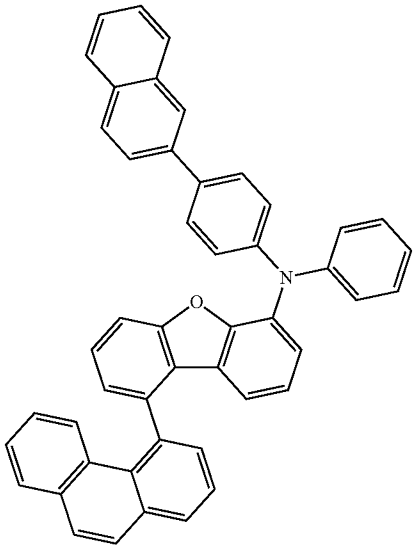
-continued
1-136
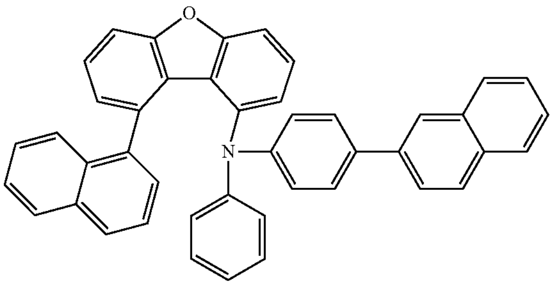
1-137
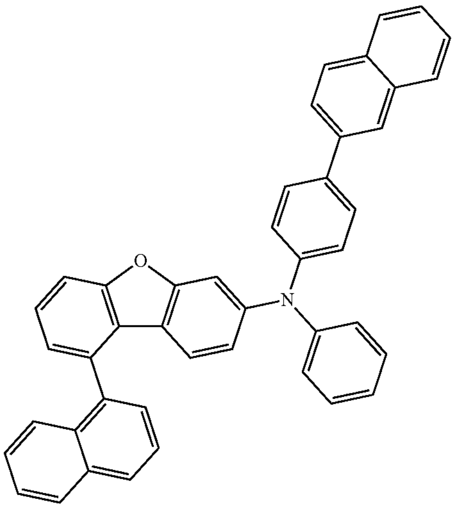
1-138
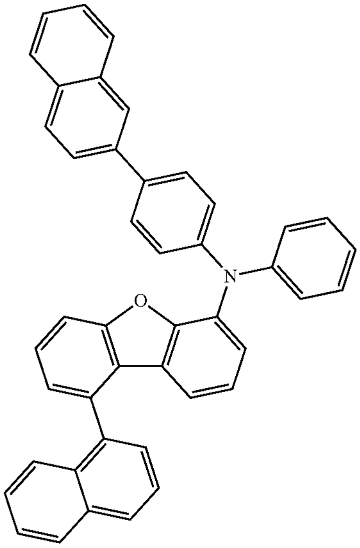

1-139
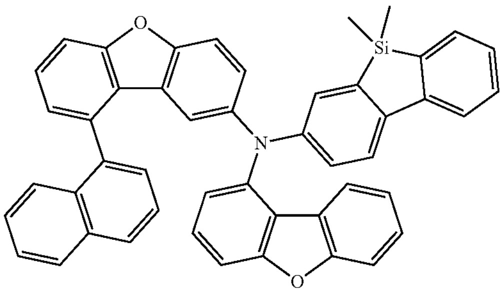
1-140
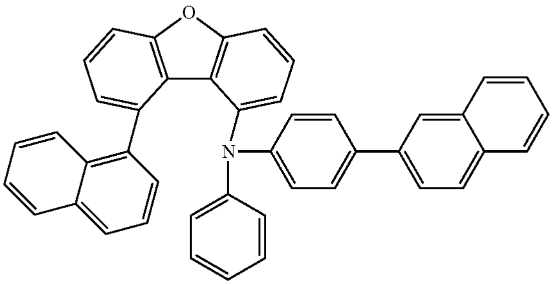
1-141
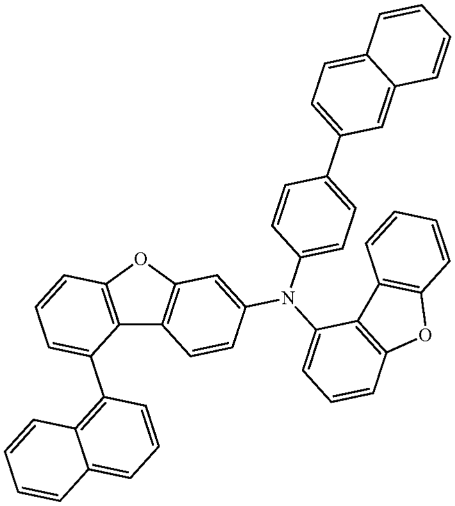
1-142
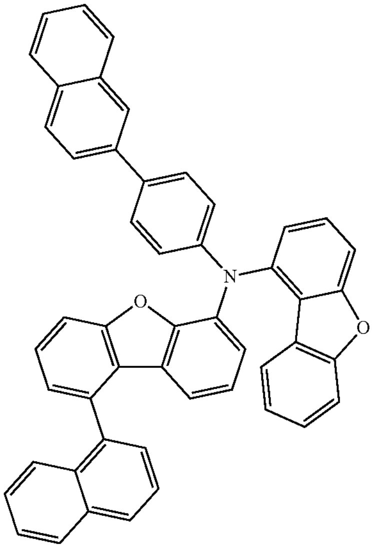
1-143
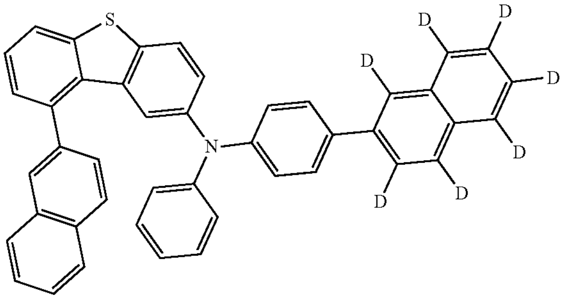
1-144
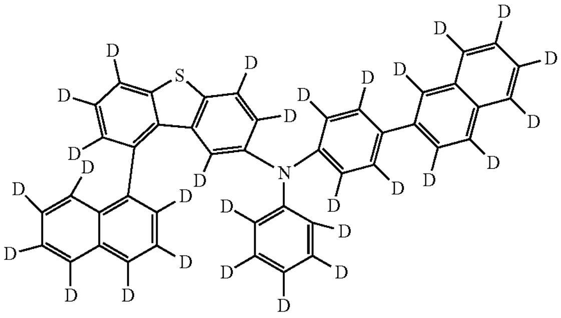
1-145
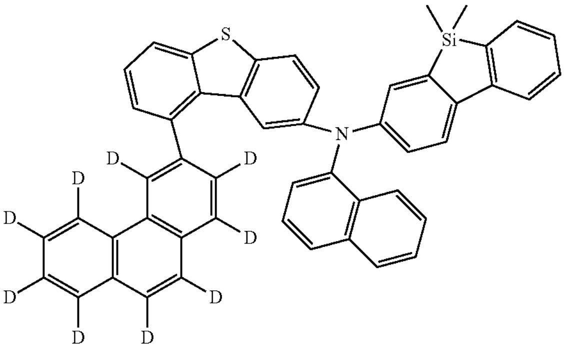

-continued
1-146
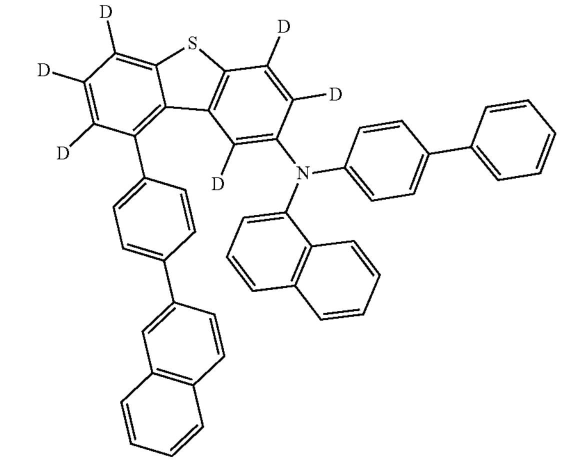
1-147
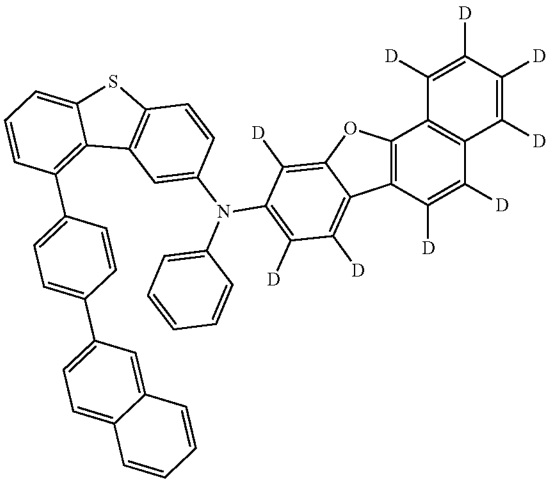
1-148
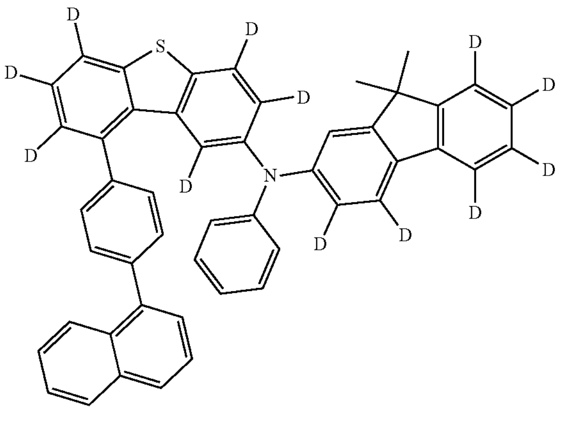
-continued
1-149
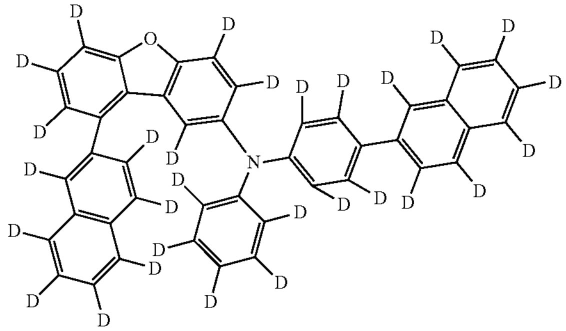
1-150
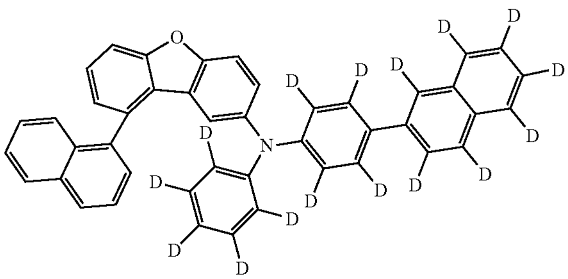
1-151
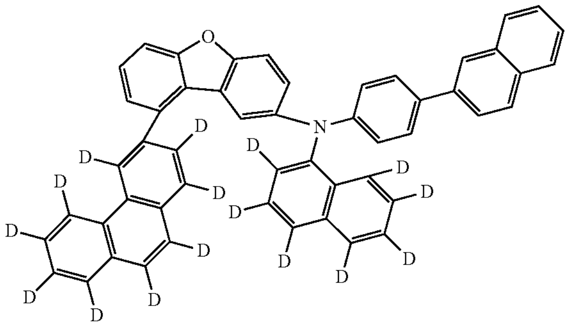
1-153
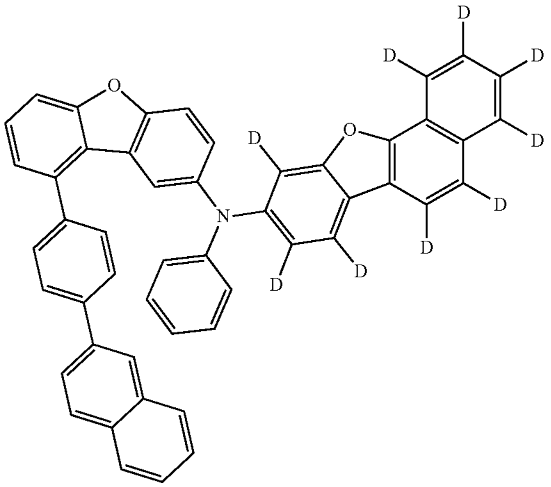

-continued 1-154

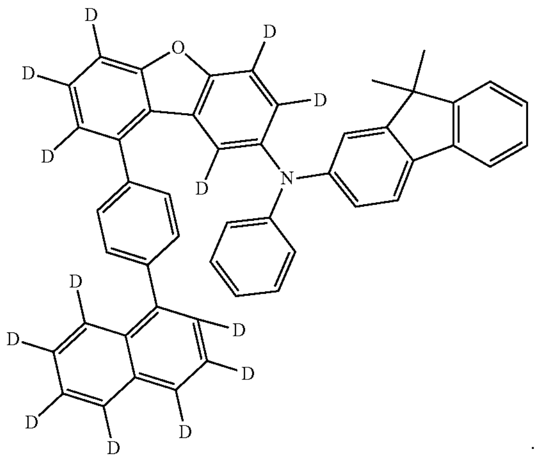

-continued

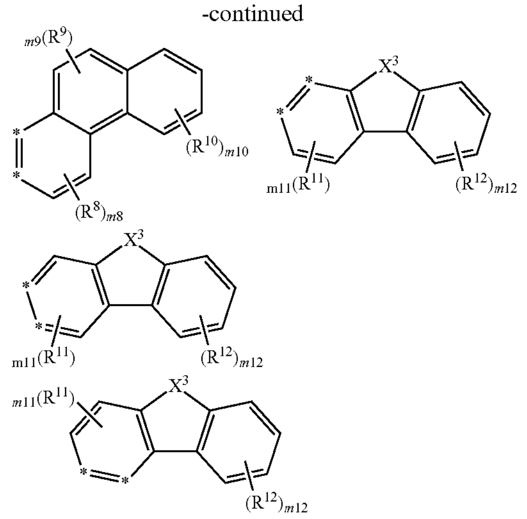

6. A composition for an organic optoelectronic device, the composition comprising:

a first compound; and a second compound, wherein:

the first compound is the compound for an organic optoelectronic device as claimed in claim 1, the second compound is a compound for an organic optoelectronic device represented by Chemical Formula 2:

[Chemical Formula 2]

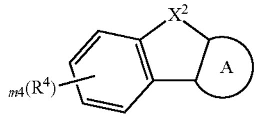

in Chemical Formula 2, $X^2$ is O, S, N-$L^a$-$R^a$, $CR^bR^c$, or $SiR^dR^e$, $L^a$ is a single bond or a substituted or unsubstituted C6 to C12 arylene group, $R^a$, $R^b$, $R^c$, $R^d$, $R^e$ and $R^4$ are each independently hydrogen, deuterium, a substituted or unsubstituted C1 to C30 alkyl group, a substituted or unsubstituted C6 to C30 aryl group, or a substituted or unsubstituted C2 to C30 heterocyclic group, m4 is an integer of 1 to 4, and A is a ring of Group II,

[Group II]

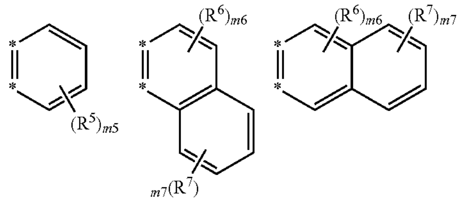

in Group II,

* is a linking point, $X^3$ is O or S, $R^5$ to $R^{12}$ are each independently hydrogen, deuterium, a substituted or unsubstituted C1 to C30 alkyl group, a substituted or unsubstituted C6 to C30 aryl group, or a substituted or unsubstituted C2 to C30 heterocyclic group, m5, m7, m10, and m12 are each independently an integer of 1 to 4, m6, m8, m9, and m11 are each independently 1 or 2, and at least one of $R^a$ and $R^4$ to $R^{12}$ is a substituted heterocyclic group represented by Chemical Formula a,

[Chemical Formula a]

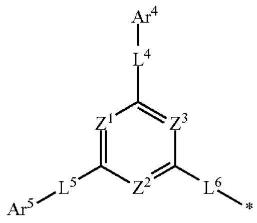

in Chemical Formula a, $Z^1$ to $Z^3$ are each independently N or $CR^f$, provided that at least two of $Z^1$ to $Z^3$ are N, $R^f$ is hydrogen, deuterium, a substituted or unsubstituted C1 to C10 alkyl group, or a substituted or unsubstituted C6 to C20 aryl group, $L^4$ to $L^6$ are each independently a single bond or a substituted or unsubstituted C6 to C30 arylene group, $Ar^4$ and $Ar^5$ are each independently a substituted or unsubstituted C6 to C30 aryl group or a substituted or unsubstituted C2 to C30 heterocyclic group, and

* is a linking point.

7. The composition as claimed in claim 6, wherein:

Chemical Formula 2 is represented by one of Chemical Formula 2-I to Chemical Formula 2-X:

[Chemical Formula 2-I]

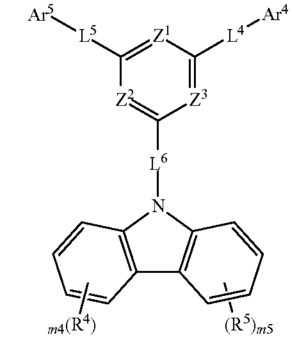

in Chemical Formula 2-1, $Z^1$ to $Z^3$, $R^4$, $R^5$, $L^4$ to $L^6$, $Ar^4$, $Ar^5$, m4, and m5 are defined the same as those of Chemical Formula 2;

[Chemical Formula 2-II]

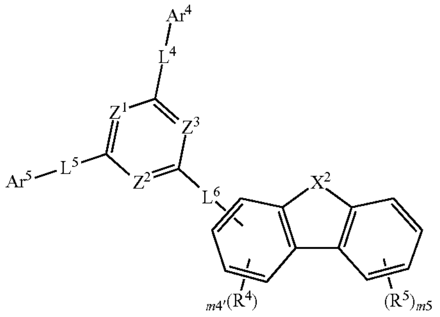

[Chemical Formula 2-III]

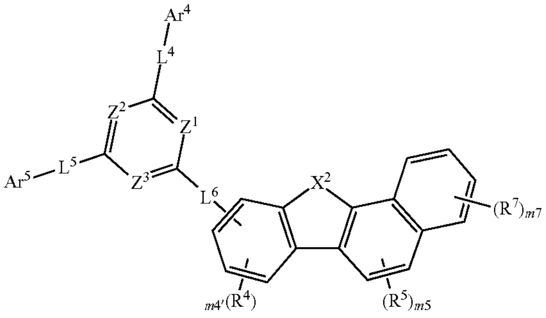

[Chemical Formula 2-IV]

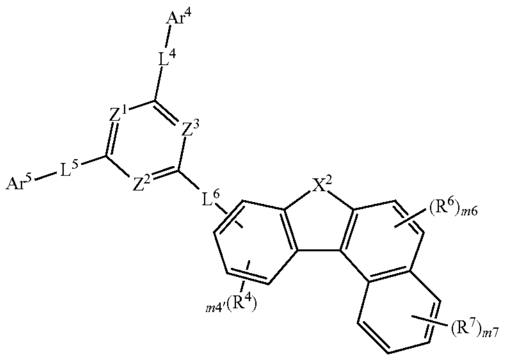

-continued

[Chemical Formula 2-V]

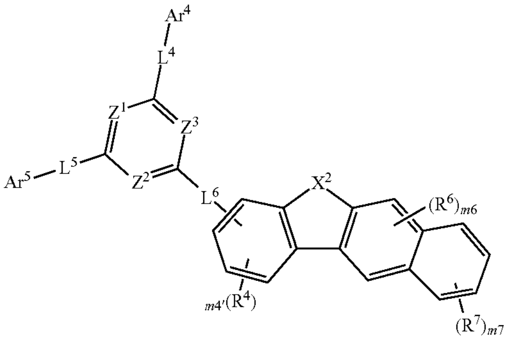

in Chemical Formula 2-II to Chemical Formula 2-V, $X^2$, $Z^1$ to $Z^3$, $R^4$ to $R^7$, $L^4$ to $L^6$, $Ar^4$, $Ar^5$, and m5 to m7 are defined the same as those of Chemical Formula 2, and m4' is an integer of 1 to 3;

[Chemical Formula 2-VI]

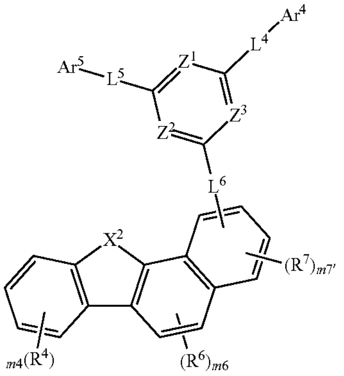

[Chemical Formula 2-VII]

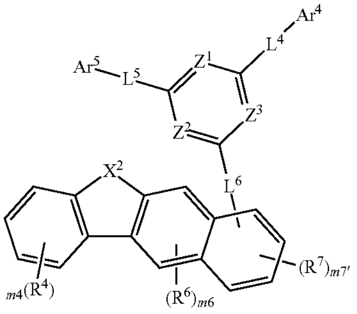

-continued

[Chemical Formula 2-VIII]

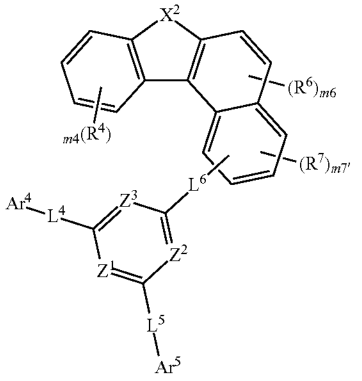

in Chemical Formula 2-VI to Chemical Formula 2-VIII, $X^2$, $Z^1$ to $Z^3$, $R^4$, $R^6$, $R^7$, $L^4$ to $L^6$, $Ar^4$, $Ar^5$, m4, and m6 are defined the same as those of Chemical Formula 2, and m7' is an integer of 1 to 3;

[Chemical Formula 2-IX]

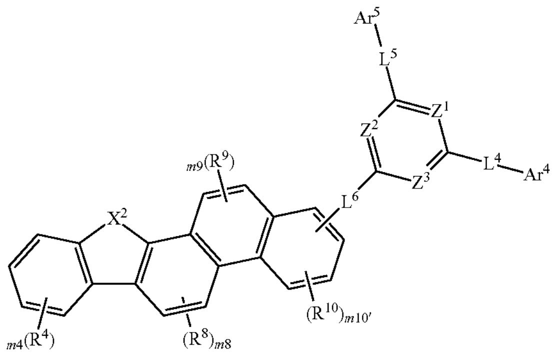

in Chemical Formula 2-IX, $X^2$, $Z^1$ to $Z^3$, $R^4$, $R^8$ to $R^{10}$, $L^4$ to $L^6$, $Ar^4$, $Ar^5$, m4, m8, and m9 are defined the same as those of Chemical Formula 2, and m10' is an integer of 1 to 3;

[Chemical Formula 2-X]

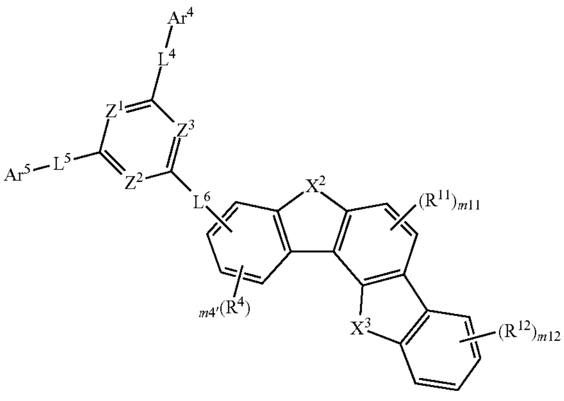

wherein, in Chemical Formula 2-X, $X^2$, $X^3$, $Z^1$ to $Z^3$, $R^4$, $R^{11}$, $R^{12}$, $L^4$ to $L^6$, $Ar^4$, $Ar^5$, m11 and m12 are defined the same as those of Chemical Formula 2, and m4' is an integer of 1 to 3.

8. The composition as claimed in claim 7, wherein the second compound is represented by Chemical Formula 2-II, Chemical Formula 2-III, or Chemical Formula 2-VI.

9. The composition as claimed in claim 6, wherein:

the second compound is represented by Chemical Formula 2-II-3, Chemical Formula 2-III-1, Chemical Formula 2-VI-1, or Chemical Formula 2-VI-3:

[Chemical Formula 2-II-3]

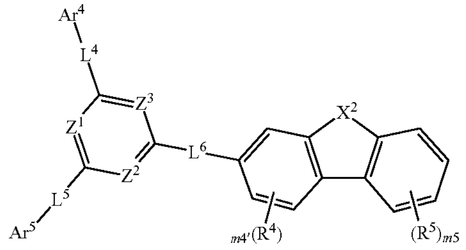

[Chemical Formula 2-III-1]

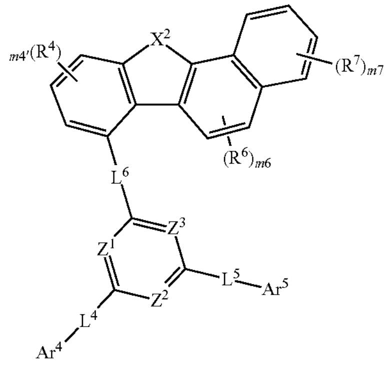

[Chemical Formula 2-VI-1]

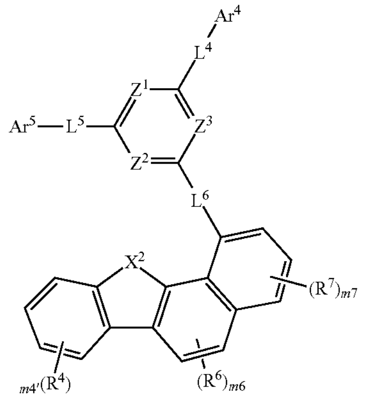

-continued

[Chemical Formula 2-VI-3]

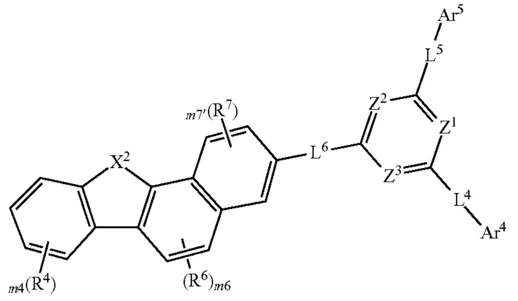

in Chemical Formula 2-II-3, Chemical Formula 2-III-1, Chemical Formula 2-VI-1, and Chemical Formula 2-VI-3, $X^2$, $Z^1$ to $Z^3$, $R^4$ to $R^7$, $L^4$ to $L^6$, $Ar^4$, $Ar^5$, m4 to m7, m4', and m7' are defined the same as those of Chemical Formulae 2-II to 2-X.

10. The composition as claimed in claim 6, wherein $Ar^4$ and $Ar^5$ are each independently a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted carbazolyl group, a substituted or unsubstituted dibenzofuranyl group, a substituted or unsubstituted dibenzothiophenyl group, or a substituted or unsubstituted dibenzosilolyl group.

11. The composition as claimed in claim 6, wherein the second compound is a compound of Group 2:

[Group 2]

A-1

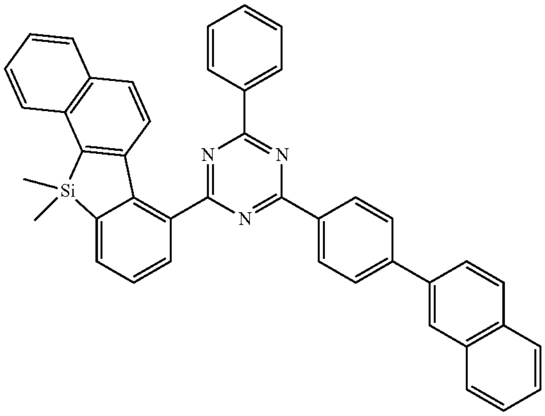

-continued

A-2

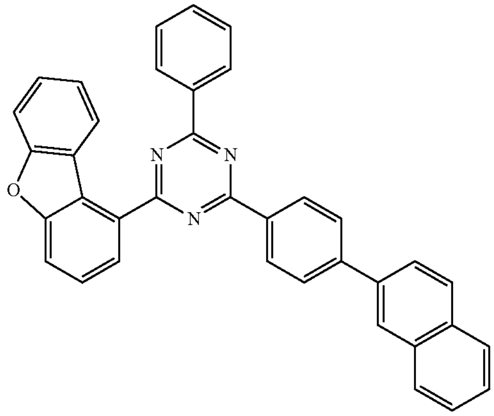

A-3

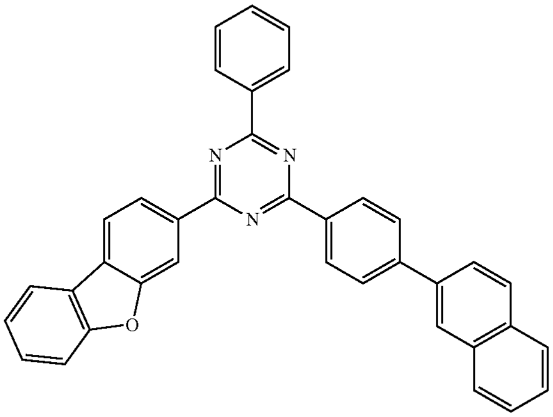

A-4

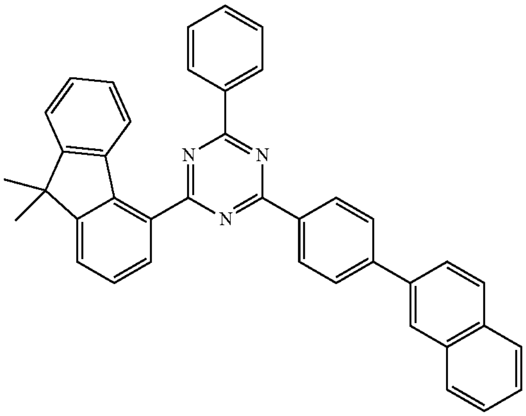

-continued
A-5
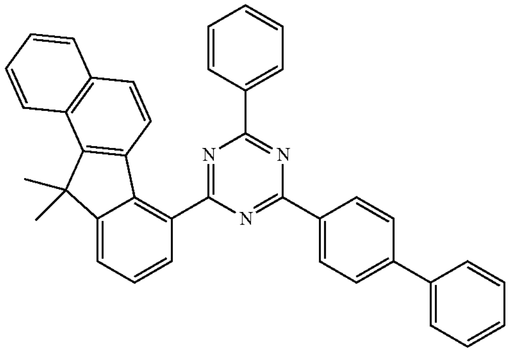
A-6
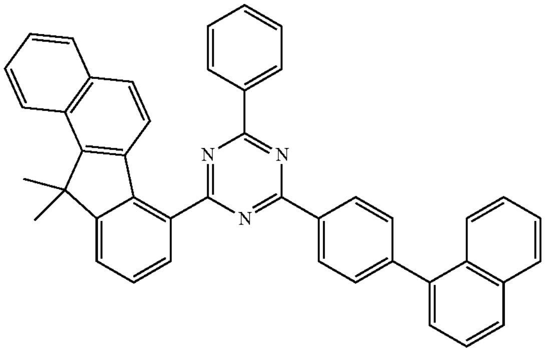
A-7
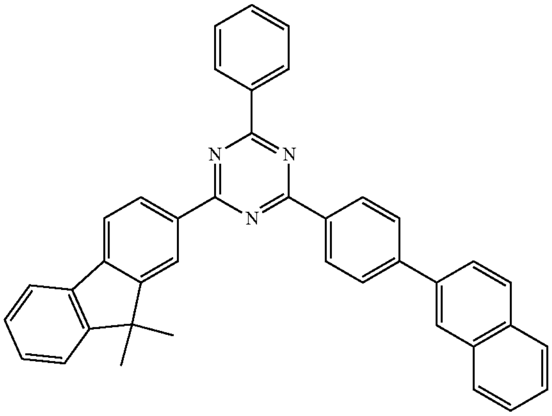
A-8
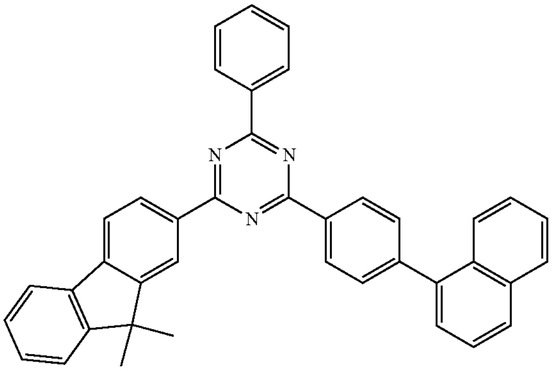
-continued
A-9
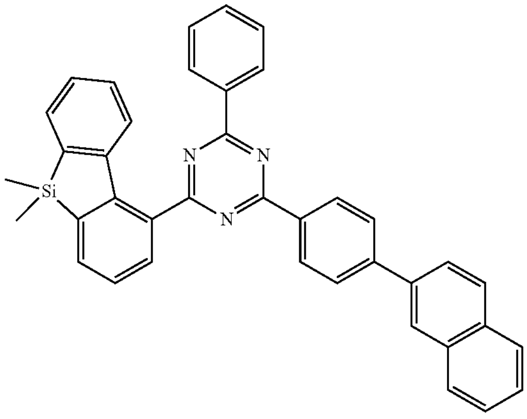
A-10
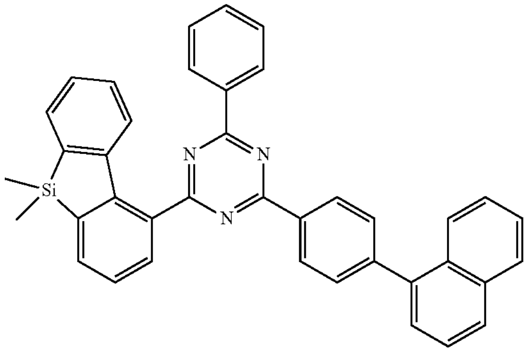
A-11
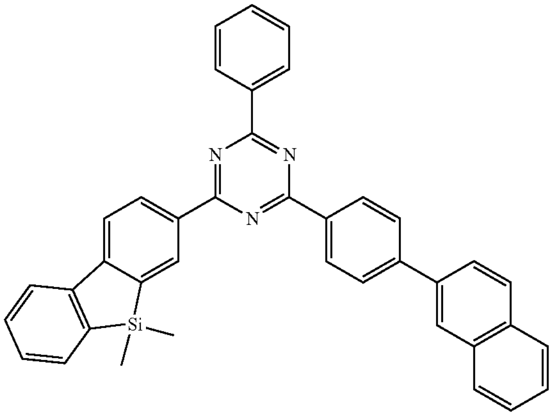
A-12
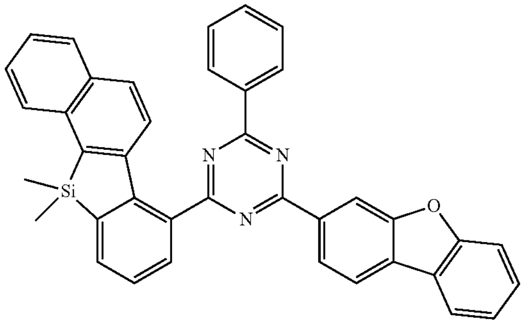

-continued
A-13
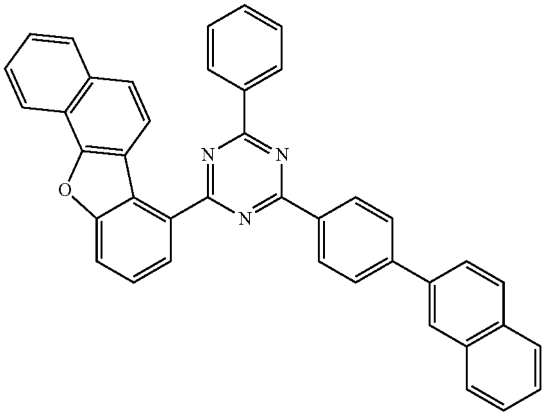
A-14
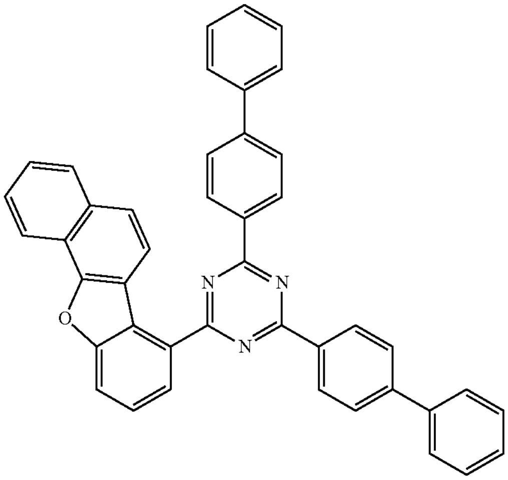
A-15
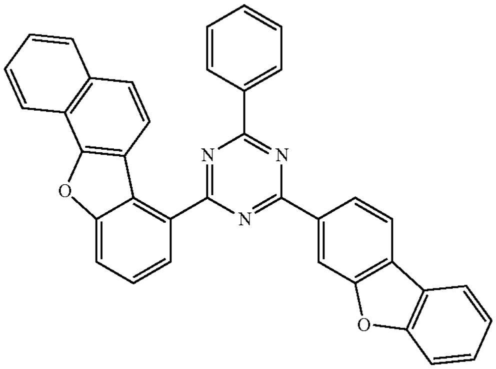
-continued
A-16
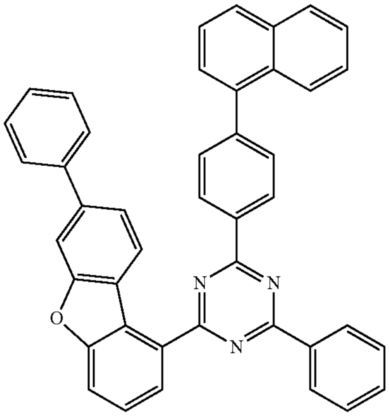
A-17
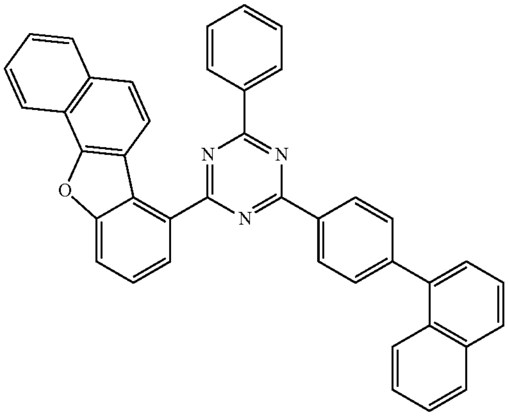
A-18
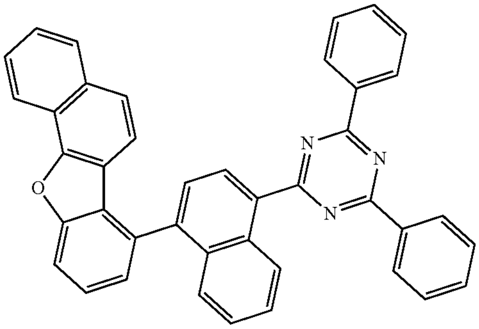
A-19
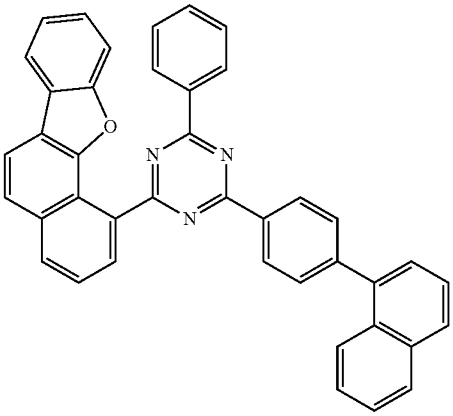

-continued
A-20
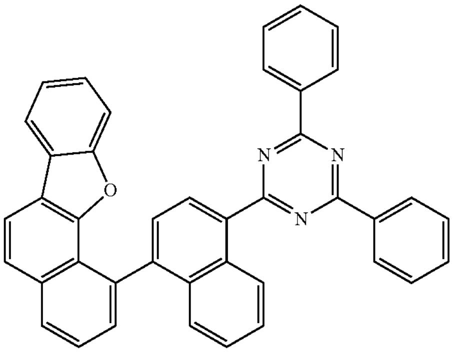
A-21
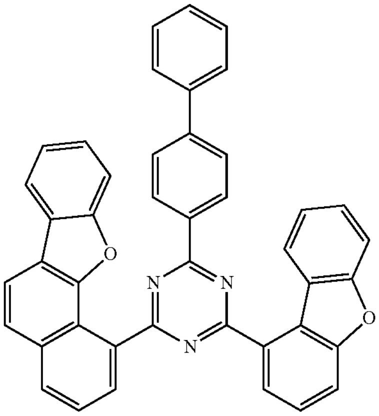
A-22
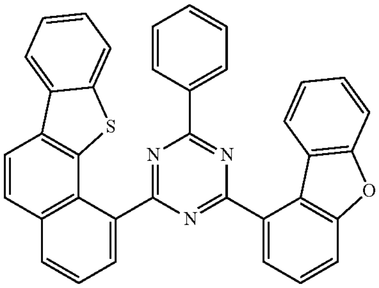
A-23
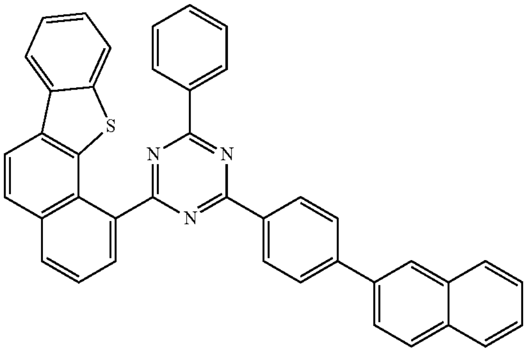
-continued
A-24
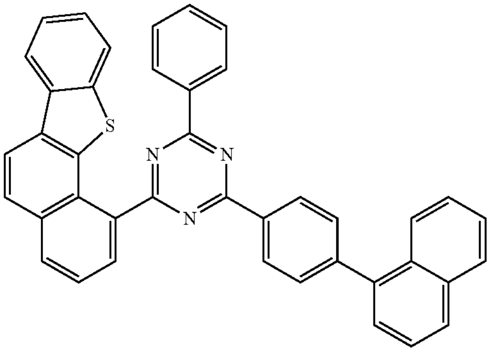
A-25
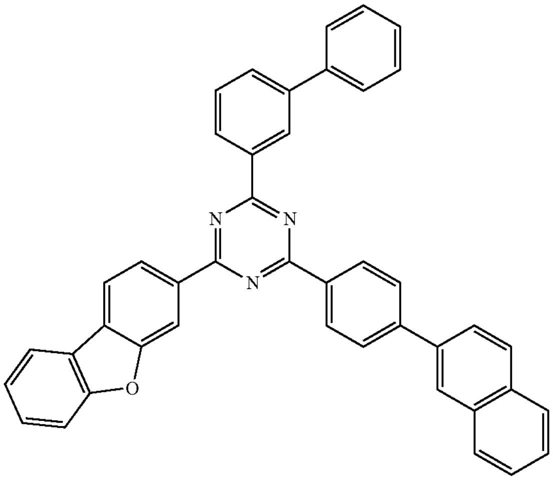
A-26
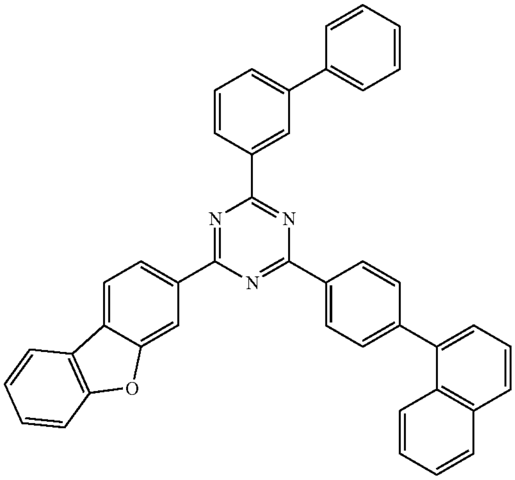

-continued
A-27
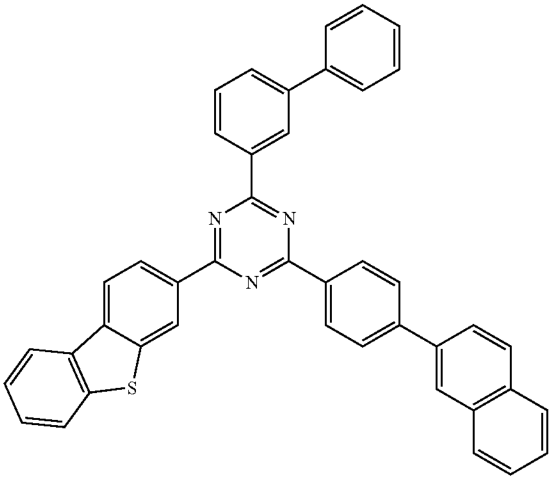
A-28
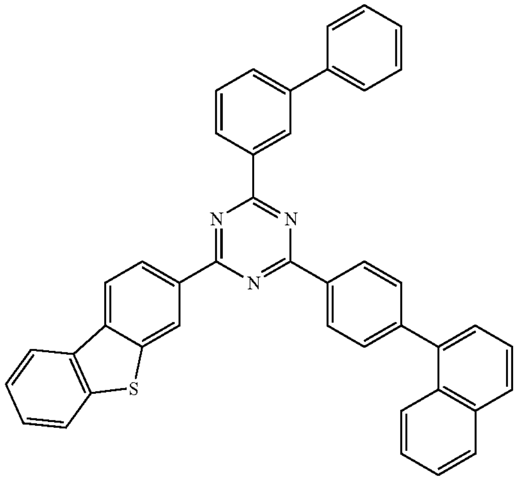
A-29
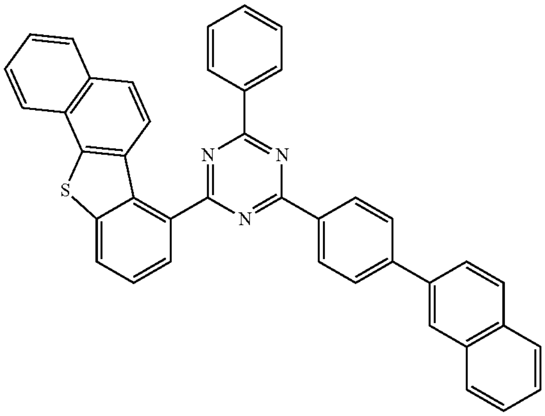
-continued
A-30
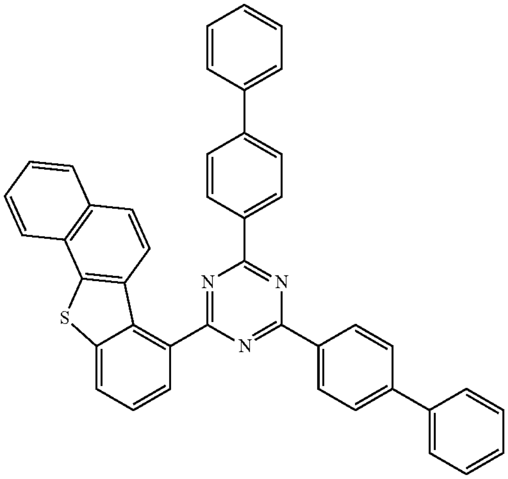
A-31
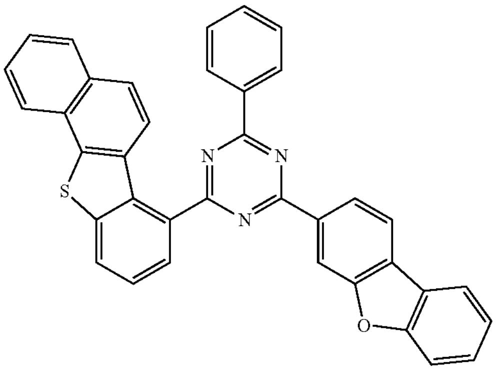
A-32
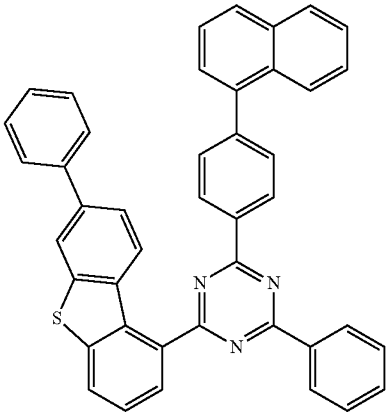

-continued
A-33
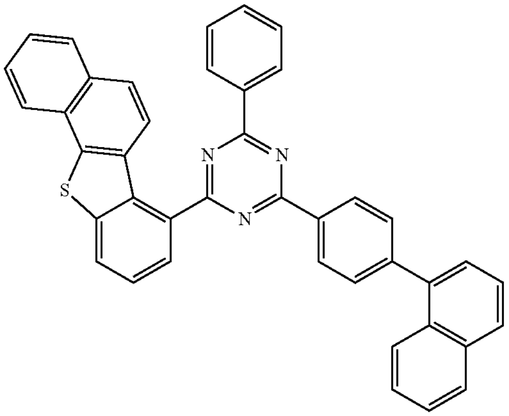
A-34
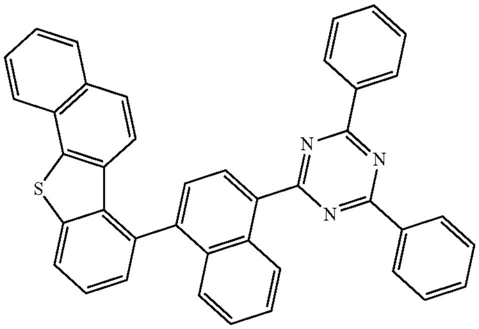
A-35
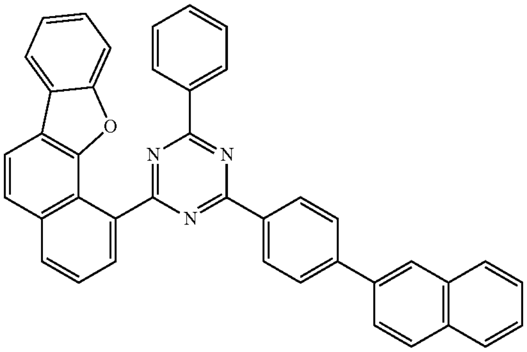
A-36
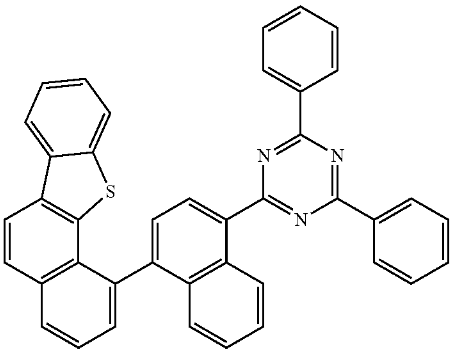
-continued
A-37
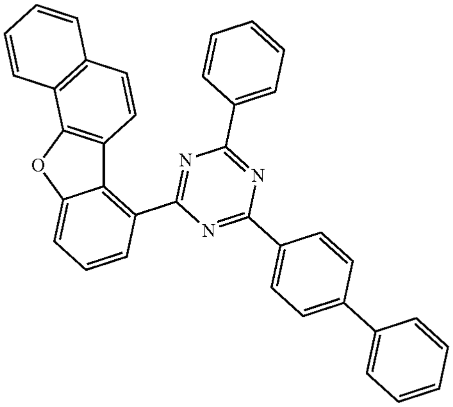
A-38
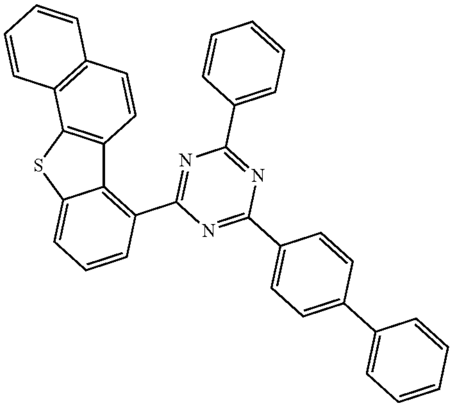
A-39
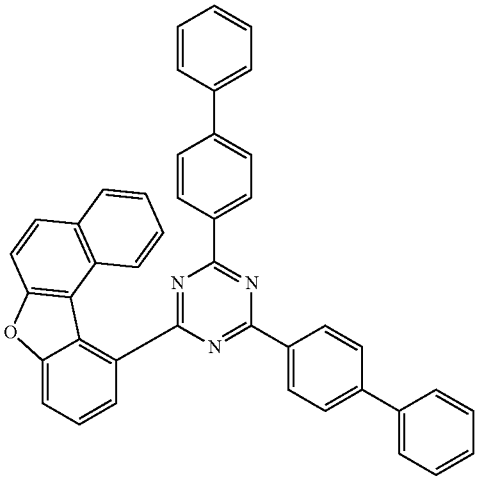

-continued
A-40
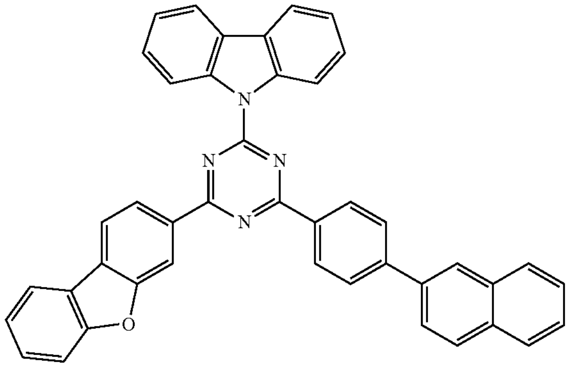
A-41
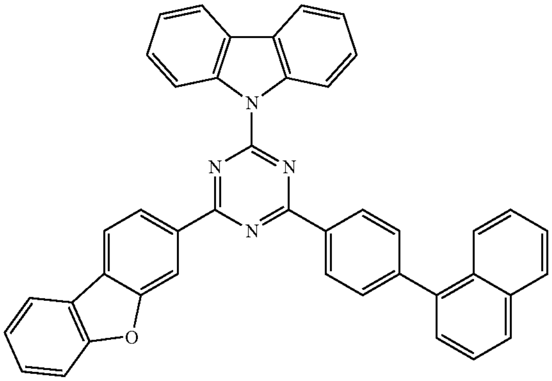
A-42
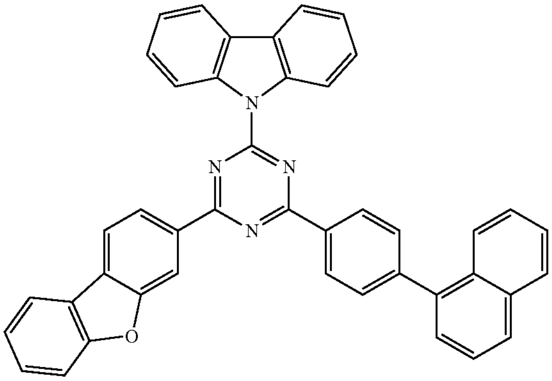
-continued
A-43
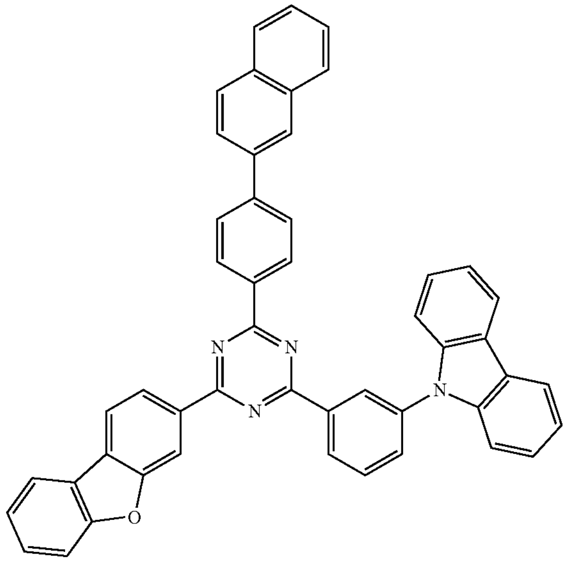
A-44
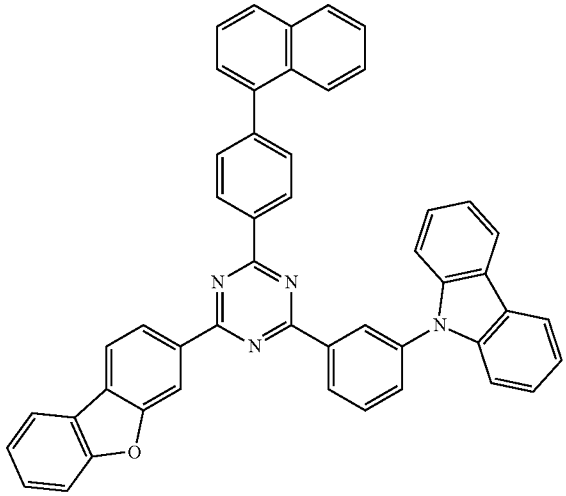
A-45
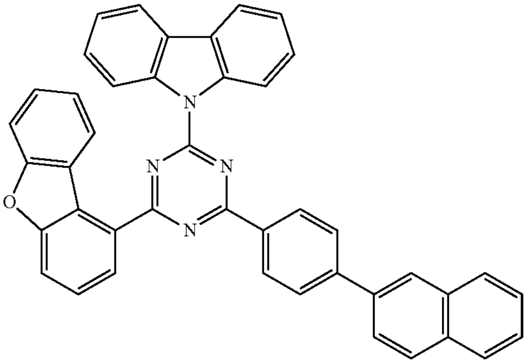

-continued
A-46
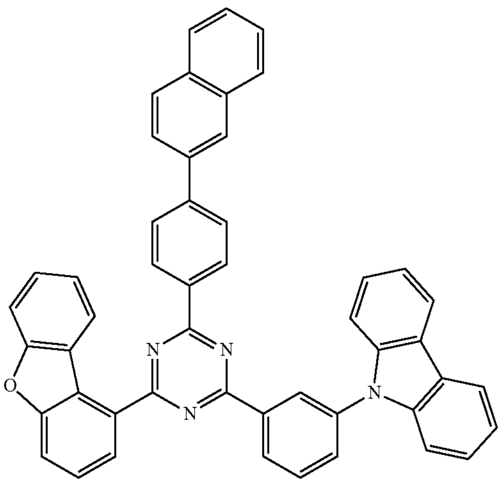
A-47
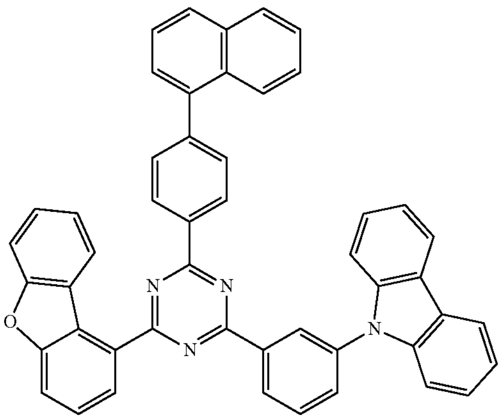
A-48
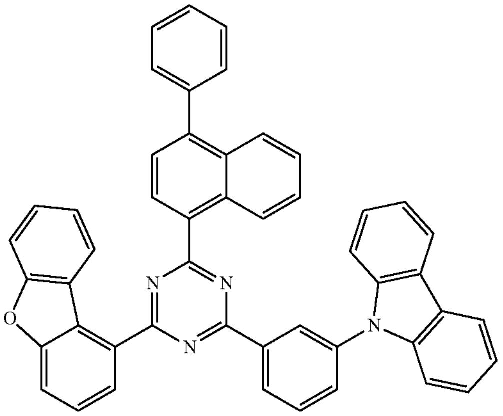
-continued
A-49
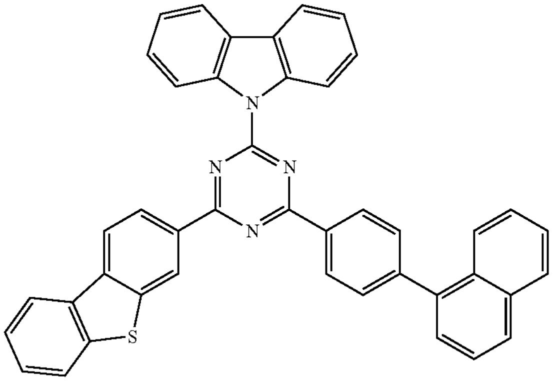
A-50
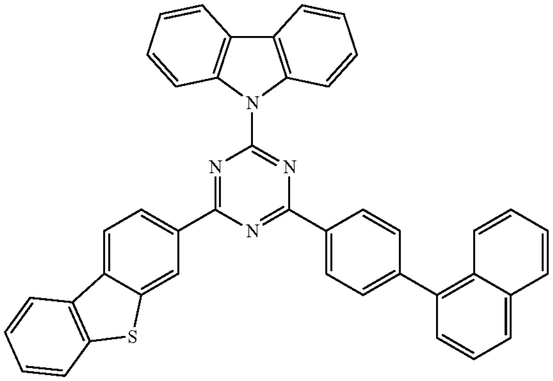
A-51
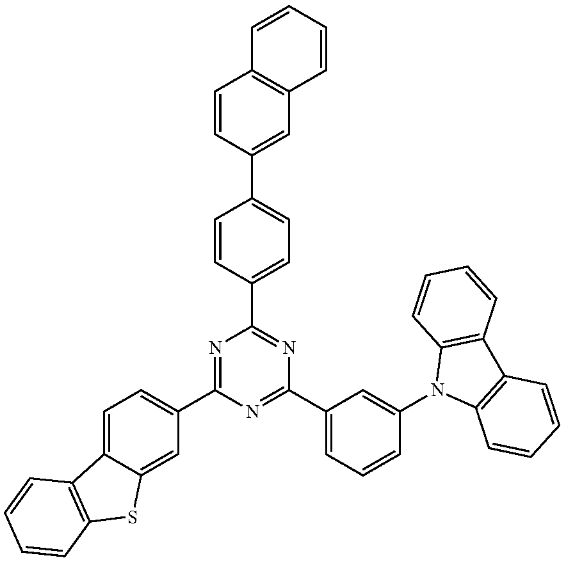

-continued
A-52
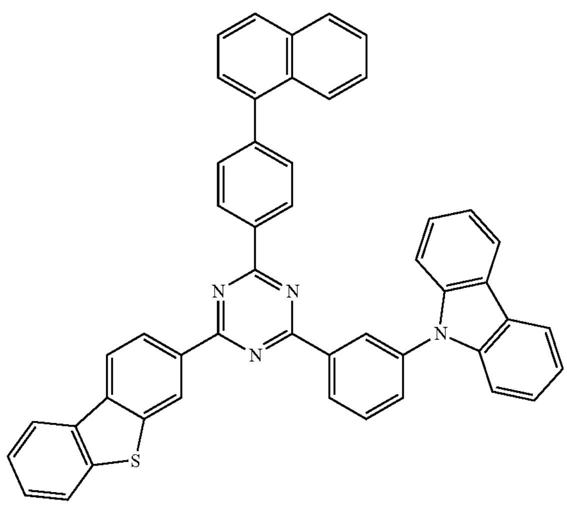
A-53
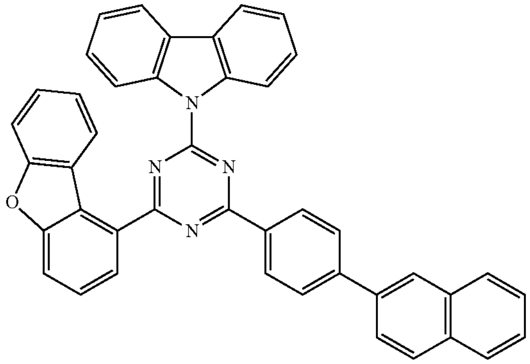
A-54
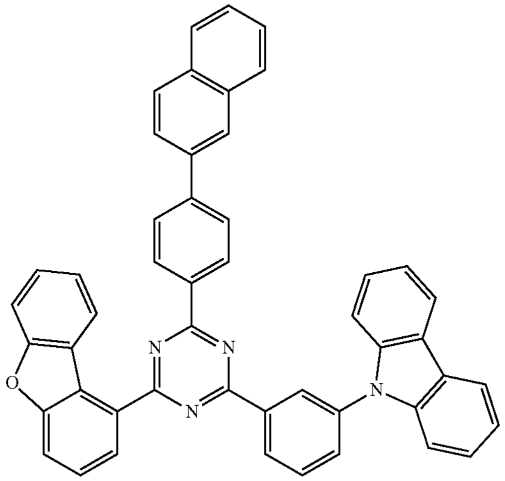
-continued
A-55
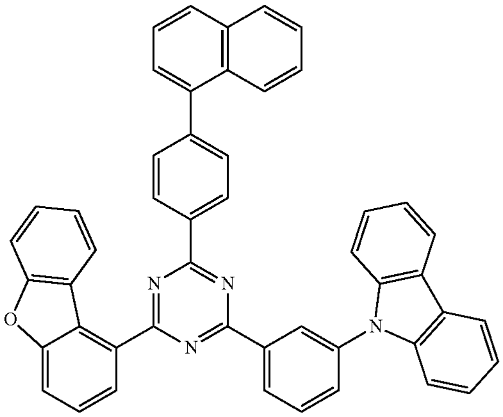
A-56
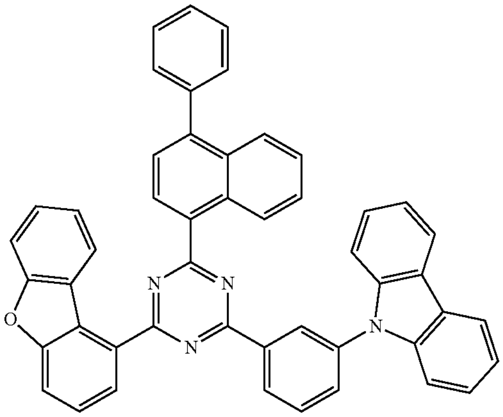
A-57
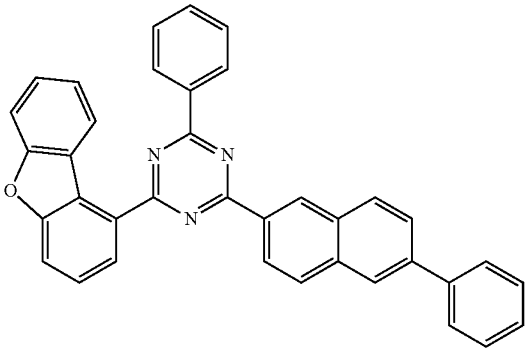
A-58
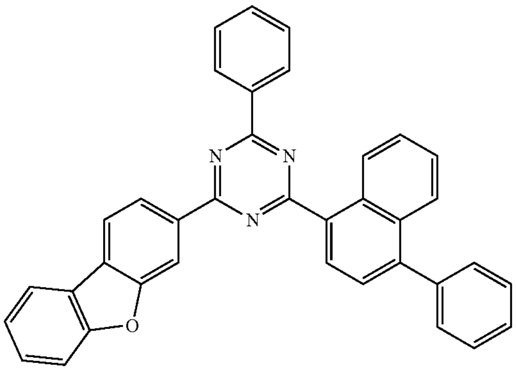

-continued
A-59
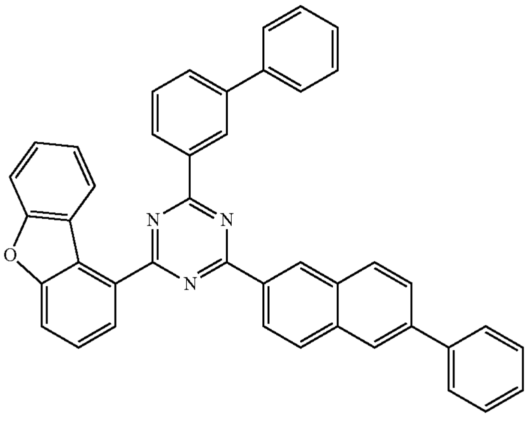
A-60
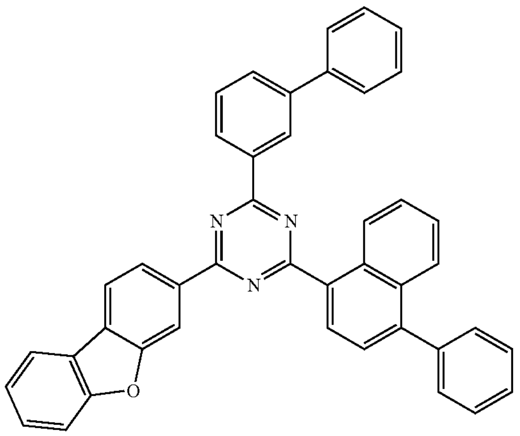
A-61
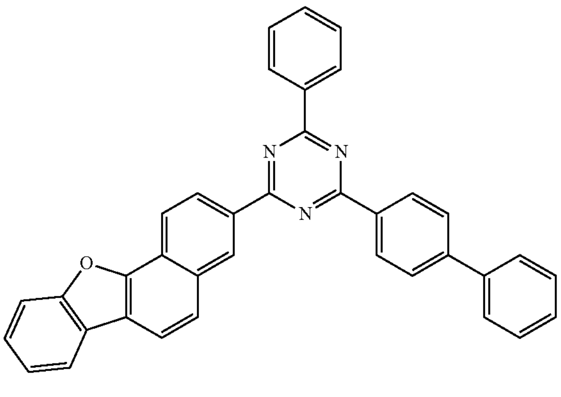
-continued
A-62
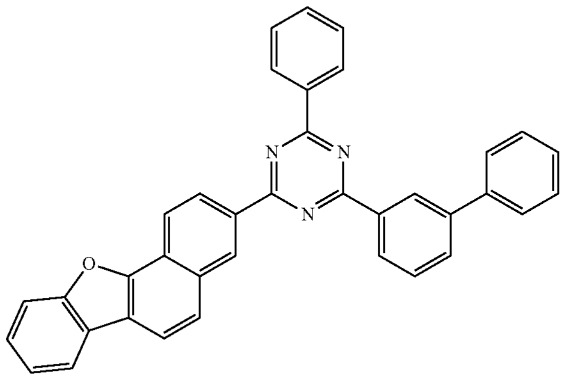
A-63
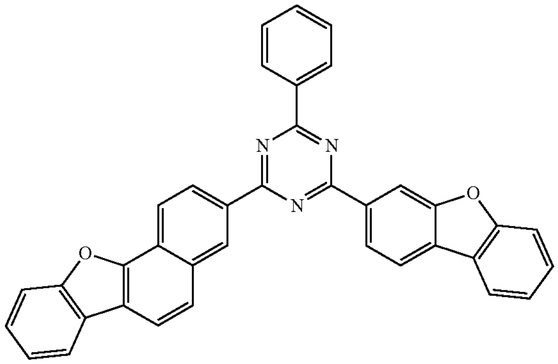
A-64
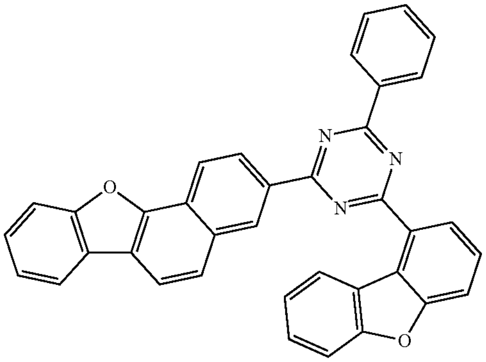
A-65
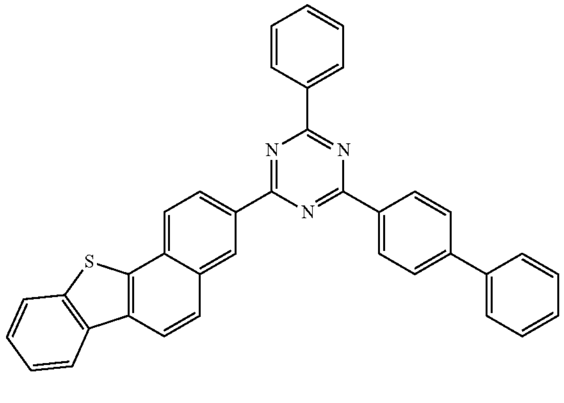

-continued
A-66
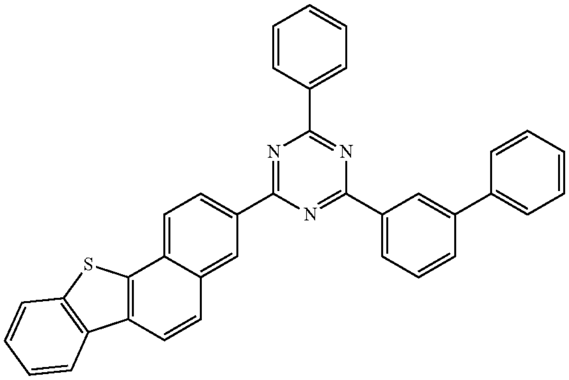
A-67
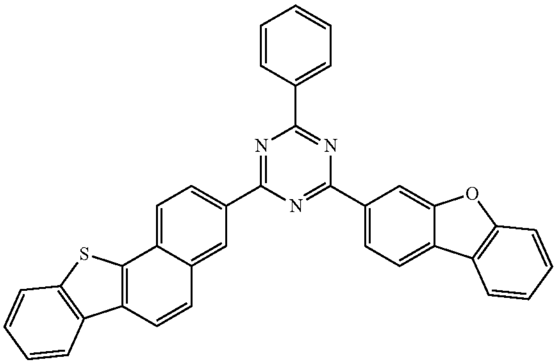
A-68
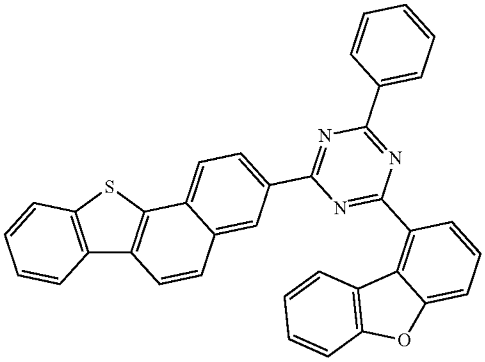
-continued
A-69
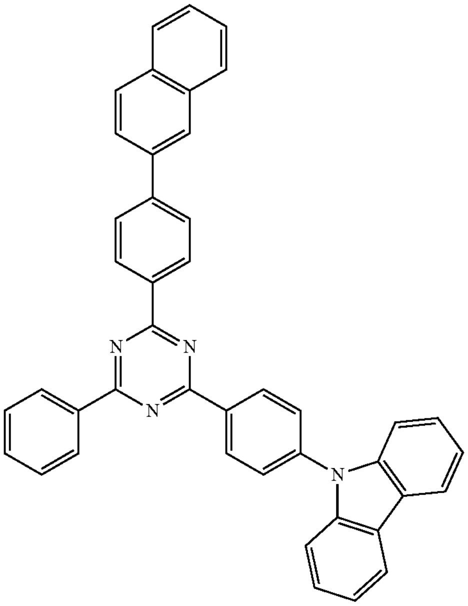
A-70
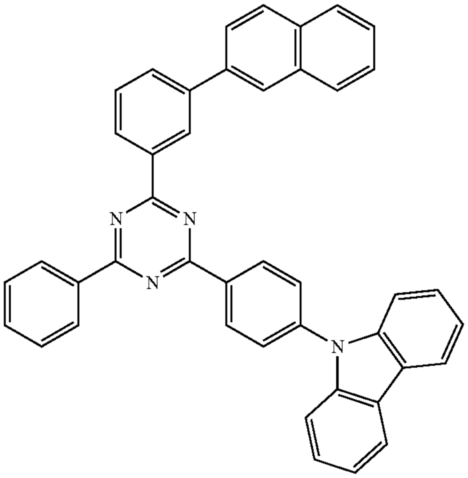
A-71
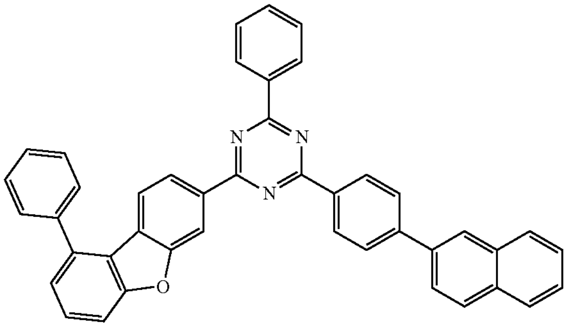

-continued
A-72
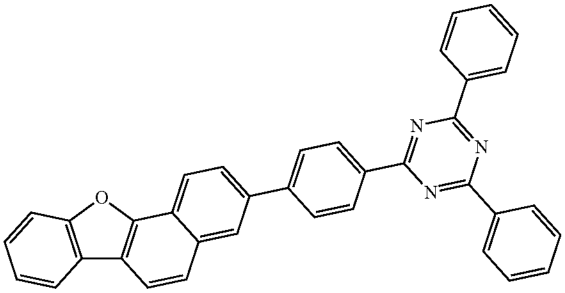
A-73
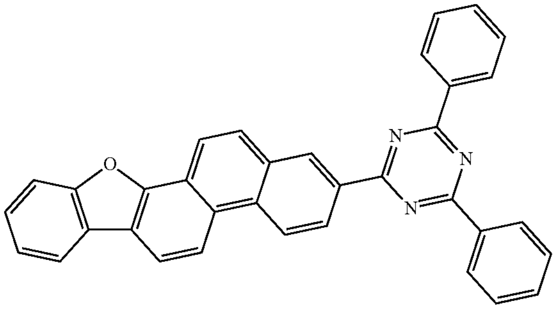
A-74
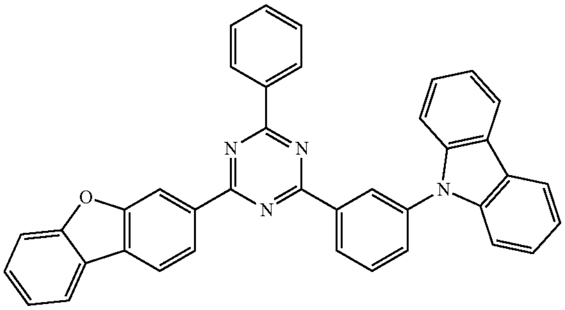
A-75
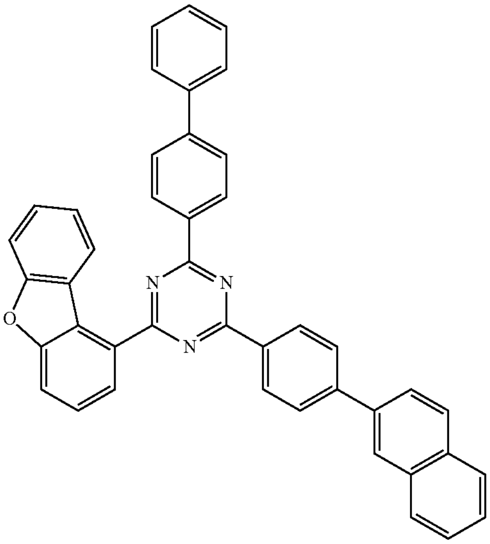
-continued
A-76
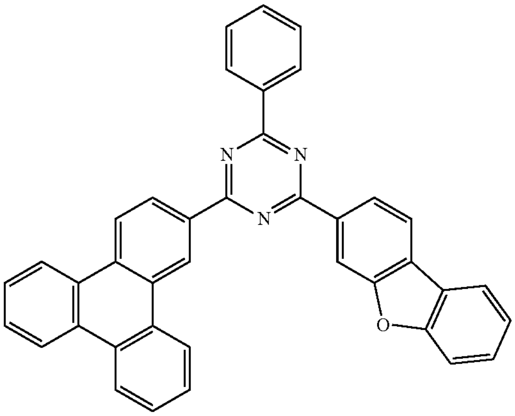
A-77
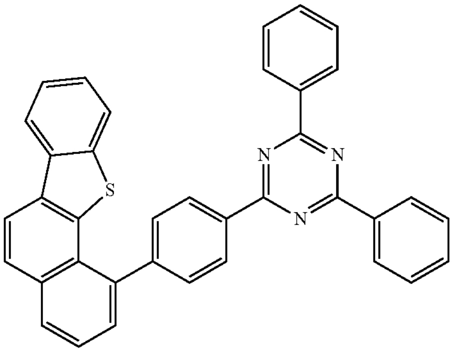
A-78
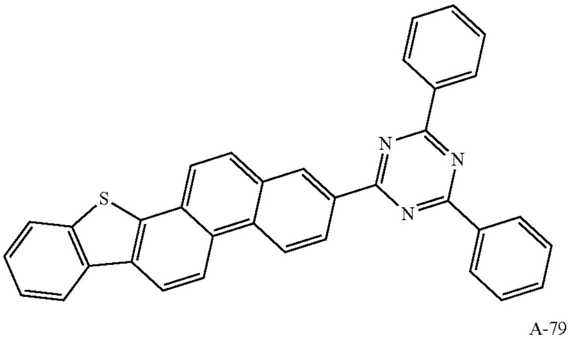
A-79
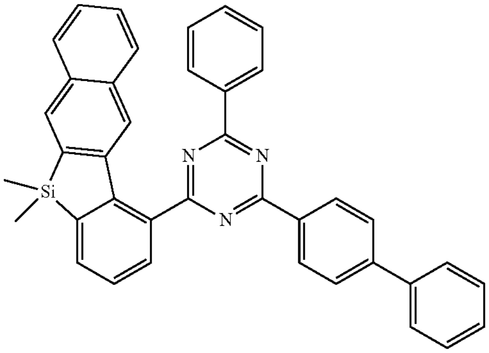

-continued
A-80
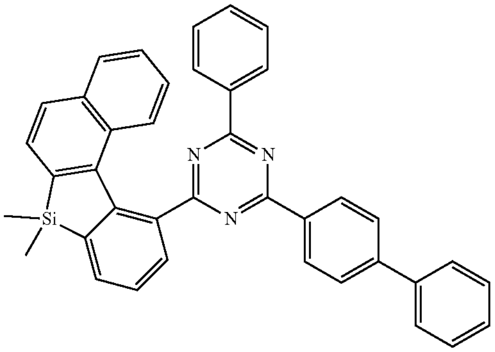
A-81
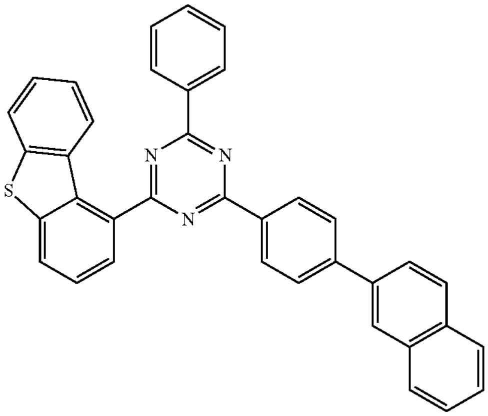
A-82
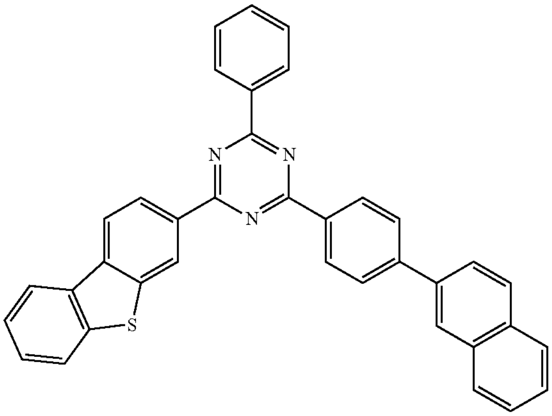
-continued
A-83
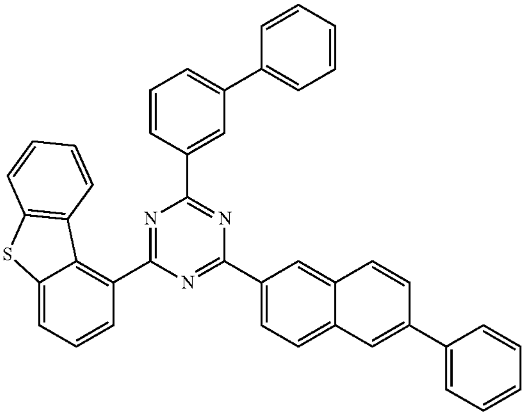
A-84
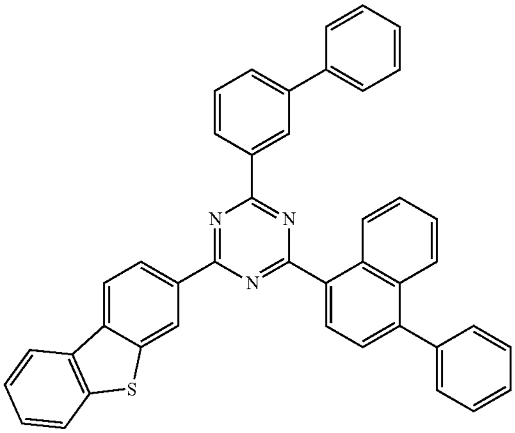
A-85
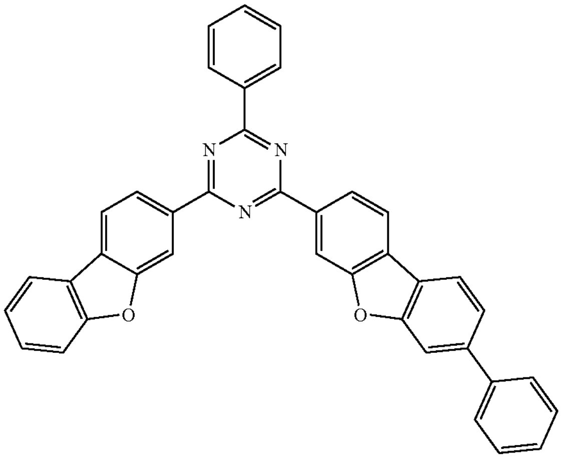

-continued
A-86
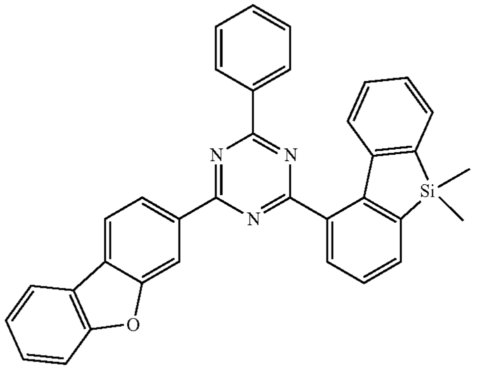
A-87
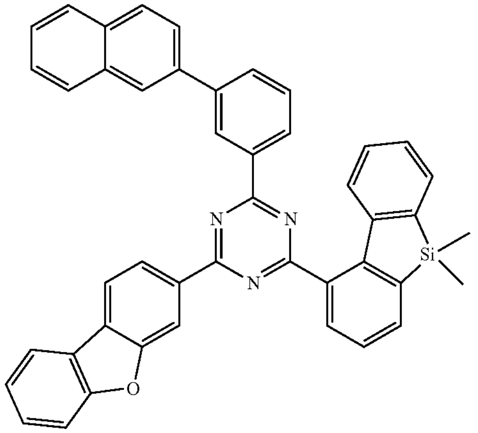
A-88
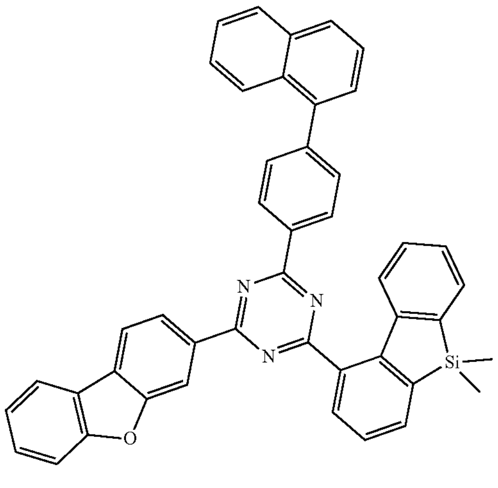
-continued
A-89
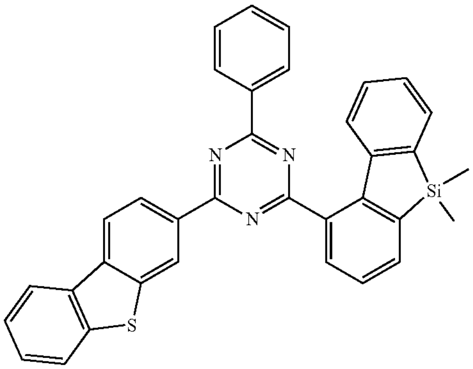
A-90
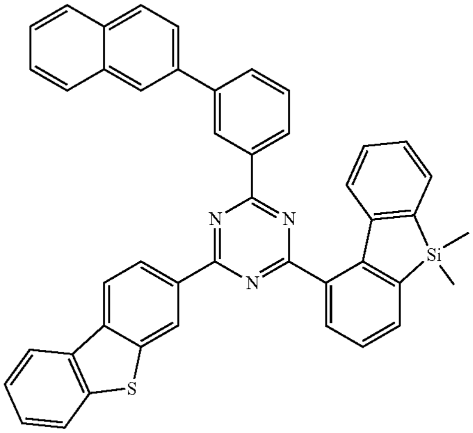
A-91
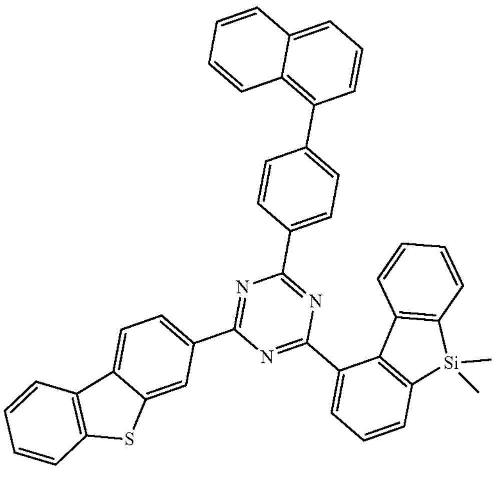

-continued
A-92
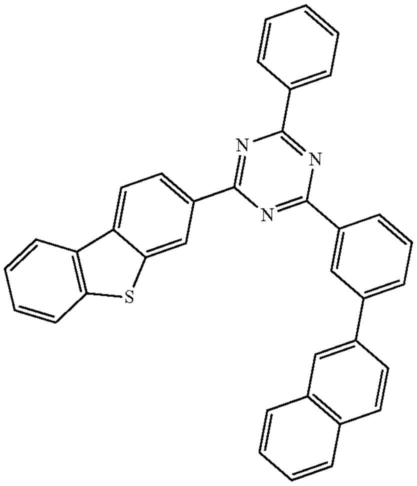
A-93
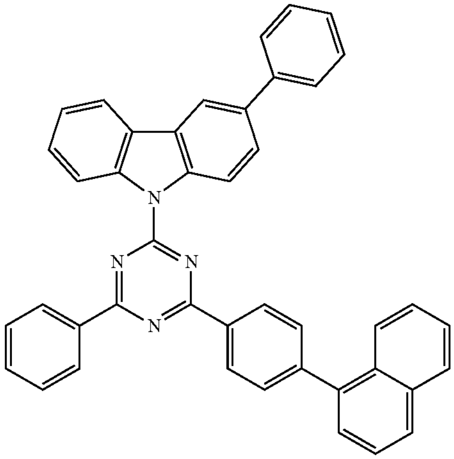
A-94
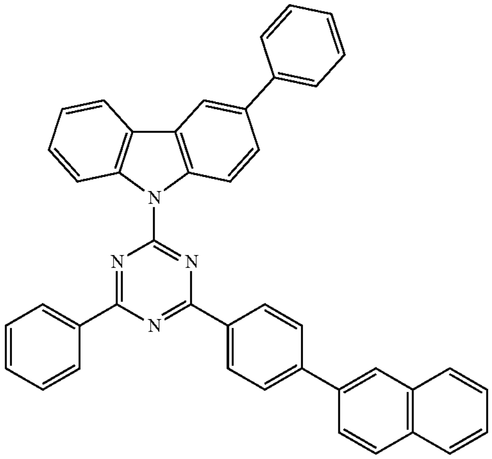
-continued
A-95
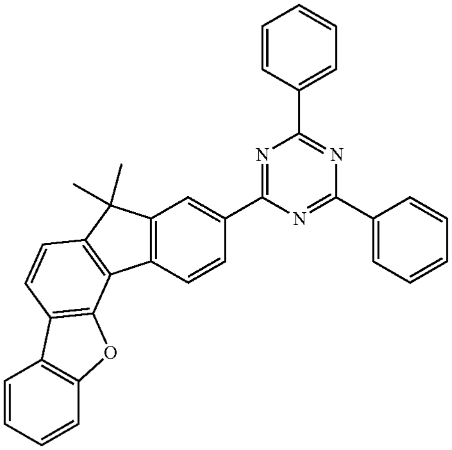
A-96
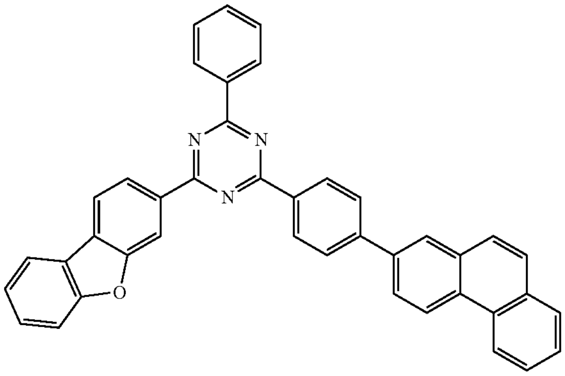
A-97
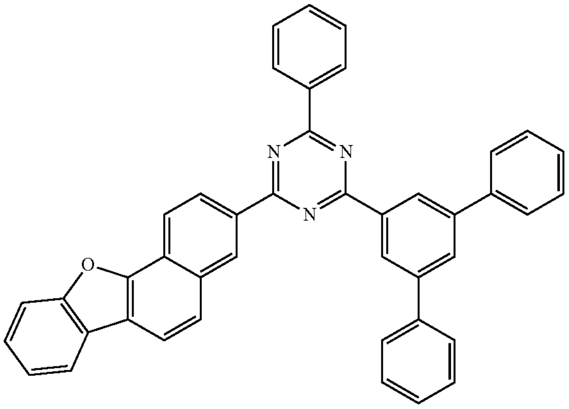

-continued
A-98
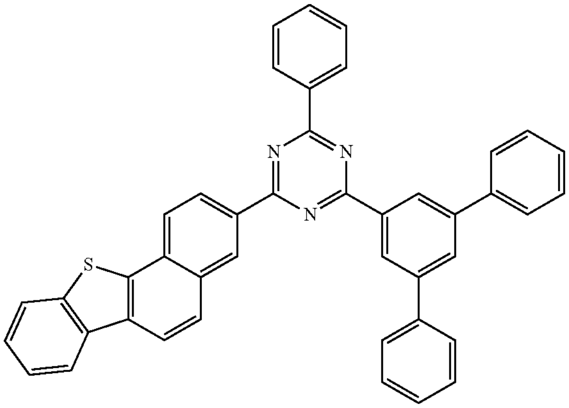
A-99
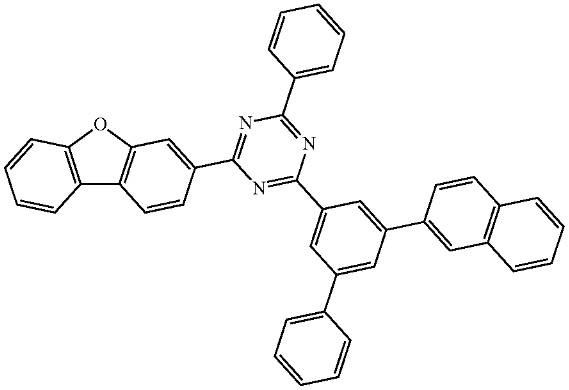
A-100
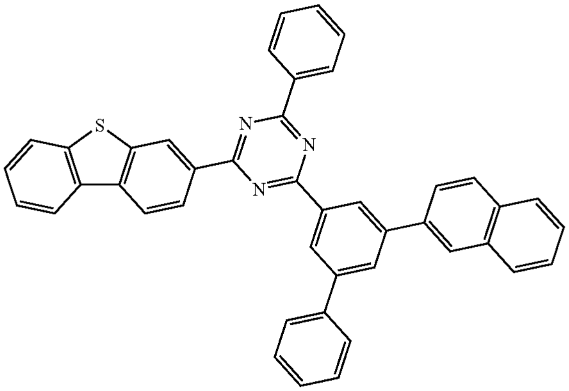
A-101
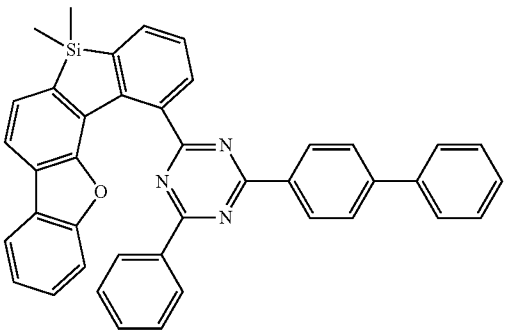
-continued
A-102
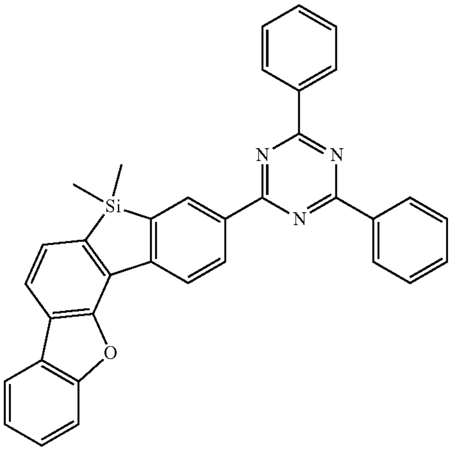
A-103
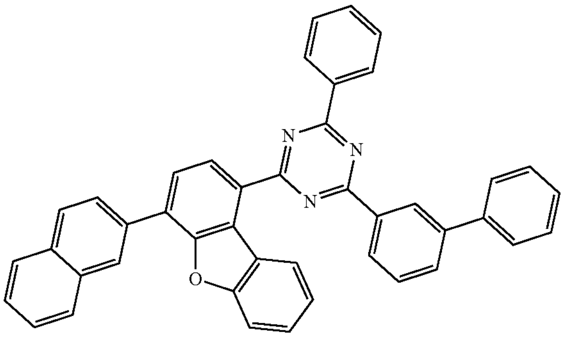
A-104
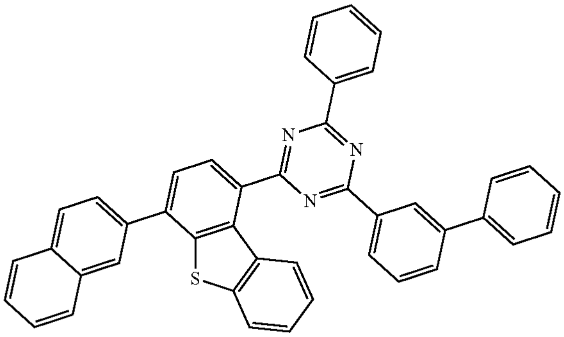
A-105
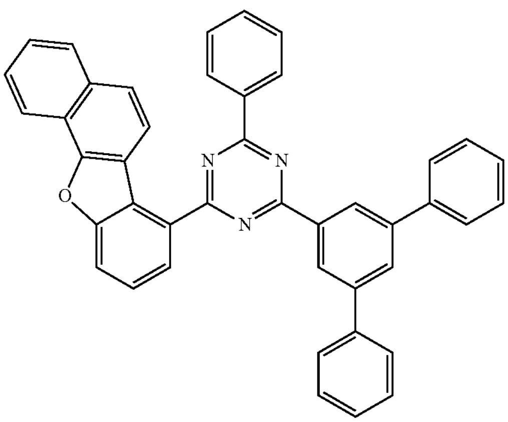

-continued
A-106
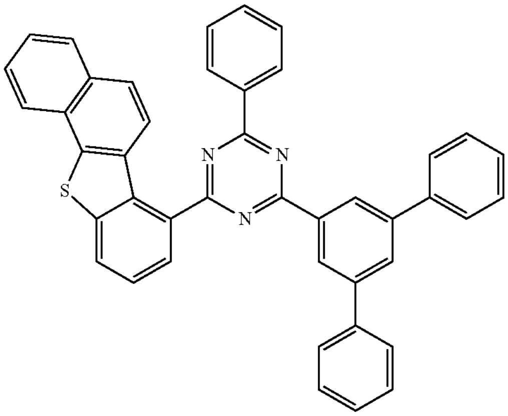
A-107
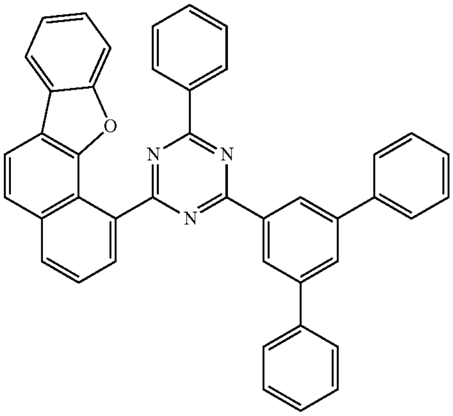
A-108
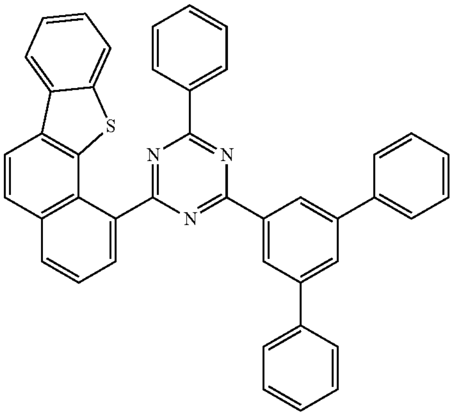
-continued
A-109
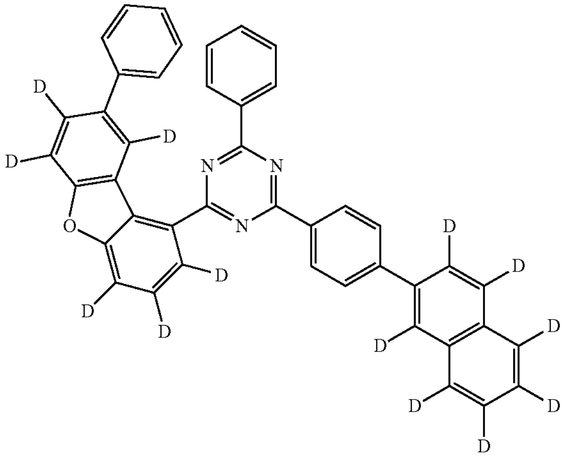
A-110
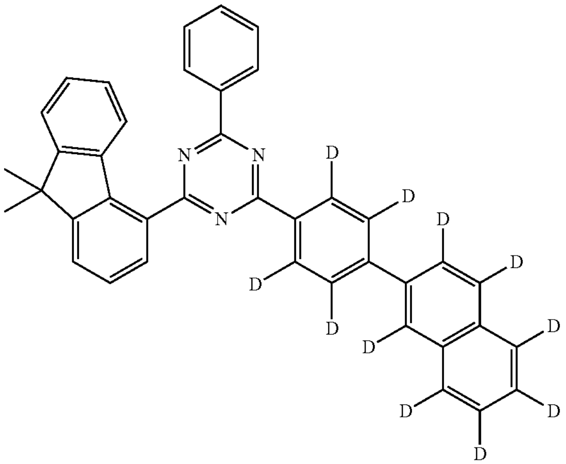
A-111
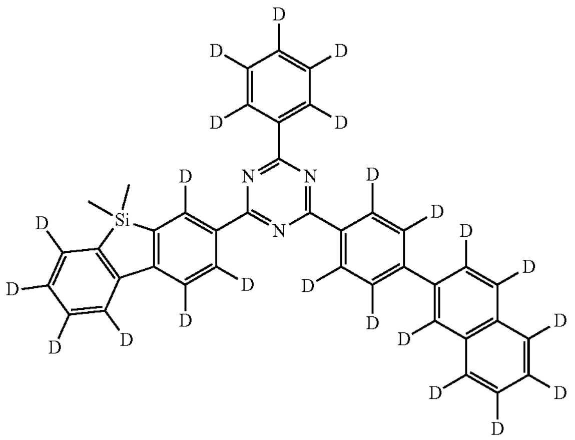

-continued
A-112
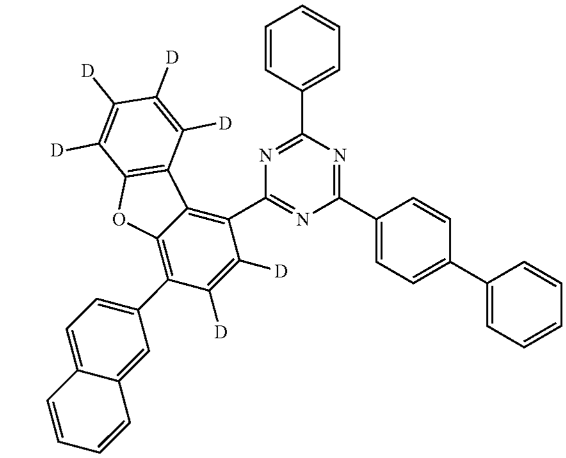
A-113
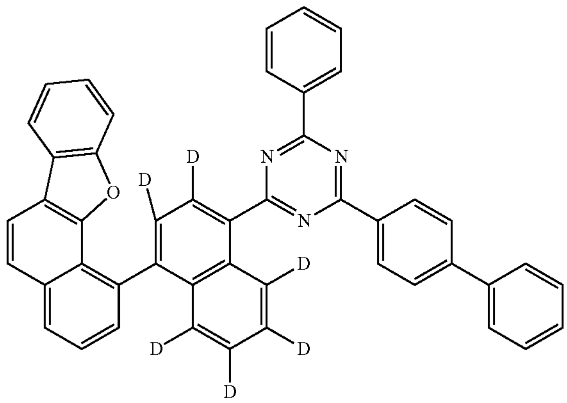
A-114
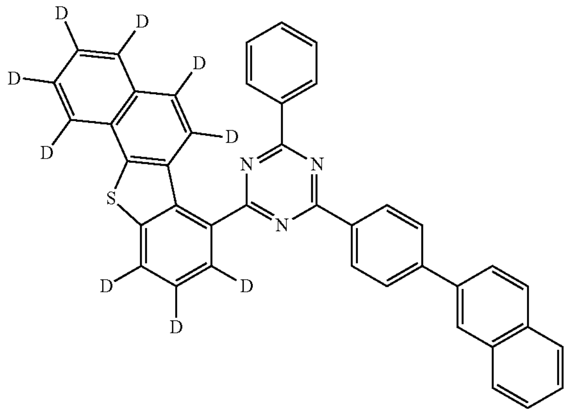
-continued
A-115
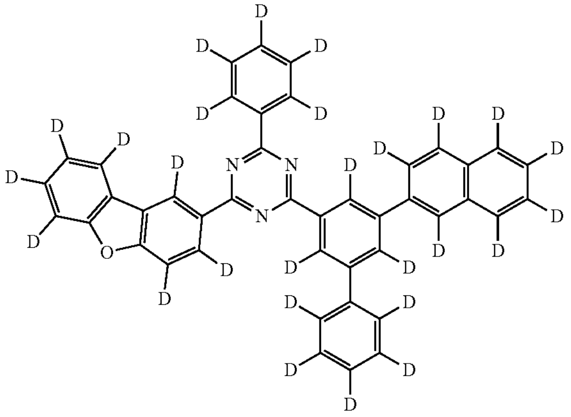
A-116
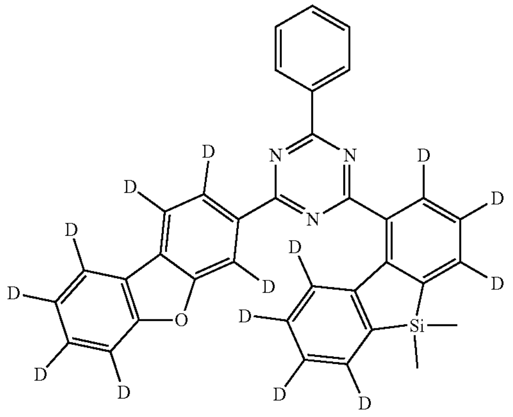
A-117
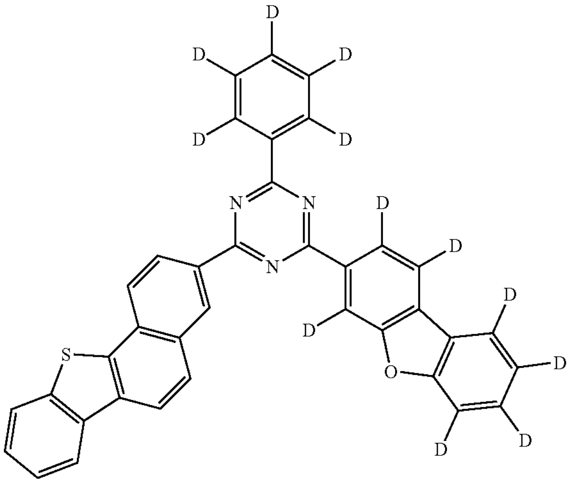

-continued

A-118

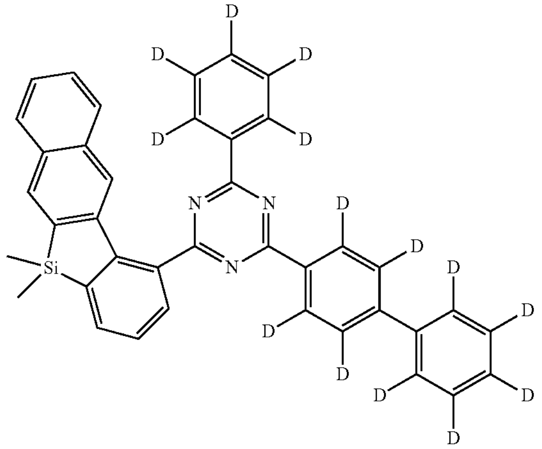

A-119

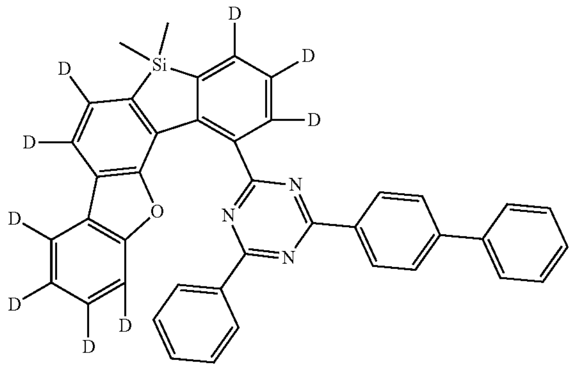

A-120

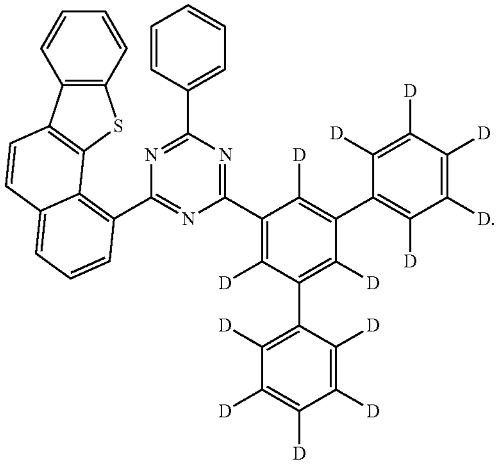

12. An organic optoelectronic device, comprising:

an anode and a cathode facing each other, and at least one organic layer between the anode and the cathode, wherein the at least one organic layer includes the compound for an organic optoelectronic device as claimed in claim 1.

13. The organic optoelectronic device as claimed in claim 12, wherein:

the at least one organic layer includes a light emitting layer, and the light emitting layer includes the compound for an organic optoelectronic device.

14. A display device comprising the organic optoelectronic device as claimed in claim 12.

15. An organic optoelectronic device, comprising:

an anode and a cathode facing each other, and at least one organic layer between the anode and the cathode, wherein the at least one organic layer includes the composition for an organic optoelectronic device as claimed in claim 6.

16. The organic optoelectronic device as claimed in claim 15, wherein:

the at least one organic layer includes a light emitting layer, and the light emitting layer includes the composition for an organic optoelectronic device.

17. A display device comprising the organic optoelectronic device as claimed in claim 15.

18. The compound as claimed in claim 1, wherein:

$Ar^1$ is a biphenyl group that is unsubstituted or substituted with deuterium or a C6 to C12 aryl group, a terphenyl group that is unsubstituted or substituted with deuterium or a C6 to C12 aryl group, a naphthyl group that is unsubstituted or substituted with deuterium or a C6 to C12 aryl group, or a phenanthrenyl group that is unsubstituted or substituted with deuterium or a C6 to C12 aryl group, and moieties $L^2$-$Ar^2$ and $L^3$-$Ar^3$ of Chemical Formula 1 are each independently a moiety of Group I:

[Group I]

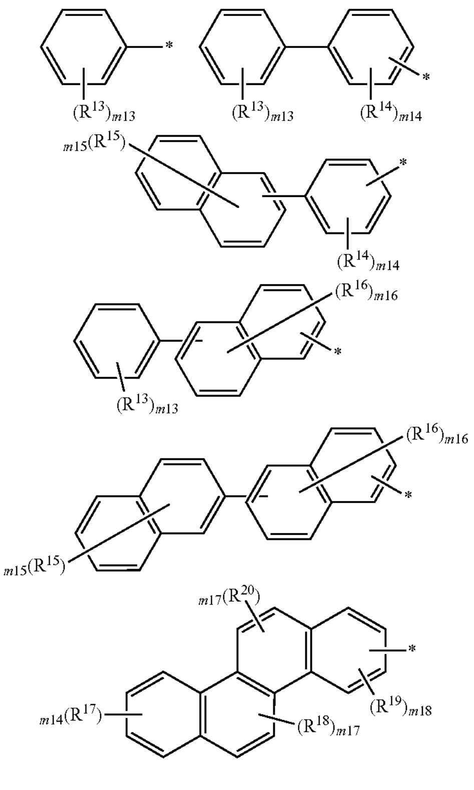

-continued

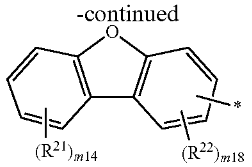

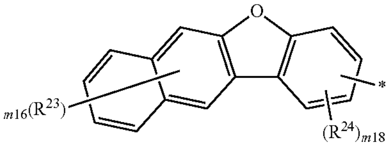

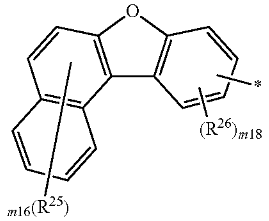

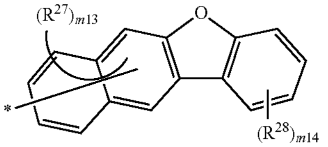

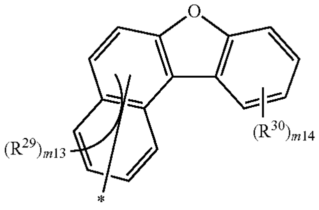

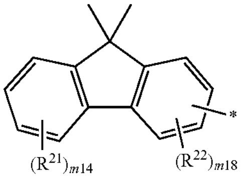

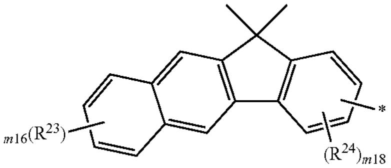

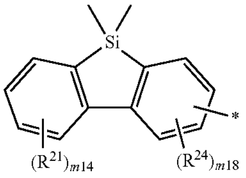

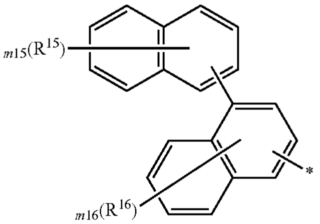

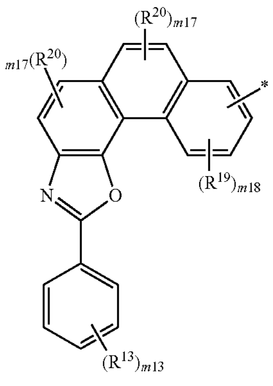

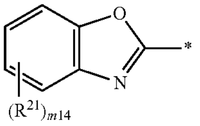

in Group I, $R^{13}$ to $R^{30}$ are each independently hydrogen, deuterium, a halogen, a C1 to C10 alkyl group, or a C6 to C12 aryl group, m13 is an integer of 1 to 5, m14 is an integer of 1 to 4, m15 is an integer of 1 to 7, m16 is an integer of 1 to 6, m17 is an integer of 1 or 2, m18 is an integer of 1 to 3, and

* is a linking point.

19. A composition for an organic optoelectronic device the composition comprising:

a first compound; and a second compound, wherein:

the first compound is a compound for an organic optoelectronic device represented by Chemical Formula 1, and the second compound is a compound for an organic optoelectronic device represented by Chemical Formula 2:

[Chemical Formula 2-IX]

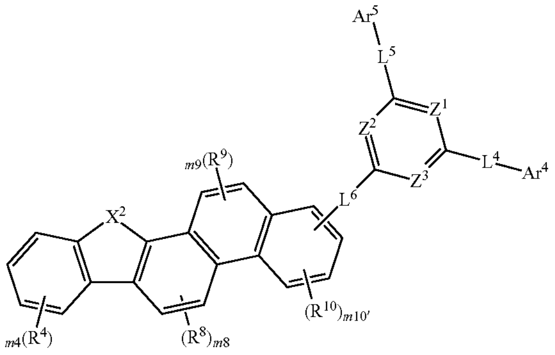

in Chemical Formula 1, $X^1$ is O or S, $L^1$ to $L^3$ are each independently a single bond, a substituted or unsubstituted C6 to C20 arylene group, or a substituted or unsubstituted C2 to C30 heterocyclic group, $Ar^1$ is a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted chrysenyl group, or a substituted or unsubstituted triphenylene group, $Ar^2$ and $Ar^3$ are each independently a substituted or unsubstituted C6 to C20 aryl group or a substituted or unsubstituted C2 to C30 heterocyclic group, $R^1$ to $R^3$ are each independently hydrogen, deuterium, a halogen, a substituted or unsubstituted C1 to C10 alkyl group, or a substituted or unsubstituted C6 to C12 aryl group, m1 and m2 are each independently an integer of 1 to 3, m3 is an integer of 1 to 4, n is 0 or 1, and "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof, and moieties *-$L^2$-$Ar^2$ and *-$L^3$-$Ar^3$ of Chemical Formula 1 do not include a thiophene group,

[Chemical Formula 2]

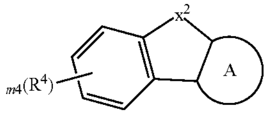

in Chemical Formula 2, $X^2$ is O, S, N-$L^a$-$R^a$, $CR^bR^c$, or $SiR^dR^e$, $L^a$ is a single bond or a substituted or unsubstituted C6 to C12 arylene group, $R^a$, $R^b$, RC, $R^d$, $R^e$ and $R^4$ are each independently hydrogen, deuterium, a substituted or unsubstituted C1 to C30 alkyl group, a substituted or unsubstituted C6 to C30 aryl group, or a substituted or unsubstituted C2 to C30 heterocyclic group, m4 is an integer of 1 to 4, and A is a ring of Group II,

[Group II]

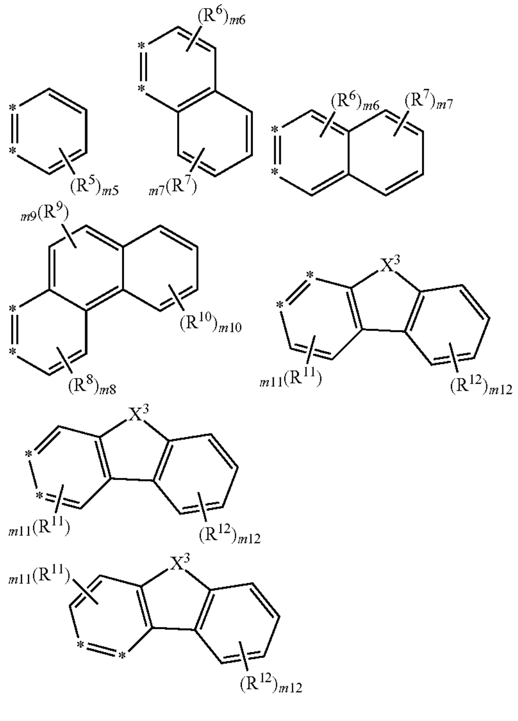

in Group II,

* is a linking point, $X^3$ is O or S, $R^5$ to $R^{12}$ are each independently hydrogen, deuterium, a substituted or unsubstituted C1 to C30 alkyl group, a substituted or unsubstituted C6 to C30 aryl group, or a substituted or unsubstituted C2 to C30 heterocyclic group, m5, m7, m10, and m12 are each independently an integer of 1 to 4, m6, m8, m9, and m11 are each independently 1 or 2, and at least one of $R^a$ and $R^4$ to $R^{12}$ is a substituted heterocyclic group represented by Chemical Formula a,

[Chemical Formula a]

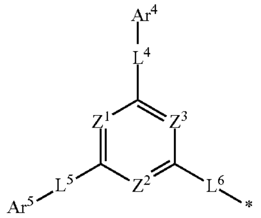

in Chemical Formula a, $Z^1$ to $Z^3$ are each independently N or CRI, provided that at least two of $Z^1$ to $Z^3$ are N, $R^f$ is hydrogen, deuterium, a substituted or unsubstituted C1 to C10 alkyl group, or a substituted or unsubstituted C6 to C20 aryl group, $L^4$ to $L^6$ are each independently a single bond or a substituted or unsubstituted C6 to C30 arylene group, $Ar^4$ and $Ar^5$ are each independently a substituted or unsubstituted C6 to C30 aryl group or a substituted or unsubstituted C2 to C30 heterocyclic group, and

* is a linking point.

20. A compound for an organic optoelectronic device, wherein the compound is a compound of Group 1:

[Group 1]

1-1

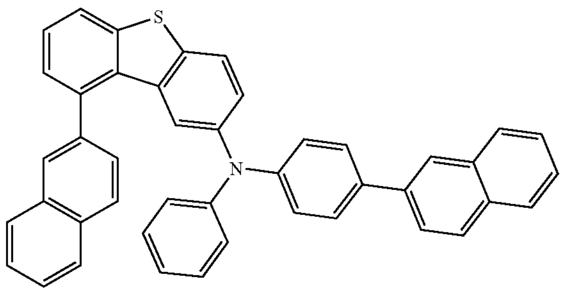

1-2

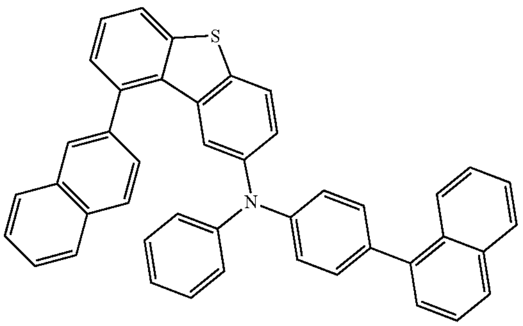

-continued
1-3
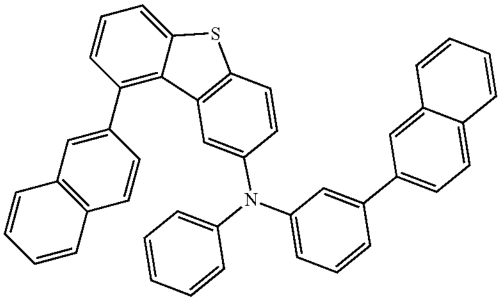
1-4
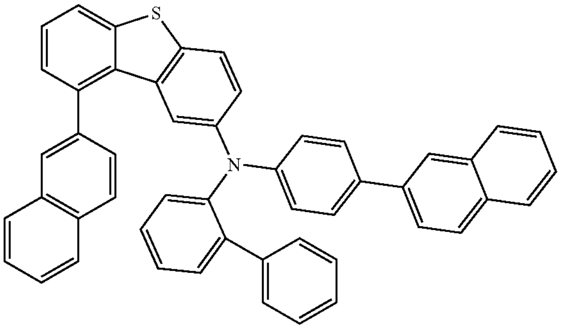
1-5
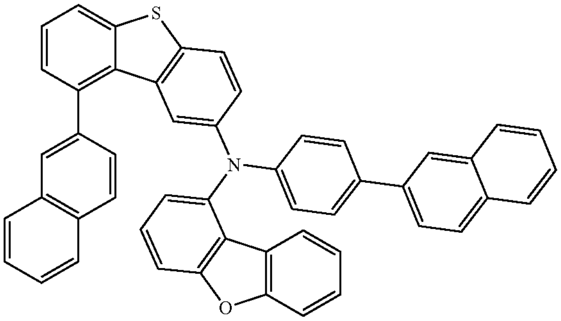
1-6
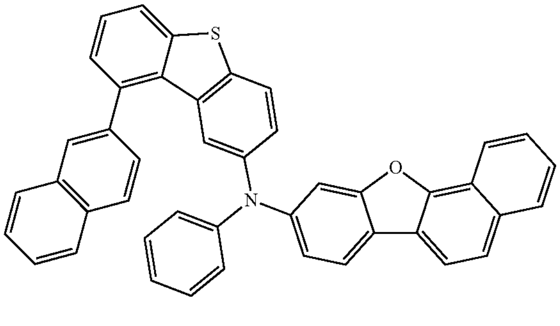
-continued
1-7
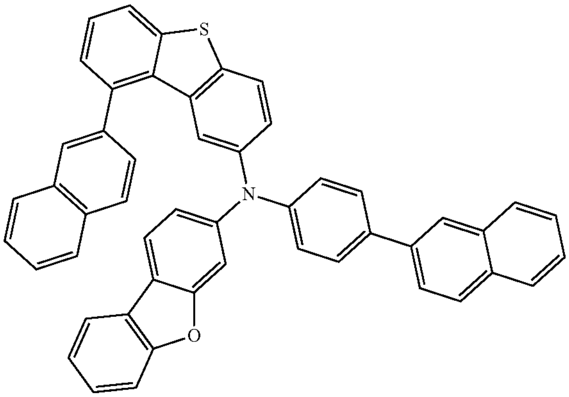
1-8
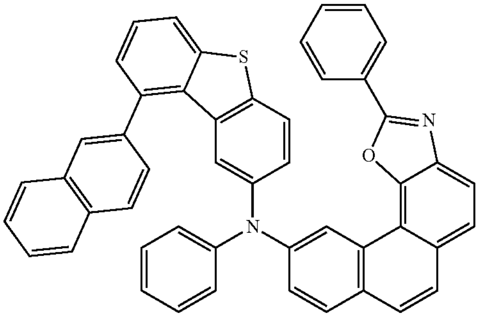
1-9
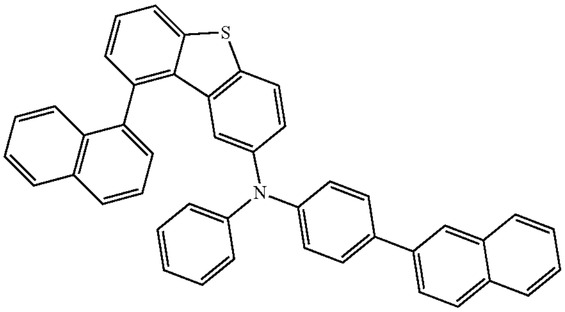
1-10
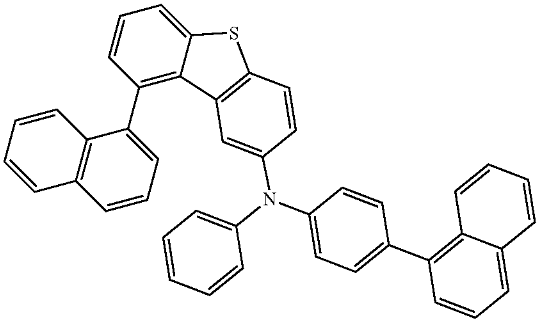

-continued
1-11
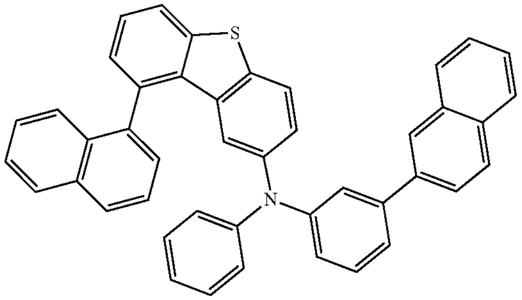
1-12
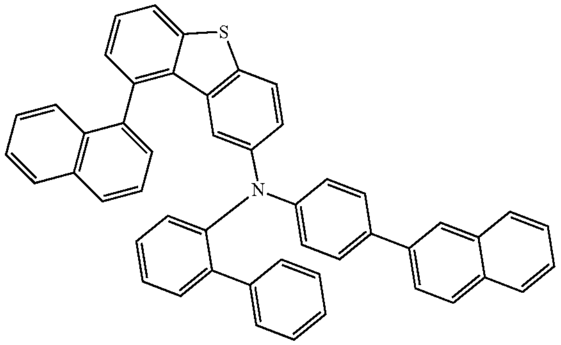
1-13
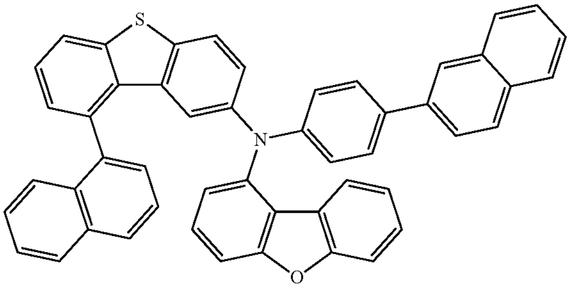
1-14
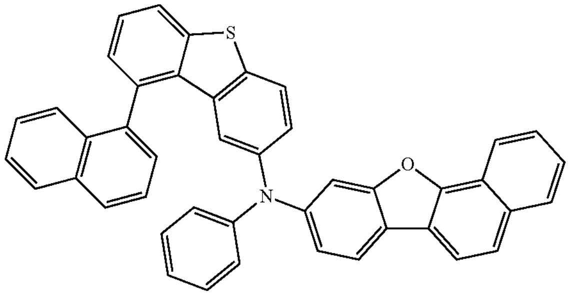
-continued
1-15
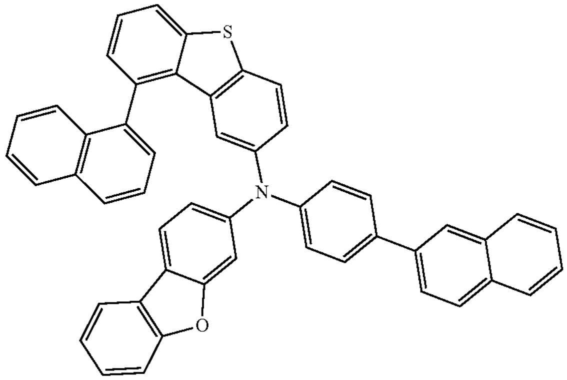
1-16
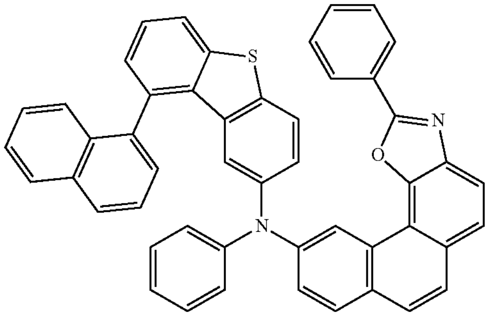
1-17
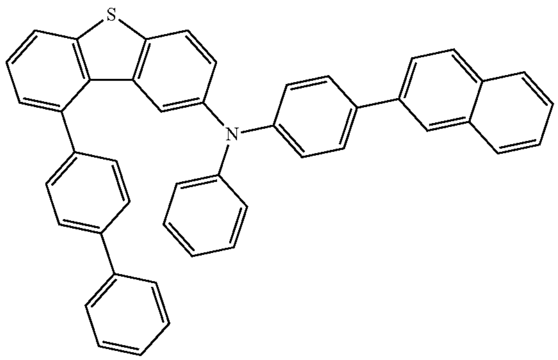
1-18
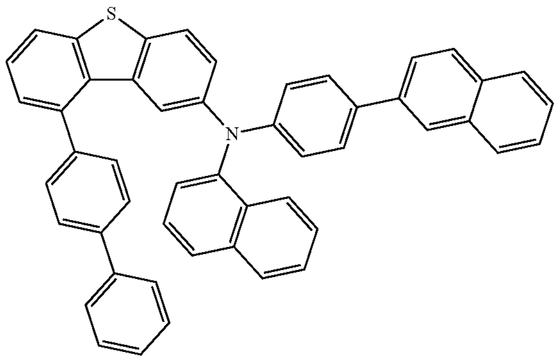

-continued
1-19
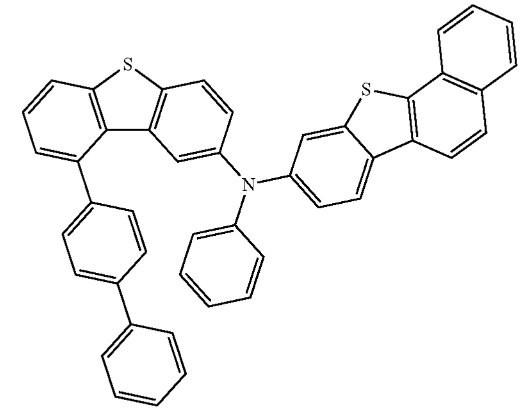
1-20
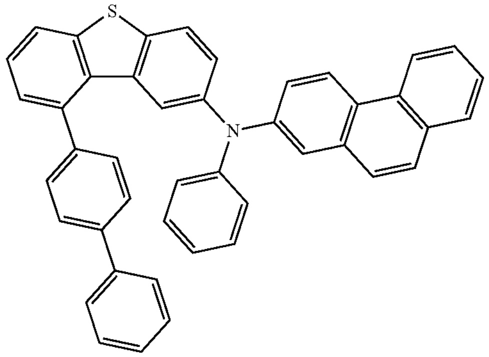
1-21
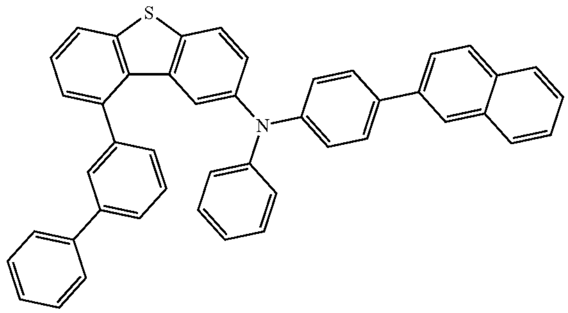
1-22
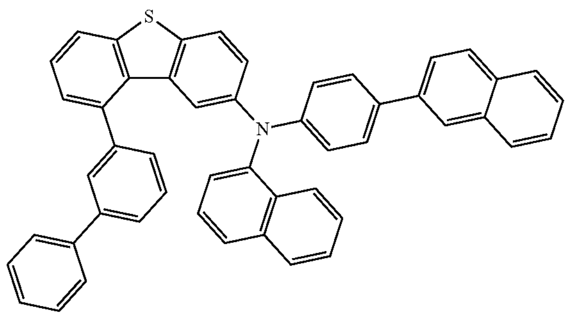
-continued
1-23
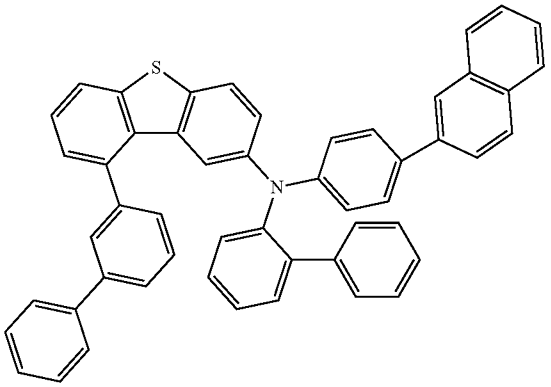
1-24
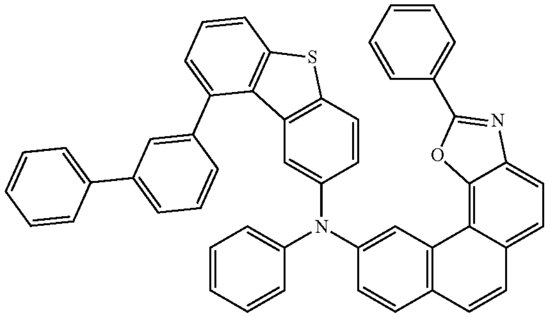
1-25
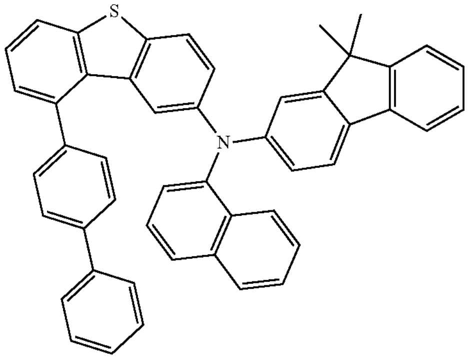
1-26
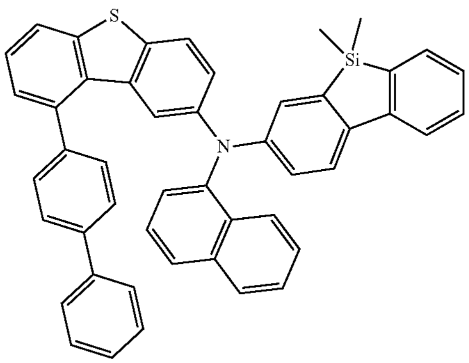

-continued
1-27
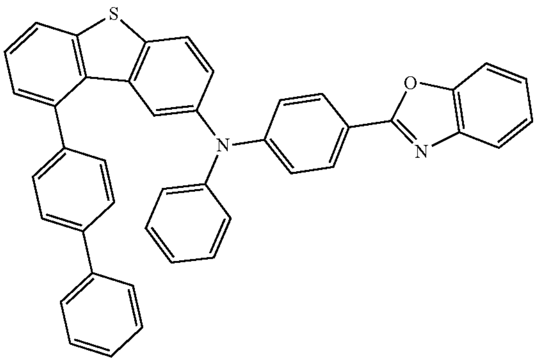
1-28
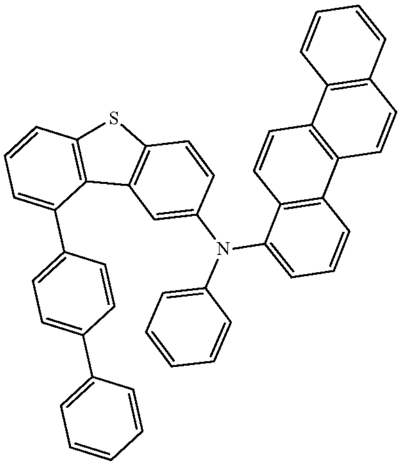
1-29
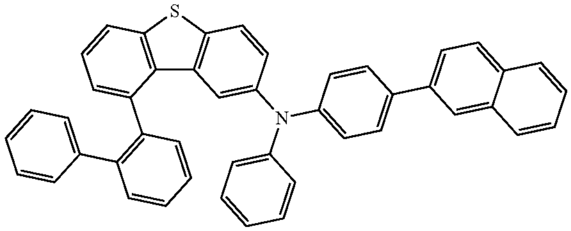
1-30
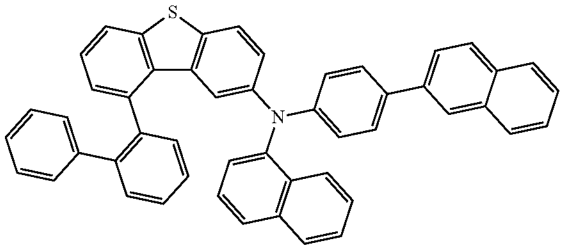
-continued
1-31
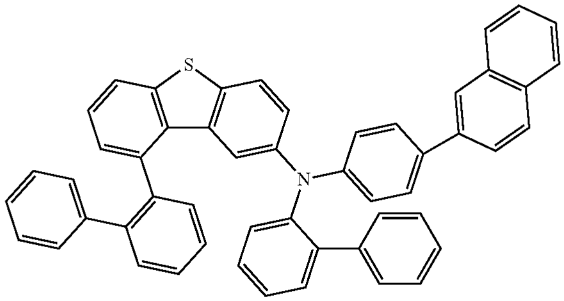
1-32
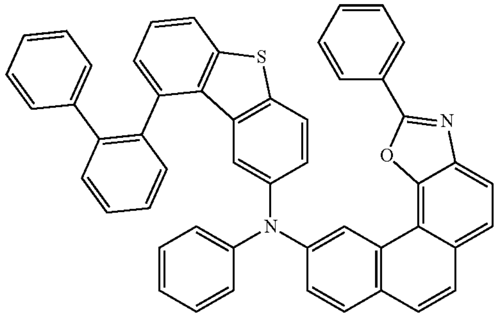
1-33
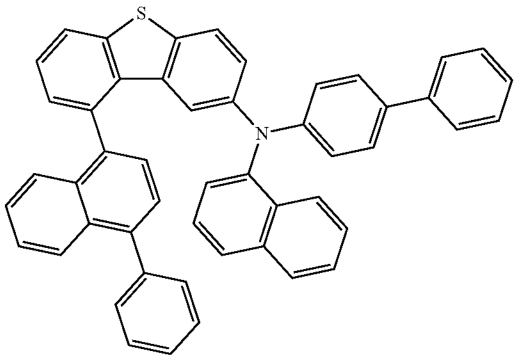
1-34
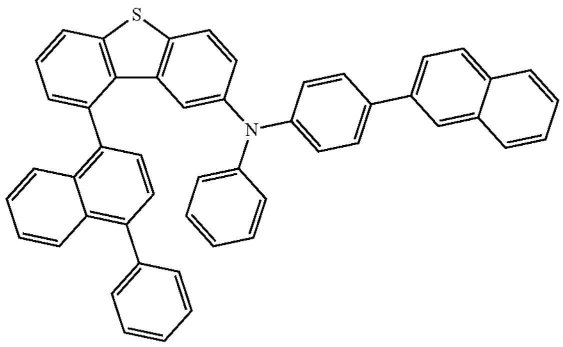

-continued
1-35
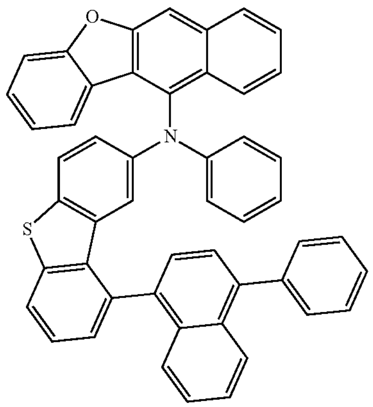
1-36
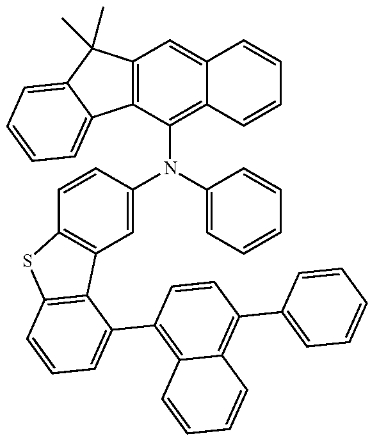
1-37
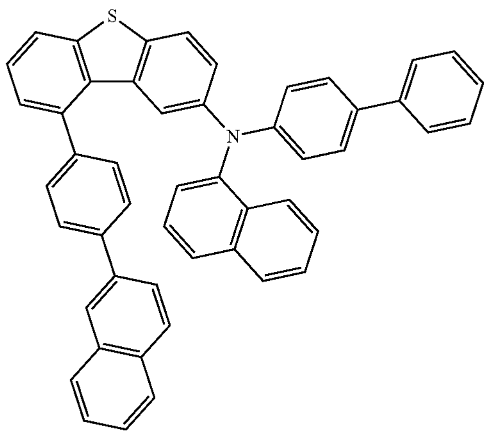
-continued
1-38
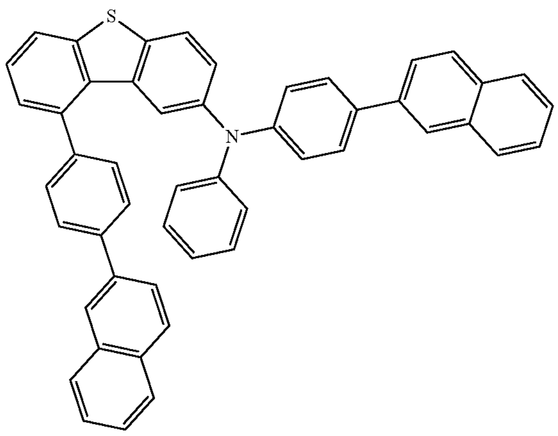
1-39
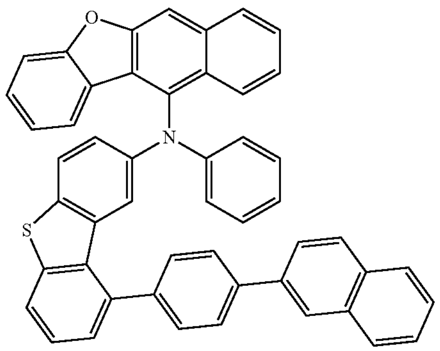
1-40
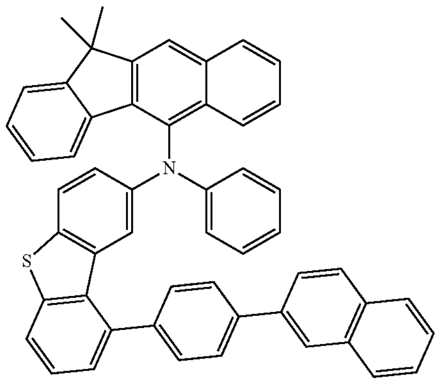

-continued
1-41
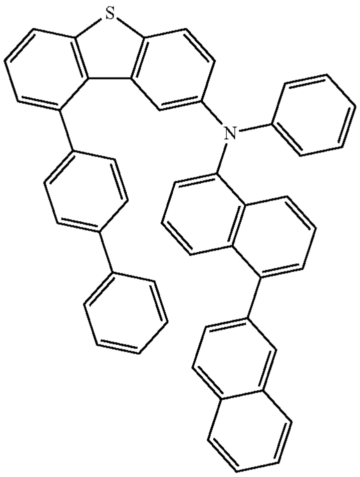
1-42
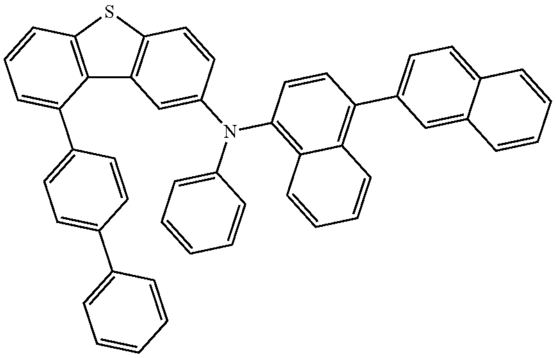
1-43
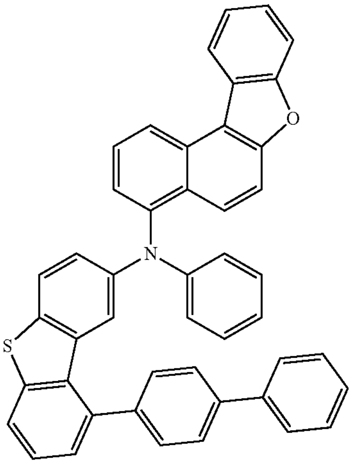
-continued
1-44
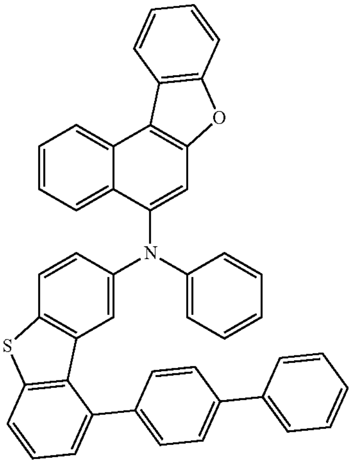
1-45
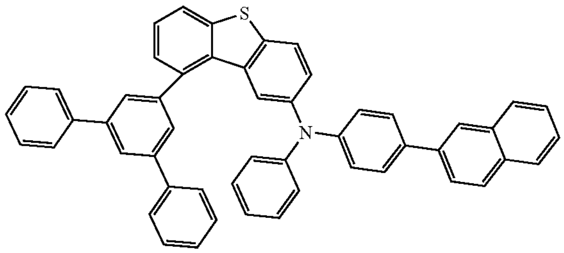
1-46
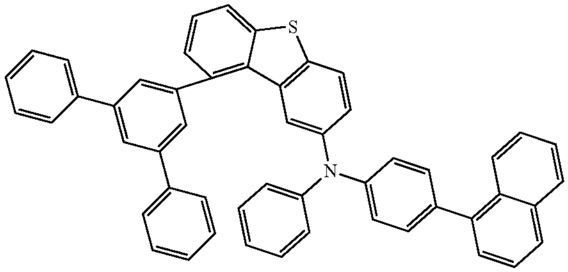
1-47
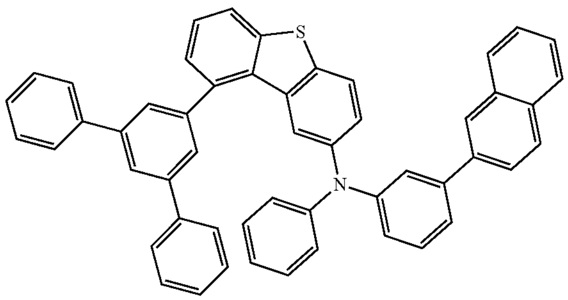

-continued
1-48
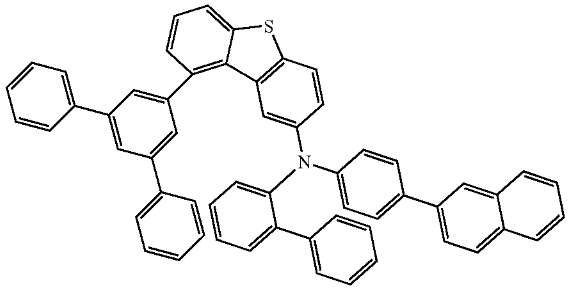
1-49
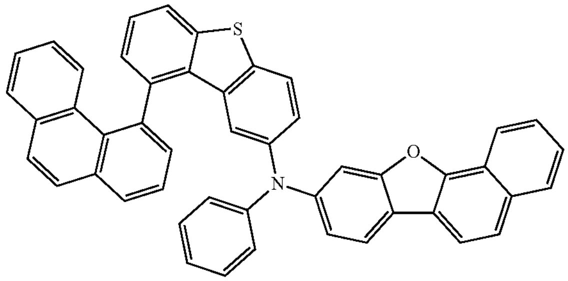
1-50
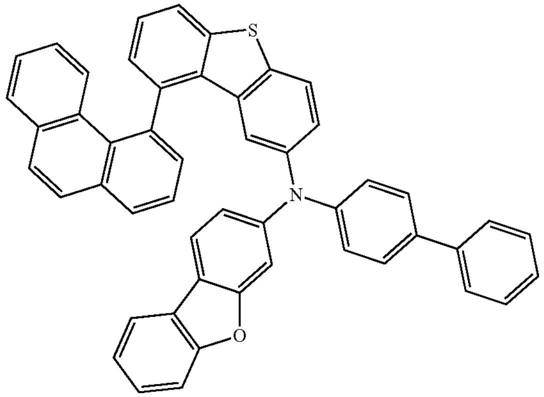
1-51
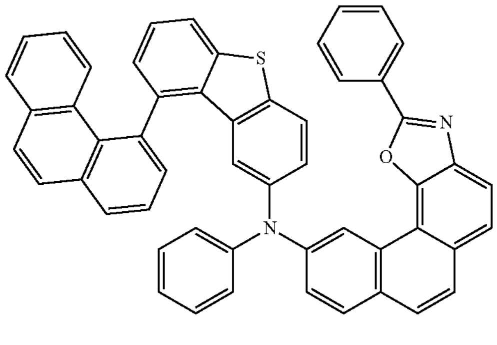
-continued
1-52
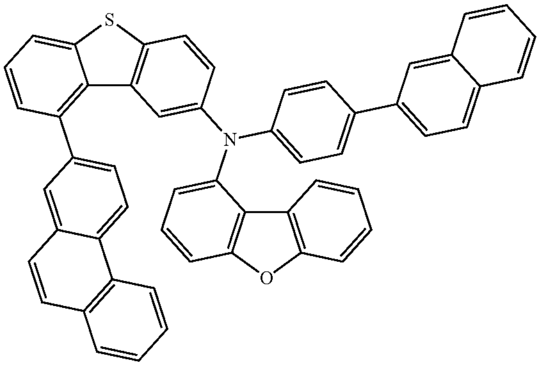
1-53
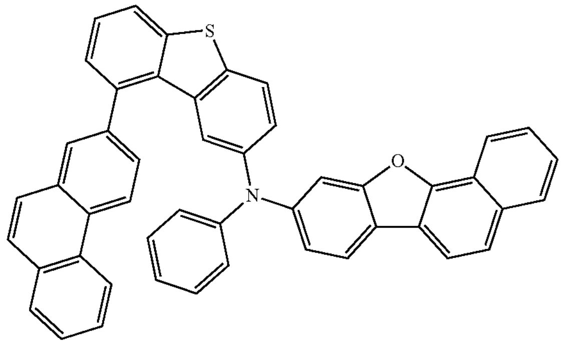
1-54
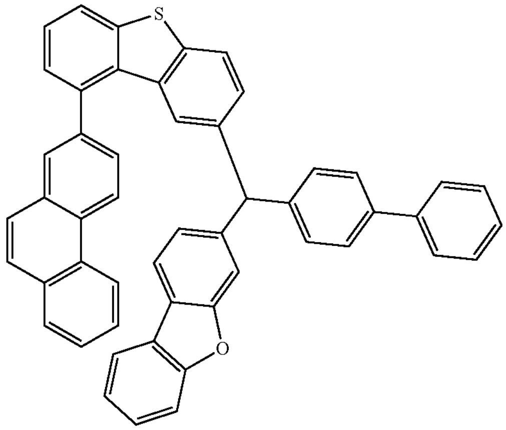
1-55
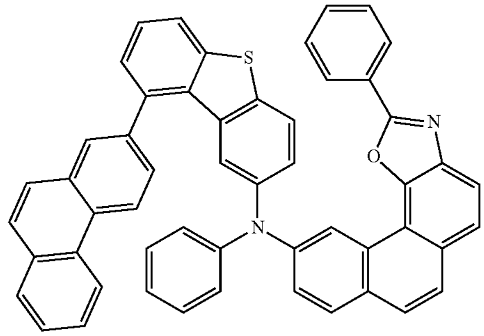

-continued
1-56
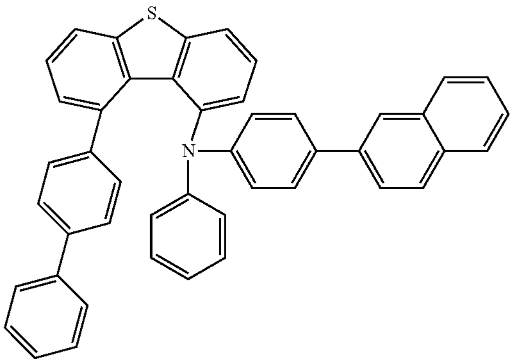
1-57
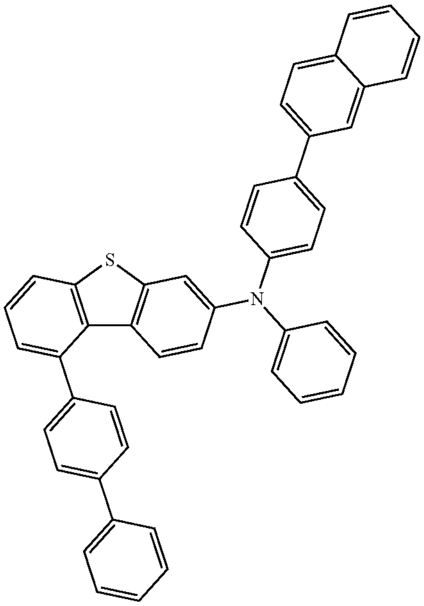
1-58
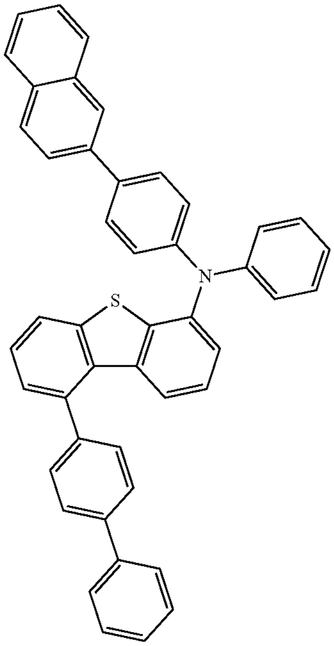
-continued
1-59
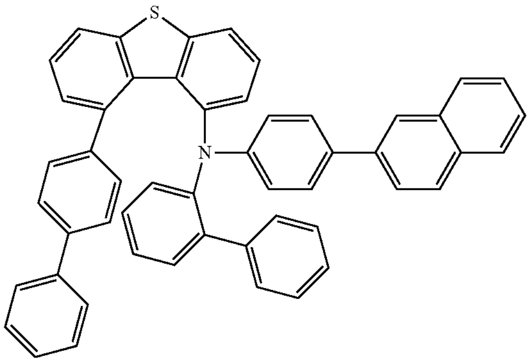
1-60
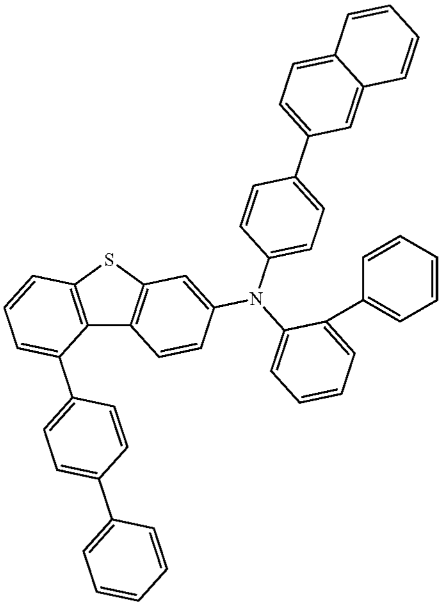
1-61
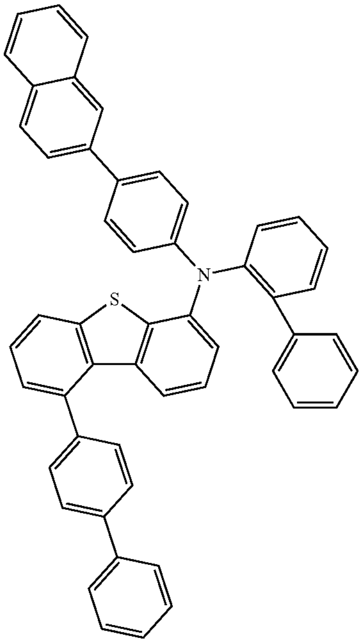

-continued
1-62
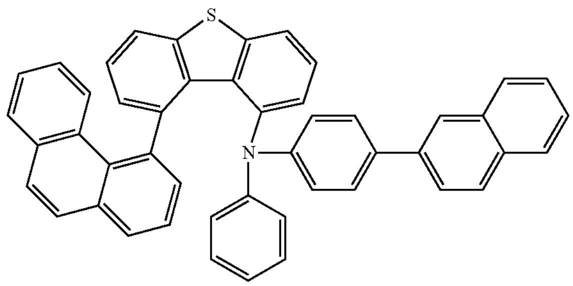
1-63
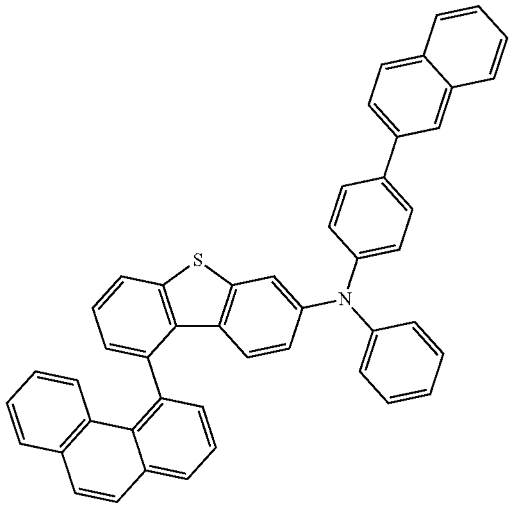
1-64
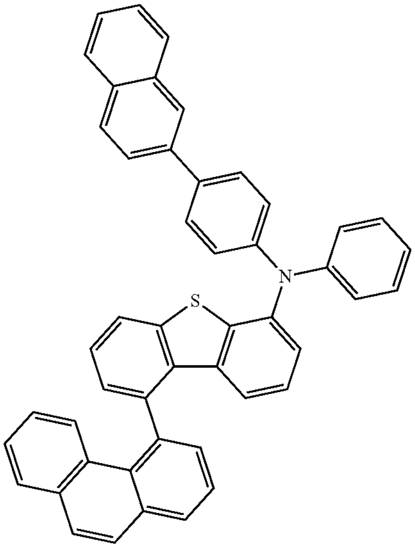
-continued
1-65
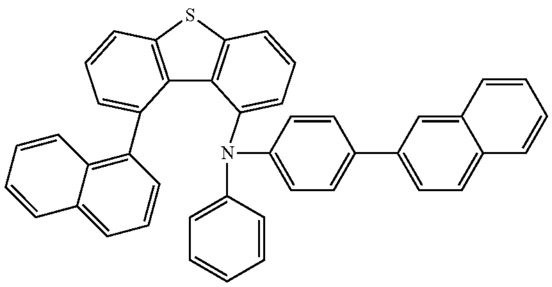
1-66
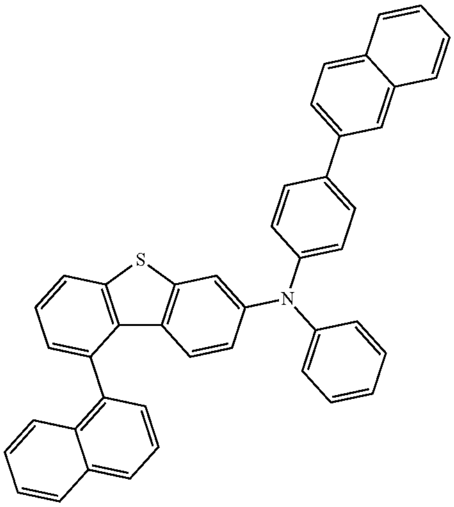
1-67
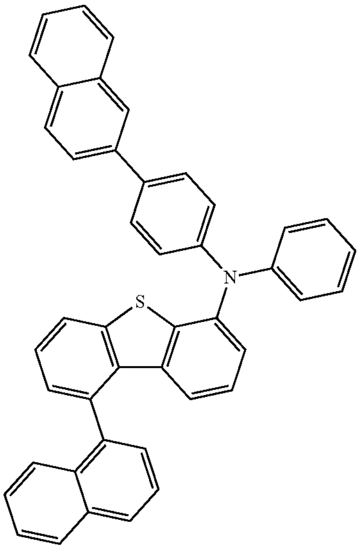

-continued
1-68
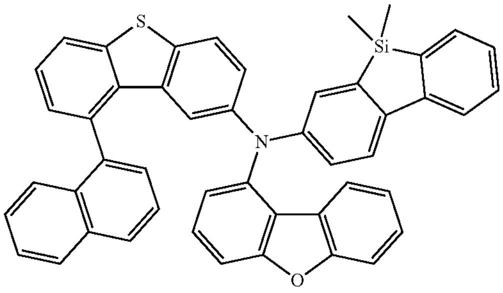
1-69
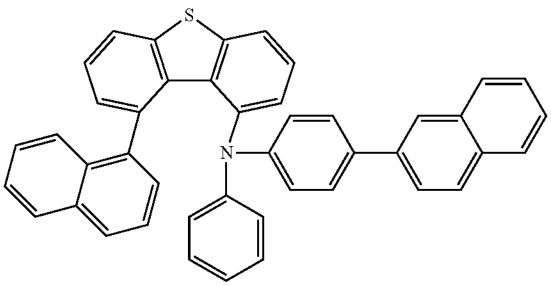
1-70
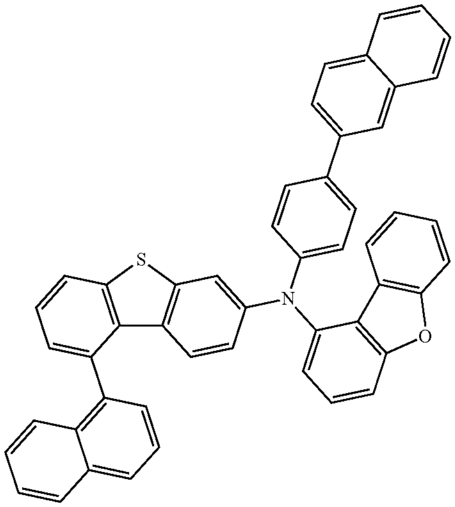
-continued
1-71
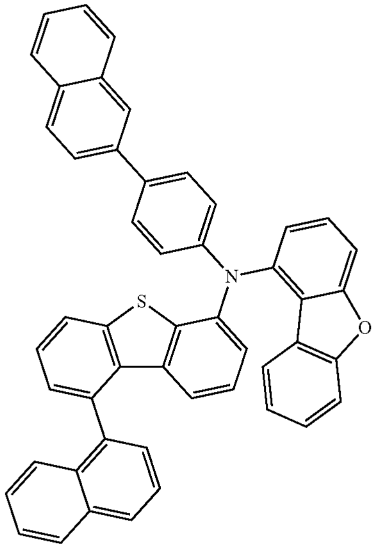
1-72
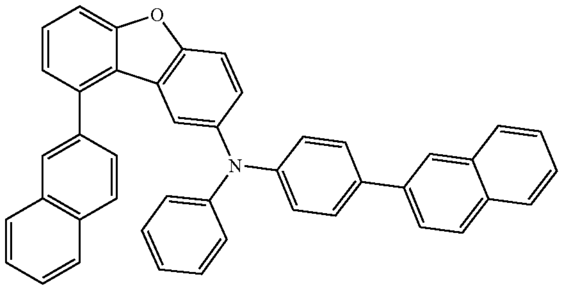
1-73
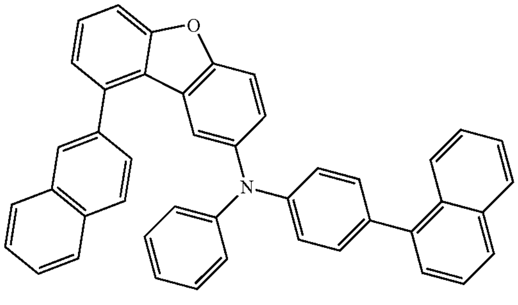
1-74
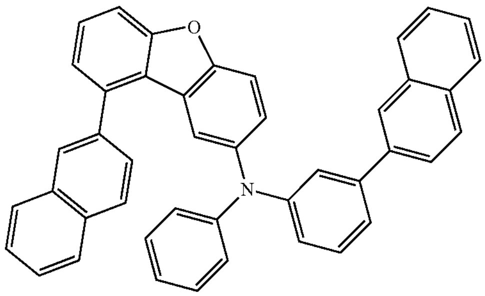

-continued
1-75
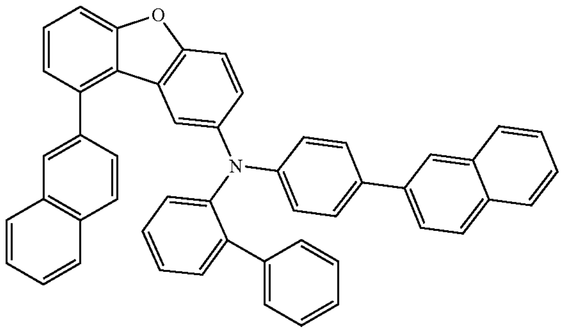
1-76
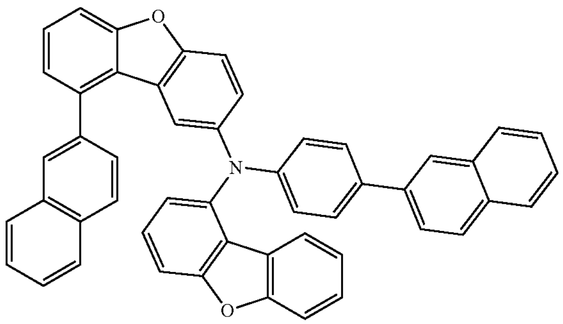
1-77
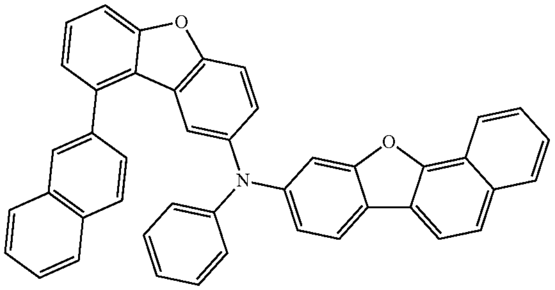
1-78
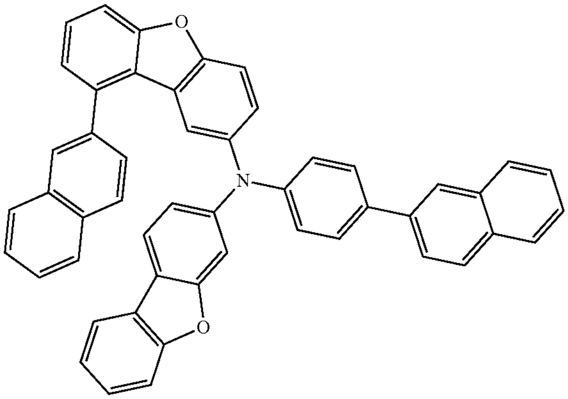
-continued
1-79
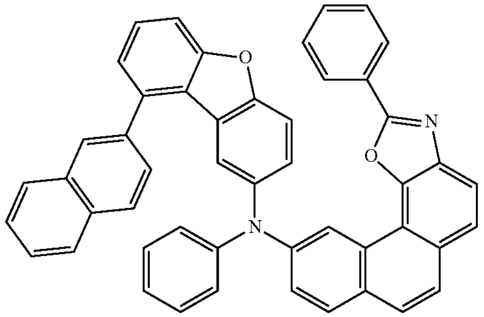
1-80
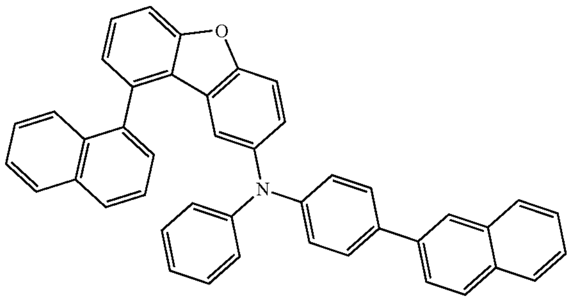
1-81
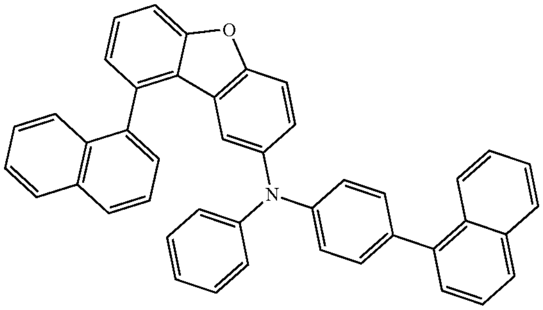
1-82
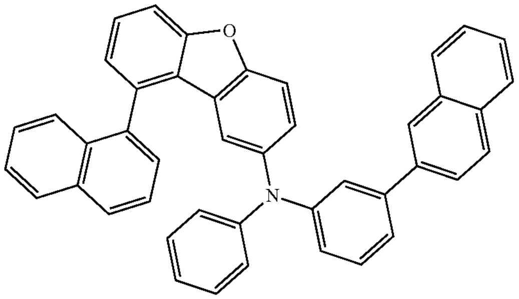

-continued
1-83
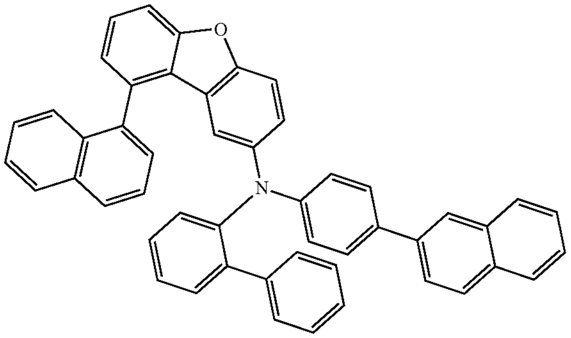
1-84
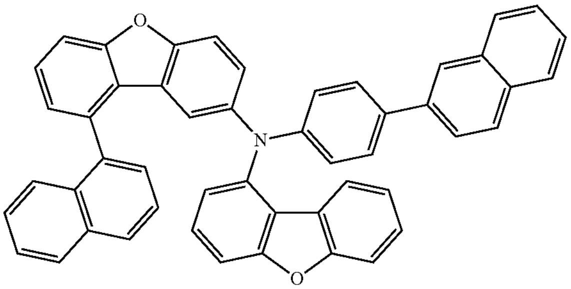
1-85
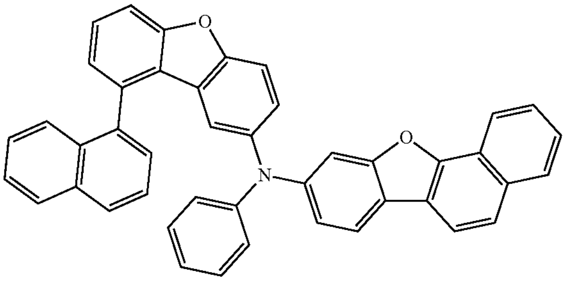
1-86
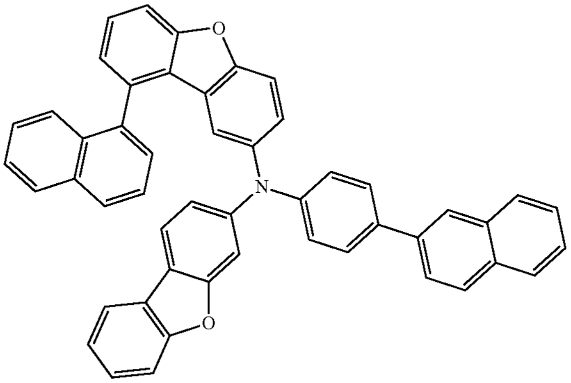
-continued
1-87
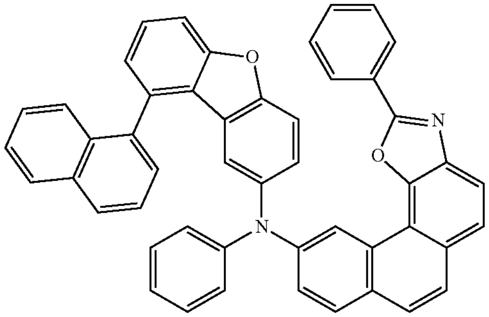
1-88
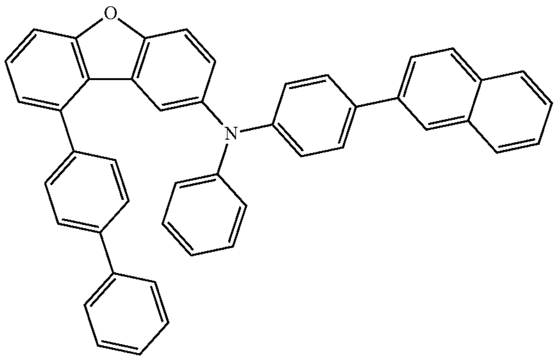
1-89
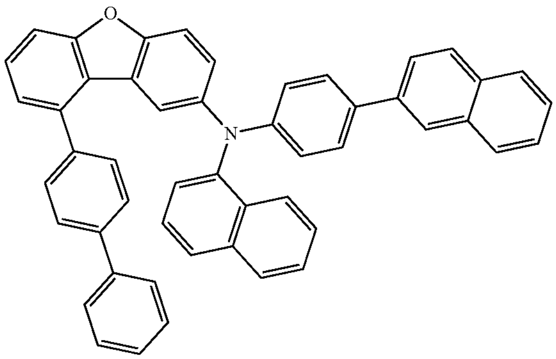
1-90
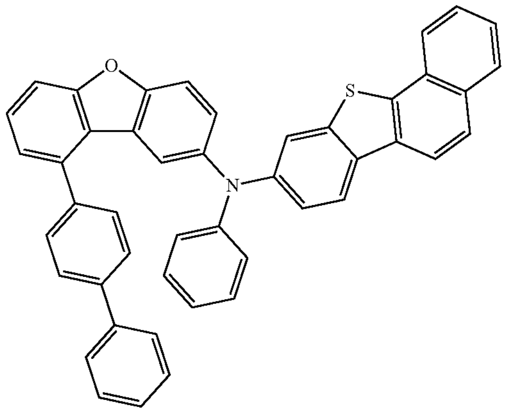

-continued
1-91
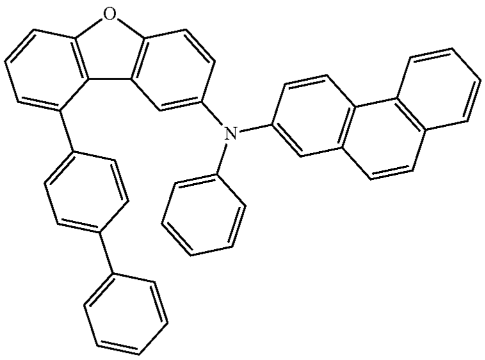
1-92
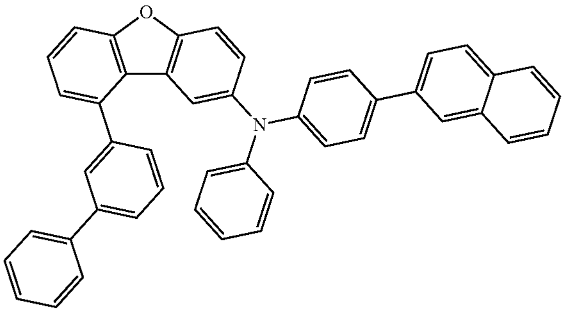
1-93
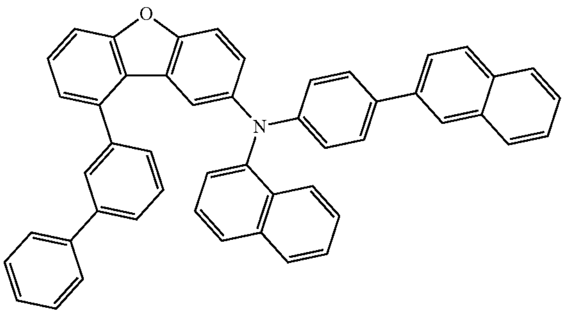
1-94
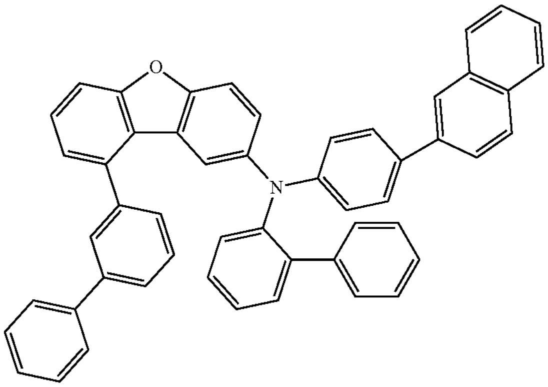
-continued
1-95
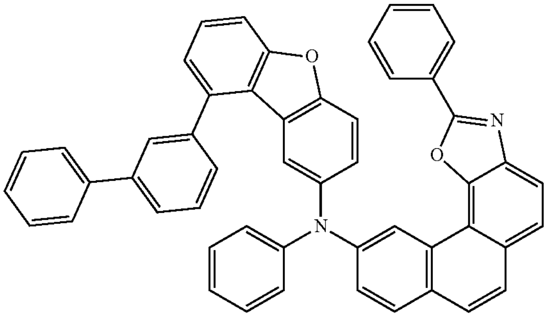
1-96
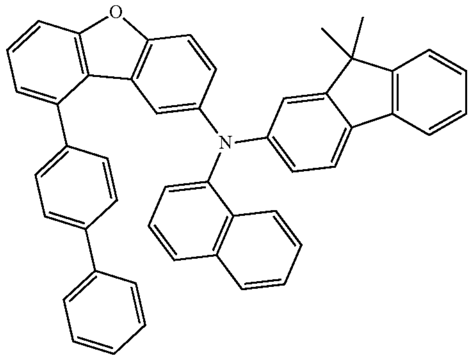
1-97
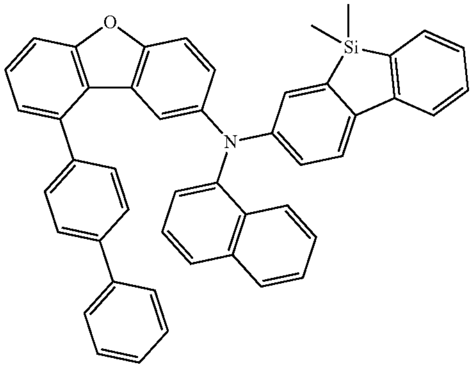
1-98
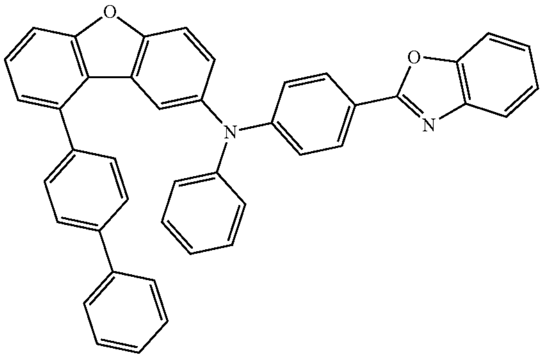

-continued
1-99
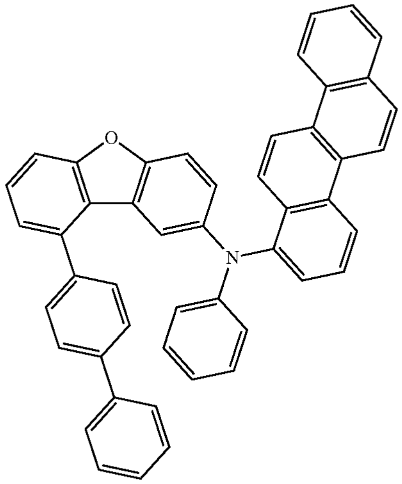
1-100
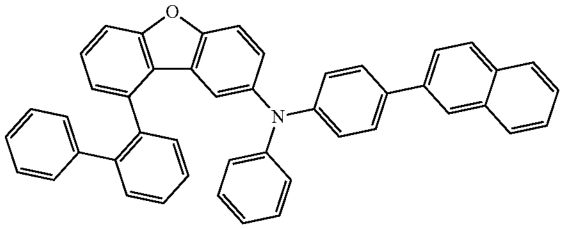
1-101
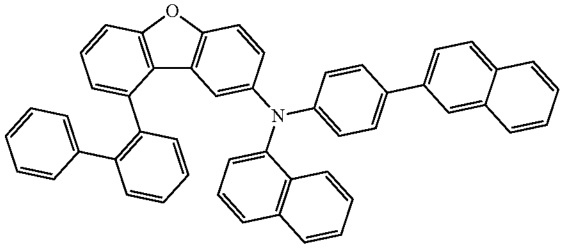
1-102
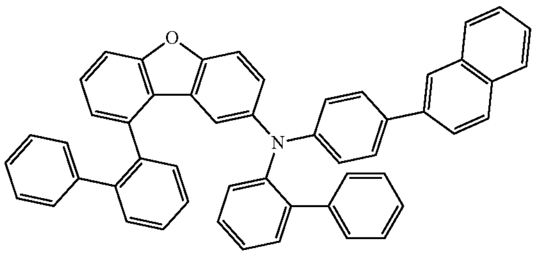
1-103
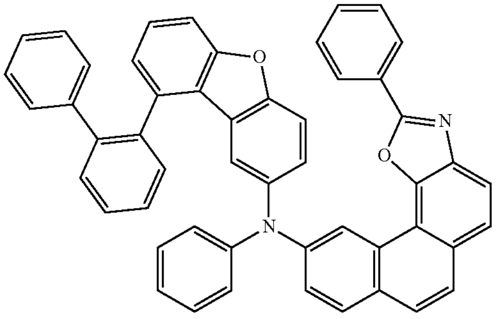
-continued
1-104
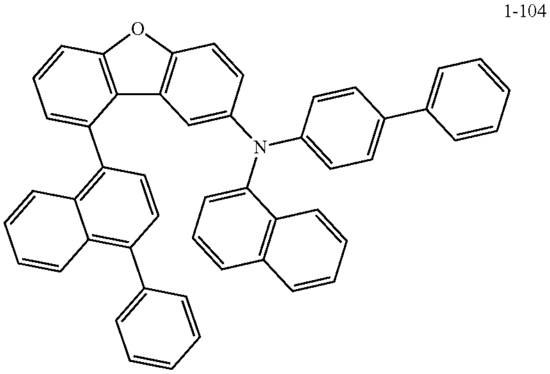
1-105
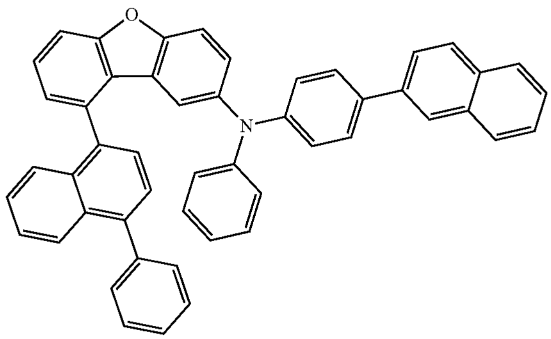
1-106
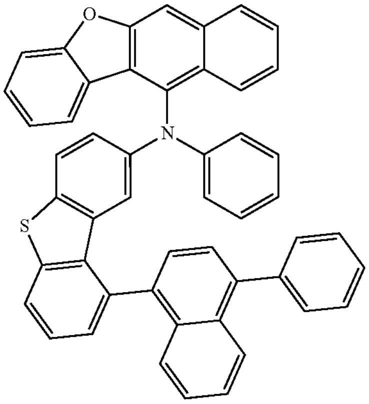
1-107
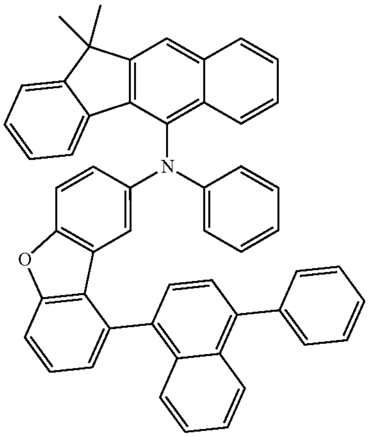

-continued
1-108
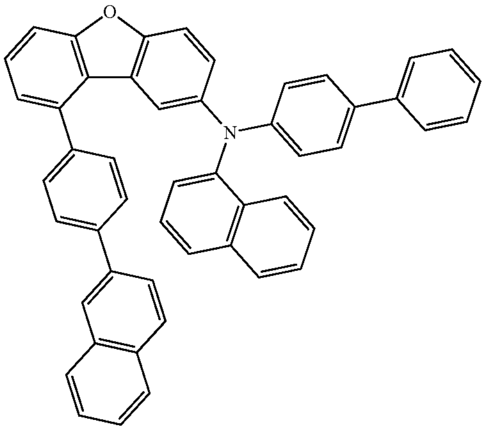
1-109
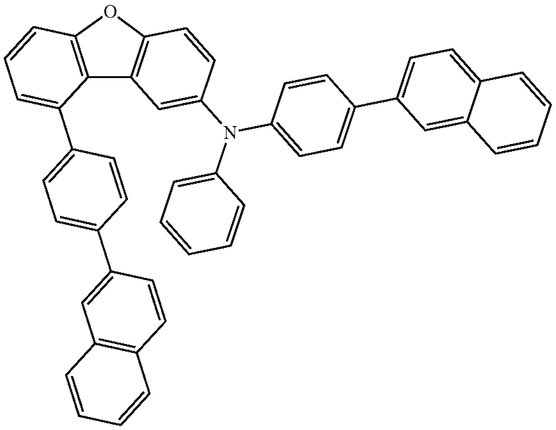
1-110
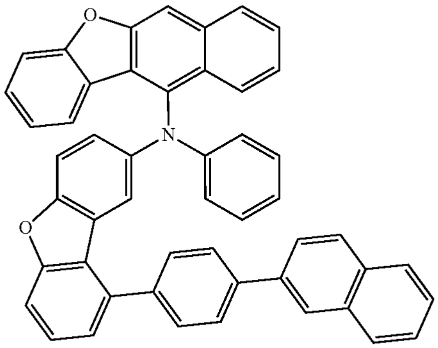
-continued
1-111
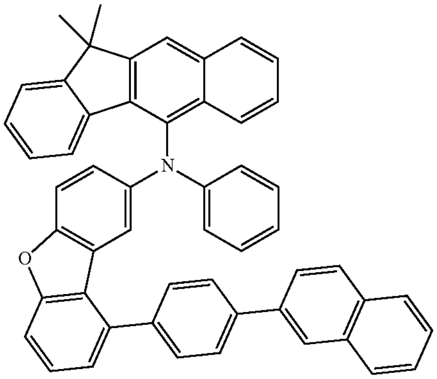
1-112
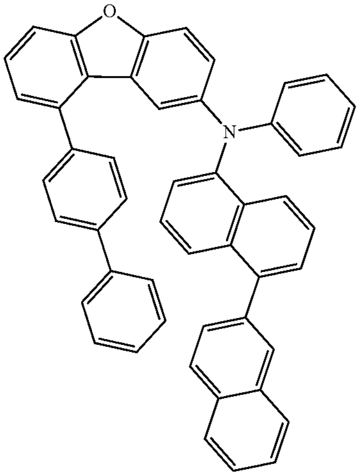
1-113
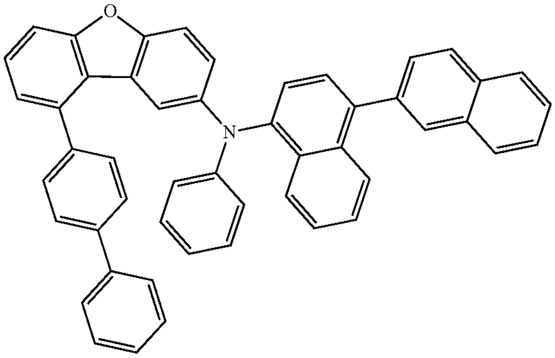

-continued
1-114
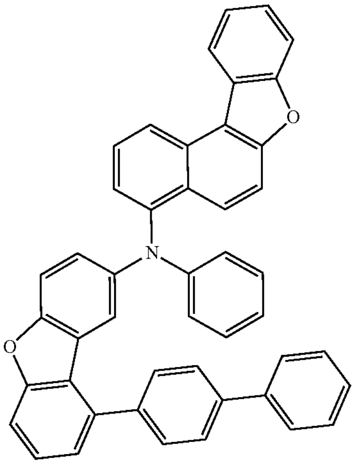
1-115
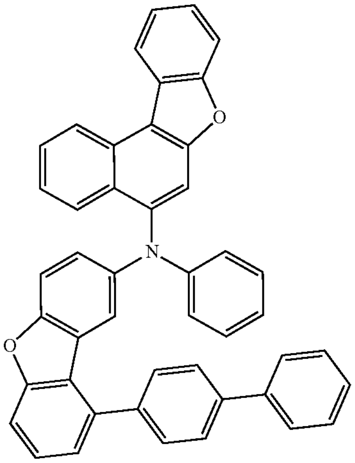
1-116
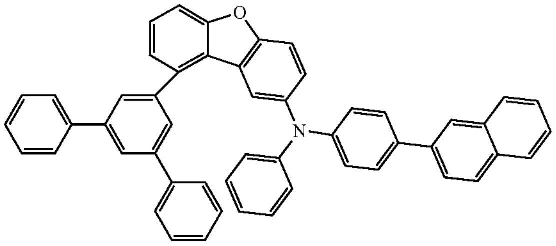
1-117
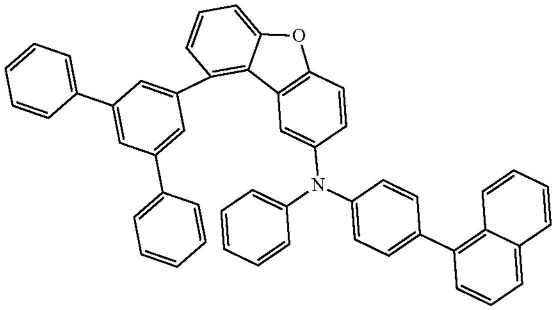
-continued
1-118
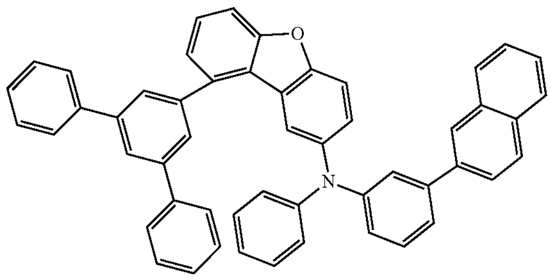
1-119
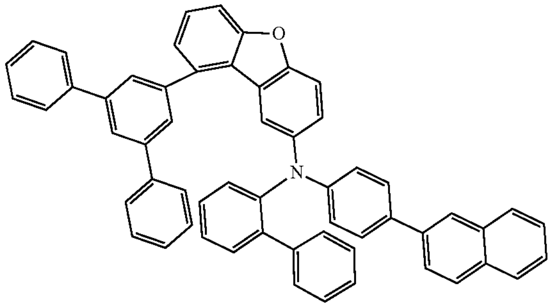
1-120
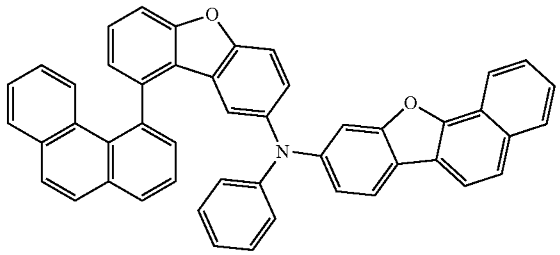
1-121
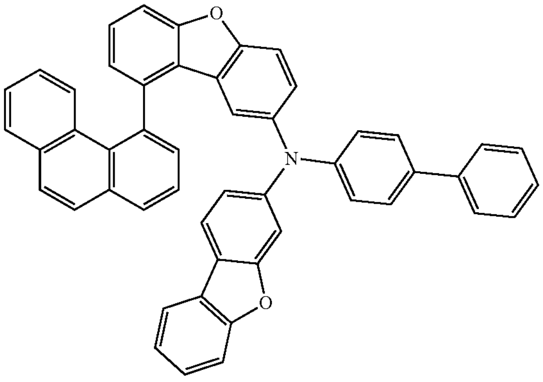
1-122
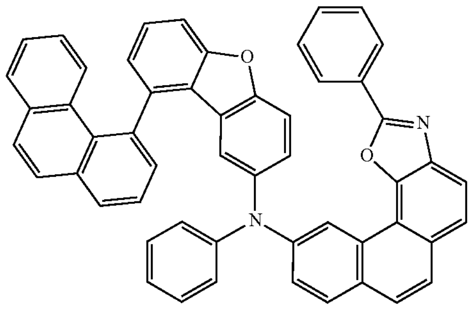

-continued
1-123
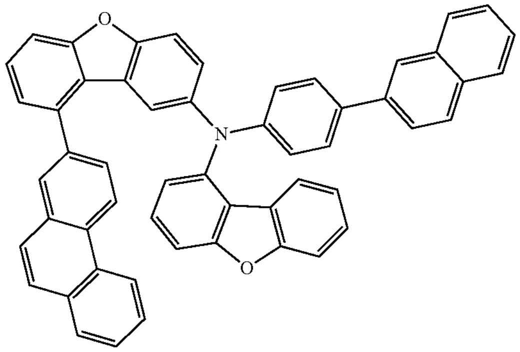
1-124
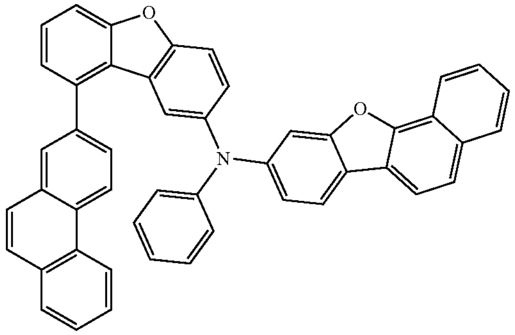
1-125
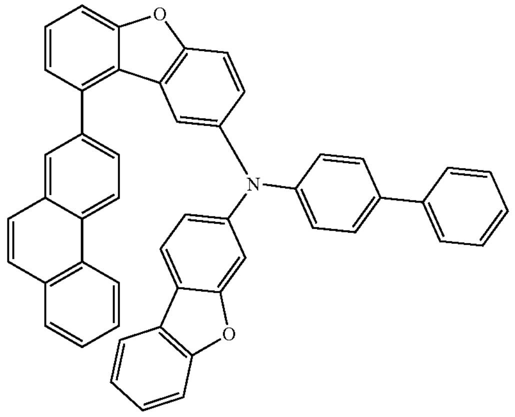
1-126
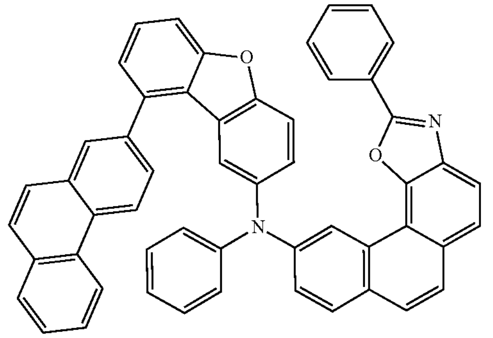
-continued
1-127
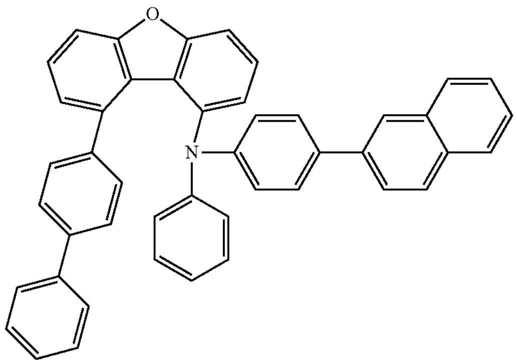
1-128
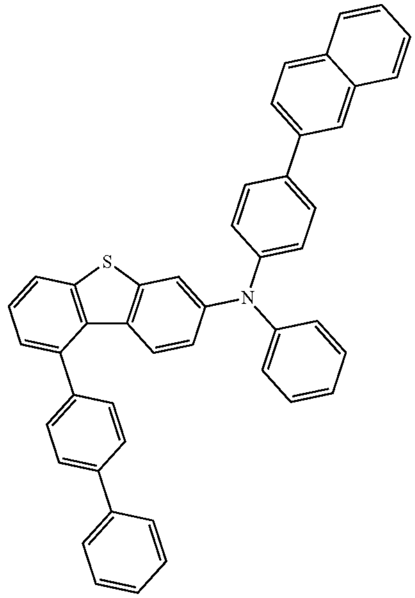
1-129
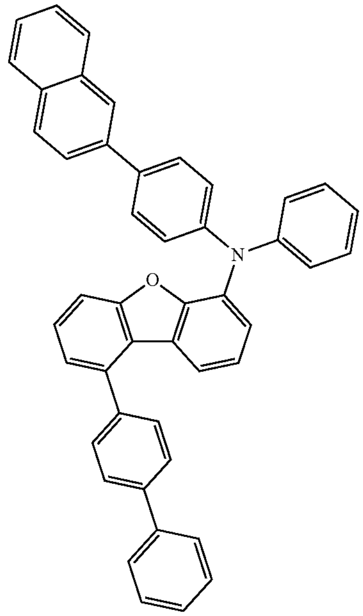

-continued
1-130
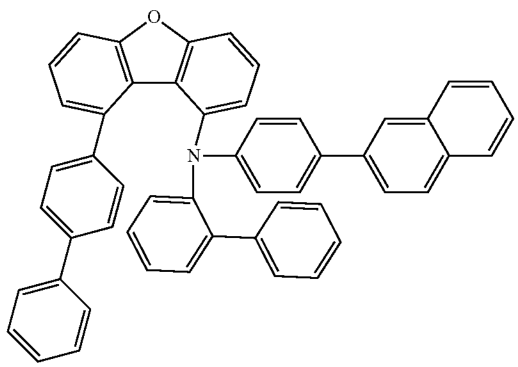
1-131
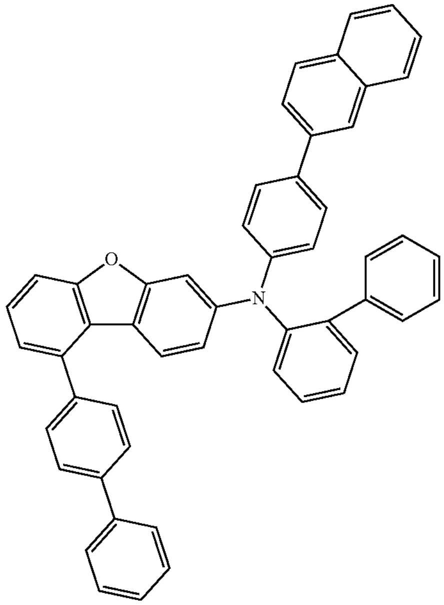
1-132
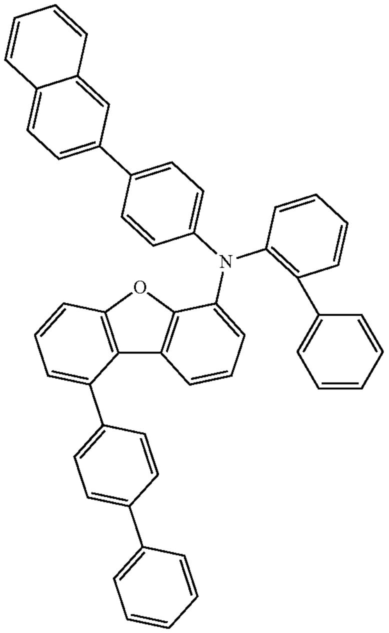
-continued
1-133
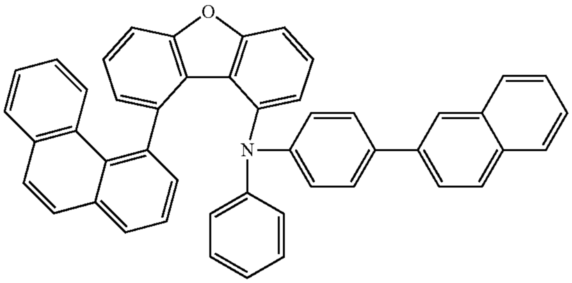
1-134
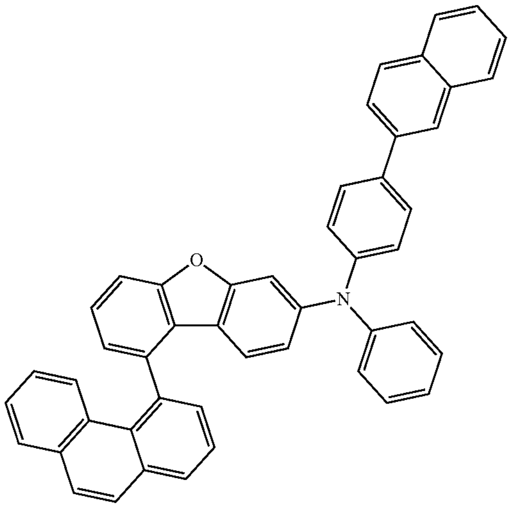
1-135
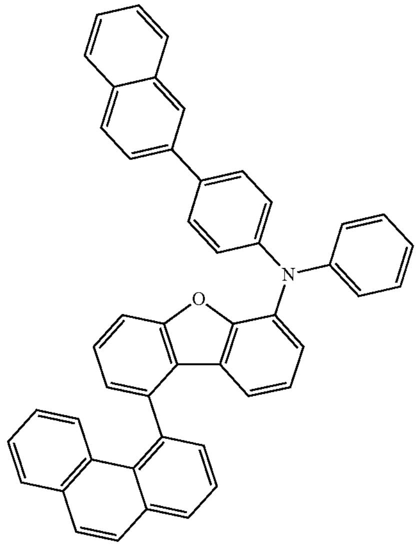

-continued
1-136
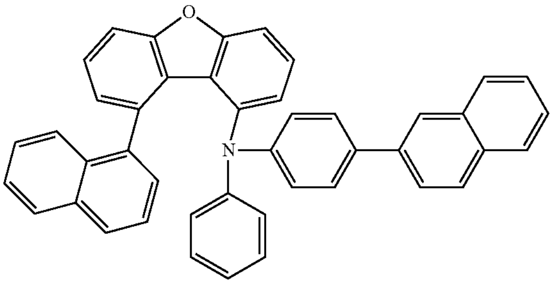
1-137
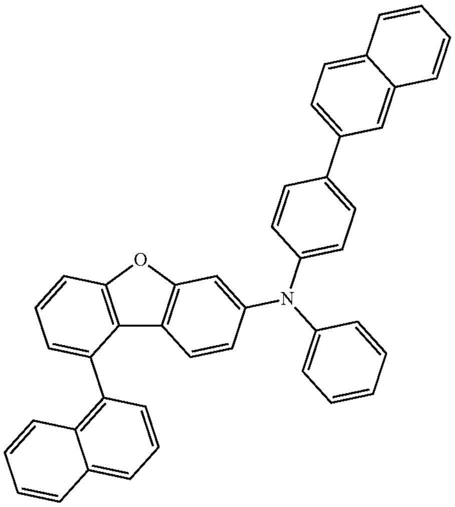
1-138
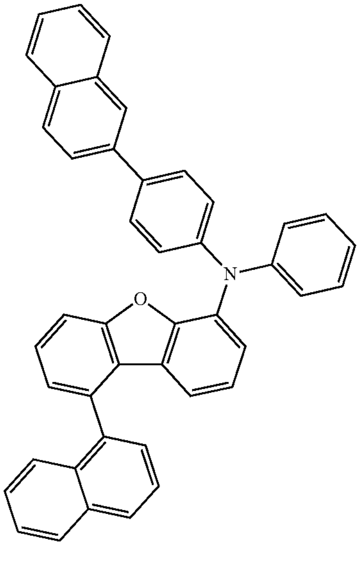
-continued
1-139
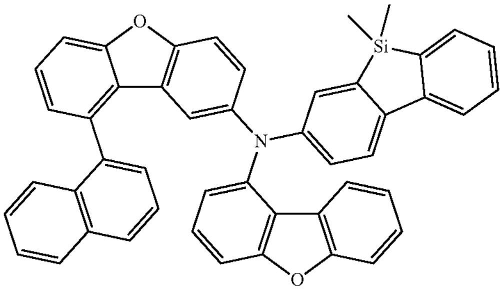
1-140
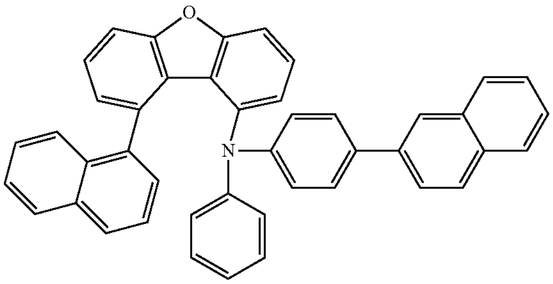
1-141
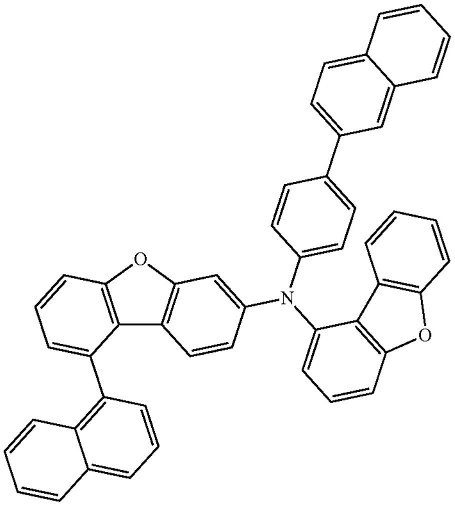

-continued
1-142
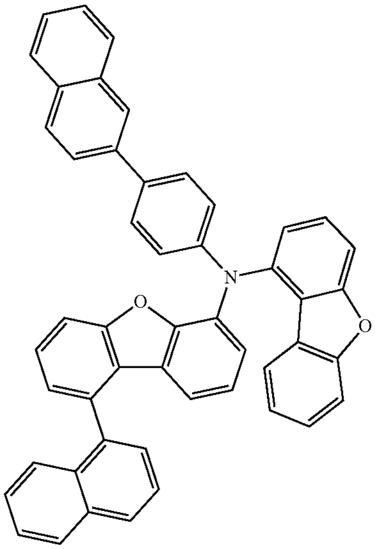
1-143
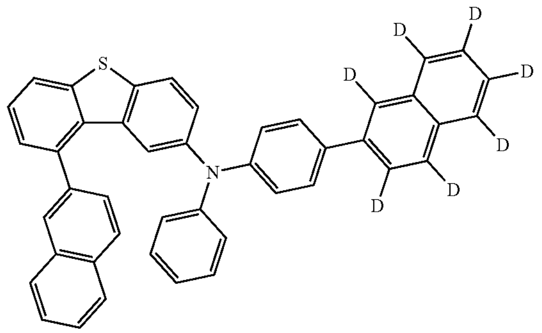
1-144
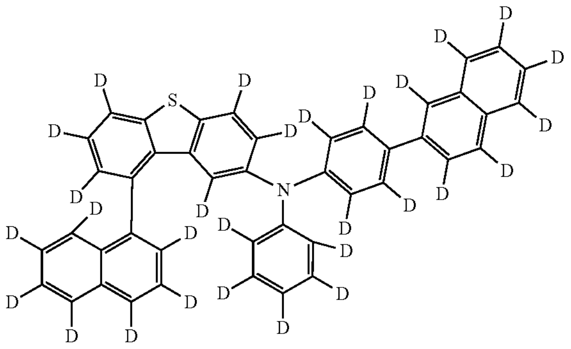
-continued
1-145
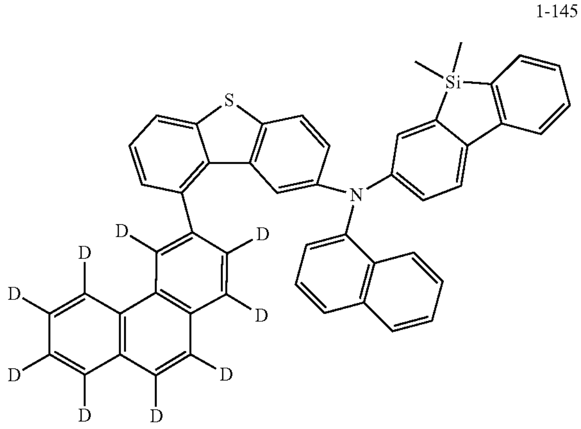
1-146
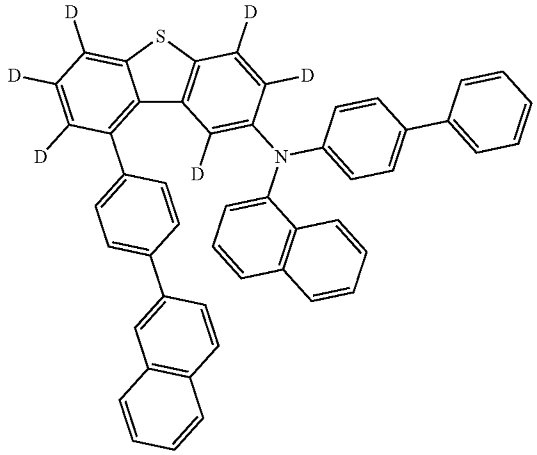
1-147
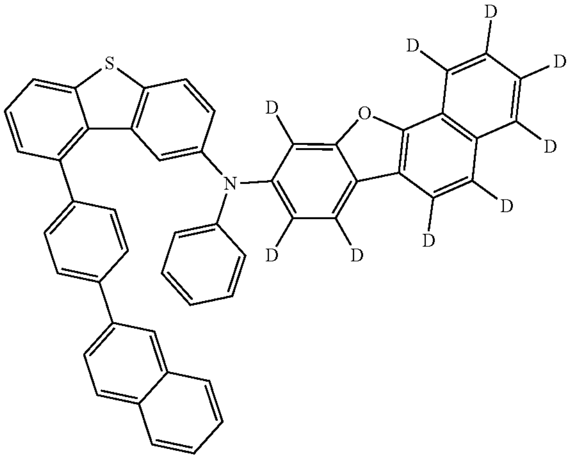

-continued
1-148
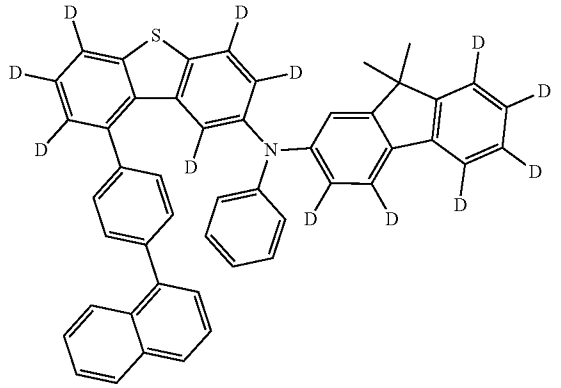
1-149
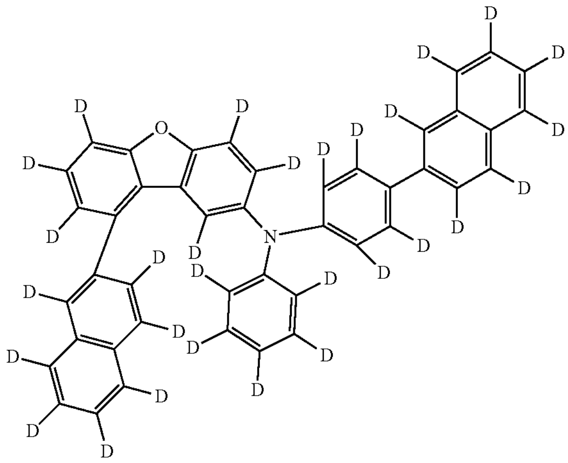
1-150
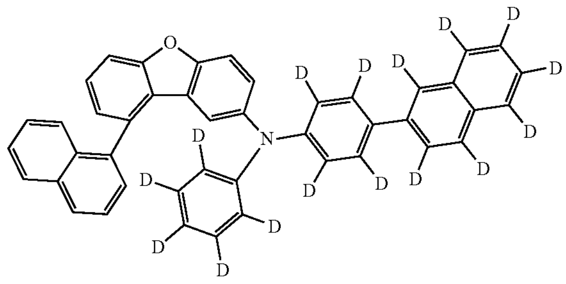
1-151
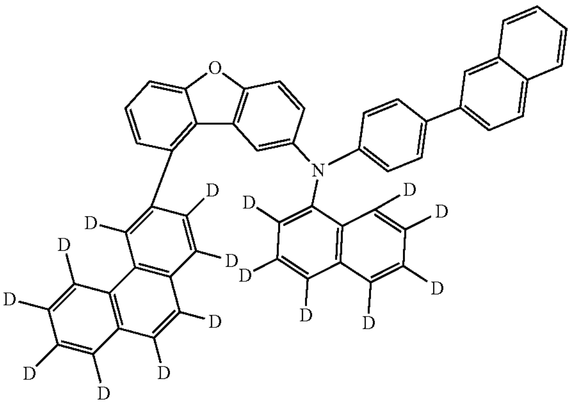
-continued
1-152
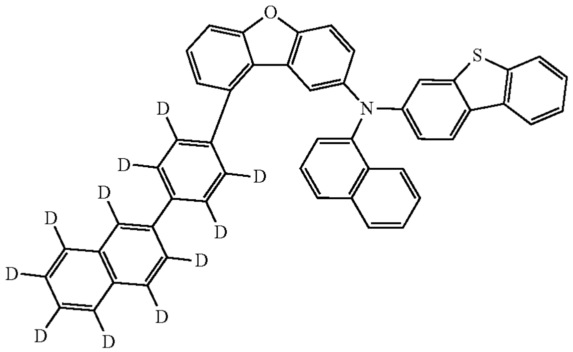
1-153
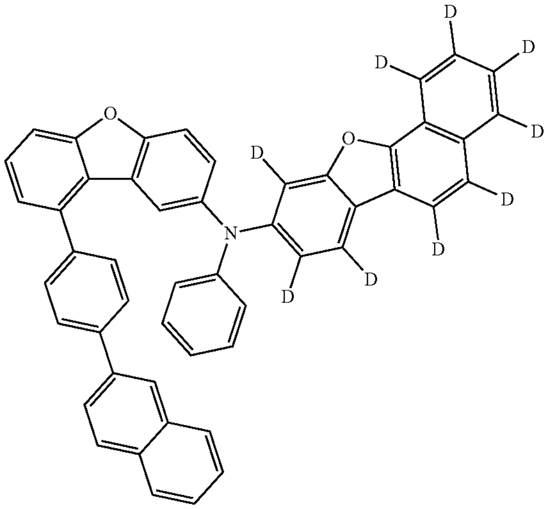
1-154
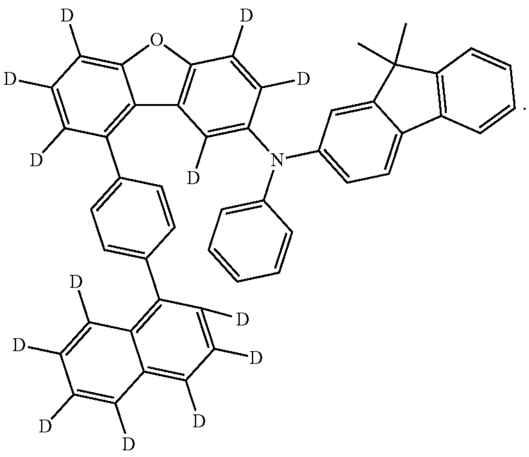
* * * * *